United States Patent
Pyun et al.

(10) Patent No.: US 11,892,353 B2
(45) Date of Patent: Feb. 6, 2024

(54) DIAGNOSIS METHOD USING LASER INDUCED BREAKDOWN SPECTROSCOPY AND DIAGNOSIS DEVICE PERFORMING THE SAME

(71) Applicant: SPECLIPSE, INC., Gyeonggi-do (KR)

(72) Inventors: Sung Hyun Pyun, Seoul (KR); Wan Ki Min, Gyeonggi-do (KR)

(73) Assignee: SPECLIPSE, INC., Gyeonggi-do (KR)

( * ) Notice: Subject to any disclaimer, the term of this patent is extended or adjusted under 35 U.S.C. 154(b) by 0 days.

(21) Appl. No.: 17/883,724

(22) Filed: Aug. 9, 2022

(65) Prior Publication Data

US 2022/0381614 A1    Dec. 1, 2022

Related U.S. Application Data

(63) Continuation of application No. 17/135,675, filed on Dec. 28, 2020, now Pat. No. 11,422,033, which is a
(Continued)

(51) Int. Cl.
*G01J 3/30* (2006.01)
*G01J 3/443* (2006.01)
(Continued)

(52) U.S. Cl.
CPC .............. *G01J 3/443* (2013.01); *B63B 25/16* (2013.01); *B63J 2/14* (2013.01); *F02M 21/0215* (2013.01);
(Continued)

(58) Field of Classification Search
CPC .. G01J 3/443; G01J 2003/423; G01N 21/718; Y10S 128/924; Y10S 128/925; Y10S 706/924
See application file for complete search history.

(56) References Cited

U.S. PATENT DOCUMENTS 5,280,788 A    1/1994  Janes et al.
5,608,520 A    3/1997  Fleming
(Continued)

FOREIGN PATENT DOCUMENTS

CN    101828902 A    9/2010
JP    H04-132540 A    5/1992
(Continued)

OTHER PUBLICATIONS

F. Anabitarte, A. Cobo, J. M. Lopez-Higuera, "Laser-Induced Breakdown Spectroscopy: Fundamentals, Applications, and Challenges", International Scholarly Research Notices, vol. 2012, Article ID 285240, 12 pages, 2012. https://doi.org/10.5402/2012/285240 (Year: 2012).*

(Continued)

*Primary Examiner* — Uzma Alam
*Assistant Examiner* — Jonathon Cook
(74) *Attorney, Agent, or Firm* — Harness, Dickey & Pierce, P.L.C.

(57) ABSTRACT

Disclosed herein are a method for diagnosing a disease of a body tissue by using LIBS (Laser-Induced Breakdown Spectroscopy) comprising: preparing a laser device including: a laser projection module, outputting the laser to a suspicious region of the body tissue, a light receiving module, receiving a plurality of light, a spectrum measurement module, and a guide unit; and projecting the laser to generate plasma by inducing tissue ablation in the suspicious region; wherein the laser projected to the suspicious region has a target area, and wherein the target area has smaller size than the suspicious region such that the target area is located inside the suspicious region.

14 Claims, 59 Drawing Sheets

Related U.S. Application Data continuation of application No. 16/863,140, filed on Apr. 30, 2020, now Pat. No. 11,079,279, which is a continuation of application No. PCT/KR2019/010811, filed on Aug. 23, 2019.

(60) Provisional application No. 62/822,634, filed on Mar. 22, 2019.

(51) Int. Cl.
| | |
|---|---|
| *B63B 25/16* | (2006.01) |
| *B63J 2/14* | (2006.01) |
| *F02M 21/02* | (2006.01) |
| *F17C 6/00* | (2006.01) |
| *F17C 9/02* | (2006.01) |
| *F17C 9/04* | (2006.01) |
| *G01J 3/42* | (2006.01) |
| *G01N 21/71* | (2006.01) |

(52) U.S. Cl.
CPC .............. *F17C 6/00* (2013.01); *F17C 9/02* (2013.01); *F17C 9/04* (2013.01); *F17C 2221/033* (2013.01); *F17C 2227/0164* (2013.01); *F17C 2227/0185* (2013.01); *F17C 2227/0339* (2013.01); *F17C 2227/0348* (2013.01); *F17C 2227/0358* (2013.01); *F17C 2265/033* (2013.01); *F17C 2265/034* (2013.01); *F17C 2265/037* (2013.01); *F17C 2265/038* (2013.01); *F17C 2265/066* (2013.01); *F17C 2270/0105* (2013.01); *G01J 2003/423* (2013.01); *G01N 21/718* (2013.01)

(56) References Cited

U.S. PATENT DOCUMENTS

| | | | |
|---|---|---|---|
| 5,720,894 | A | 2/1998 | Neev et al. |
| 6,008,896 | A * | 12/1999 | Sabsabi ................ G01N 21/718 |
| | | | 356/318 |
| 6,135,965 | A | 10/2000 | Tumer et al. |
| 6,392,683 | B1 | 5/2002 | Hayashi |
| 6,463,314 | B1 * | 10/2002 | Haruna .................. G01N 21/25 |
| | | | 600/407 |
| 6,529,767 | B1 | 3/2003 | Woo et al. |
| 6,605,466 | B1 | 8/2003 | Pageon et al. |
| 7,092,087 | B2 | 8/2006 | Kumar et al. |
| 7,322,972 | B2 | 1/2008 | Viator et al. |
| 8,243,269 | B2 | 8/2012 | Matousek et al. |
| 8,310,671 | B1 * | 11/2012 | Nguyen .................... G01J 3/44 |
| | | | 356/315 |
| 8,319,964 | B2 * | 11/2012 | Hahn .................. G01N 21/718 |
| | | | 356/318 |
| 9,117,133 | B2 | 8/2015 | Barnes et al. |
| 9,877,655 | B2 | 1/2018 | Huang et al. |
| 10,393,587 | B1 | 8/2019 | Yoo et al. |
| 2003/0109787 | A1 | 6/2003 | Black |
| 2003/0231306 | A1 * | 12/2003 | Gornushkin ......... G01N 21/718 |
| | | | 356/318 |
| 2004/0010197 | A1 | 1/2004 | Faupel et al. |
| 2004/0073119 | A1 | 4/2004 | Mycek et al. |
| 2005/0090751 | A1 | 4/2005 | Balas |
| 2005/0200843 | A1 | 9/2005 | Kumar et al. |
| 2006/0025692 | A1 | 2/2006 | Ishihara |
| 2006/0089556 | A1 | 4/2006 | Bambot et al. |
| 2006/0095096 | A1 | 5/2006 | DeBenedictis et al. |
| 2006/0247531 | A1 | 11/2006 | Pogue et al. |
| 2007/0005393 | A1 | 1/2007 | Cole et al. |
| 2007/0232874 | A1 | 10/2007 | Ince |
| 2007/0296966 | A1 | 12/2007 | Benicewicz et al. |
| 2008/0076985 | A1 | 3/2008 | Matousek et al. |
| 2008/0129992 | A1 | 6/2008 | Matousek et al. |
| 2008/0147053 | A1 | 6/2008 | Kang et al. |
| 2008/0154257 | A1 | 6/2008 | Sharareh et al. |
| 2008/0194928 | A1 | 8/2008 | Bandic et al. |
| 2008/0204715 | A1 | 8/2008 | Klehr et al. |
| 2008/0221457 | A1 | 9/2008 | Zeng et al. |
| 2008/0269578 | A1 | 10/2008 | Goris et al. |
| 2008/0275315 | A1 | 11/2008 | Oka et al. |
| 2009/0023991 | A1 | 1/2009 | Gono et al. |
| 2009/0281536 | A1 | 11/2009 | Beckman et al. |
| 2010/0091276 | A1 | 4/2010 | Matousek et al. |
| 2010/0134605 | A1 | 6/2010 | Demos et al. |
| 2010/0185064 | A1 | 7/2010 | Bandic et al. |
| 2010/0280504 | A1 | 11/2010 | Manzke et al. |
| 2010/0292676 | A1 | 11/2010 | Larsen |
| 2011/0085165 | A1 | 4/2011 | Beckstead et al. |
| 2011/0105339 | A1 | 5/2011 | Al Moussalami |
| 2011/0218428 | A1 | 9/2011 | Westmoreland et al. |
| 2012/0041315 | A1 | 2/2012 | Mycek et al. |
| 2012/0044484 | A1 | 2/2012 | Henneberg |
| 2012/0057145 | A1 | 3/2012 | Tunnell et al. |
| 2012/0081704 | A1 | 4/2012 | Morrow et al. |
| 2012/0123275 | A1 | 5/2012 | Ortonne |
| 2012/0150044 | A1 | 6/2012 | Kim |
| 2012/0190990 | A1 | 7/2012 | Ohzawa et al. |
| 2012/0302892 | A1 | 11/2012 | Lue et al. |
| 2013/0079649 | A1 | 3/2013 | Mestha et al. |
| 2013/0116521 | A1 | 5/2013 | Inoue et al. |
| 2013/0303921 | A1 | 11/2013 | Chu et al. |
| 2014/0058244 | A1 | 2/2014 | Krocak |
| 2014/0066781 | A1 | 3/2014 | Park et al. |
| 2014/0270457 | A1 | 9/2014 | Bhargava |
| 2014/0275941 | A1 | 9/2014 | Kang et al. |
| 2015/0038824 | A1 | 2/2015 | Lupotti |
| 2015/0044098 | A1 | 2/2015 | Smart et al. |
| 2015/0148633 | A1 | 5/2015 | Park |
| 2015/0157253 | A1 | 6/2015 | Sun et al. |
| 2015/0377787 | A1 | 12/2015 | Zeng et al. |
| 2016/0062009 | A1 | 3/2016 | Wach |
| 2016/0169805 | A1 | 6/2016 | Wang |
| 2016/0231235 | A1 | 8/2016 | Gulati et al. |
| 2016/0235372 | A1 | 8/2016 | Schneider et al. |
| 2017/0035348 | A1 | 2/2017 | Bandic et al. |
| 2017/0175169 | A1 | 6/2017 | Lee et al. |
| 2018/0098726 | A1 | 4/2018 | Pyun et al. |
| 2018/0360390 | A1 | 12/2018 | Gaudiuso et al. |
| 2019/0033231 | A1 | 1/2019 | Connell et al. |
| 2019/0246908 | A1 | 8/2019 | Pyun et al. |
| 2019/0246971 | A1 | 8/2019 | Pyun et al. |

FOREIGN PATENT DOCUMENTS

| | | |
|---|---|---|
| JP | H06-000222 A | 1/1994 |
| JP | H11-230823 A | 8/1999 |
| JP | 2001-505113 A | 4/2001 |
| JP | 2003-512085 A | 4/2003 |
| JP | 2005-504561 A | 2/2005 |
| JP | 2005-192944 A | 7/2005 |
| JP | 2006-061683 A | 3/2006 |
| JP | 2008-522697 A | 7/2008 |
| JP | 2009-300131 A | 12/2009 |
| JP | 2010-249835 A | 11/2010 |
| JP | 2011-507651 A | 3/2011 |
| JP | 2012-519862 A | 8/2012 |
| JP | 2013-500464 A | 1/2013 |
| JP | 5435134 B2 | 3/2014 |
| JP | 5519711 B2 | 6/2014 |
| JP | 2016-510245 A | 4/2016 |
| JP | 5915543 B2 | 5/2016 |
| JP | 2016-530917 A | 10/2016 |
| KR | 97-0061214 A | 9/1997 |
| KR | 10-2002-0018254 A | 3/2002 |
| KR | 10-2005-0102524 A | 10/2005 |
| KR | 10-2007-0004144 A | 1/2007 |
| KR | 10-2007-0108132 A | 11/2007 |
| KR | 10-2008-0056034 A | 6/2008 |
| KR | 10-2009-0059667 A | 6/2009 |
| KR | 10-2009-0097904 A | 9/2009 |
| KR | 10-2009-0102751 A | 9/2009 |
| KR | 10-2010-0056000 A | 5/2010 |
| KR | 10-2010-0132841 A | 12/2010 |
| KR | 10-2011-0011009 A | 2/2011 |

(56) References Cited

FOREIGN PATENT DOCUMENTS

| | | |
|---|---|---|
| KR | 10-2012-0066286 A | 6/2012 |
| KR | 10-1168044 B1 | 7/2012 |
| KR | 10-2012-0111900 A | 10/2012 |
| KR | 10-2013-0075571 A | 7/2013 |
| KR | 10-2014-0028358 A | 3/2014 |
| KR | 10-1480337 B1 | 1/2015 |
| KR | 10-2015-0036345 A | 4/2015 |
| KR | 10-1506978 B1 | 4/2015 |
| KR | 10-2015-0061218 A | 6/2015 |
| KR | 10-2015-0061914 A | 6/2015 |
| KR | 10-2016-0007170 A | 1/2016 |
| KR | 10-2017-0058958 A | 5/2017 |
| KR | 10-2017-0106776 A | 9/2017 |
| KR | 10-2017-0114897 A | 10/2017 |
| KR | 10-2017-0114973 A | 10/2017 |
| KR | 10-2018-0011646 A | 2/2018 |
| WO | WO-2003/087793 A1 | 10/2003 |
| WO | WO-2009/103154 A1 | 8/2009 |
| WO | WO-2009/137740 A1 | 11/2009 |
| WO | WO-2011/162342 A1 | 12/2011 |
| WO | WO-2012/008047 A1 | 1/2012 |
| WO | WO-2014/007759 A1 | 1/2014 |
| WO | WO-2018/075679 A1 | 4/2018 |

OTHER PUBLICATIONS

Extended European Seach Report from corresponding European Patent Application No. 19921463.6, dated Nov. 28, 2022.
Gaudiuso, R., et al.; "Laser-induced breakdown spectroscopy for human and animal health: A review", Spectrochimica Acta Part B, 2018, pp. 1-26.
Mehari, F., et al.; "Investigation of Laser Induced Breakdown Spectroscopy (LIBS) for the Di® erentiation of Nerve and Gland Tissue{A Possible Application for a Laser Surgery Feedback Control Mechanism", Plasma Science and Technology, vol. 18, No. 6, Jun. 2016, pp. 654-660.
El Sherbini, A. M., et al.; "Diagnosis and Classification of Liver Cancer using LIBS Technique and Artificial Neural Network", International Journal of Science and Research (IJSR), vol. 4 Issue 5, May 2015, pp. 1153-1158.
International Search Report of PCT Application No. PCT/KR2018/007301, dated Oct. 17, 2018.
Written Opinion of PCT Application No. PCT/KR2018/007301, dated Oct. 17, 2018.
International Search Report of PCT Application No. PCT/KR2018/007297, dated Oct. 26, 2018.
Written Opinion of PCT Application No. PCT/KR2018/007297, dated Oct. 26, 2018.
International Search Report of PCT Application No. PCT/KR2019/010811, dated Dec. 28, 2019.
Written Opinion of PCT Application No. PCT/KR2019/010811, dated Dec. 28, 2019.
2nd Office Action of Korean Patent Application No. 10-2019-0104041, dated Dec. 26, 2019.
Office Action of Korean Patent Application No. 10-2018-0073304, dated Jan. 17, 2020.
Office Action of Korean Patent Application No. 10-2018-0073310, dated Jan. 17, 2020.
Final Rejection of Korean Patent Application No. 10-2019-0104041, dated Apr. 17, 2020.
Notice of Allowance of Korean Patent Application No. 10-2019-0104041, dated Jun. 12, 2020.
Notice of Allowance of Korean Patent Application No. 10-2018-0073304. dated Sep. 18, 2020.
Office Action of U.S. Appl. No. 16/101,928, dated Nov. 19, 2020.
2nd Notice of Allowance of U.S. Appl. No. 16/863,140_dated Dec. 3, 2020.
3rd Notice of Allowance of U.S. Appl. No. 16/863,140_dated Mar. 31, 2021.
Office Action from corresponding Korean Patent Application No. 10-2019-0104043, dated Jun. 8, 2021.
Office Action from corresponding U.S. Appl. No. 17/084,334, dated Oct. 4, 2021.
Kumar, A., et al.; "Characterization of malignant tissue cells by laser-induced breakdown spectroscopy", Appl. Opt. 43, 5399-5403, 2004.
Myers, et al.; "Non-invasive in-situ detection of malignant skin tissue and other abnormalities using portable LIBS system with fiber spectrometer and eye-safe erbium glass laser", Proc SPIE 6863, Optical Diagnositc and Sensing VIII, 2008.
Notice of Allowance of U.S. Appl. No. 16/863,140 dated Jul. 14, 2020—18 pages.
Office Action of KR Patent Application No. 10-2016-0041313 dated May 11, 2016—3 pages.
Office Action of KR Patent Application No. 10-2016-0115669 dated Oct. 7, 2016—4 pages.
Notice of Allowance of KR Patent Application No. 10-2016-0115669 dated Jun. 14, 2017—1 page.
International Search Report of PCT Application No. PCT/KR2016/005515 dated—Jan. 3, 2017—3 pages.
Office Action of KR Patent Application No. 10-2016-0158195 dated Apr. 3, 2017—4 pages.
Notice of Allowance of KR Patent Application No. 10-2016-0158195 dated Oct. 25, 2017—2 pages.
Office Action of KR Patent Application No. 10-2016-0023734 dated Apr. 16, 2017—7 pages.
Notice of Allowance of KR Patent Application No. 10-2016-0023734 dated Sep. 18, 2017—1 pages.
Office Action of KR Patent Application No. 10-2016-0041992 dated Jun. 1, 2017—4 pages.
Notice of Allowance of KR Patent Application No. 10-2016-0041992 dated Apr. 6, 2018—1 page.
International Search Report of PCT Application No. PCT/KR2017/003703 dated—Jun. 15, 2017—8 pages.
International Search Report of PCT Application No. PCT/KR2017/003701 dated Jun. 19, 2017—3 pages.
Office Action of KR Patent Application No. 10-2017-0088575 dated Aug. 16, 2017—4 pages.
Notice of Allowance of KR Patent Application No. 10-2017-0088575 dated Dec. 27, 2017—2 pages.
Notice of Allowance of KR Patent Application No. 10-2016-0074609 dated Jun. 14, 2018—2 pages.
Notice of Allowance of KR Patent Application No. 10-2016-0078830 dated Aug. 28, 2017—2 pages.
Office Action of KR Patent Application No. 10-2016-0150932 dated Jan. 8, 2018—7 pages.
Office Action of KR Patent Application No. 10-2016-0089921 dated Sep. 22, 2017v4 pages.
Notice of Allowance of KR Patent Application No. 10-2016-0089921 dated Jul. 5, 2018—2 pages.
International Search Report of PCT Application No. PCT/KR2018/001074 dated May 28, 2018 - 3 pages.
International Search Report of PCT Application No. PCT/KR2018/001071 dated Jun. 28, 2018 - 3 pages.
Office Action of KR Patent Application No. 10-2017-0043700 dated Jun. 28, 2018—4 pages.
Office Action 2 of KR Patent Application No. 10-2017-0043700 dated May 20, 2019—4 pages.
Notice of Allowance of KR Patent Application No. 10-2017-0043700 dated Oct. 31, 2019—2 pages.
Office Action of KR Patent Application No. 10-2017-0043705 dated Jul. 17, 2018—6 pages.
Notice of Allowance of KR Patent Application No. 10-2017-0043705 dated Oct. 31, 2019—2 pages.
Search Report of European Patent Application No. 17779337.9 dated Feb. 5, 2019—10 pages.
Office Action of KR Patent Application No. 10-2018-0008736 dated May 27, 2019—5 pages.
Office Action of U.S. Appl. No. 15/540,366 dated Oct. 31, 2019—43 pages.
Final Office Action of U.S. Appl. No. 15/540,366 dated May 8, 2020—36 pages.

(56) References Cited

OTHER PUBLICATIONS

Office Action of U.S. Appl. No. 15/540,364 dated Apr. 13, 2020—18 pages.
Office Action 1 of U.S. Appl. No. 15/540,364 dated Aug. 6, 2019—23 pages.
Final Office Action of U.S. Appl. No. 15/540,364 dated Dec. 2, 2019—21 pages.
Office Action of U.S. Appl. No. 15/477,995 dated Dec. 6, 2019—21 pages.
Final Office Action of U.S. Appl. No. 15/477,995 dated May 6, 2020—16 pages.
Advisory Action of U.S. Appl. No. 15/477,995 dated Aug. 10, 2020—4 pages.
Christopher P. Favazza et al., "In vivo photoacoustic microscopy of human cutaneous microvasculature and a nevus", Journal of Biomedical Optics, Jan. 2011 · vol. 16(1), 016015-1-016015-6.
Giakoumaki, et al., "Spectroscopic analysis using a hybrid LIBS-Raman system", Appl. Phys. A 83, 537-541 (2006).
Akshaya Kumar et al., "Characterization of malignant tissue cells by laser-induced breakdown spectroscopy", Optical Society of America, Oct. 1, 2004, vol. 43, No. 28, p. 5398-5403.
S. J. Rehse, et al., "Laser-induced breakdown spectroscopy (LIBS): an overview of recent progress and future potential for biomedical applications", Journal of Medical Engineering & Technology, 2012; 36:2, pp. 77-89.
0. Samek, et al., "Quantitative laser-induced breakdown spectroscopy analysis of calcified tissue samples", Spectrochimica Acta Part B 56 (2001) 865-875.
International Search Report of corresponding PCT Application No. PCT/KR2019/010811—6 pages (dated Dec. 18, 2019).
Office Action of KR 10-2019-0104039—4 pages, dated Nov. 20, 2020.
Office Action of KR 10-2019-0104040—7 pages, dated Nov. 20, 2020.
Office Action of KR 10-2019-0104042—4 pages, dated Nov. 20, 2020.
Office Action of KR 10-2019-0104043—5 pages, dated Nov. 20, 2020.

* cited by examiner

100

100a

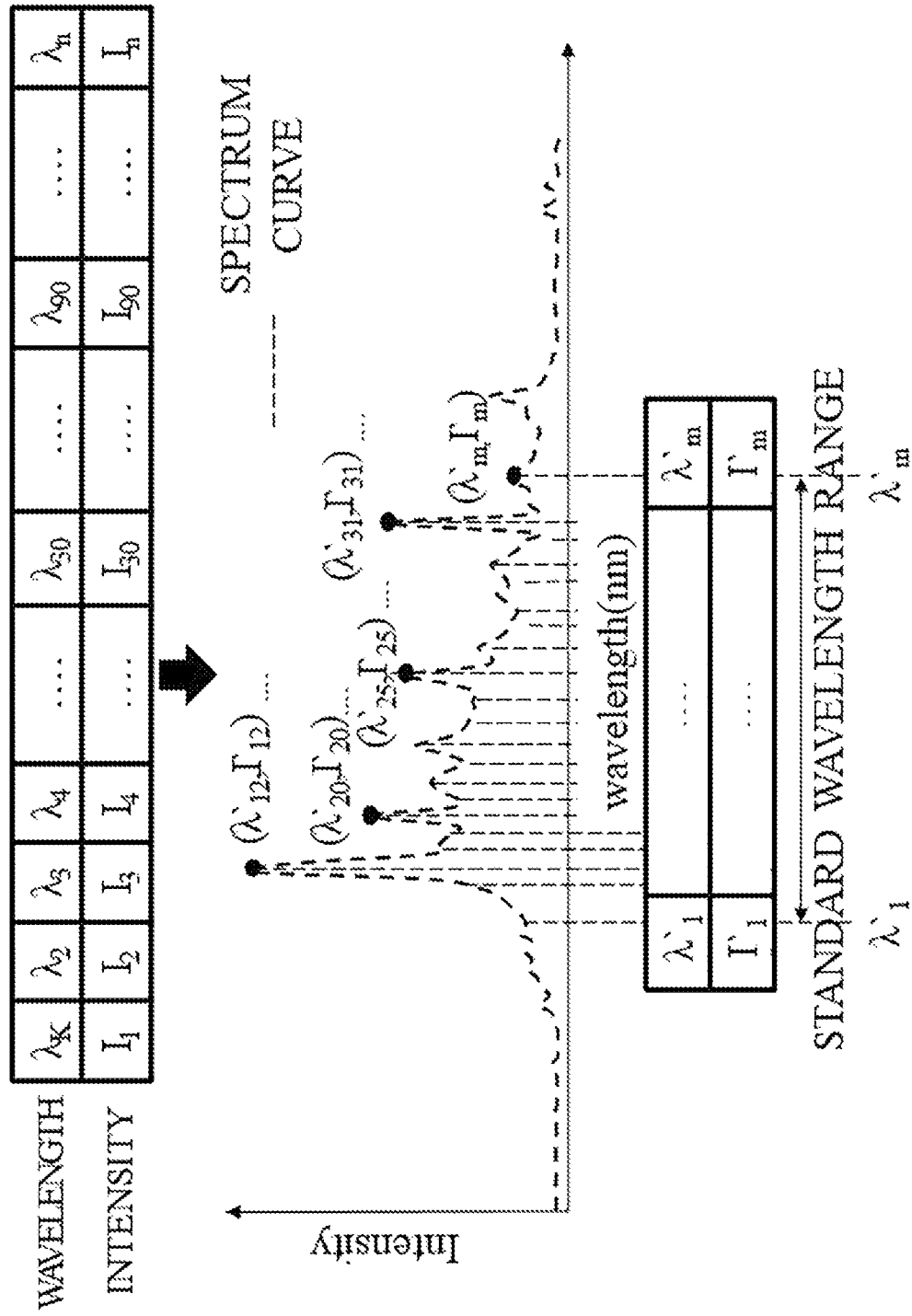

FIG.36

| SPECTRUM DATA | | |
|---|---|---|
| WAVELENGTH | INTENSITY | FEATURE IMPORTANCE(F) |
| $\lambda_1$ | $I_1$ | $F_1$ |
| $\lambda_2$ | $I_2$ | $F_2$ |
| $\lambda_3$ | $I_3$ | $F_3$ |
| .... | .... | .... |
| $\lambda_{11}$ | $I_{11}$ | $F_{11}$ |
| $\lambda_{12}$ | $I_{12}$ | $F_{12}$ |
| $\lambda_{13}$ | $I_{13}$ | $F_{13}$ |
| $\lambda_{14}$ | $I_{14}$ | $F_{14}$ |
| .... | .... | .... |
| $\lambda_{21}$ | $I_{21}$ | $F_{21}$ |
| $\lambda_{22}$ | $I_{22}$ | $F_{22}$ |
| $\lambda_{23}$ | $I_{23}$ | $F_{23}$ |
| .... | .... | .... |
| $\lambda_{31}$ | $I_{31}$ | $F_{31}$ |
| $\lambda_{32}$ | $I_{32}$ | $F_{32}$ |
| $\lambda_{33}$ | $I_{33}$ | $F_{33}$ |
| .... | .... | .... |
| $\lambda_{n-2}$ | $I_{n-2}$ | $F_{n-2}$ |
| $\lambda_{n-1}$ | $I_{n-1}$ | $F_{n-1}$ |
| $\lambda_{n}$ | $I_{n}$ | $F_{n}$ |

 LESS THAN THRESHOLD

 GREATER THAN OR EQUAL TO THRESHOLD

DIAGNOSIS METHOD USING LASER INDUCED BREAKDOWN SPECTROSCOPY AND DIAGNOSIS DEVICE PERFORMING THE SAME

This application is a continuation of U.S. application Ser. No. 17/135,675, filed on 28 Dec. 2020, which is a continuation of U.S. application Ser. No. 16/863,140, filed on 30 Apr. 2020, now U.S. Pat. No. 11,079,279, issued on 3 Aug. 2021, which is a continuation of PCT Application No. PCT/KR2019/010811, filed on 23 Aug. 2019, which claims priority to U.S. Application No. 62/822,634, filed on 22 Mar. 2019, the entire contents of which are incorporated herein by references.

BACKGROUND

1. Field of the Invention

The present disclosure relates to a diagnostic method using laser induced breakdown spectrum analysis and a diagnostic device for performing the same, and more particularly, to a diagnostic method of performing diagnosis using spectrum data of light collected from a specimen, to which a laser is projected, and a diagnostic device performing the same.

2. Discussion of Related Art

In the field of modern medical technology, there is an increasing demand for various techniques for more accurate diagnosis in a non-invasive manner that minimizes inconvenience of the existing biopsy. In this trend, a spectrum analysis method, which is conventionally used to analyze a composition of a material, can be used to detect a composition of biological tissue or a harmful substances and further used for diagnosis of diseases such that the spectrum analysis method is getting attention as next generation medical technology.

The spectrum analysis method may be broadly divided into Raman spectroscopy which analyzes a spectrum of scattered light of a laser projected onto a specimen, and laser induced breakdown spectroscopy (LIB S) which analyzes a spectrum of a plasma induced by a high-power laser.

However, since the conventional spectrum analysis method, which is mainly used to analyze inorganic materials, is performed through spectrum analysis in a specific wavelength range with respect to some elements, in analysis of biological tissue which is relatively complicated in composition and difficult to control environmental variables, the spectrum analysis method has limitations of a lack of accuracy or in that analysis results are affected by patient specificity.

SUMMARY OF THE INVENTION

The present disclosure is directed to providing a diagnostic method of non-invasively performing a disease diagnosis of body tissue using a laser induced breakdown spectroscopy (LIES) and a diagnostic device for performing the same.

The present disclosure is also directed to providing a diagnostic method of performing a disease diagnosis by collecting various and a large amount of information from a patient so as to increase accuracy or reliability of the disease diagnosis on the patient and a diagnostic device for performing the same.

The present disclosure is also directed to providing a diagnostic method of performing a diagnosis on a patient using light having various spectra generated from a specimen immediately after a plasma is generated in the specimen and a diagnostic device for performing the same.

The present disclosure is also directed to providing a diagnostic method of minimizing damage to a patient while using LIBS and a diagnostic device for performing the same.

The present disclosure is also directed to providing a diagnostic method of minimizing damage that may occur to a patient due to external factors such as hand shaking of a user and the like while using LIBS and a diagnostic device for performing the same.

The present disclosure is also directed to providing a diagnostic method of commonly performing a disease diagnosis on various patients using LIBS and a diagnostic device for performing the same.

The present disclosure is also directed to providing a diagnostic device for projecting a laser onto a specimen, receiving at least a part of light generated from the specimen, and providing a trigger signal on the basis of a triggering event.

The present disclosure is also directed to providing a diagnostic method of minimizing an influence due to environmental factors included in spectrum data while performing a disease diagnosis from the spectrum data using an artificial neural network and a diagnostic device for performing the same.

The present disclosure is also directed to providing a diagnostic method of minimizing an influence due to a mechanical off-set of a device for obtaining spectrum data while performing a disease diagnosis from the spectrum data using an artificial neural network and a diagnostic device for performing the same.

The technical problems to be solved by the present disclosure are not limited to the above-described technical problems and other technical problems which are not described can be clearly understood by those skilled in the art to which the present disclosure pertains from the following description and the accompanying drawings.

According to an aspect of the present disclosure, there is provided a diagnostic device comprising: a laser projection module projecting a pulsed laser to a specimen; a light receiving module receiving a light generated by a plasma ablation induced at the specimen by the pulsed laser; a spectral member receiving and dividing the light generated by the plasma ablation; a sensor array including a plurality of sensors arranged to receive the divided light for each wavelength, alternately and continuously repeating an exposure period which accumulates electric energy according to received light and a reset period which initialize the electric energy accumulated during the exposure period and generating spectrum data related to a light received in the exposure period, wherein a time interval of the exposure period is set in order to receive a light having a continuous spectrum characteristic and a light having a discontinuous spectrum characteristic during an exposure period which includes a projecting time point of the pulsed laser; and a controller obtaining spectrum data of the light generated by the plasma ablation from a specific exposure period, where the light generated by the plasma ablation is received, among the repeated plurality of exposure periods, and determining whether or not the specimen is diseased based on the spectrum data of the light generated by the plasma ablation.

According to another aspect of the present disclosure, there is provided a method for diagnosing a disease of a body tissue of a patient by using LIBS (Laser-Induced Breakdown Spectroscopy), comprising: by using the sensor array which includes a plurality of sensors arrayed to receive a spectroscopic light for each wavelength, repeating alternately and continuously an exposure period in which electric energy is accumulated related to the spectroscopic light received and a reset period in which the accumulated electric energy during the exposure period is reset; projecting a pulsed laser to a specimen; collecting a light generated by plasma ablation induced at the specimen by the pulsed laser; dividing the light generated by the plasma ablation; generating, by using the sensor array, spectrum data related to the light generated by the plasma ablation during a specific exposure period which is one of the repeated plurality of exposure periods; recognizing the specific exposure period among the plurality of exposure periods; obtaining spectrum data related to the light generated by the plasma ablation from the specific exposure period; and determining whether or not the specimen is diseased based on the obtained spectrum data related to the light generated by the plasma ablation.

According to another aspect of the present disclosure, there is provided a method for diagnosing a disease of a body tissue of a patient by using LIBS (Laser-Induced Breakdown Spectroscopy), comprising: by using the sensor array which includes a plurality of sensors arrayed to receive a spectroscopic light for each wavelength, repeating alternately and continuously an exposure period in which electric energy is accumulated related to the spectroscopic light received and a reset period in which the accumulated electric energy during the exposure period is reset; projecting a first pulsed laser to a first specimen at a first time point; detecting, by using the sensor array, spectrum related to first light generated by plasma ablation induced at the first specimen by the first pulsed laser through a first exposure period including the first time point; projecting a second pulsed laser to a second specimen at a second time point; detecting, by using the sensor array, spectrum related to second light generated by plasma ablation induced at the second specimen by the second pulsed laser through a second exposure period including the second time point; obtaining first spectrum data and second spectrum data which are respectively obtained at the first exposure period and the second exposure period among the repeated plurality of exposure periods; and determining whether or not the specimen is diseased based on the first spectrum data and the second spectrum data.

According to an aspect of the present disclosure, there is provided a diagnostic device comprising: a laser module projecting a pulsed laser to a specimen; a light collecting module receiving a light generated by plasma ablation induced at the specimen by the pulsed laser; a triggering module receiving a light from the specimen and outputting a triggering signal; a spectral member dividing the light generated by the plasma ablation offered from the light collecting module; a sensor array including a plurality of sensors arrayed to receive the spectroscopic light for each wavelength and generating spectrum data of the light generated by the plasma ablation through generating an electric signal related to incident light during a predetermined time interval from a time point when the triggering signal is outputted; and a controller performing a disease diagnosis to a patient based on the spectrum data.

According to another aspect of the present disclosure, there is provided a method for diagnosing a disease of a body tissue of a patient by using LIBS (Laser-Induced Breakdown Spectroscopy), comprising: projecting a pulsed laser to a specimen; outputting a triggering signal according to reflected light of the pulsed laser; generating spectrum data of light generated by plasma ablation induced at the specimen by the pulsed laser through detecting a spectrum of incident light during a predetermined time interval from an output time point of the triggering signal; and performing a disease diagnosis to the patient based on the spectrum data.

According to another aspect of the present disclosure, there is provided a method for diagnosing a disease of a body tissue of a patient by using LIBS (Laser-Induced Breakdown Spectroscopy), comprising: projecting a first pulsed laser to a first specimen which is a subject to disease examination; outputting a first triggering signal by receiving reflected light of the first pulsed laser; receiving light from the first specimen during a predetermined time interval from a output time point of the first triggering signal and obtaining first spectrum data related to light received from the first specimen; projecting a second pulsed laser to a second specimen which is normal; outputting a second triggering signal by receiving reflected light of the second pulsed laser; receiving light from the second specimen during the predetermined time interval from a output time point of the second triggering signal and obtaining second spectrum data related to light received from the second specimen; obtaining comparison spectrum data of the first spectrum data and the second spectrum data; and determining whether or not the first specimen is diseased based on the comparison spectrum data.

According to an aspect of the present disclosure, there is provided a method for diagnosing a disease of a body tissue of a patient by using LIBS (Laser-Induced Breakdown Spectroscopy) comprising: projecting a pulsed laser to a suspicious specimen; receiving a light generated by a plasma ablation induced at the suspicious specimen by the pulsed laser; obtaining a first spectrum data related to the light received from the suspicious specimen; projecting a light generated by plasma ablation induced at the non-diseased specimen by the pulsed laser; obtaining a second spectrum data related to the light received from the non-disease d specimen; and determining whether or not the suspicious specimen is diseased based on a comparison data of the first spectrum data and the second spectrum data by using an artificial neural network learned with a learning-set including the comparison data of two spectrum data related to light generated by the plasma ablation induced at two different non-diseased tissues, respectively, labeled with a first class value indicating a non-disease status, and the comparison data of two spectrum data related to light generated by the plasma ablation induced at a non-diseased tissue and at a diseased tissue, respectively, labeled with a second class value indicating a disease status.

According to another aspect of the present disclosure, there is provided a method for diagnosing a disease of a body tissue of a patient by using LIBS (Laser-Induced Breakdown Spectroscopy), comprising: obtaining a first spectrum data related to a light received from a suspicious specimen which is induced a plasma ablation by projected the pulsed laser; obtaining a second spectrum data related to a light collected from a non-diseased specimen which is induced a plasma ablation by projected the pulsed laser; and determining whether or not the suspicious specimen is diseased based on a comparison data of the first spectrum data and the second spectrum data by using an artificial neural network learned with a learning-set including the comparison data of two spectrum data related to light generated by the plasma ablation induced at two different non-diseased tissues, respectively, labeled with a first class value indicating a non-disease status, and the comparison data of two spectrum data related to light generated by the plasma ablation induced at a non-diseased tissue and at a diseased tissue, respectively, labeled with a second class value indicating a disease status.

According to another aspect of the present disclosure, there is provided a diagnostic device comprising: a laser projection module projecting a pulsed laser to a specimen; a light receiving module receiving a light generated by a plasma ablation induced at the specimen by the pulsed laser, wherein the light generated by plasma ablation includes plasma emission light having a continuum spectrum characteristic and specific element emission light having a discontinued spectrum characteristic; spectrum measurement module obtaining a spectrum data from the received light; and a controller: obtaining a first spectrum data related to a light received from a target specimen projected the pulsed laser by the laser projection module and second spectrum data related to a light received from a reference specimen, non-diseased, projected the pulsed laser by the laser projection module, and determining whether or not the target specimen is diseased based on a comparison data of the first spectrum data and the second spectrum data by using an artificial neural network which is learned with a first learning set including the comparison data of two spectrum data related to light generated by the plasma ablation induced at two different non-diseased tissues, respectively, labeled with a class value indicating a non-diseased status and a second learning set including the comparison data, of two spectrum data related to light generated by the plasma ablation induced at a non-diseased tissue and at a diseased tissue, respectively, labeled with a class value indicating a diseased status.

According to an aspect of the present disclosure, there is provided a method for diagnosing a disease of a body tissue by using LIBS (Laser-Induced Breakdown Spectroscopy) comprising: preparing a laser device including: a light emitting unit generating a laser induced to have prescribed wavelength and outputting the laser to a objective area of the body tissue, a light collecting unit receiving a plurality of light occurred when a portion of the body tissue is ablated as a result of the laser entering to the body tissue, being arranged with a prescribed angle to the light emitting unit toward to the objective area where the laser enters, and receiving the plurality of light, a optical signal converter generating a detecting signal by detecting a portion of the plurality of light, a guide unit adjusting a projecting distance of the pulsed laser from an end of the light emitting unit to the objective area; and projecting a laser to occurring plasma by inducing tissue ablation at the objective area of the body tissue; wherein a target area of the laser, which is projected to the objective area by adjusting an optical value or an optical path of the laser and by combining a length guided by the guide unit, is provided, and wherein the target area is located inside the objective area such that it has smaller area than the objective area.

According to another aspect of the present disclosure, there is provided a diagnosis device for diagnosing a disease of a body tissue by using LIBS (Laser-Induced Breakdown Spectroscopy) comprising: a housing provided with a gripping portion gripped by a user on its outer surface; a laser output unit installed inside the housing and emitting a high power pulsed laser to induce tissue ablation in an objective area where a tissue to be diagnosed is located; a light control unit which includes: a light path control means installed inside the housing to be located on a path of the pulsed laser and passing the pulsed laser such that a light path of at least a part of the pulsed laser is controlled, wherein an energy intensity received per area of a cross-section area perpendicular to a traveling direction of the pulsed laser becomes maximum at a point of a first distance from the laser output unit when the pulsed laser passes the light path control means; a light collecting unit being arranged with a prescribed angle to the light emitting unit toward to the objective area and receiving light generated according to the tissue ablation from the objective area; and a guide unit including: an extension portion extending from the housing along the traveling direction of the pulsed laser and a contact portion formed at an end of the extension portion to contact the body tissue, wherein the extension portion extends such that the contact portion is to be located at a point of a second distance from the laser output unit when the contact portion contacts the body tissue.

According to another aspect of the present disclosure, there is provided a diagnosis device for diagnosing a disease of a body tissue by using LIBS (Laser-Induced Breakdown Spectroscopy) comprising: a laser output module emitting a high power pulsed laser to induce tissue ablation in an objective area where a tissue to be diagnosed is located and including: a light control lens changing a light path of the pulsed laser to control an energy of the pulsed laser for inducing the tissue ablation at the objective area and a guide unit for controlling a projection distance of the pulsed laser from the light control lens to the objective area; a light collecting module having a prescribed angle to a projection path of the pulsed laser, arranged toward the objective area, and obtaining plasma light related to tissue ablation induced by the pulsed laser; an analysis module obtaining target spectrum information related to spectrum of light generated by tissue ablation induced at the objective area and determining a disease in the objective area; wherein the light control lens is defined as a first region and a second region, wherein refractive index of the first region and the second region is different to prevent over-concentrated projection on the projection distance of the pulsed laser for inducing the tissue ablation, wherein a light-focused area is occurred in a predetermined region in a projection direction of the pulsed laser from a position which is a focal length of the light control lens apart due to a difference between the refractive index of the first region and the second region, and wherein the guide unit has predetermined length such that the objective area is located in the light-focused area in order to prevent impact in a lower tissue which is at a predetermined depth deeper than a position of the objective area when the pulsed laser is projected to the objective area.

According to one aspect of the present disclosure, there is provided a diagnosis device comprising: a housing where an opening toward a specimen located at a point of patient's skin is formed at one end; a laser projecting module installed inside the housing and projecting a pulsed laser toward the specimen; and a triggering module located at rear side of the laser projecting module while installed inside the housing and outputting a triggering signal by receiving reflected light of the pulsed laser reflected from the specimen.

The technical solutions of the present disclosure are not limited to the above-described technical solutions and other technical solutions which are not described can be clearly understood by those skilled in the art to which the present disclosure pertains from the following description and the accompanying drawings.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which:

FIG. 35 is a diagram illustrating another example of the process of obtaining processed spectrum data according to one embodiment of the present disclosure;

FIG. 36 is a diagram illustrating feature importance for each wavelength included in spectrum data according to one embodiment of the present disclosure;

DETAILED DESCRIPTION OF EXEMPLARY EMBODIMENTS

Figure 1:
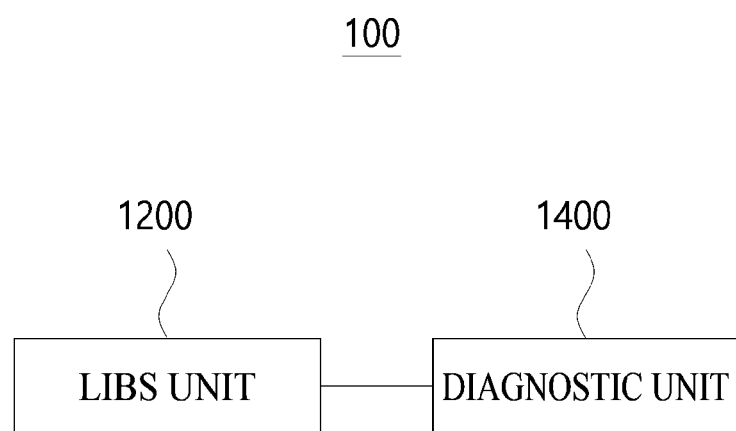
FIG. 1 is a block diagram illustrating a diagnostic system according to one embodiment of the present disclosure.

The above and other objectives, features, and advantages of the present disclosure will become more apparent from the following description with reference to the accompanying drawings. However, the present disclosure may be modified into various forms and may have a variety of embodiments, and, therefore, specific embodiments will be illustrated in the drawings and described in detail below.

The embodiments described herein are intended to clearly describe the spirit of the present disclosure to those skilled in the art to which the present disclosure pertains, and thus the present disclosure is not limited to these embodiments described herein, and the scope of the present disclosure should be construed as including alternations or modifications without departing from the spirit of the present disclosure.

The drawings accompanied to the present disclosure are provided to easily describe the present disclosure, and shapes shown in the drawings may be exaggerated and illustrated as necessary to help understanding of the present disclosure, and thus the present disclosure is not limited to the drawings.

When a detailed description of a known function or configuration related to the present disclosure is determined to unnecessarily obscure the gist of the present disclosure, the detailed description thereof will be omitted herein. Also, numbers (e.g., a first, a second, and the like) used in the description of the present disclosure are merely identification symbols for distinguishing one component from another component.

Further, suffixes "unit," "module," and "part" for components used in the following description are given or interchanged in consideration of only convenience of description, and thus these suffixes do not have distinctive meanings or functions.

According to an aspect of the present disclosure, there is provided a diagnostic device comprising: a laser projection module projecting a pulsed laser to a specimen; a light receiving module receiving a light generated by a plasma ablation induced at the specimen by the pulsed laser; a spectral member receiving and dividing the light generated by the plasma ablation; a sensor array including a plurality of sensors arranged to receive the divided light for each wavelength, alternately and continuously repeating an exposure period which accumulates electric energy according to received light and a reset period which initialize the electric energy accumulated during the exposure period and generating spectrum data related to a light received in the exposure period, wherein a time interval of the exposure period is set in order to receive a light having a continuous spectrum characteristic and a light having a discontinuous spectrum characteristic during an exposure period which includes a projecting time point of the pulsed laser; and a controller obtaining spectrum data of the light generated by the plasma ablation from a specific exposure period, where the light generated by the plasma ablation is received, among the repeated plurality of exposure periods, and determining whether or not the specimen is diseased based on the spectrum data of the light generated by the plasma ablation.

In addition, the controller, by using the projection time point of the pulsed laser, obtains spectrum data of the light generated by the plasma ablation from the specific exposure period among the plurality of exposure periods.

In addition, the diagnosis device further includes a triggering module outputting a triggering signal by receiving a light from the specimen, wherein the controller, by using the triggering signal, obtains spectrum data of the light generated by the plasma ablation from the specific exposure period among the plurality of exposure periods.

In addition, the triggering module outputs the triggering signal when a reflected light of the pulsed laser is received.

In addition, the triggering module is a photo diode which outputs a triggering signal when a light above a threshold is received, wherein the threshold is smaller than a peak value of an electric signal generated by an input of a reflected light of the pulsed laser and is bigger than a peak value of an electric signal generated by an input of a light occurred by the plasma ablation.

In addition, the controller determines whether or not the specimen is diseased from spectrum data of the light generated by the plasma ablation by using an artificial neural network learned with a first learning set including spectrum data obtained related to a normal tissue labeled with a class value indicating normal and a second learning set including spectrum data obtained related to a disease tissue labeled with a class value indicating disease.

According to another aspect of the present disclosure, there is provided a method for diagnosing a disease of a body tissue of a patient by using LIBS (Laser-Induced Breakdown Spectroscopy), comprising: by using the sensor array which includes a plurality of sensors arrayed to receive a spectroscopic light for each wavelength, repeating alternately and continuously an exposure period in which electric energy is accumulated related to the spectroscopic light received and a reset period in which the accumulated electric energy during the exposure period is reset; projecting a pulsed laser to a specimen; collecting a light generated by plasma ablation induced at the specimen by the pulsed laser; dividing the light generated by the plasma ablation; generating, by using the sensor array, spectrum data related to the light generated by the plasma ablation during a specific exposure period which is one of the repeated plurality of exposure periods; recognizing the specific exposure period among the plurality of exposure periods; obtaining spectrum data related to the light generated by the plasma ablation from the specific exposure period; and determining whether or not the specimen is diseased based on the obtained spectrum data related to the light generated by the plasma ablation.

In addition, the specimen is a skin tissue and the disease is a skin cancer.

In addition, a time period of the exposure period is at least above 1ms.

In addition, the recognizing includes recognizing the specific exposure period using the projection time point of the pulsed laser.

In addition, the recognizing includes recognizing the specific exposure period based on an accumulated electric energy during the exposure period.

In addition, the recognizing step recognizes an exposure period, where a difference between accumulated energy during a previous exposure period and accumulated energy during an arbitral exposure period and a difference between accumulated energy during a previous exposure period close to the arbitral exposure period and accumulated energy during the arbitral exposure period is larger than a predetermined threshold, as the specific exposure period.

In addition, the method further comprises: outputting a triggering signal upon the reflected light of the pulsed laser is received, wherein the recognizing step includes determining an exposure period corresponding to an output time point of the triggering signal as the specific exposure period.

In addition, the step of determining whether the specimen is diseased comprises: inputting spectrum data related to the light generated by the plasma ablation into an input layer of an artificial neural network, wherein the artificial neural network is learned with a first learning set including obtained spectrum data related to a normal tissue and labeled with a class value indicating normal and a second learning set including obtained spectrum data related to a disease tissue and labeled with a class value indicating disease; and determining whether the specimen is diseased based on an output value of the artificial neural network.

In addition, the method further comprises: recognizing the specific exposure period among the plurality of exposure periods.

According to another aspect of the present disclosure, there is provided a method for diagnosing a disease of a body tissue of a patient by using LIBS (Laser-Induced Breakdown Spectroscopy), comprising: by using the sensor array which includes a plurality of sensors arrayed to receive a spectroscopic light for each wavelength, repeating alternately and continuously an exposure period in which electric energy is accumulated related to the spectroscopic light received and a reset period in which the accumulated electric energy during the exposure period is reset; projecting a first pulsed laser to a first specimen at a first time point; detecting, by using the sensor array, spectrum related to first light generated by plasma ablation induced at the first specimen by the first pulsed laser through a first exposure period including the first time point; projecting a second pulsed laser to a second specimen at a second time point; detecting, by using the sensor array, spectrum related to second light generated by plasma ablation induced at the second specimen by the second pulsed laser through a second exposure period including the second time point; obtaining first spectrum data and second spectrum data which are respectively obtained at the first exposure period and the second exposure period among the repeated plurality of exposure periods; and determining whether or not the specimen is diseased based on the first spectrum data and the second spectrum data.

In addition, the method further comprises: outputting a first triggering signal and a second triggering signal at the first time point and the second time point respectively, by a triggering module which outputs a triggering signal upon receiving reflected light of the pulsed laser; and acquiring, by using the first triggering signal and the second triggering signal, the first spectrum data and the second spectrum data from the first exposure period and the second exposure period respectively among the plurality of repeated exposure periods.

In addition, one of the first specimen and the second specimen is a normal specimen and the other is a specimen to be examined to have a disease.

In addition, the step of performing the disease diagnosis includes: obtaining a comparison value between the first spectrum data and the second spectrum data; and performing a disease diagnosis to the patient by using the comparison value.

In addition, the comparison value is one of a difference between the first spectrum data and the second spectrum data or a ratio of the second spectrum data to the first spectrum data.

In addition, the step of performing the disease diagnosis includes: determining whether the disease-suspicious specimen is diseased from a comparison value of the first spectrum data and the second spectrum data, by using an artificial neural network learned with a learning set including a comparison value between spectrum data related to light generated by plasma ablation induced at a normal tissue and spectrum data related to light generated by plasma ablation induced a disease tissue labeled a class value indicating disease and a comparison value between two spectrum data related to light generated by plasma ablation induced at two different normal tissues labeled a class value indicating normal According to an aspect of the present disclosure, there is provided a diagnostic device comprising: a laser module projecting a pulsed laser to a specimen; a light collecting module receiving a light generated by plasma ablation induced at the specimen by the pulsed laser; a triggering module receiving a light from the specimen and outputting a triggering signal; a spectral member dividing the light generated by the plasma ablation offered from the light collecting module; a sensor array including a plurality of sensors arrayed to receive the spectroscopic light for each wavelength and generating spectrum data of the light generated by the plasma ablation through generating an electric signal related to incident light during a predetermined time interval from a time point when the triggering signal is outputted; and a controller performing a disease diagnosis to a patient based on the spectrum data.

In addition, the sensor array generates an electric signal for the incident light immediately without a time delay from the output time point of the triggering signal such that the spectrum information on light of continuous spectral property according to plasma emission related to the plasma ablation in the spectrum data.

In addition, the predetermined time interval is set such that spectrum information about light of continuous spectral property according to plasma emission related to the plasma ablation and spectrum information about light of discontinuous (discrete) spectral property according to element specific emission is included in the spectrum data.

In addition, the predetermined time interval is bigger than a time interval from the projection time point of the pulsed laser to a time point when the element specific emission starts.

In addition, the predetermined time interval is at least above 1 us.

In addition, the triggering module outputs the triggering signal according to the reflected light of the pulsed laser.

In addition, the triggering module includes a photo diode outputting a triggering signal when light, having intensity above threshold which is smaller than an intensity of the reflected light of the pulsed laser and larger than an intensity of the light generated by the plasma ablation, is input.

In addition, the triggering module is a photo diode outputting a triggering signal upon light above a threshold is input, wherein a rising time that an intensity of an electric signal generated by the reflected light of the pulsed laser approaches the threshold is at least shorter than the time interval from the projection time point of the pulsed laser to the time point when the plasma emission starts.

In addition, the triggering module is a photo diode outputting a triggering signal upon light above a threshold is input, wherein a rising time that an intensity of an electric signal generated by the reflected light of the pulsed laser approaches the threshold is at least shorter than 100 ns.

In addition, the controller determines whether or not the specimen is diseased from the light generated by the plasma ablation by using an artificial neural network, wherein the artificial neural network is learned with a first learning set including obtained spectrum data related to a normal tissue and labeled with a class value indicating normal and a second learning set including obtained spectrum data related to a disease tissue and labeled with a class value indicating disease According to another aspect of the present disclosure, there is provided a method for diagnosing a disease of a body tissue of a patient by using LIBS (Laser-Induced Breakdown Spectroscopy), comprising: projecting a pulsed laser to a specimen; outputting a triggering signal according to reflected light of the pulsed laser; generating spectrum data of light generated by plasma ablation induced at the specimen by the pulsed laser through detecting a spectrum of incident light during a predetermined time interval from an output time point of the triggering signal; and performing a disease diagnosis to the patient based on the spectrum data.

In addition, the step of generating includes: measuring spectrum for the incident light immediately without a time delay from the output time point of the triggering signal such that the spectrum information on light of continuous spectral property according to plasma emission related to the plasma ablation in the spectrum data.

In addition, the predetermined time interval is set such that spectrum information about light of continuous spectral property according to plasma emission related to the plasma ablation and spectrum information about light of discontinuous (discrete) spectral property according to element specific emission is included in the spectrum data.

In addition, the predetermined time interval is bigger than a time interval from the projection time point of the pulsed laser to a time point when the element specific emission starts.

In addition, the predetermined time interval is at least above 1 us.

In addition, the step of outputting the triggering signal includes outputting the triggering signal according to the reflected light of the pulsed laser.

In addition, in the step of outputting the triggering signal, a time interval from an incident time point of the reflected light of the pulsed laser to an output time point of the triggering signal is shorter than a time interval from the projection time point of the pulsed laser to a starting time point of the plasma emission.

In addition, in the step of outputting the triggering signal, a time interval from an incident time point of the reflected light of the pulsed laser to an output time point of the triggering signal is set to be at least shorter than 10 ns.

In addition, the step of performing the diagnosis includes: storing an artificial neural network is learned with a first learning set including obtained spectrum data related to a normal tissue and labeled with a class value indicating normal and a second learning set including obtained spectrum data related to a disease tissue and labeled with a class value indicating disease; inputting spectrum data related to the light generated by the plasma ablation into the artificial neural network and determining existence of the disease according to output of the artificial neural network.

According to another aspect of the present disclosure, there is provided a method for diagnosing a disease of a body tissue of a patient by using LIBS (Laser-Induced Breakdown Spectroscopy), comprising: projecting a first pulsed laser to a first specimen which is a subject to disease examination; outputting a first triggering signal by receiving reflected light of the first pulsed laser; receiving light from the first specimen during a predetermined time interval from a output time point of the first triggering signal and obtaining first spectrum data related to light received from the first specimen; projecting a second pulsed laser to a second specimen which is normal; outputting a second triggering signal by receiving reflected light of the second pulsed laser; receiving light from the second specimen during the predetermined time interval from a output time point of the second triggering signal and obtaining second spectrum data related to light received from the second specimen; obtaining comparison spectrum data of the first spectrum data and the second spectrum data; and determining whether or not the first specimen is diseased based on the comparison spectrum data.

According to an aspect of the present disclosure, there is provided a method for diagnosing a disease of a body tissue of a patient by using LIBS (Laser-Induced Breakdown Spectroscopy) comprising: projecting a pulsed laser to a suspicious specimen; receiving a light generated by a plasma ablation induced at the suspicious specimen by the pulsed laser; obtaining a first spectrum data related to the light received from the suspicious specimen; projecting a light generated by plasma ablation induced at the non-diseased specimen by the pulsed laser; obtaining a second spectrum data related to the light received from the non-disease d specimen; and determining whether or not the suspicious specimen is diseased based on a comparison data of the first spectrum data and the second spectrum data by using an artificial neural network learned with a learning-set including the comparison data of two spectrum data related to light generated by the plasma ablation induced at two different non-diseased tissues, respectively, labeled with a first class value indicating a non-disease status, and the comparison data of two spectrum data related to light generated by the plasma ablation induced at a non-diseased tissue and at a diseased tissue, respectively, labeled with a second class value indicating a disease status.

In addition, the comparison data is a difference of two spectrum data.

In addition, the comparison data includes a ratio of two spectrum data.

In addition, the body tissue includes a skin and the disease includes a skin cancer.

In addition, the suspicious specimen and the normal specimen have substantially same skin characteristics.

In addition, a distance between the suspicious specimen and the normal specimen is smaller than a predetermined distance.

In addition, the method further comprises normalizing the first spectrum data and the second spectrum data.

In addition, the normalizing includes processing the first spectrum data based on energy of the first spectrum data, and processing the second spectrum data based on energy of the second spectrum data.

In addition, the normalizing includes adjusting an intensity of at least one of the first spectrum data and the second spectrum data so as to the first spectrum data and the second spectrum data have equal energy.

In addition, the method further comprises: when energy of the first spectrum data is less than a first threshold, outputting a message indicating re-projecting the pulsed laser to the suspicious specimen; and when energy of the second spectrum data is less than the first threshold, Outputting a message indicating re-projecting the pulsed laser to the normal specimen.

In addition, outputting a message indicating projecting the pulsed laser to the suspicious specimen when a max peak value of the first spectrum data is above a first threshold; and outputting a message indicating projecting the pulsed laser to the normal specimen when a max peak value of the second spectrum data is above the first threshold.

In addition, the method further comprises standardizing the first spectrum data and the second spectrum data.

In addition, the standardizing includes: generating a first spectrum curve based on a plurality of intensity values of the first spectrum data corresponding to a plurality of measured wavelengths, a processing the first spectrum data by extracting a plurality of intensity values corresponding to a plurality of predetermined standard wavelengths from the first spectrum curve; generating a second spectrum curve based on a plurality of intensity values of the second spectrum data corresponding to a plurality of measured wavelengths; and processing the second spectrum data by extracting a plurality of intensity values corresponding to a plurality of predetermined standard wavelengths from the second spectrum curve.

In addition, the processed first and second spectrum data include a same number of intensity values corresponding to a plurality of wavelengths, and each includes a more number of intensity values corresponding to a plurality wavelengths than a number of intensity values corresponding to a plurality of wavelengths of the first and second spectrum data before processing.

In addition, a number of input nodes of an input layer of the artificial neural network is equal as the number of the predetermined standard wavelengths; and each intensity value corresponding to the each predetermined standard wavelength is inputted to the each input node respectively.

According to another aspect of the present disclosure, there is provided a method for diagnosing a disease of a body tissue of a patient by using LIBS (Laser-Induced Breakdown Spectroscopy), comprising: obtaining a first spectrum data related to a light received from a suspicious specimen which is induced a plasma ablation by projected the pulsed laser; obtaining a second spectrum data related to a light collected from a non-diseased specimen which is induced a plasma ablation by projected the pulsed laser; and determining whether or not the suspicious specimen is diseased based on a comparison data of the first spectrum data and the second spectrum data by using an artificial neural network learned with a learning-set including the comparison data of two spectrum data related to light generated by the plasma ablation induced at two different non-diseased tissues, respectively, labeled with a first class value indicating a non-disease status, and the comparison data of two spectrum data related to light generated by the plasma ablation induced at a non-diseased tissue and at a diseased tissue, respectively, labeled with a second class value indicating a disease status.

According to another aspect of the present disclosure, there is provided a diagnostic device comprising: a laser projection module projecting a pulsed laser to a specimen; a light receiving module receiving a light generated by a plasma ablation induced at the specimen by the pulsed laser, wherein the light generated by plasma ablation includes plasma emission light having a continuum spectrum characteristic and specific element emission light having a discontinued spectrum characteristic; spectrum measurement module obtaining a spectrum data from the received light; and a controller: obtaining a first spectrum data related to a light received from a target specimen projected the pulsed laser by the laser projection module and second spectrum data related to a light received from a reference specimen, non-diseased, projected the pulsed laser by the laser projection module, and determining whether or not the target specimen is diseased based on a comparison data of the first spectrum data and the second spectrum data by using an artificial neural network which is learned with a first learning set including the comparison data of two spectrum data related to light generated by the plasma ablation induced at two different non-diseased tissues, respectively, labeled with a class value indicating a non-diseased status and a second learning set including the comparison data, of two spectrum data related to light generated by the plasma ablation induced at a non-diseased tissue and at a diseased tissue, respectively, labeled with a class value indicating a diseased status.

In addition, the laser projection module irradiates the pulsed laser which has nano second, pico second or femto second pulse duration.

In addition, the light receiving module receives the light from a first time point to a second time point, wherein the first time point is before 100 ns after pulsed laser projected, and wherein the second time point is later than 1 us after the pulsed laser is projected.

In addition, the light receiving module measures a spectrum related to a wavelength range, wherein the wavelength range is between first wavelength less than 300 nm and second wavelength larger than 700 nm.

According to an aspect of the present disclosure, there is provided a method for diagnosing a disease of a body tissue by using LIBS (Laser-Induced Breakdown Spectroscopy) comprising: preparing a laser device including: a light emitting unit generating a laser induced to have prescribed wavelength and outputting the laser to a objective area of the body tissue, a light collecting unit receiving a plurality of light occurred when a portion of the body tissue is ablated as a result of the laser entering to the body tissue, being arranged with a prescribed angle to the light emitting unit toward to the objective area where the laser enters, and receiving the plurality of light, a optical signal converter generating a detecting signal by detecting a portion of the plurality of light, a guide unit adjusting a projecting distance of the pulsed laser from an end of the light emitting unit to the objective area; and projecting a laser to occurring plasma by inducing tissue ablation at the objective area of the body tissue; wherein a target area of the laser, which is projected to the objective area by adjusting an optical value or an optical path of the laser and by combining a length guided by the guide unit, is provided, and wherein the target area is located inside the objective area such that it has smaller area than the objective area.

In addition, the light emitting unit has a predetermined pulse energy and pulse duration to have a power density of 0.1 GW/cm2 or more based on an area of the target area in order to generate plasma at the objective area.

In addition, an amount of laser for the objective area is less than 40 J/cm2 to minimize a tissue damage occurring at a position a predetermined depth deeper than the objective area except for tissue ablation at the objective area.

According to another aspect of the present disclosure, there is provided a diagnosis device for diagnosing a disease of a body tissue by using LIBS (Laser-Induced Breakdown Spectroscopy) comprising: a housing provided with a gripping portion gripped by a user on its outer surface; a laser output unit installed inside the housing and emitting a high power pulsed laser to induce tissue ablation in an objective area where a tissue to be diagnosed is located; a light control unit which includes: a light path control means installed inside the housing to be located on a path of the pulsed laser and passing the pulsed laser such that a light path of at least a part of the pulsed laser is controlled, wherein an energy intensity received per area of a cross-section area perpendicular to a traveling direction of the pulsed laser becomes maximum at a point of a first distance from the laser output unit when the pulsed laser passes the light path control means; a light collecting unit being arranged with a prescribed angle to the light emitting unit toward to the objective area and receiving light generated according to the tissue ablation from the objective area; and a guide unit including: an extension portion extending from the housing along the traveling direction of the pulsed laser and a contact portion formed at an end of the extension portion to contact the body tissue, wherein the extension portion extends such that the contact portion is to be located at a point of a second distance from the laser output unit when the contact portion contacts the body tissue.

In addition, an energy intensity received per area of a cross-section area perpendicular to the traveling direction of the pulsed laser at a point of the second distance from the laser output unit is bigger than an energy intensity received per area for inducing tissue ablation.

According to another aspect of the present disclosure, there is provided a diagnosis device for diagnosing a disease of a body tissue by using LIBS (Laser-Induced Breakdown Spectroscopy) comprising: a laser output module emitting a high power pulsed laser to induce tissue ablation in an objective area where a tissue to be diagnosed is located and including: a light control lens changing a light path of the pulsed laser to control an energy of the pulsed laser for inducing the tissue ablation at the objective area and a guide unit for controlling a projection distance of the pulsed laser from the light control lens to the objective area; a light collecting module having a prescribed angle to a projection path of the pulsed laser, arranged toward the objective area, and obtaining plasma light related to tissue ablation induced by the pulsed laser; an analysis module obtaining target spectrum information related to spectrum of light generated by tissue ablation induced at the objective area and determining a disease in the objective area; wherein the light control lens is defined as a first region and a second region, wherein refractive index of the first region and the second region is different to prevent over-concentrated projection on the projection distance of the pulsed laser for inducing the tissue ablation, wherein a light-focused area is occurred in a predetermined region in a projection direction of the pulsed laser from a position which is a focal length of the light control lens apart due to a difference between the refractive index of the first region and the second region, and wherein the guide unit has predetermined length such that the objective area is located in the light-focused area in order to prevent impact in a lower tissue which is at a predetermined depth deeper than a position of the objective area when the pulsed laser is projected to the objective area.

According to one aspect of the present disclosure, there is provided a diagnosis device comprising: a housing where an opening toward a specimen located at a point of patient's skin is formed at one end; a laser projecting module installed inside the housing and projecting a pulsed laser toward the specimen; and a triggering module located at rear side of the laser projecting module while installed inside the housing and outputting a triggering signal by receiving reflected light of the pulsed laser reflected from the specimen.

In addition, the triggering module receives a reflected light, which is the pulse laser outputted from the laser projecting module and reflected from the specimen, through the laser projecting module.

In addition, the diagnosis device further comprises a guide frame extended from one end of the housing toward the specimen and having an end thereof in contact with the patient's skin.

In addition, the guide frame extends such that a focal point of the pulsed laser is located on the specimen when the end of the guide frame contacts to the skin.

In addition, the diagnosis device further includes a light collecting unit located at an exterior of the housing and receiving the light generated by plasma ablation induced at the specimen by the pulsed laser.

In addition, the light collecting module provides the collected light to a spectroscopic module for spectroscopically analyzing the light generated by the plasma ablation.

In addition, the spectroscopic module generates spectrum data of plasma emission light having a property of continuous spectrum and element specific emission light having a property of discontinuous spectrum by the plasma ablation by measuring spectrum of incident light during a predetermined time interval from immediately after the output of the triggering signal.

In addition, the triggering module outputs the triggering signal in at least 10 ns from an incident time point of the pulsed laser for the spectroscopic module to detect the plasma emission light having continuous spectrum property.

In addition, the predetermined time interval is set at least equal or more than 1 us such that the spectroscopic module detects the element specific emission light having discontinuous spectrum property.

In addition, the spectroscopic module is offered as a sensor with a non-gated type repeating an exposure period and a reset period and generates spectrum data of the light by the plasma ablation through an exposure period, which includes an output time point of the triggering signal, among the continuously repeated plurality of exposure periods.

The present specification relates to a diagnostic method using laser induced breakdown spectrum analysis and a diagnostic device for performing the same.

Here, the LIBS is a technique of projecting a short pulsed laser of high power to a target, which will be diagnosed, to form a plasma and performing spectroscopic analysis on light generated from the plasma.

The plasma means a phase of a material that receives high energy so that electrons with negative charges are separated from ions with positive charges. In the plasma, particles continuously move and react with each other to gain or lose energy, and in such a process, the particles transmit and receive electromagnetic waves to and from each other. Some of the electromagnetic waves are emitted to the outside. Electromagnetic waves emitted from the plasma may include electromagnetic waves generated over a wide wavelength range and emitted while free electrons in the plasma undergo routing changes due to magnetic fields or electromagnetic forces of surrounding particles, and electromagnetic waves of specific wavelengths corresponding to energy losses which are generated when energy levels of electrons confined to nuclei are transitioned.

Here, it is possible to determine a composition and a state of a material by analyzing the electromagnetic waves emitted from the plasma. The LIBS examines a characteristic including a composition and a state of a target which will be examined by projecting a laser to the target to induce a plasma and analyzing a spectrum of light generated by the plasma. In the present disclosure, the spectrum means an indicator capable of indicating a characteristic or feature of light. For example, the indicator may be expressed as a quantity of light for each wavelength, an intensity of the light, or energy thereof.

Hereinafter, a target to which a laser is projected, that is, a target of the LIBS will be referred to as a "specimen." That is, in the present disclosure, the "specimen" may refer to an object that is a target of spectrum analysis. Therefore, the "specimen" may be understood as an object to which a laser is projected in a LIBS process.

Generally, in the present disclosure, the specimen may be an object of diagnosis, that is, a target of diagnosis or examination, but the object of spectrum analysis does not necessarily coincide with the object of diagnosis. For example, the specimen may include an object that undergoes LIBS for comparison with the object of diagnosis. Thus, the specimen is not limited to the object of diagnosis but should be understood as a comprehensive meaning encompassing all targets of spectrum analysis.

In the present disclosure, various objects may become the specimen. For example, when disease diagnosis or the like is performed on a patient, the specimen may be a part of a component constituting a body of a patient in addition to skin, pieces of internal and external tissue, various cells, blood, saliva, and the like. In addition to the above description, when diagnosis on various non-biological materials in addition to chemicals will be performed, the specimen may include various materials such as metals or nonmetals, inorganic materials, and the like. In other words, in the present disclosure, the specimen should be understood as a comprehensive concept including any material which will be a target of spectrum analysis.

Further, in the present disclosure, "diagnosis" has a comprehensive concept including determination of a characteristic in addition to a state or composition of an object which will be analyzed using LIBS and second determination on the basis of the characteristic determination. For example, the diagnosis may include analysis of a composition of a specific material. Alternatively, the diagnosis may include not only determination of specific information on object analysis, such as a nature, a characteristic, and the like of the specimen, but also determination of a disease of a patient or determination of similarity between a previously analyzed specimen and a newly analyzed specimen. As a specific example, diagnosis using LIBS in the present disclosure may be used to determine whether a human body has a disease or an illness or to obtain biometric data such as a specific cell content, skin age, and a harmful substance content of a human body.

Hereinafter, a diagnostic system 100 according to one embodiment of the present disclosure will be described with reference to FIGS. 1 to 4.

The diagnostic system 100 according to one embodiment of the present disclosure is a system for performing diagnosis on a specimen using LIBS.

FIG. 1 is a block diagram illustrating the diagnostic system 100 according to one embodiment of the present disclosure.

Referring to FIG. 1, the diagnostic system 100 may include a LIBS unit 1200 and a diagnostic unit 1400. In the diagnostic system 100, the LIBS unit 1200 may project a laser to a specimen to form a plasma and obtain spectrum data from the plasma, and the diagnostic unit 1400 may perform diagnosis on a diagnostic target on the basis of the spectrum data obtained from the LIBS unit 1200.

The LIBS unit 1200 may project the laser to the specimen. Plasma ablation may be generated in the specimen to which the laser is projected. In this case, a plasma may be formed in the specimen in which the plasma ablation is generated. That is, the LIBS unit 1200 may form the plasma by projecting the laser to the specimen to induce the plasma ablation to the specimen.

The LIBS unit 1200 may collect light from the specimen. Here, the light collected by the LIBS unit 1200 may include laser-derived light which is derived from the laser projected to the specimen, and light generated due to the plasma ablation induced in the specimen. The laser-derived light may include reflected light, scattered light, and fluorescent light due to the laser projected to the specimen. The light generated due to the plasma ablation may include light according to plasma emission and light according to element specific emission. The light according to the plasma emission and the light according to the element specific emission will be described in more detail below.

The LIBS unit 1200 may obtain spectrum data by spectroscopically analyzing the collected light. Here, the spectrum data may include information on a spectrum of the light. Specifically, the spectrum data may include data on an intensity measured for each wavelength of the light. Here, the spectrum data may include information obtained by sampling and digitizing a spectrum of the light. For example, when the LIBS unit 1200 spectroscopically divides the light collected to measure an intensity for each wavelength for a predetermined time, the spectrum data may include a set of intensity values proportional to measured quantities of light. In the present disclosure, the spectrum data may be obtained by spectroscopically dividing the light collected by the LIBS unit 1200. Accordingly, the spectrum data may have a specific wavelength range according to a configuration of spectroscopically dividing the light or sensing the light. The spectrum data obtained in the LIBS unit 1200 may be used for diagnosis in the diagnostic unit 1400.

The diagnostic unit 1400 may perform diagnosis on the basis of the spectrum data. Specifically, the diagnostic unit 1400 may obtain the spectrum data from the LIBS unit 1200 and perform diagnosis on the basis of the spectrum data.

In order to perform diagnosis, the diagnostic unit 1400 may use techniques for big data and artificial intelligence. For example, the diagnostic unit 1400 may execute a machine-learned program to perform diagnosis on the specimen. Examples in which the diagnosis is performed in the diagnostic unit 1400 will be described in more detailed below.

The above-described diagnostic system 100 may be physically provided as a single device or a plurality of devices. For example, the diagnostic system 100 may be provided as a single diagnostic device in which the LIBS unit 1200 and the diagnostic unit 1400 are physically integrated. That is, the diagnostic system 100 may be implemented as a physically single device. Alternatively, the diagnostic system 100 may be implemented as a system including a plurality of devices when the LIBS unit 1200 and the diagnostic unit 1400 are provided as physically separate devices. That is, the diagnostic system 100 may be implemented as two devices such as a LIBS device and a diagnostic device. Alternatively, it should be noted that the physical implementation of the diagnostic system 100 is not limited to the above-described examples.

The above-described diagnostic system 100 may be implemented in various forms. Hereinafter, some examples of the diagnostic system 100 according to one embodiment of the present disclosure will be described.

According to one example, the diagnostic system 100 may be implemented in a stand-alone type system. Here, the stand-alone type may refer to a form capable of independently performing a diagnostic method according to one embodiment of the present disclosure without additional external equipment.

Figure 2:
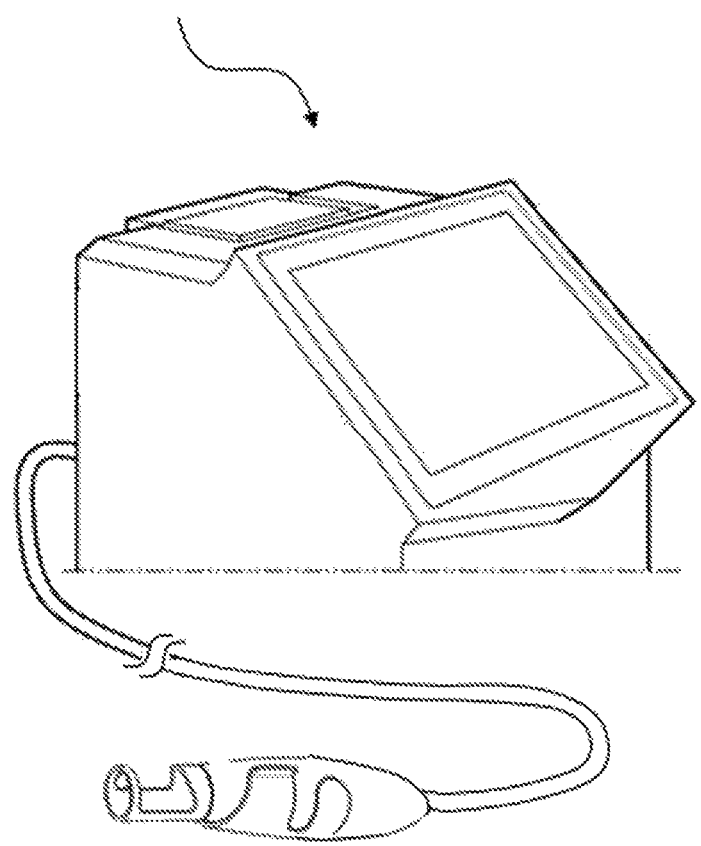
FIGS. 2 and 3 are perspective views illustrating examples of the diagnostic system according to one embodiment of the present disclosure.

FIG. 2 is a block diagram illustrating an example 100*a* of the diagnostic system 100 according to one embodiment of the present disclosure.

Referring to FIG. 2, the stand-alone type diagnostic system 100*a* may include a component for projecting a laser to a specimen, a component for collecting light generated from a plasma formed in the specimen, a component for obtaining spectrum data on the collected light, and a component for analyzing the spectrum data to perform diagnosis on the specimen, thereby independently performing an entire process of the diagnostic method without the external equipment.

Alternatively, the diagnostic system 100 may be implemented in an add-on type system. Here, the add-on type may refer to a form capable of performing the diagnostic method according to one embodiment of the present disclosure in cooperation with external equipment.

Figure 3:
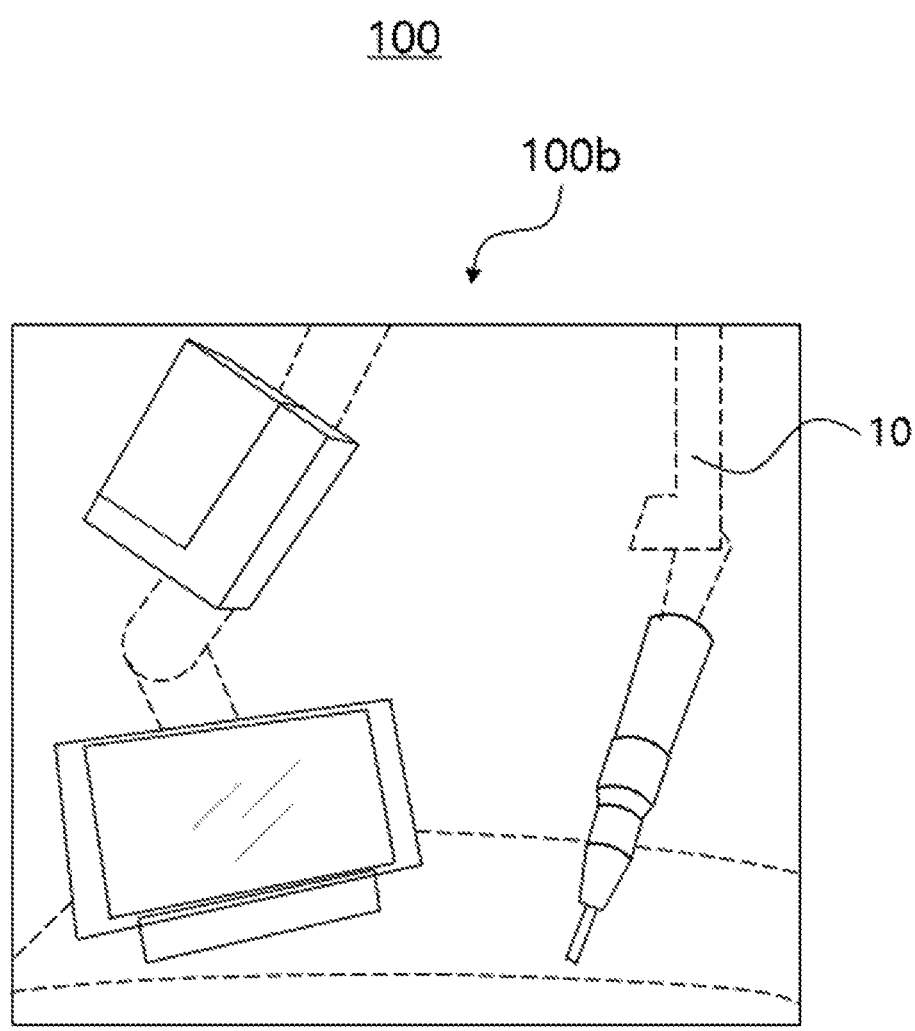

FIG. 3 is a block diagram illustrating another example 100*b* of the diagnostic system 100 according to one embodiment of the present disclosure.

The add-on type diagnostic system 100*b* may be provided in the form in which some components are omitted from the stand-alone type diagnostic system 100*a*. For example, the add-on type diagnostic system 100*b* may be constituted except for the component of projecting a laser to a specimen. In this case, as shown in FIG. 3, the diagnostic method according to one embodiment of the present disclosure may be performed by cooperating external equipment 10 for projecting a laser to a specimen with the add-on type diagnostic system 100*b*. Alternatively, the external equipment 10 may be provided as a laser projecting device, a light collector, a spectroscopy device, or a combination thereof. In this case, a component for performing a processing function of the external equipment 10 may be omitted from the add-on type diagnostic system 100*b*. Meanwhile, the add-on type diagnostic system 100*b* may be used in a state in which some or all components of the diagnostic system are mounted in the external equipment 10. In FIG. 3, a portion corresponding to the external equipment 10 is illustrated by a dotted line, and a portion corresponding to the diagnostic system 100 is illustrated by a solid line.

Hereinafter, the LIBS unit 1200 according to one embodiment of the present disclosure will be described.

According to one embodiment of the present disclosure, in order to perform diagnosis, the LIBS unit 1200 may project a laser to a specimen. Further, the LIBS unit 1200 may collect light from a plasma formed on the specimen due to the laser projection. Further, the LIBS unit 1200 may obtain spectrum data from the collected light.

Figure 4:
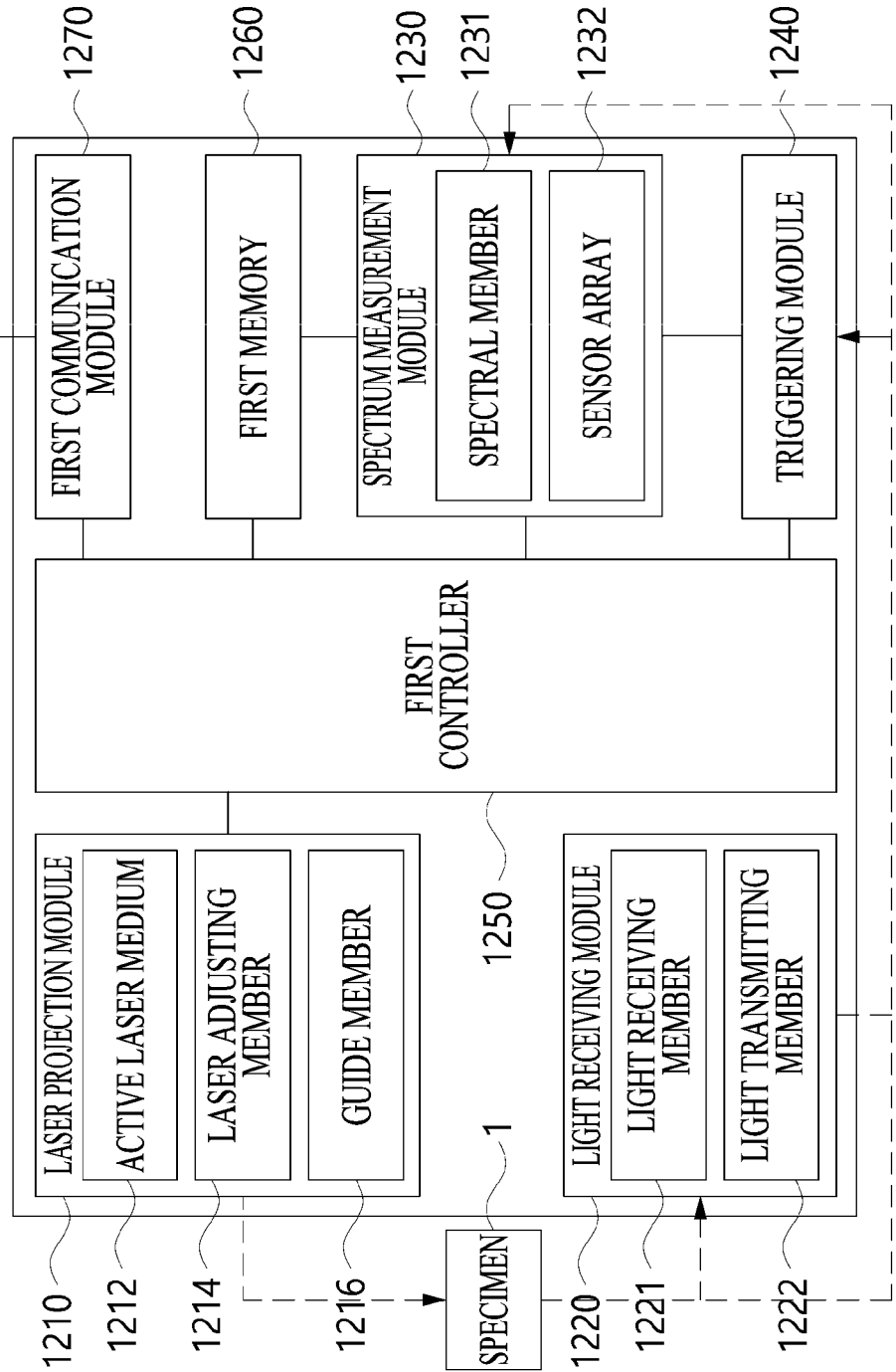
FIG. 4 is a block diagram illustrating a laser induced breakdown spectroscopy (LIB S) unit according to one embodiment of the present disclosure.

FIG. 4 is a block diagram illustrating the LIBS unit 1200 according to one embodiment of the present disclosure.

Referring to FIG. 4, the LIBS unit 1200 may include a laser projection module 1210, a light receiving module 1220, a spectrum measurement module 1230, a triggering module 1240, a first controller 1250, a first memory 1260, and a first communication module 1270.

According to one embodiment of the present disclosure, the laser projection module 1210 projects a laser to the specimen 1, the light receiving module 1220 collects light from the specimen 1 to which the laser is projected, the spectrum measurement module 1230 detects an intensity of each wavelength of the collected light, and the first controller 1250 generates spectrum data on the basis of the detection result of the spectrum measurement module 1230 such that the LIBS unit 1200 may obtain the spectrum data on the specimen 1.

Hereinafter, each configuration of the LIBS unit 1200 according to one embodiment of the present disclosure will be described.

The laser projection module 1210 may project a laser to the specimen 1. Alternatively, the laser projection module 1210 may guide a laser output from the external equipment 10 to be projected to the specimen 1.

A laser induced breakdown phenomenon may be generated in the specimen 1 to which the laser is projected. Specifically, when the laser is projected to body tissue by the laser projection module 1210, a part of the body tissue is ablated such that a plasma may be formed. As described above, in order for generation of the laser induced breakdown phenomenon, characteristics such as a laser intensity, a projection area, and the like should satisfy specific conditions. To the present end, the laser projection module 1210 may adjust a characteristic of the laser projected to the specimen 1. Here, the projection area may mean an area in which the laser projected to the specimen 1 is incident thereto.

Hereinafter, a detailed configuration of a laser projection module will be described in detail.

Referring to FIG. 4 again, the laser projection module 1210 may include an active laser medium 1212, a laser adjusting member 1214, and a guide member 1216.

According to one embodiment of the present disclosure, the laser projection module 1210 may generate a laser using the active laser medium 1212. Further, the laser adjusting member 1214 may set or change characteristics such as an intensity, a projection area, a focal length, and the like of the laser. The guide member 1216 may set a positional relationship between the specimen 1 and the laser projection module 1210 such that the laser is appropriately projected to the specimen 1.

The active laser medium 1212 may receive energy to generate a laser. The laser projection module 1210 may output the laser generated from the active laser medium 1212 in the form of a continuous beam or a pulsed beam. Here, when a pulsed laser is output, the laser generated from the active laser medium 1212 may be excited by a pulse signal, or Q-switching and mode synchronization may be used, and a pulse duration is adjusted such that an output intensity (energy per unit time) may be adjusted by the laser. Further, the laser projection module 1210 may output a laser having a specific wavelength. In this case, a wavelength of the laser being output may be determined by a kind of the active laser medium 1212. For example, when the active laser medium 1212 is provided as Nd:YAG material, the laser projection module 1210 may output a laser having a wavelength of 1064 nm, a laser having a harmonic wavelength of 1064 nm, or a harmonic laser of the 1064 nm laser.

The laser adjusting member 1214 may change characteristics of the laser projected to the specimen 1. Specifically, the laser adjusting member 1214 may adjust characteristics of a laser generated in the active laser medium 1212 or external equipment. In other words, the laser adjusting member 1214 may change the characteristics of the laser generated in the active laser medium 1212 or the external equipment and then input to the laser adjusting member 1214 to output a laser having the changed characteristics. For example, the characteristics of the laser may include an intensity, a shape, a focal length, a projection area at a specific distance, and the like of the laser.

The laser adjusting member 1214 may adjust the characteristics of the laser to satisfy a specific condition.

For example, the laser adjusting member 1214 may adjust the intensity of the laser. For example, the laser adjusting member 1214 may adjust the intensity of the laser projected to the specimen 1 to be greater than or equal to an intensity for forming a plasma in the specimen 1. For example, the laser adjusting member 1214 may also adjust the intensity of the laser projected to the specimen 1 to be less than or equal to an intensity at which damage occurs in the specimen 1. The laser adjusting member 1214 may perform a non-destructive test on the specimen 1 by adjusting the intensity of the laser to be greater than the intensity for forming the plasma in the specimen 1 and to be less than the intensity at which the damage occurs in the specimen 1.

Alternatively, the laser adjusting member 1214 may change the form of the laser. Here, the form of the laser may include a collimated beam, a focused beam, and a defocused beam. For example, the laser adjusting member 1214 may change the laser input as a collimated beam into a laser of a focused beam and output the focused laser. For example, the laser adjusting member 1214 may also change the laser input as a focused beam into a laser of a collimated beam and output the collimated laser.

Meanwhile, when the form of the laser is changed, the projection area of the laser projected to the specimen 1 may be determined. Accordingly, an intensity of energy applied to the specimen 1 by the laser may be determined.

Here, the laser adjusting member 1214 may be provided as an optical part including optical elements such as a lens, a filter, a mirror, a pinhole, and the like so as to change the characteristics of the laser projected to the specimen 1. For example, the laser adjusting member 1214 may be provided as a filter having specific transmittance to reduce the intensity of the laser. Alternatively, the laser adjusting member 1214 may be provided as a collimating lens to output an input focused laser as a collimated laser. Also alternatively, the laser adjusting member 1214 may be provided as a focus lens which changes a focal length of the laser to a specific length.

The guide member 1216 may set the positional relationship between the specimen 1 and the laser projection module 1210. Accordingly, the guide member 1216 may set a projection distance of the laser projected to the specimen 1. Here, the projection distance refers to a distance between the laser emitted from the laser projection module 1210 and the specimen 1 and should be understood as a different concept from the focal length of the laser. Further, the guide member 1216 may set the projection area of the laser with respect to the specimen 1 by setting the projection distance of the laser.

The guide member 1216 may extend from one point of the laser projection module 1210 in a projection direction of the laser. For example, one end of the guide member 1216 is connected to an end portion of the laser projection module 1210 from which the laser is emitted, and the guide member 1216 may be provided in the form of a rod, a bar, a hollow cylinder, or the like, which extends in a direction in which the laser is emitted from the end portion of the laser projection module 1210. Alternatively, it is noted in advance that the shape of the guide member 1216 is not limited to the above-described examples. For example, the guide member 1216 may be provided as a solid cylinder of a transparent material.

The other end of the guide member 1216 may be in contact with the specimen 1 or a periphery thereof. Thus, owing to an extension length of the guide member 1216, the positional relationship between the specimen 1 and the laser projection module 1210 and the projection distance may be set.

Further, the guide member 1216 may set the projection area of the laser, thereby setting energy per unit area, which is applied to the specimen 1 by the laser projected to the specimen 1.

For example, when the shape of the laser projected to the specimen 1 is a focused beam, as the guide member 1216 sets the projection distance of the laser to become away from a focal point of the laser, the projection area may be set to be larger, and an energy intensity per unit area, which is applied to the specimen 1, may be reduced.

Here, the energy intensity per unit area applied to the specimen 1 may be determined by not only the projection area determined by the extension length of the guide member 1216 but also the characteristic of the laser output from the active laser medium 1212 and the characteristic of the laser changed in the laser adjusting member 1214. A more detailed description thereof will be described below.

Meanwhile, all the components of the above-described laser projection module 1210 are not essential. Thus, some of the above-described components may be omitted from the laser projection module 1210. For example, when it is not necessary to adjust the intensity of the laser projected to the specimen 1, the laser adjusting member 1214 may be omitted. Alternatively, the active laser medium 1212 may be omitted from the add-on type diagnostic system 100*b*.

According to one embodiment of the present disclosure, the light receiving module 1220 may collect light from the specimen 1. Further, the light receiving module 1220 may provide the collected light to the spectrum measurement module 1230 and/or the triggering module 1240.

Referring to FIG. 4 again, the light receiving module 1220 according to one embodiment of the present disclosure may include a light receiving member 1221 and a light transmitting member 1222.

The light receiving member 1221 may collect light from the specimen 1. For example, the light receiving member 1221 may be an incident part such as a lens or the like disposed to receive the light from the specimen 1. Thus, the light receiving member 1221 may receive laser-derived light caused when the laser is projected to the specimen 1 and plasma light generated due to the laser projection.

The light transmitting member 1222 may transmit the collected light to the spectrum measurement module 1230 and/or the triggering module 1240. For example, the light transmitting member 1222 may be provided as one of various parts such as an optical cable, an optical fiber, or the like for transmitting light.

The spectrum measurement module 1230 may detect an intensity for each wavelength of input light. For example, the spectrum measurement module 1230 may detect an intensity of each wavelength of light which is collected by receiving the light collected by the light receiving module 1220 through the light transmitting member 1222.

Here, the spectrum measurement module 1230 may detect the intensity of each wavelength by spectroscopically dividing the light being input and outputting an electrical signal according to the intensity of each wavelength of the spectroscopically divided light. As described below, the first controller 1250 may generate spectrum data using the detection result (e.g., an electrical signal) of the spectrum measurement module 1230.

Referring to FIG. 4 again, the spectrum measurement module 1230 according to one embodiment of the present disclosure may include a spectral member 1231 and a sensor array 1232.

The spectral member 1231 may spectroscopically divide light input to the spectrum measurement module 1230. Here, the light input to the spectrum measurement module 1230 may be light collected from the specimen 1 by the light receiving module 1220.

The spectral member 1231 may separate a propagation path of the light according to a wavelength or frequency of the light using at least one among a light interference phenomenon, a light diffraction phenomenon, and a light refraction phenomenon. A typical example of the spectral member 1231 is a diffraction grating or a prism.

The sensor array 1232 may detect an intensity of the light, which is separated for each wavelength. The sensor array 1232 may be provided such that a plurality of sensors for receiving light of different wavelengths are arranged in an array form on a propagation path of the light, which is separated according to a wavelength. Each of the sensors may output an electrical signal having a voltage value or a current value which corresponds to the intensity or a quantity of light being received. Thus, the sensor array 1232 may detect an intensity of the light for each wavelength.

The sensor array 1232 may include various kinds of devices. For example, the sensor array 1232 may include at least one among a photodiode, a photo transistor, a photo interrupter, a photo coupler, a cadmium sulfide (CdS) cell, a solar cell, and a charged coupled device (CCD), a complementary metal-oxide semiconductor (CMOS) sensor, and an avalanche photo diode (APD).

A wavelength range detected by the sensor array 1232 may be set according to a relative position of the sensor array 1232 from the spectral member 1231. For example, as the sensor array 1232 is disposed farther away from the spectral member 1231, a wider wavelength range may be detected. Meanwhile, when an array interval of the plurality of sensors is constant in the sensor array 1232, resolution with respect to a wavelength may be lowered as a detected wavelength range is increased.

Meanwhile, it may be necessary to set a wavelength range in which the sensor array 1232 detects light so as to exclude a wavelength of a laser projected to the specimen 1 (hereinafter referred to as a "projection wavelength"). For example, the sensor array 1232 may be disposed outside of a propagation path of a propagation wavelength such that the light of the projection wavelength is not received by the sensor array 1232. Specifically, for example, when a laser having a wavelength of 1064 nm is projected to the specimen 1, the sensor array 1232 may be disposed on a propagation path of light having wavelengths of 200 nm to 800 nm. Alternatively, the sensor array 1232 is disposed on a propagation path of a projection wavelength and a specific sensor located on the propagation path of the projection wavelength undergoes a blind process or is masked such that the sensor array 1232 may not receive the light of the propagation wavelength.

As described above, the sensor array 1232 in which the propagation wavelength is excluded from a detection wavelength range may not detect laser-derived light having a wavelength similar to the propagation wavelength. Meanwhile, when an optical device detects laser-derived light, since an intensity or energy of the laser-derived light is high, the optical device may be damaged. For example, when the sensor array 1232 detects the propagation laser or the laser-derived light, the sensor array 1232 may be saturated to not perform a light detection function. Therefore, as described above, the sensor array 1232 may be prevented from being damaged by not receiving the light of the propagation wavelength such as the laser-derived light.

The triggering module 1240 may perform a triggering operation. Here, the triggering operation may mean an operation of indicating at least one among a laser projection time, a start time of laser induced breakdown, and a plasma generation time. As described below, the triggering operation may be used to determine a period in which a spectroscopic measurement module starts spectroscopic measurement on light generated due to laser induced breakdown or performs the spectroscopic measurement on the light generated due to the laser induced breakdown.

For example, when the triggering module 1240 receives a laser projected to the specimen 1 or receives reflected light from the specimen 1, the triggering module 1240 may output a trigger signal to perform a triggering operation. In this case, the triggering module 1240 may be provided as an optical sensor for outputting an electrical signal according to reception of light. Here, a specific sensor of the sensor array 1232 disposed at a position receiving the projection wavelength may operate as the triggering module 1240.

Alternatively, when the triggering module 1240 receives an electrical signal for generating a laser which will be projected to the specimen 1, the triggering module 1240 may outputting a trigger signal to perform a triggering operation. In addition to the above description, the electrical signal for generating the laser may be used as the trigger signal.

The first communication module 1270 may perform communication with an external device. The LIBS unit 1200 may transmit and receive data to and from the diagnostic unit 1400 or an external server through the first communication module 1270. For example, the LIBS unit 1200 may transmit spectrum data or an electrical signal on the basis of quantity of light detected by the spectrum measurement module 1230 to the diagnostic unit 1400 through the first communication module 1270. Alternatively, the LIBS unit 1200 may upload spectrum data by accessing the Internet through the first communication module 1270.

The first communication module 1270 is broadly divided into a wired type module and a wireless type module. Since each of the wired type module and the wireless type module has an advantage and a disadvantage, in some cases, the wired type module and the wireless type module may be simultaneously provided in the LIBS unit 1200.

Here, in the case of the wired type module, a local area network (LAN) or a Universal Serial Bus (USB) communication is a typical example, and other methods are possible. Here, in the case of the wireless type module, a wireless personal area network (WPAN)-based communication method such as Bluetooth or ZigBee may be mainly used. However, since a wireless communication protocol is not limited thereto, the wireless type communication module may use a wireless local area network (WLAN)-based communication method such as Wi-Fi or other known communication methods.

The first memory 1260 may store various pieces of information. Various pieces of data may be temporarily or semi-permanently stored in the first memory 1260. Examples of the first memory 1260 include a hard disk drive (HDD), a solid state drive (SSD), a flash memory, a read-only memory (ROM), a random access memory (RAM), and the like. The first memory 1260 may be provided in the form of being embedded in the LIBS unit 1200 or being detachable therefrom.

The first memory 1260 may store various pieces of data required for an operation of the LIBS unit 1200 in addition to an operating system (OS) for operating the LIBS unit 1200 or a program for operating each component of the LIBS unit 1200. For example, the first memory 1260 may store spectrum data and electrical signals generated on the basis of a quantity of light detected by the spectrum measurement module 1230.

The first controller 1250 may control an overall operation of the LIBS unit 1200. For example, the first controller 1250 may load a program for an operation of the spectrum measurement module 1230 from the first memory 1260 and execute the program, generate a control signal so as to control projection of a laser from the laser projection module 1210, receive a trigger signal from the triggering module 1240 to transmit the trigger signal to the spectrum measurement module 1230.

The first controller 1250 may be implemented as a central processing unit (CPU) or a device similar to the CPU according to hardware, software, or a combination thereof. The first controller 1250 may be provided in a hardware form of an electronic circuit for processing an electrical signal to perform a control function. The first controller 1250 may be provided in a software form of a program or a code for driving a hardware circuit.

The LIBS unit 1200 may have a separate power supply unit or receive power from the outside in a wired or wireless manner. The LIBS unit 1200 may have a separate switch for controlling the power supply unit.

Hereinafter, the diagnostic unit 1400 according to one embodiment of the present disclosure will be described.

According to one embodiment of the present disclosure, the diagnostic unit 1400 may perform diagnosis on the specimen 1. Further, the diagnostic unit 1400 may provide a user with a result of diagnosis performed on the specimen 1.

In diagnosing the specimen 1, the diagnostic unit 1400 may use various pieces of data. For example, the diagnostic unit 1400 may use at least one among spectrum data, image data, and acoustic data.

Here, the diagnostic unit 1400 may receive data for diagnosing the specimen 1 from the LIBS unit 1200. The diagnostic unit 1400 may obtain spectrum data from the LIBS unit 1200 and use the spectrum data to perform diagnosis on the specimen 1. Specifically, for example, when the LIBS unit 1200 projects a laser to the specimen 1 to form a plasma and provides the diagnostic unit 1400 with spectrum data obtained by spectroscopically analyzing plasma light from the plasma, the diagnostic unit 1400 may use the spectrum data to determine whether a disease is present in the specimen 1.

Figure 5:
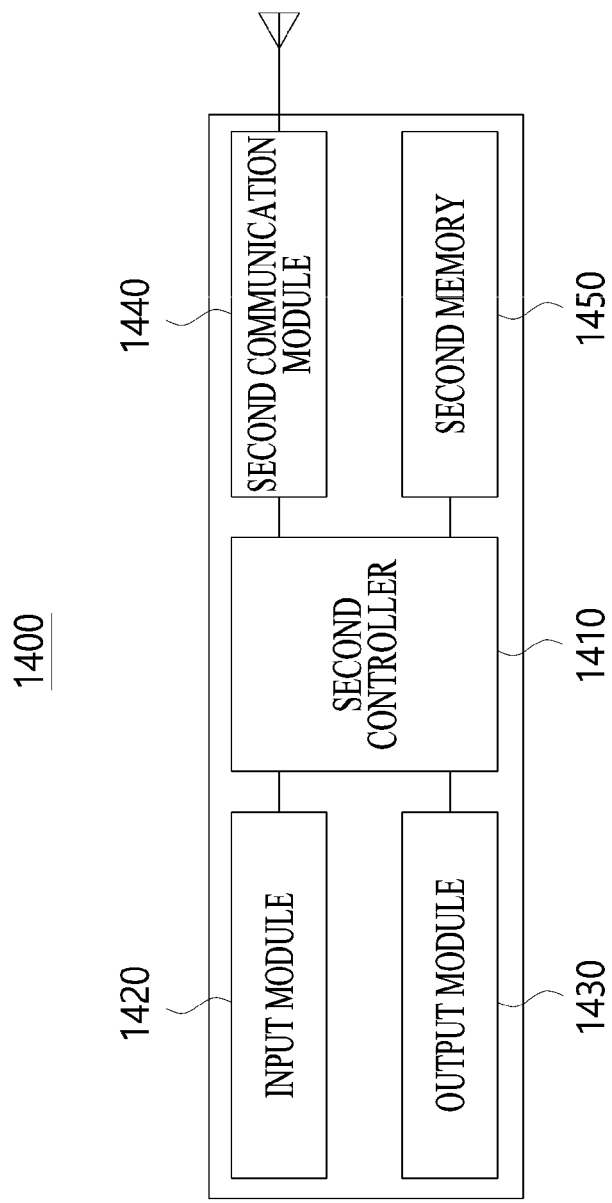
FIG. 5 is a block diagram illustrating a diagnostic unit according to one embodiment of the present disclosure.

FIG. 5 is a block diagram illustrating the diagnostic unit 1400 according to one embodiment of the present disclosure.

Referring to FIG. 5, the diagnostic unit 1400 may include a second controller 1410, an input module 1420, an output module 1430, a second communication module 1440, and a second memory 1450.

According to one embodiment of the present disclosure, the second controller 1410 obtains spectrum data with respect to the specimen 1 from the LIBS unit 1200 using the second communication module 1440, determines a state of the specimen 1, such as the presence of absence of a disease, a health status, a composition, and the like, using a diagnostic program stored in the second memory 1450, and outputs the determination result to the output module 1430 such that the diagnostic unit 1400 may perform diagnosis on the specimen 1.

Hereinafter, each component of the diagnostic unit 1400 according to one embodiment of the present disclosure will be described.

The second communication module 1440 may perform communication with an external device. The diagnostic unit 1400 may perform data communication with the LIBS unit 1200 or an external server using the second communication module 1440. For example, the diagnostic unit 1400 may obtain data required for diagnosis on the specimen 1 from the LIBS unit 1200 using the second communication module 1440.

The second communication module 1440 may be provided similar to the first communication module 1270, and thus a more detailed description thereof will be omitted herein.

The second memory 1450 may store various pieces of information of the diagnostic unit 1400.

The second memory 1450 may store various pieces of data required for an operation of the diagnostic unit 1400 in addition to an OS for driving the diagnostic unit 1400 or a program for operating each configuration of the diagnostic unit 1400. For example, the second memory 1450 may store a program for processing spectrum data with respect to the specimen 1 and an artificial neural network for data analysis.

The second memory 1450 may be provided similar to the first memory 1260, and thus a more detailed description thereof will be omitted herein.

The input module 1420 may receive a user input from a user. The user input may be made in various forms such as a key input, a touch input, and a voice input. The input module 1420 is a comprehensive concept encompassing not only a keypad, a keyboard, and a mouse which have a traditional form as well as a touch sensor for sensing a touch of a user, but also various types of input parts for sensing or receiving various types of user inputs. Further, the input module 1420 may be implemented in the form of an input interface (a USB port, a PS/2 port, and the like) for connecting an external input device for receiving a user input to an electronic device instead of a device for directly sensing a user input.

The output module 1430 may output and provide various pieces of information to the user. The output module 1430 is a comprehensive concept encompassing a display for outputting an image, a speaker for outputting a sound, a haptic device for generating vibrations, and various types of output parts. In addition to the above description, the output module 1430 may be implemented in the form of a port type output interface for connecting individual output parts to an electronic device.

The second controller 1410 may control an overall operation of the diagnostic unit 1400. For example, the second controller 1410 may generate a control signal so as to load a program for processing and analyzing data from the second memory 1450, process and analyze data obtained from the LIBS unit 1200, and provide the result of the processing and analysis to a user through the output module 1430.

The second controller 1410 may be provided similar to the first controller 1250, and thus a more detailed description thereof will be omitted herein.

The diagnostic unit 1400 may have a separate power supply unit or receive power from the outside in a wired or wireless manner. The diagnostic unit 1400 may have a separate switch for controlling the power supply unit.

Hereinafter, a diagnostic method according to one embodiment of the present disclosure will be described. In the following description, the diagnostic method according to one embodiment of the present disclosure will be described as being performed by the above-described diagnostic system 100. However, since this is only for convenience of description, the diagnostic method according to one embodiment of the present disclosure is not limited to being performed by the above-described diagnostic system 100. That is, the diagnostic method, which will be described below, is not necessarily to be performed by only the above-described diagnostic system 100 and may be performed by another system or device having a function similar to that of the above-described diagnostic system 100.

Figure 6:
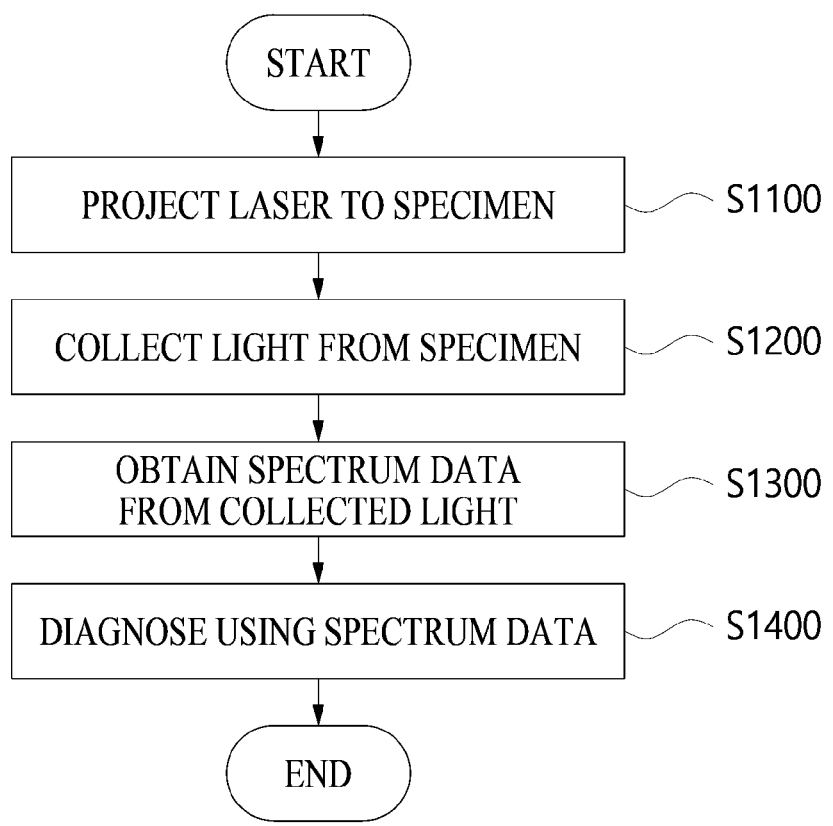
FIG. 6 is a flowchart illustrating a diagnostic method according to one embodiment of the present disclosure.
Figure 7:
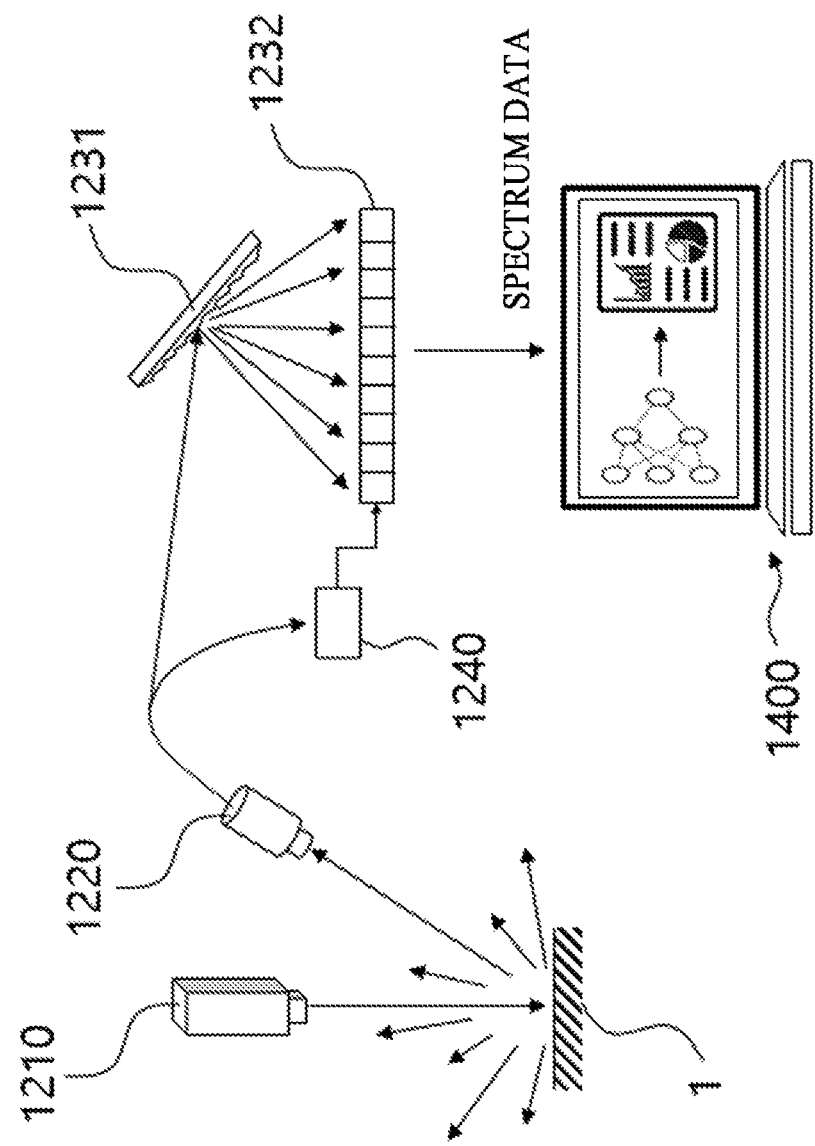
FIG. 7 is an exemplary diagram illustrating a procedure in which the diagnostic method according to one embodiment of the present disclosure is performed.

FIG. 6 is a flowchart illustrating a diagnostic method according to one embodiment of the present disclosure, and FIG. 7 is an exemplary diagram illustrating a procedure in which the diagnostic method according to one embodiment of the present disclosure is performed;

Referring to FIG. 6, the diagnostic method according to one embodiment of the present disclosure may include projecting a laser to a specimen (S1100), collecting light from the specimen (S1200), obtaining spectrum data from the collected light (S1300), and diagnosing the specimen using the obtained spectrum data (S1400).

Hereinafter, the above-described operations will be described in more detail.

The diagnostic system 100 may project a laser to the specimen 1 (S1100). Specifically, as shown in FIG. 7, the laser projection module 1210 of the LIBS unit 1200 may project a laser to the specimen 1. Here, the laser projection module 1210 may directly generate a laser to output the laser to the specimen 1 or receive a laser from the external equipment 10 to output the laser to the specimen 1.

Plasma ablation is induced to the specimen 1 to which the laser is projected such that a plasma may be formed in the specimen 1 or a periphery thereof. Here, the laser projected to the specimen 1 may include a pulsed laser having a predetermined intensity, a predetermined period, and a predetermined form so as to induce ablation in the specimen 1 and form a plasma. The intensity, period, and shape of the laser projected to the specimen 1 may be set or adjusted by the laser projection module 1210.

The diagnostic system 100 may collect light related to or caused due to the laser projection from the specimen 1 (S1200). Specifically, as shown in FIG. 7, the light receiving module 1220 of the LIBS unit 1200 may receive the light from the specimen 1.

For example, as shown in FIG. 7, when the laser is projected to the specimen 1, light may be emitted in various directions, and the light receiving module 1220 may receive at least a part of the diverging light.

Here, the collected light may be provided to the spectrum measurement module 1230 and/or the triggering module 1240 through the light transmitting member 1222.

The diagnostic system 100 may obtain spectrum data on the collected light (S1300). Specifically, the spectrum measurement module 1230 of the LIBS unit 1200 may receive the collected light from the light receiving module 1220 and generate the spectrum data on the collected light. More specifically, as shown in FIG. 7, the spectral member 1231 may receive the collected light from the light receiving module 1220 and spectroscopically divide the collected light according to a wavelength, and the sensor array 1232 may measure an intensity of the spectroscopically divided light for each wavelength. Here, when the light is received, the triggering module 1240 may generate a trigger signal and output the trigger signal to the sensor array 1232. The sensor array 1232 may measure the intensity for each wavelength using the trigger signal.

The diagnostic system 100 may perform diagnosis on the specimen 1 using the obtained spectrum data (S1400). More specifically, the diagnostic unit 1400 may perform diagnosis using the spectrum data obtained by the LIBS unit 1200. For example, as illustrated in FIG. 7, the diagnostic unit 1400 may process the spectrum data and determine whether a disease is present in the specimen 1 or a state of the specimen 1 using a data analysis program and the like. In analyzing the spectrum data, the diagnostic unit 1400 may use an artificial neural network, a diagnostic algorithm utilizing machine learning or big data analysis, and the like. Further, the diagnostic unit 1400 may provide the user with a result of performing the diagnosis on the specimen 1 through the output module 1430.

Hereinafter, some operations performed by the diagnostic system 100 in conjunction with the diagnostic method will be described in more detail.

An operation of obtaining the spectrum data among the operations performed by the diagnostic system 100 in conjunction with the diagnostic method will be described below. However, prior to describing the operation of obtaining the spectrum data, the spectrum data, which will be obtained by the diagnostic system 100 according to one embodiment of the present disclosure, will be described.

According to one embodiment of the present disclosure, the diagnostic system 100 may perform diagnosis on the specimen 1 using the spectrum data.

Figure 8:
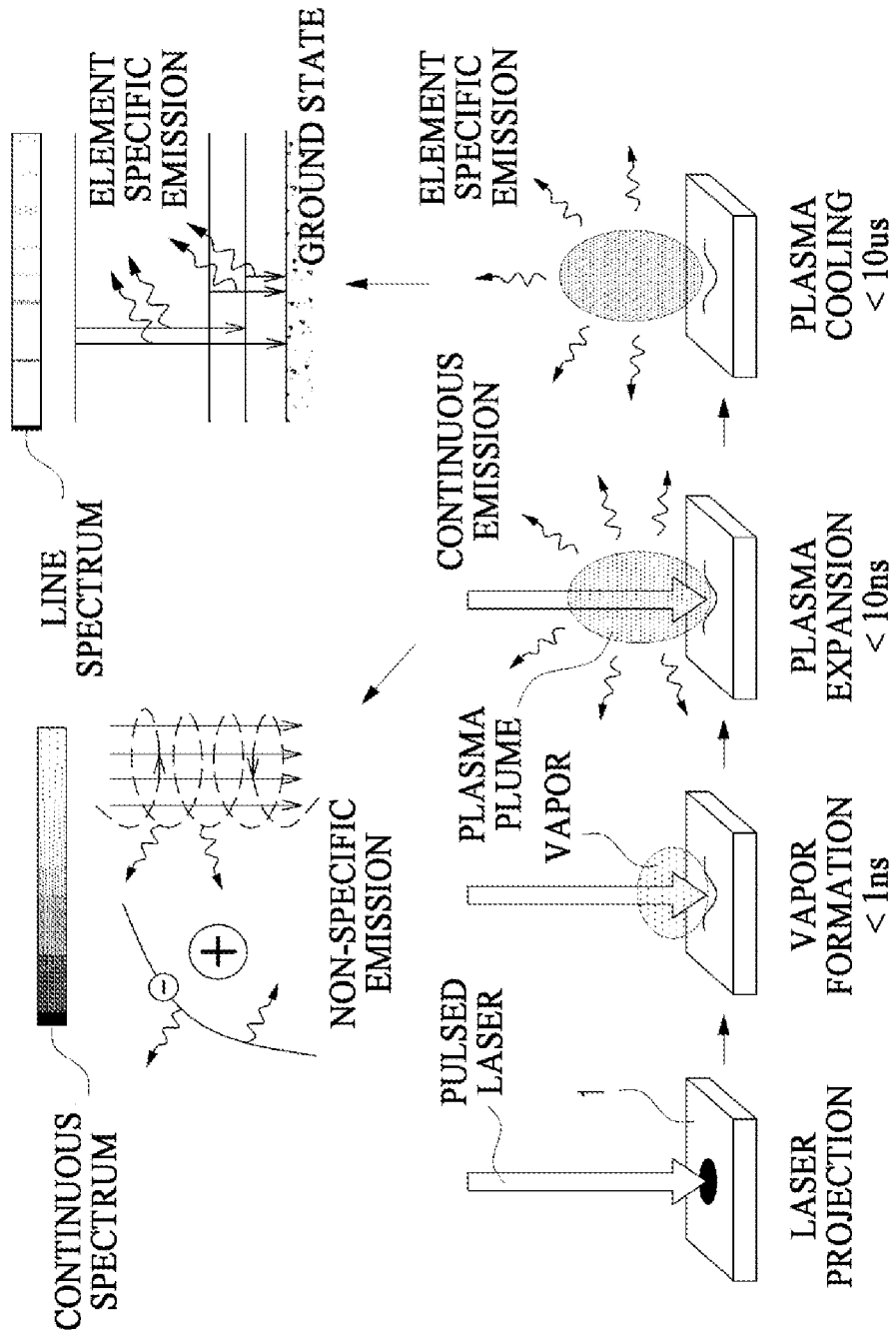
FIG. 8 is a diagram illustrating laser induced breakdown according to one embodiment of the present disclosure.

FIG. 8 is a diagram illustrating laser induced breakdown according to one embodiment of the present disclosure;

According to one embodiment of the present disclosure, when a pulsed laser having a predetermined intensity or more is projected to the specimen 1, laser induced breakdown may occur. Here, various phenomena may be induced to the specimen 1 according to an elapsed time after the laser is projected to the specimen 1.

When a predetermined amount of energy is applied to the specimen 1 due to the laser projection, a part of the specimen 1 may be broken and separated to form a vapor and then a plasma may be induced. For example, referring to FIG. 8, when energy of a predetermined intensity or more is applied to the specimen 1 due to a pulsed laser, some of particles of the specimen 1 may be broken at a time of about 1 ns after the laser is projected and, vapor may be formed, and plasma plume may be begun to be formed to extend to an elapsed time of about 10 ns to several tens of nanoseconds. Here, plasma emission may occur from the plasma such that plasma light may be emitted. Here, the plasma emission has a characteristic of non-specific emission such as electron cyclotron emission (ECE) due to free electrons in the plasma, emission due to bremsstrahlung radiation and recombination reaction, and the like, or a continuous spectrum having a non-specific wavelength due to continuous emission.

The plasma formed in the specimen 1 extends and is cooled over time such that light emission may occur as the excited electrons transition to specific energy levels. For example, referring to FIG. 8 again, element specific emission may actively occur from the specimen 1 at a time of about 1 μs after the laser is projected to the specimen 1. Here, the element specific emission occurs due to the transition of electrons from specific energy levels to another specific energy levels in a process in which the plasma returns to a state such as ions, atoms, or molecules such that, the element specific emission may have a characteristic of a line spectrum or a discrete spectrum. Alternatively, the element specific emission does not necessarily occur at the time of about 1 μs after the laser is projected to the specimen 1 and may occur earlier than the time of about 1 μs after the laser is projected.

Figure 9:
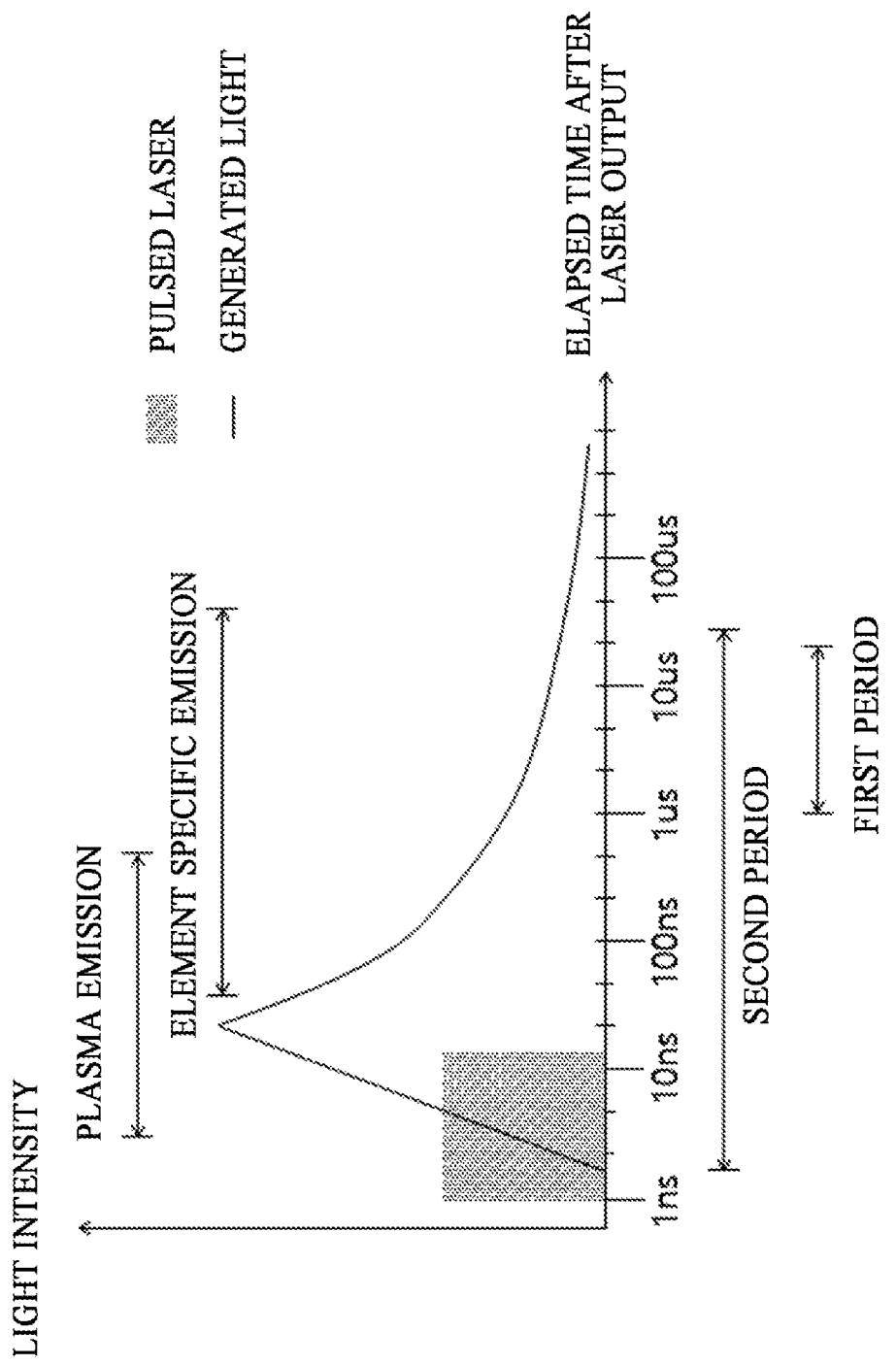
FIG. 9 is a graph showing light emitted during the laser induced breakdown according to one embodiment of the present disclosure.

FIG. 9 is a graph showing light emitted during the laser induced breakdown according to one embodiment of the present disclosure;

Referring to FIG. 9, it may take a predetermined time in order that the laser is output to reach the specimen 1. For example, it may take a predetermined time (e.g., 1 ns) based on a distance between the laser projection module 1210 and the specimen 1 until the pulsed laser is output from the laser projection module 1210 and reaches the specimen 1. Further, the pulsed laser may continue within a pulse duration, and an intensity of an optical signal of the pulsed laser may be set according to output energy and the pulse duration of the pulsed laser.

Referring to FIG. 9 again, after the laser is projected to the specimen 1, non-specific emission may be dominantly exhibited at an early stage and then element specific emission may be dominantly exhibited at a later stage. For example, in a period from about 1 ns to about 1 μs after the laser is projected to the specimen 1, the non-specific emission may be dominantly exhibited and light having a continuous spectrum may be mainly emitted. Further, in a period from about 1 μs to about 10 μs after the laser is projected to the specimen 1, the element specific emission may be dominantly exhibited and light having a line spectrum may be mainly emitted. Further, an intensity of the generated light which is emitted due to the laser projection to the specimen 1 may be increase at the early stage and then decreased at the later stage.

Therefore, a spectrum being observed may be varied according to how to set a spectrum measurement period after the laser projection. Thus, the spectrum measurement period may be appropriately selected according to a shape of a spectrum which will be obtained. For example, when a specific element content of the specimen 1 is examined, in order to obtain an element specific spectrum, a spectrum observation period may be set after plasma emission is terminated or reduced. For example, when non-specific emission generated from specimen 1 is analyzed, an observation period may be set to include an initial time at which plasma emission is maintained after the laser projection.

Meanwhile, since the time or the time periods described in conjunction with the laser induced breakdown phenomenon with reference to FIGS. 8 and 9 are merely illustrative, the embodiments of the present disclosure are not limited thereto. For example, it is noted in advance that the above-described time or time periods may be varied according to a kind or state of the specimen and the characteristic of the laser being projected, and the above examples are merely for convenience of description.

Next, a spectrum observed in some periods will be described below.

Figure 10:
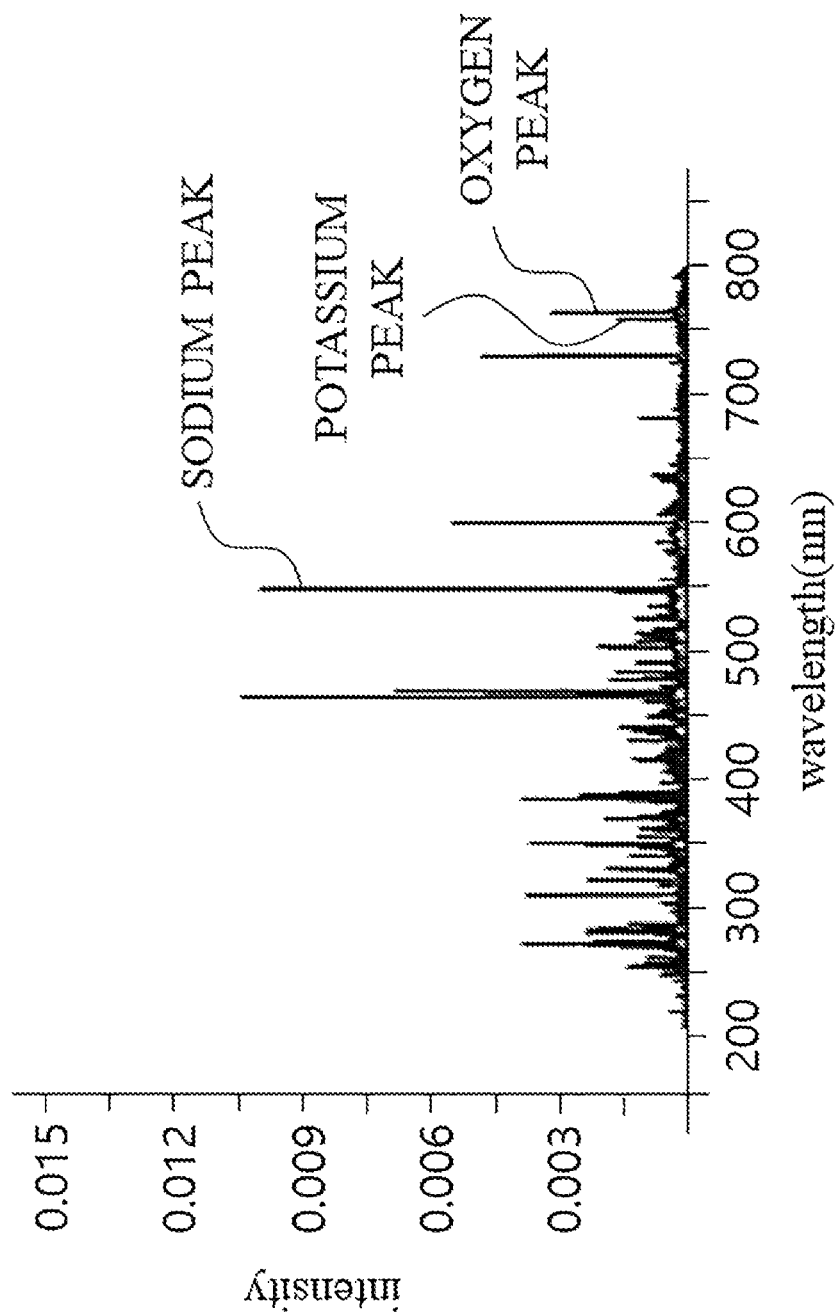
FIG. 10 is a graph showing spectra observed in a first period according to one embodiment of the present disclosure.

FIG. 10 is a graph showing spectra observed in a first period according to one embodiment of the present disclosure;

Referring to FIG. 9 again, a first period may be a period which is set for observing a spectrum of the element specific emission.

Thus, the first period may be set as a period after the plasma emission, i.e., after the non-specific emission having a continuous spectrum is substantially terminated. That is, the first period may be set as a period in which a ratio of the element specific emission among the emission occurring in the specimen 1 is dominant. For example, the first period may be a period from a time of about 1 μs after the laser is projected to the specimen 1 to a time of about 10 μs after the laser is projected.

Accordingly, a substantial line spectrum in which element peaks are dominant may be observed in the first period. Here, the element peak may mean a peak displayed at a corresponding wavelength on a spectrum as a specific element or component emits light having a unique wavelength. More specifically, when light emitted from a specific element due to electron transition and having a specific wavelength is detected in a relatively large amount as compared to surrounding light having another wavelength, the element peak may be interpreted as a peak displayed in a spectrum by corresponding to a light intensity value measured at the specific wavelength. For example, a spectrum observed in the first period shown in FIG. 10 may include a sodium element peak in a wavelength around about 600 nm and include a potassium peak, an oxygen peak, and the like in a wavelength region from about 750 nm to about 800 nm. Meanwhile, a wavelength at which an element peak exhibits in a spectrum may be referred to as a peak wavelength.

Physically speaking, as shown in FIG. 10, a small amount of continuous spectrum due to plasma emission is included in the spectrum observed in the first period, but the continuous spectrum is negligible compared to the line spectrum due to element specific emission or has only a level that does not affect a result during data analysis so that, in this specification, the spectrum shown in FIG. 10 may be understood as a discontinuous spectrum or a line spectrum.

Figure 11:
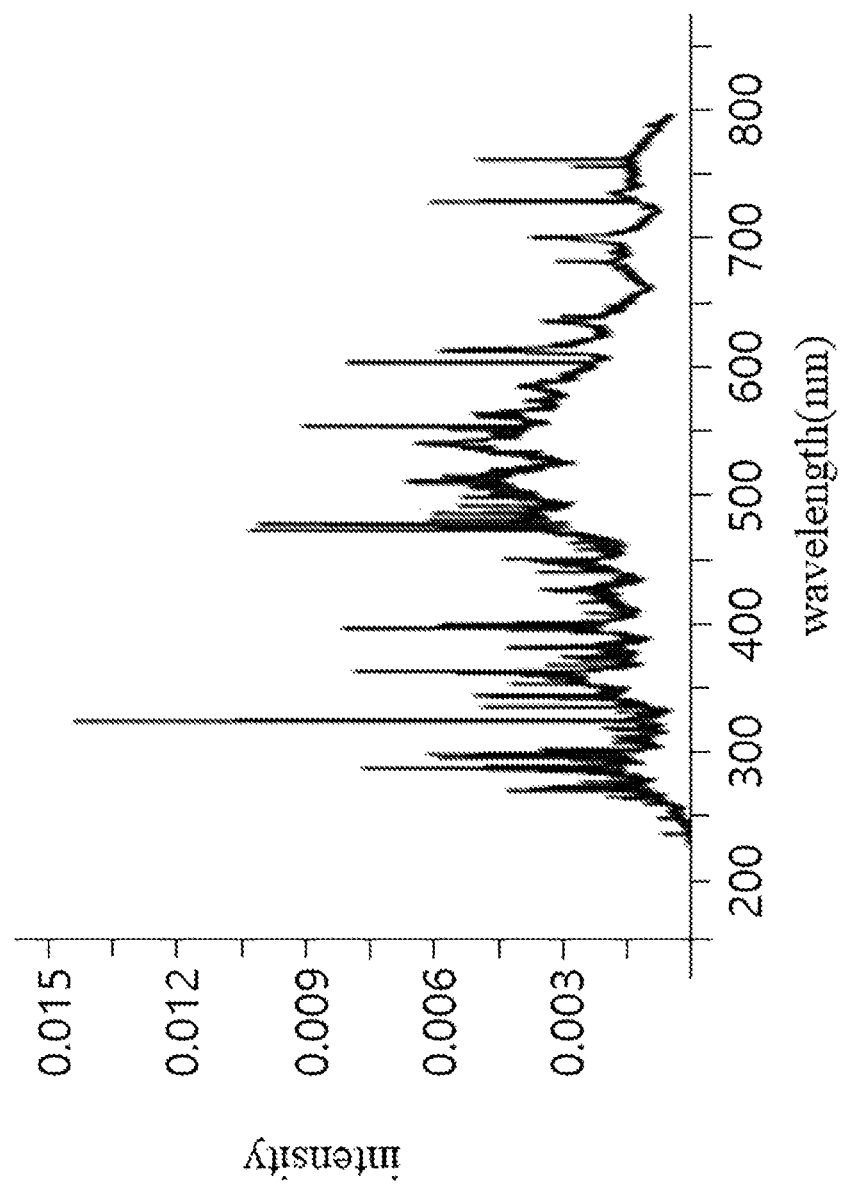
FIG. 11 is a graph showing spectra observed in a second period according to one embodiment of the present disclosure.

FIG. 11 is a graph showing spectra observed in a second period according to one embodiment of the present disclosure;

Referring to FIG. 9 again, the second period may be a period which is set for observing all spectra of the plasma emission (i.e., the non-specific emission) and the element specific emission.

Therefore, a start time point of the second period may be set to a time point at which the plasma emission, i.e., the non-specific emission having a continuous spectrum, is started. For example, the start time point of the second period may be set to a time point of about 1 ns after the laser is projected to the specimen 1.

Here, when the plasma emission is observed for diagnosis of the specimen 1, since observation of an entirety of the plasma emission is not necessary, the start time point of the second period is not necessarily set to a time point at which the non-specific emission is started, and it is also possible to set a time point at which the non-specific emission is sufficiently maintained to the start time point of the second period. For example, when actual plasma emission is made in a period from 1 ns to 100 ns after the laser projection, the start time point of the second period may be set to a previous time point of at least 100 ns after the laser is projected to the specimen 1. In this case, when at least 30% of the plasma emission with respect to a specific observation area is required for analysis of the specimen 1, the start time point of the second section may be set to a time point at which at least 30% of a quantity of light according to the total plasma emission with respect to the specific observation area may be collected (e.g., a time point of several tens of nanoseconds after the laser projection). Here, the specific observation area may mean a specific area observed by an observation part such as the light receiving module 1220. Accordingly, the specific observation area may be different according to a positional relationship between the observation tool and the specimen 1, and the plasma emission with respect to the specific observation area may be understood as plasma emission, which is observed in a specific area by the observation part, of the plasma emission generated due to the laser projection. That is, an entirety of light due to the plasma emission with respect to the specific observation area may be a part of an entirety of light due to the plasma formed in the specimen 1.

However, when the diagnosis is performed on the specimen 1 using the spectrum of the plasma emission, as a quantity of light is increased, accuracy of the diagnosis may increase so that it may be preferable that the start time point of the second period is set to a previous time point of 10 ns after the laser projection.

Here, in the second period, when the spectrum due to the plasma emission and the spectrum due to the element specific emission are to be observed, an end time point of the second period may be set such that the second period includes over a certain level of a period in which the element specific emission occurs. For example, the end time point of the second period may be set to a time point of about 10 μs after the laser is projected to the specimen 1. Accordingly, when the spectrum due to the plasma emission and the spectrum due to the element specific emission are to be observed, the second period may be set to include the first period. Here, the end time point of the second period is not necessarily specified. For example, when a factor with respect to external light such as sunlight or the like may be sufficiently suppressed, the end time point of the second period may be set to any time point at which a plasma ablation process is completely terminated (e.g., a time of 1 ms or 1 second after the laser projection).

Meanwhile, when it is necessary to observe only the spectrum of the plasma emission (i.e., the non-specific emission) as necessary, a start time point of the plasma observation period may be set to the start time point of the second period, and an end time point of the plasma observation period may be set to a previous time point at which an amount of the element specific emission becomes a predetermined level or more. That is, for example, the end time point of the plasma observation period may be set to a time point of about 1 μs after the laser is projected to the specimen 1.

As shown in FIG. 11, the spectrum detected in the second period may include the continuous spectrum due to the plasma emission and the line spectrum due to the element specific emission.

As described above, as shown in FIG. 10, the spectrum observed in the first period also includes a small amount of the continuous spectrum due to the plasma emission, but the continuous spectrum is negligible compared to the line spectrum due to element specific emission or has only a level that does not affect a result during data analysis, whereas, the spectrum observed in the second period significantly includes the continuous spectrum due to the plasma emission and the line spectrum due to the element specific emission.

The spectrum detected in the second period is also a kind of continuous spectrum in a physical sense. However, the spectrum observed in the second period has a form in which the continuous spectrum due to the plasma emission and the line spectrum due to the element specific emission are combined so that, in this specification, the spectrum observed in the second period will be referred to as a composite spectrum (a combined or mixed spectrum).

Meanwhile, the composite spectrum significantly including the continuous spectrum due to the plasma emission and the line spectrum due to the element specific emission may mean that, in performing the diagnosis using the spectrum data in this disclosure, both the continuous spectrum due to the plasma emission and the line spectrum due to the element specific emission are included to an extent sufficient to be considered.

For example, light detected in the second period may include a specific ratio or more of the entirety of the light due to the plasma emission with respect to a specific observation area. Further, the light detected in the second period may include a specific ratio or more of the entirety of the light due to the element specific emission with respect to the specific observation area. Here, like the plasma emission with respect to the specific observation area, the element specific emission with respect to the specific observation area may mean an element specific emission of the element specific emission occurring as the laser is projected to the specimen 1 within a specific area observed by the observation tool such as the light receiving module 1220. For example, a spectrum of the light detected in the second period may include a spectrum of 30% or more of entire light due to the plasma emission with respect to the specific observation area. Alternatively, the spectrum of the light detected in the second period may include a spectrum of 50% or more of entire light due to the plasma emission with respect to the specific observation area. It is noted that 30% and 50% are merely exemplary ratios.

Also, alternatively, in the spectrum of the light detected in the second period, an intensity value of a specific element peak within a specific wavelength range, and a maximum intensity value among intensity values within a wavelength range not corresponding to a peak wavelength may be each greater than or equal to a predetermined threshold.

Further alternatively, in the spectrum of the light detected in the second period, the sum of intensity values within a wavelength range out of a peak wavelength in a specific wavelength range, and overall intensity values of element peaks may be each greater than or equal to a predetermined threshold.

Further alternatively, in the spectrum of the light detected in the second period, overall intensity values within a specific wavelength range may be greater than or equal to a predetermined threshold, and a ratio of a maximum intensity value among an intensity value of a specific element peak and intensity values not corresponding to a specific element peak may be within a predetermined ratio range.

Further alternatively, in the spectrum of the light detected in the second period, overall intensity values within a specific wavelength range are greater than or equal to a predetermined threshold, and a ratio of the sum of overall intensity values of element peaks and intensity values not corresponding to the element peaks may be within a predetermined ratio range.

Further alternatively, in the spectrum of the light detected in the second period, a ratio of entire intensity values of an element peak to overall intensity values within a specific wavelength range, and a ratio of the sum of intensity values not corresponding to the element peak to the entire intensity values may be each within a predetermined ratio range.

In one embodiment of the present disclosure, the diagnosis may be performed using the above-described composite spectrum.

In a conventional LIB S, a method of inspecting a content ratio of an element or the like is mostly performed using a line spectrum shown in FIG. 10. For example, U.S. Patent entitled "Laser-induced breakdown spectroscopy for specimen analysis (application number: U.S. Ser. No. 10/662, 347)" discloses a method of detecting the presence or absence of a trace element in a sample using LIBS on a biological sample. Here, the trace element means sodium, iron, aluminum calcium, potassium, and the like and a method of using discrete spectral signature so as to determine a trace element content is disclosed in the U.S. Patent. Meanwhile, such a method has an excellent effect in analysis of a metal or an inanimate object of which element content is relatively specified, but there is a limit of accuracy in the analysis or diagnosis of an organism having a different characteristic for each sample due to a lack of information.

While the line spectrum used in the conventional LIBS dominantly includes the element peak due to the element specific emission, the above-described composite spectrum includes not only the element peak but also intensity values in a wavelength range out of the peak wavelength due to the plasma emission. Therefore, when the composite spectrum is used, diagnosis may be performed using more information than the line spectrum such that accuracy of sensitivity and/or specificity of the diagnosis may be increased.

Here, in the existing LIBS, an intensity value in a wavelength range out of the peak wavelength in the composite spectrum is treated as noise or unnecessary information, and a quantity of the intensity value is large so that there is difficult to process or analyze the intensity value. According to one embodiment of the present disclosure, as described below, a large amount of data included in the composite spectrum may be analyzed using machine learning or artificial intelligence technology, and thus it is necessary to obtain the composite spectrum from the specimen 1.

An operation of obtaining spectrum data according to one embodiment of the present disclosure may be interpreted as the above-described operation of obtaining an intensity value for each wavelength with respect to the composite spectrum. Specifically, the diagnostic system 100 according to one embodiment of the present disclosure may obtain spectrum data with respect to the composite spectrum in at least a part of the second period through a spectrum data obtaining operation.

Hereinafter, some embodiments in which the diagnostic system 100 obtains a composite spectrum or spectrum data with respect to the composite spectrum (hereinafter, referred to as the composite spectrum and the like) will be described.

According to one embodiment of the present disclosure, the diagnostic system 100 may obtain a composite spectrum and the like through a gated manner.

According to one embodiment of the present disclosure, the sensor array 1232 of the spectrum measurement module 1230 may operate in a gated manner. Here, the gated manner refers to a manner of receiving light using the sensor array 1232 which initiates light detection based on a start signal. For example, when the start signal is applied, the sensor array 1232 operating in the gated manner may perform light detection for a predetermined time from a time point at which a predetermined delay time elapses. Alternatively, the sensor array 1232 operating in the gated manner may perform light detection from a time point of application of the start signal to a time point of application of an end signal.

Hereinafter, when the LIBS unit 1200 operates in a gated manner according to one embodiment of the present disclosure, an operating method of the sensor array 1232 will be described with reference to FIG. 12.

According to one embodiment of the present disclosure, when the LIBS unit 1200 operates in a gated manner, the sensor array 1232 may perform a light detection operation when a specific condition is satisfied. For example, when the sensor array 1232 obtain a control signal from the first controller 1250, the sensor array 1232 may detect light which is spectroscopically divided in the spectral member 1231 and output an electrical signal. Alternatively, when the sensor array 1232 obtain a trigger signal from the triggering module 1240, the sensor array 1232 may detect light which is spectroscopically divided in the spectral member 1231 and output an electrical signal.

Figure 12:
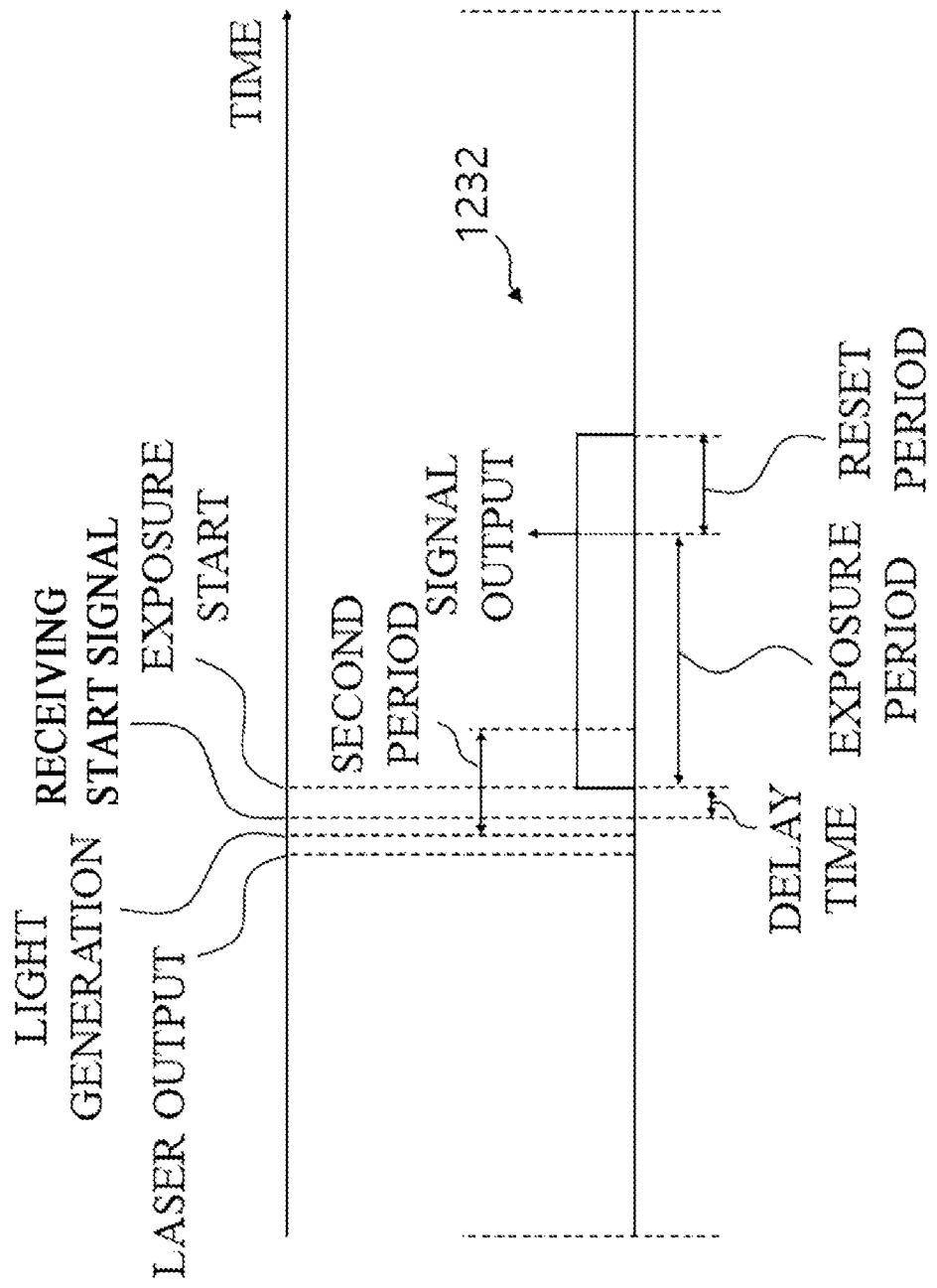
FIG. 12 is an exemplary diagram illustrating a LIBS unit operating in a gated manner according to one embodiment of the present disclosure.

FIG. 12 is a diagram illustrating the sensor array 1232 operating in a gated manner according to one embodiment of the present disclosure.

Referring to FIG. 12, the sensor array 1232 may have an exposure period or integration period and a reset period or readout period. Here, in the exposure period, the sensor array 1232 may accumulate incident light. When the light is accumulated, due to a photoelectric effect, the sensor array 1232 generated an electrical signal reflecting an intensity, an amount, and energy of the accumulated light. In the reset period, the sensor array 1232 may output the electrical signal generated according to the light incident during the exposure period. Alternatively, during the exposure period, the electrical signal may be externally read from the sensor array 1232. Each of individual sensors of the sensor array 1232 outputs the intensity of the light for each wavelength according to the above-described method such that spectrum data is generated. Further, in the reset period, the electrical signal or electrical energy due to the light accumulated in the sensor array 1232 may be reset so as to detect light in a next exposure period.

The exposure period may have a predetermined exposure time. Here, the exposure time may be set to be longer than a time at which plasma light exhibits or a time at which the plasma emission exhibits. Alternatively, the exposure time may be set to be longer than a length of the second period. For example, the exposure time may be set to about 1 ms or more. Since the exposure time is set to be longer than the time at which the plasma light exhibits or a plasma emission period, the sensor array 1232 may detect a continuous spectrum, a composite spectrum, or the like.

In the reset period, the sensor array 1232 may output an electrical signal corresponding to a quantity of light accumulated in the exposure period or perform a reset operation of removing the light accumulated in the exposure period. Here, the reset period may have a predetermined reset time for performing the reset operation, and the reset time may be set to be relatively shorter than the exposure time. For example, the reset time may be set within a range of 1 μs to 2 μs.

Meanwhile, the above-described exposure time and reset time are merely illustrative, and thus the embodiments of the present disclosure are not limited thereto. For example, the exposure time may be set to about 100 ns so as to detect only an initial spectrum after the laser is projected to the specimen 1.

After the start signal is obtained, the sensor array 1232 operating in the gated manner may have the above-described exposure period and reset period, thereby performing the light detection operation. Here, the start signal may include a signal for instructing the sensor array 1232 to perform the light detection operation. Here, for example, the start signal may be a trigger signal which will be described below.

According to an example, when the start signal is received, the sensor array 1232 operating in the gated manner may enter the exposure period after a delay time elapses and start light detection. In this case, a start time point of the light detection may be a time point at which, after the laser is output, a time interval from an output time point of the laser to a time point of receiving the start signal, and a delay time from a time point of receiving the start signal to a time point of entering the exposure period elapsed.

When the start signal is the trigger signal which will be described below, the time point of receiving the start signal of the sensor array 1232 may be a time point after a predetermined time elapses from the time point of the laser projection or output. For example, until the sensor array 1232 obtains the start signal from the first controller 1250 and/or the triggering module 1240, it may take a predetermined time from the output of the laser which will be projected to the specimen 1 or after the laser is projected to the specimen 1.

The delay time is a time for which the sensor array 1232 obtains the start signal and then starts light detection. The delay time may be predetermined by specifications of the sensor array 1232 or defined by a user.

Conventionally, when spectrum data due to element specific emission is analyzed, the sensor array 1232 operating in the gated manner was mainly designed to have a delay time of about 1 μs such that the exposure period started after the plasma emission was terminated or become very small. However, in the present disclosure, when the delay time is set to about 1 μs, it may be difficult for the sensor array 1232 to substantially receive the composite spectrum.

In order for the sensor array 1232 to receive the composite spectrum, the delay time may be set to be shorter than a time point at which the plasma emission is at least maintained at a level of a predetermined amount or more. In other words, the delay time may be set such that the sensor array 1232 detects light in at least a part of the second period. For example, the delay time of the sensor array 1232 may be set within a range of 1 ns to 1 μs.

Further, as the delay time becomes shorter, a time point at which the sensor array 1232 detects light becomes faster, and as the time point at which the sensor array 1232 detects light becomes faster, the sensor array 1232 may detect more light with respect to the plasma emission, and a ratio of the continuous spectrum in the obtained composite spectrum may increase. Accordingly, in order to detect the composite spectrum in which the continuous spectrum has a predetermined ratio or more in the sensor array 1232, the delay time may be set to 100 ns or less, and more preferably, 10 ns or less.

All the above time values are merely illustrative, and thus the delay time is not limited to the above-described example.

Further, as described above, until the sensor array 1232 starts the light detection after the laser projection/output, in addition to the delay time, since a time for receiving the start signal after the time point of the laser output/projection additionally elapses, a value of the delay time may be determined by further considering how long the time takes. For example, when light is to be detected before at least 5 ns elapses after the laser projection and 2 ns elapses for the sensor array 1232 to receive the start signal after the laser projection, the delay time should be set to be less than or equal to 3 ns.

According to another example, when the start signal is received, the sensor array 1232 operating in the gated manner may immediately enter the exposure period to start the light detection. When the exposure period begins immediately upon reception of the start signal without an intentional delay time, the sensor array 1232 may detect a large amount of the plasma emission as possible.

According to one embodiment of the present disclosure, the diagnostic system 100 may obtain the composite spectrum and the like through a non-gated manner.

According to one embodiment of the present disclosure, the sensor array 1232 of the spectrum measurement module 1230 may operate in a non-gated manner. Here, the non-gated manner may mean a manner of continuously performing the light detection regardless of the start signal. For example, when power is supplied, the sensor array 1232 operating in the non-gated manner may perform the light detection according to a predetermined cycle to output an electrical signal.

Hereinafter, when the LIBS unit 1200 operates in a non-gated manner according to one embodiment of the present disclosure, an operating method of the sensor array 1232 will be described with reference to FIG. 13.

Figure 13:
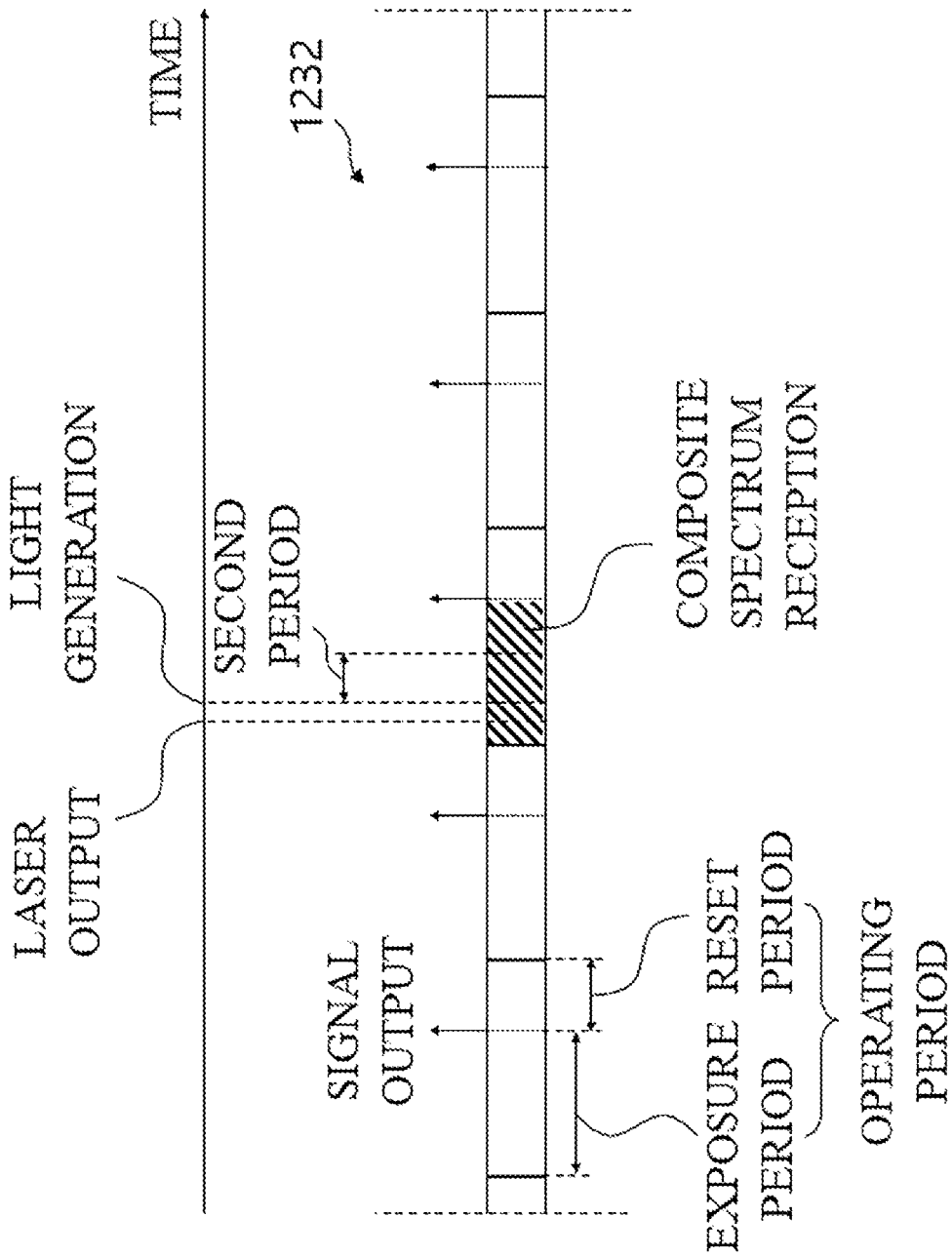
FIG. 13 is an exemplary diagram illustrating a LIBS unit operating in a non-gated manner according to one embodiment of the present disclosure.

FIG. 13 is an exemplary diagram illustrating the LIBS unit 1200 operating in a non-gated manner according to one embodiment of the present disclosure.

The sensor array 1232 operating in the non-gated manner may repeat an exposure period and a reset period, thereby performing a light detection operation.

Referring to FIG. 13, the sensor array 1232 may repeat operation periods. Each of the operation periods may detect light and output an electrical signal. Here, the operation period may include the exposure period and the reset period. Unless otherwise noted, the exposure period and the reset period of the non-gated manner may be understood to have the same characteristics as the exposure period and the reset period of the above-described gated manner. Therefore, the non-gated type sensor array may generate an electrical signal according to light incident in the exposure period and output the electrical signal in the reset period.

Referring to FIG. 13 again, since the sensor array 1232 operating in the non-gated manner continuously repeats the operation period, when the laser is projected to the specimen 1 during the operation of the sensor array 1232, the sensor array 1232 may receive light from the specimen 1, which is induced due to the laser projection, in the exposure period of any one operation period. Here, the exposure period of the operation period may be set to be sufficiently longer than a time interval in which the light is generated from the specimen 1 due to tissue ablation or the laser projection. When the exposure period is set to be sufficiently longer than the time interval in which the light is generated from the specimen 1, all or most of the second period in which the plasma emission is mainly generated may be belonged to one of the repeated exposure periods except for a specific case, and at least a part of the first period in which the element specific emission is mainly generated may also be belonged to one of the repeated exposure periods such that the non-gated type sensor array 1232 may obtain a composite spectrum in at least one among the repeated operation period.

Meanwhile, since the sensor array 1232 continuously repeats the operation periods without considering the time point of the laser projection regardless of the laser projection, when at least a part of the plasma ablation is generated in the reset period, a correct composite spectrum may not be obtained. For example, when all or a large portion (e.g., 70% or more) of the second period in which the plasma emission is mainly generated is included in the reset period, a continuous spectrum due to the plasma emission is not present or is present in a small amount such that there is high probability in that the sensor array 1232 detects a spectrum closer to the line spectrum due to the element specific emission than the composite spectrum. For example, when overall energy of the light received in the non-gated type sensor array 1232 is lower than a predetermined value, the diagnostic system 100 may determine that all or a large portion of the light generated due to the plasma ablation is not detected by the sensor array 1232 and provide an error notification to the user. In order to prevent such an error from being frequently generated, the exposure period may be set to be sufficiently longer or the reset period may be set to be sufficiently shorter in the non-gated type sensor array 1232, and as the exposure period becomes longer or the reset period becomes shorter, probability of receiving the light generated due to the plasma ablation in the exposure period becomes higher. For example, when the light generated for 1 ns to 10 µs after the laser projection is used for analysis, an exposure time is set to 10 ms, and the reset period is set to 10 µs, only an error less than one will be generated during LIBS of 1000 times.

Meanwhile, when the non-gated type sensor array 1232 is used, the operation period is continuously repeated irrespective of the laser projection such that the composite spectrum may be detected in any operation period. Therefore, in order to obtain the spectrum data according to the composite spectrum, it is necessary to specify an operation period in which the composite spectrum is received.

According to an example, the sensor array 1232 may continuously output the electrical signal for each operation period. In this case, the electrical signal output in the operation period in which the complex spectrum is received may be different from the electrical signal output in the operation period in which the complex spectrum is not received.

Figure 14:
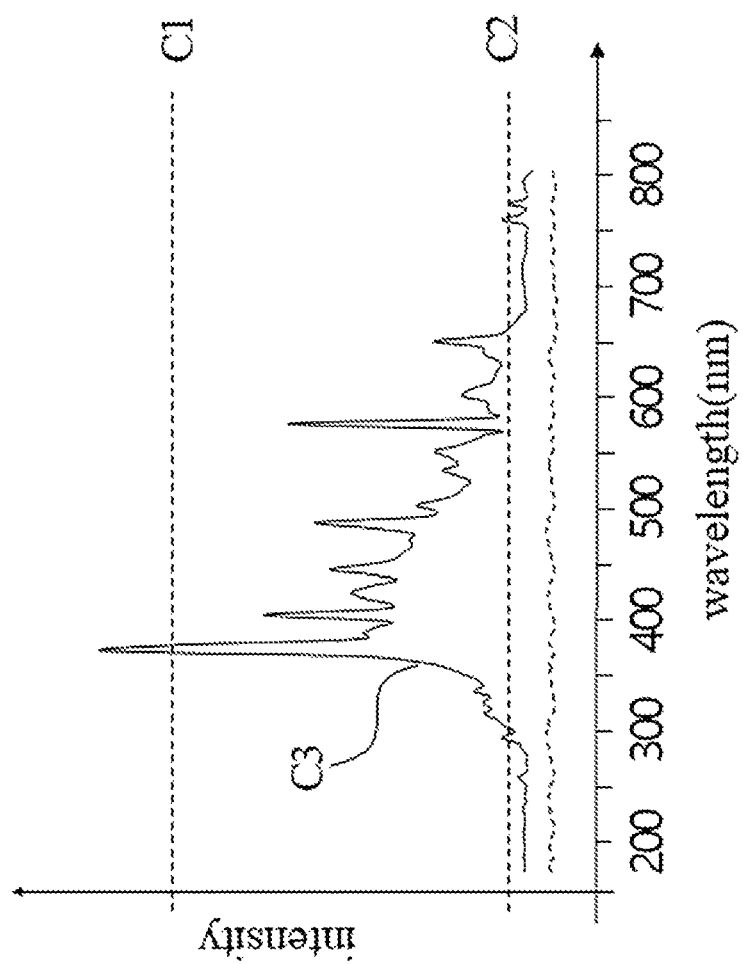
FIG. 14 is a spectrum graph observed by a non-gated sensor array according to one embodiment of the present disclosure.

FIG. 14 is a spectrum graph observed by a non-gated sensor array according to one embodiment of the present disclosure;

Specifically, as shown in FIG. 14, as the light due to the plasma ablation is received, the electrical signal of the operation period in which the composite spectrum is received has an intensity value for each wavelength corresponding to the light, whereas, as shown in FIG. 14, the electrical signal in the operation period in which the composite spectrum is not received is only a low level intensity value for each wavelength corresponding to external light such as sunlight or the like because the light due to the plasma ablation is not received. Although the external light is received even in the operation period in which the composite spectrum is received, the external light has an intensity that is much weaker than that of the light due to the plasma ablation.

Therefore, in consideration of the electrical signal being output, it is possible to specify more specifically an operation period in which the composite spectrum is received among arbitrary operation periods on the basis of a characteristic of the electrical signal being output. Here, the characteristic of the electrical signal may be an intensity value at a specific wavelength, an average value of overall intensity values for each wavelength, or the sum of intensity values of an overall wavelength range (corresponding to a total amount of received energy).

The sensor array 1232 may periodically perform the light detection operation to output an electrical signal at each reset period on the basis of a quantity of light measured during the exposure period. The first controller 1250 may obtain the electrical signal output from the sensor array 1232 and determine whether the operation period in conjunction with the electrical signal is an operation period in which the light due to the plasma ablation is received according to whether at least one among an intensity value, an average value of intensity values for overall wavelengths, the sum of the intensity values for the overall wavelengths, and an amount of received energy at a specific wavelength of the obtained electrical signal is greater than or equal to a predetermined threshold C1, C2, C3, or the like for each characteristic. In other words, the first controller 1250 may obtain the electrical signal at each operation period and select an electrical signal, in which at least one among an intensity value, the sum of intensity values for overall wavelengths, and an amount of received energy at a specific wavelength of the obtained electrical signal is greater than or equal to a predetermined threshold, as the electrical signal with respect to the composite spectrum. Alternatively, the first controller 1250 may obtain the electrical signal output from sensor array 1232, compares the obtained electrical signal with an electrical signal obtained in at least one of a previous operation period and a subsequent operation period, and select the electrical signal of which difference is greater than a predetermined threshold as the electrical signal with respect to the composite spectrum.

Also alternatively, it is also possible to specify an operation period based on the trigger signal.

Figure 15:
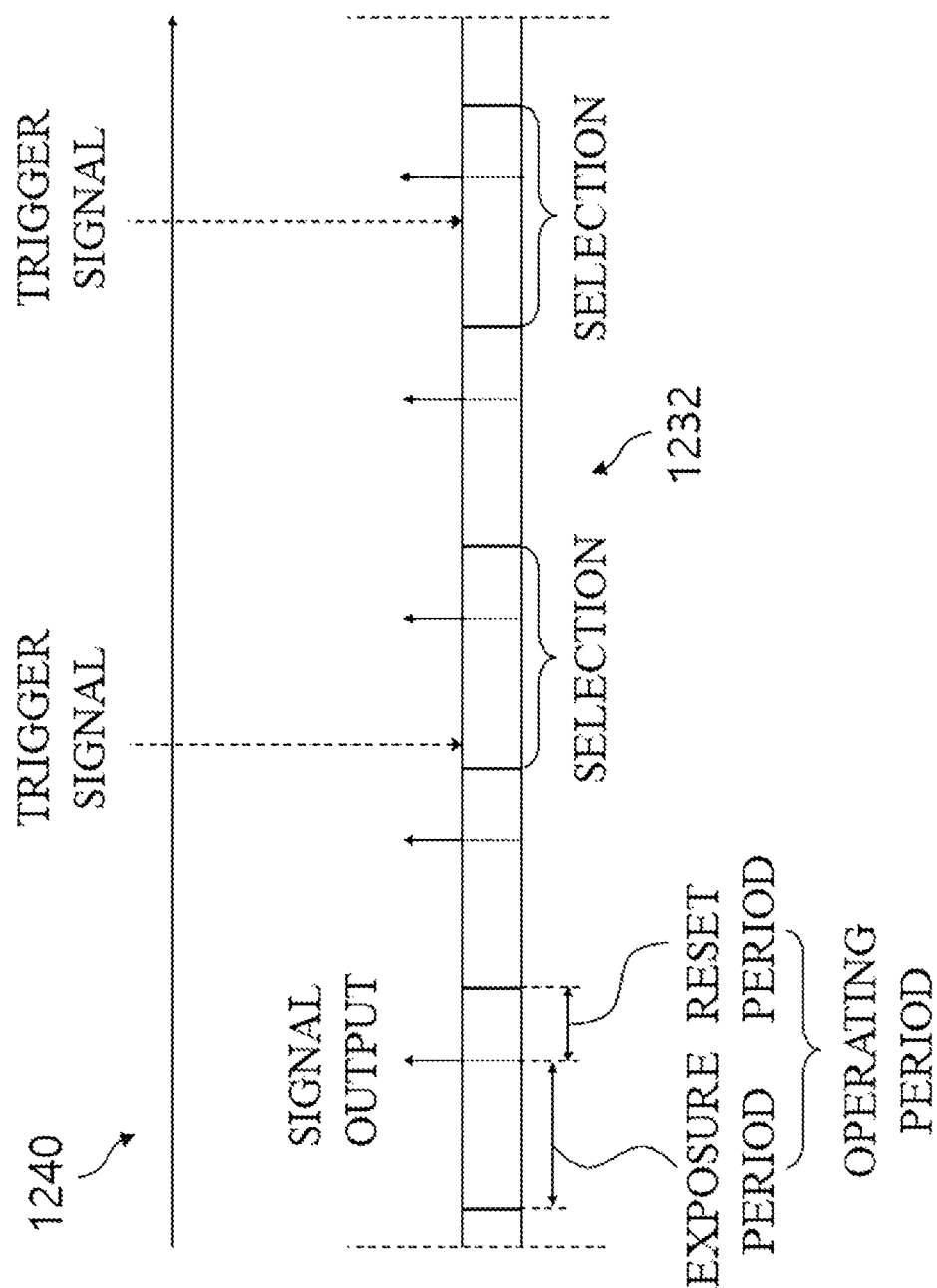
FIG. 15 is a diagram illustrating that an operating period receiving a composite spectrum is specified using a trigger signal when the non-gated sensor array is used according to one embodiment of the present disclosure.

FIG. 15 is a diagram illustrating that an operating period receiving a composite spectrum is specified using a trigger signal when the non-gated sensor array is used according to one embodiment of the present disclosure;

Referring to FIG. 15, when the non-gated type sensor array 1232 repeatedly operates in the operation period including the exposure period and the reset period, the LIBS unit 1200, for example, the triggering module 1240, may generate a trigger signal corresponding to the time point of the laser projection. Descriptions of the triggering module 1240 and the trigger signal will be described in more detail below. The first controller 1250 may determine an operation period in which the composite spectrum is received as an operation period corresponding to the trigger signal among the repeated operation periods. In other words, the first controller 1250 may obtain an electrical signal output immediately after the trigger signal is received among the electrical signals of the sensor array 1232 as an electrical signal with respect to the composite spectrum.

Meanwhile, although the first controller 1250 has been described as selecting the electrical signal in conjunction with the composite spectrum among the electrical signals continuously output from the sensor array 1232 or as specifying the operation period in conjunction with the plasma ablation among the continuously repeated operation period, it is also possible for the LIBS unit 1200 to transmit all the electrical signals being output to the diagnostic unit 1400 and is also possible for the second controller 1410 of the diagnostic unit 1400 to perform the above-described operation (selection of the electrical signal or specifying of the operation period).

According to one embodiment of the present disclosure, the LIBS unit 1200 may use the trigger signal so as to obtain the composite spectrum. In other words, the sensor array 1232 may use the trigger signal so as to generate spectrum data in conjunction with the plasma ablation.

The triggering module 1240 may generate the trigger signal. Here, the triggering operation may mean an operation of indicating at least one among a laser projection time, a start time of laser induced breakdown, and a plasma generation time. Hereinafter, an operation in which the triggering module 1240 generates the trigger signal will be referred to as a triggering operation.

Hereinafter, the triggering operation according to one embodiment of the present disclosure will be described.

Figure 16:
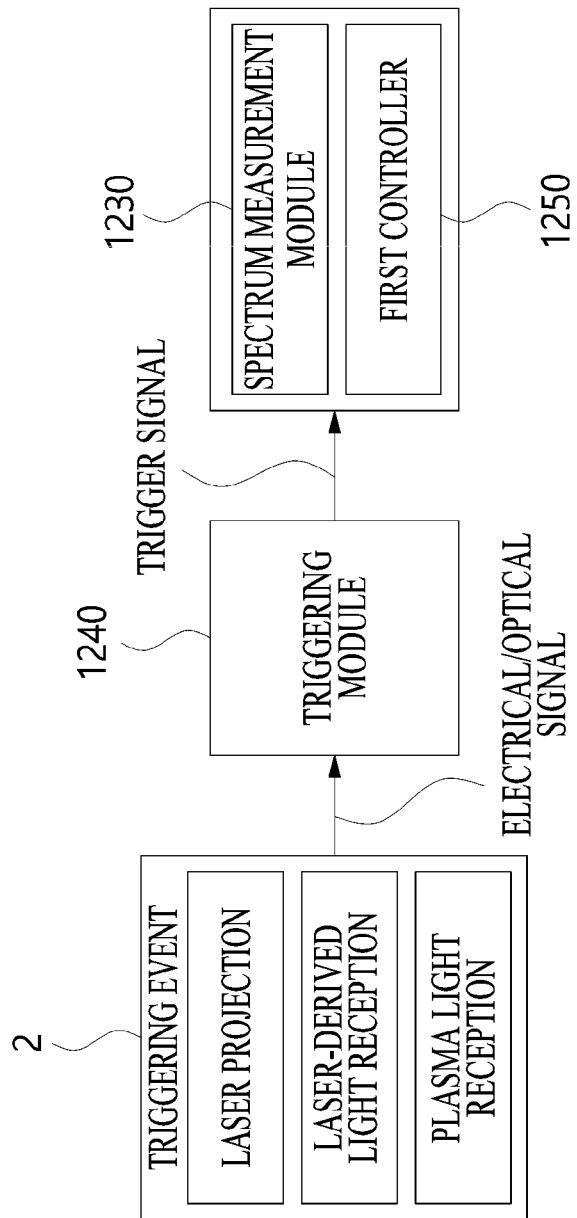
FIG. 16 is a diagram illustrating a triggering operation according to one embodiment of the present disclosure.

FIG. 16 is a diagram illustrating a triggering operation according to one embodiment of the present disclosure.

The triggering module 1240 may generate the trigger signal according to a triggering event 2. Further, the triggering module 1240 may provide the generated trigger signal to at least one among the first controller 1250, the second controller 1410, and the spectroscopic measurement module 1230.

Referring to FIG. 16, the triggering event 2 may include projection of a laser, reception of laser-derived light, and reception of plasma light. For example, the triggering module 1240 may detect the projection of a laser toward the specimen 1 and thus generate the trigger signal.

For example, the triggering module 1240 receives a control signal to be input to the laser projection module 1210 for controlling the first controller 1250 to perform laser projection so as to oscillate the laser or a drive signal input to the laser projection module 1210 for laser oscillation and thus generate the trigger signal.

Alternatively, the triggering module 1240 may generate the trigger signal by detecting the laser projected to the specimen 1. Specifically, the triggering module 1240 may include a light detection device, may be disposed in the vicinity of the projected laser, and may directly detect the projected laser or indirectly detect the projected laser through an optical part to generate the trigger signal. Here, the light detection device may be a device which responds to a wavelength of the projected laser, or a pass filter for allowing the wavelength of the projected laser to pass therethrough may be disposed on a light receiving path of the light detection device. Alternatively, a response threshold of the light detection device may be set to be greater than or equal to a specific value. Thus, malfunction due to external light such as sunlight and the like may be prevented.

Also alternatively, the triggering module 1240 may generate the trigger signal by detecting a laser-derived light including at least one among reflected light, scattered light, and fluorescent light which are generated when the laser is projected to the specimen 1. In this case, the triggering module 1240 may include a light detection device, the light detection device disposed in the vicinity of the specimen 1 may directly detect the laser-derived light or indirectly detect the laser-derived light through an optical part, or the triggering module 1240 may receive the laser-derived light from the light receiving module 1220 and detect the laser-derived light through the light detection device, thereby generating the trigger signal. Here, since the laser-derived light has a wavelength range similar to that of the projected laser, the light detection device may be a device which responds to a wavelength of the projected laser, and a pass filter for allowing the wavelength of the projected laser to pass therethrough may be disposed on a light receiving path of the light detection device. Alternatively, a response threshold of the light detection device may be set to be greater than or equal to a specific value. Thus, malfunction due to external light such as sunlight and the like may be prevented.

Further alternatively, the triggering module 1240 may generate the trigger signal by detecting plasma light generated in the specimen 1 to which the laser is projected. In this case, the triggering module 1240 may include a light detection device, the light detection device disposed in the vicinity of the specimen 1 may directly detect the plasma light or indirectly detect the plasma light through an optical part, or the triggering module 1240 may receive the plasma light from the light receiving module 1220 and detect the plasma light through the light detection device, thereby generating the trigger signal. Here, the light detection device is a device which responds to a specific wavelength range generated due to the plasma ablation (e.g., a wavelength range of a specific element peak having a high intensity value among element peaks), and a pass filter for allowing a specific wavelength range to pass therethrough may be disposed on the light receiving path of the light detection device. Alternatively, a response threshold of the light detection device may be set to be greater than or equal to a specific value. Thus, malfunction due to external light such as sunlight and the like may be prevented.

The above-described triggering module 1240 may be provided as an independent component in the LIBS unit 1200 or provided in the form of being combined with at least one among the first controller 1250, the second controller 1410, the light receiving module 1220, and the spectrum measurement module 1230.

The trigger signal generated by the above-described triggering operation may be used to obtain the composite spectrum.

According to an example, when the sensor array 1232 operates in a gated manner, the trigger signal may be used as a start signal of the sensor array 1232. Specifically, when the trigger signal is received, the sensor array 1232 may start an operation in response to the trigger signal. More specifically, when the trigger signal is received, the sensor array 1232 may enter the exposure period or enter the exposure period after the trigger signal is received and then a delay time elapses.

Alternatively, when the sensor array 1232 operates in a non-gated manner, the trigger signal may be used to select a specific operation period in which the composite spectrum is received among the repeated operation periods. Specifically, the sensor array 1232 may select an operation period corresponding to a reception time point of the trigger signal among the repeated operation periods as the specific operation period in which the composite spectrum is received.

Meanwhile, the trigger signal may be generated in the form of a time stamp generated at a detection time point of the triggering event 2. Since the trigger signal in the form of a time stamp reflects a generation time point of the triggering event 2, the non-gated type sensor array 1232 may select a specific operation period of arbitrary operation periods using event generation time information included in the trigger signal instead of the reception time point of the trigger signal.

The triggering module 1240 may have various rising times according to a time for generating the trigger signal. When the LIBS unit 1200 operating in the above-described gated method uses the trigger signal as a start signal, as the rising time increases, a time required to enter the exposure period from the time of the laser projection or the generation time of the plasma ablation increases such that, when the rising time is greater than or equal to a predetermined time interval, the gated-type sensor array 1232 may be difficult to obtain a complete composite spectrum. For example, the triggering module 1240 may have a rising time ranging from about 30 ps to 400 ns. In order for the sensor array 1232 to obtain the composite spectrum and the like, the rising time of the triggering module 1240 may be set to be less than or equal to about 100 ns.

As described above, the LIBS unit 1200 has been described as performing diagnosis using the laser induced breakdown phenomenon generated as the laser is projected to the specimen 1. Therefore, in the embodiments of the present disclosure, the laser should be projected such that the plasma ablation is induced in the target specimen 1, and, simultaneously, in the case of a human or animal body, body damage caused by the laser projection is minimized.

In the embodiments of the present disclosure, as described above, some items in conjunction with projection of the laser to the target specimen 1 and the laser projected to induce the plasma ablation while minimizing damage to the specimen 1 will be described.

In the present disclosure, damage to the specimen 1 may mean that the specimen 1 is lost/destructed to a predetermined depth or more from a surface of specimen 1, abnormality occurs in a function of the specimen 1, or a state of the specimen 1 is severe. Strictly physically, formation of a plasma as the laser is projected to the specimen 1 causes a part of the specimen 1 to be ablated, but, when ablation is generated on a surface to which the laser is projected or generated to a predetermined depth or less from the surface so that only a very small amount of the specimen 1 is substantially lost/destructed, it may be interpreted as not corresponding to the "damage" according to the present disclosure. For example, when skin is the specimen 1 and LIBS is performed on only a part of an epidermal tissue, this may be regarded as a substantial non-destructive test.

Figure 17:
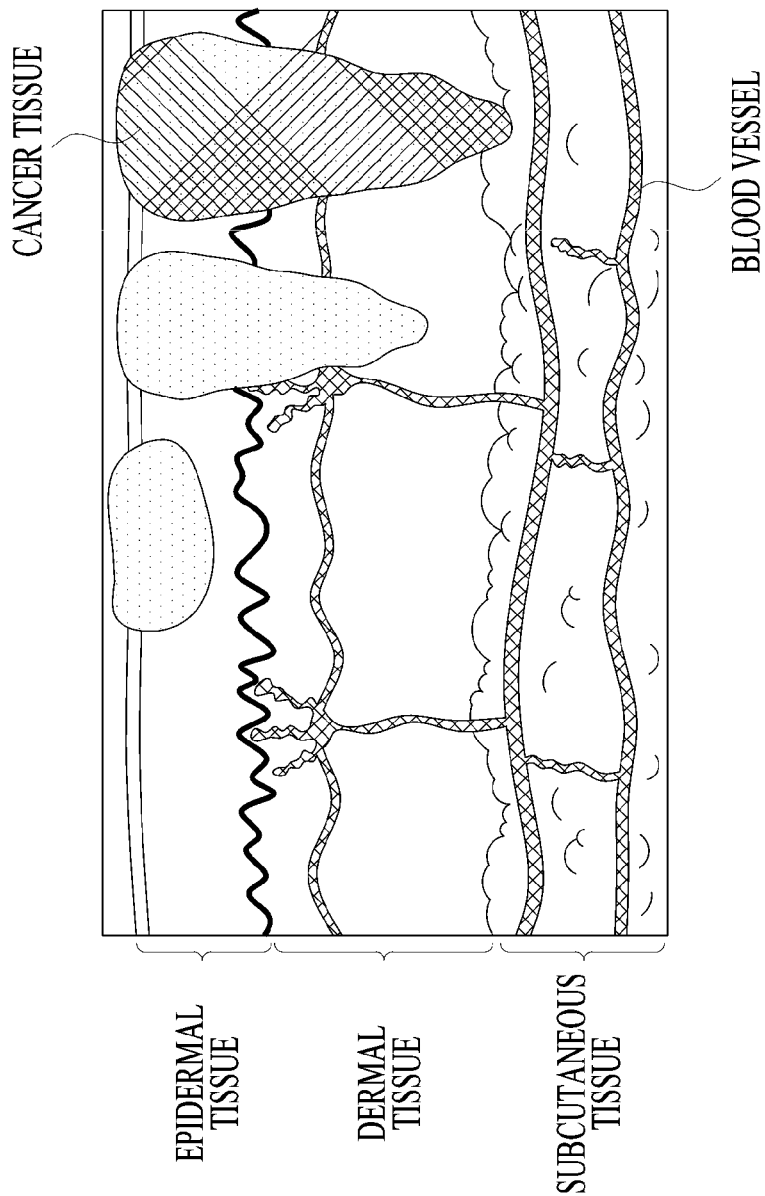
FIG. 17 is a diagram illustrating specimen damage according to one embodiment of the present disclosure.

FIG. 17 is a diagram illustrating damage of the specimen 1 according to one embodiment of the present disclosure.

Referring to FIG. 17, the skin may include the epidermal tissue, dermal tissue, and subcutaneous tissue from a surface of the skin. For example, in the case of average skin of an ordinary person, depending on a type of skin and a position of the skin in the body, an epidermal tissue may be distributed in a depth ranging from 10 to 20 μm from a surface of the skin, dermal tissue may be distributed in a depth ranging from several hundred micrometers to several millimeters from the surface, and subcutaneous tissue may be distributed below the dermal tissue. Blood vessels are located in the subcutaneous tissue, and the blood vessels of the subcutaneous tissue extend to the dermal tissue. A skin cancer may mainly occur from the epidermal tissue and gradually grow toward the dermal tissue and the subcutaneous tissue. In this case, when cancer cells metastasize to other parts of the body along the blood vessels, the cancer may metastasize to an entirety of the body.

When LIBS is performed on the specimen 1, which is skin, for diagnosis of the skin cancer and plasma ablation is generated in blood vessels or cancerous tissue around the blood vessels, bleeding may occur or cancer cells are introduced into the blood vessels to cause cancer metastasis.

Thus, for example, in the present disclosure, preferably, in order to prevent damage to the subcutaneous tissue in which at least a large amount of the blood vessels are located when the diagnostic system 100 performs the LIBS on the specimen 1, plasma ablation may be induced up to only the dermal tissue. Further, for example, in the present disclosure, more preferably, in order to prevent damage to the blood vessels or peripheries of the blood vessels when the diagnostic system 100 performs the LIBS on the specimen 1, the plasma ablation may be induced up to only the epidermal tissue in which the blood vessels are not present. Here, the diagnostic system 100 may control a depth of the plasma ablation by adjusting an intensity, fluence, a power density, a pulse duration, energy per pulse, and the like of the projected laser.

As an example of a specific numerical value, the plasma ablation may be induced to a depth of, preferably, 20 μm or less.

The above description is merely illustrative, and it is noted in advance that whether the specimen 1 is damaged may be varied according to a kind of a target, which will be diagnosed, or the purpose of diagnosis.

In one embodiment of the present disclosure, the diagnostic system 100 may project a laser to the specimen 1 so as to obtain spectrum data on the specimen 1. In this case, in order to project the laser to the diagnostic target, a laser spot should be included in the diagnostic target. Specifically, in order to project the laser to the specimen 1 which is the diagnostic target, the laser spot should be included in an area occupied by the specimen 1.

Here, the area occupied by the specimen 1 may mean an area of a target which will be diagnosed by the diagnostic system 100. For example, when diagnosis of a skin cancer is performed on human or animal skin, the area occupied by the specimen 1 may include at least a part of a region of the skin in which a pigmented region or a skin cancer such as melanoma is suspected to be present.

Figure 18:
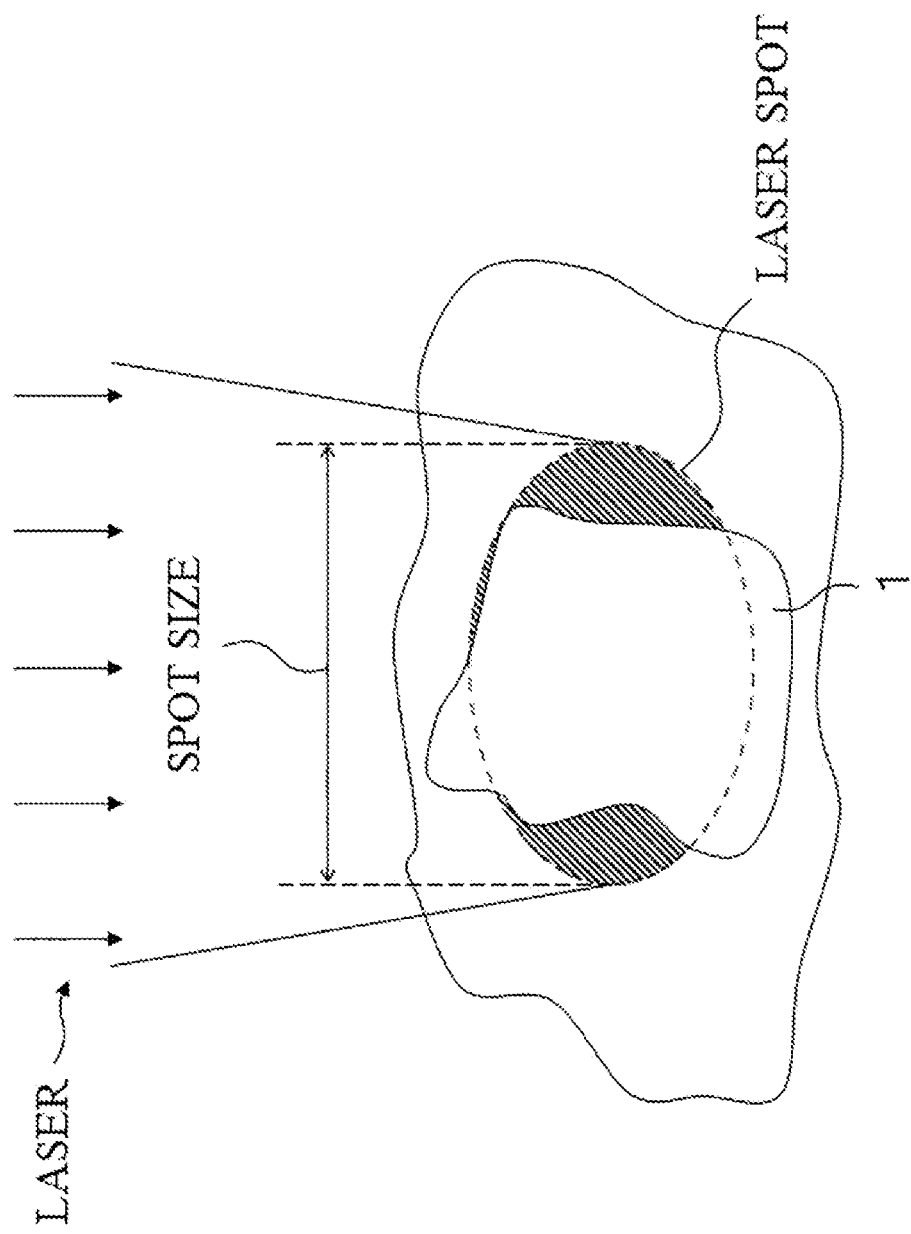
FIGS. 18 and 19 are diagrams illustrating a specimen and a laser spot according to one embodiment of the present disclosure.
Figure 19:
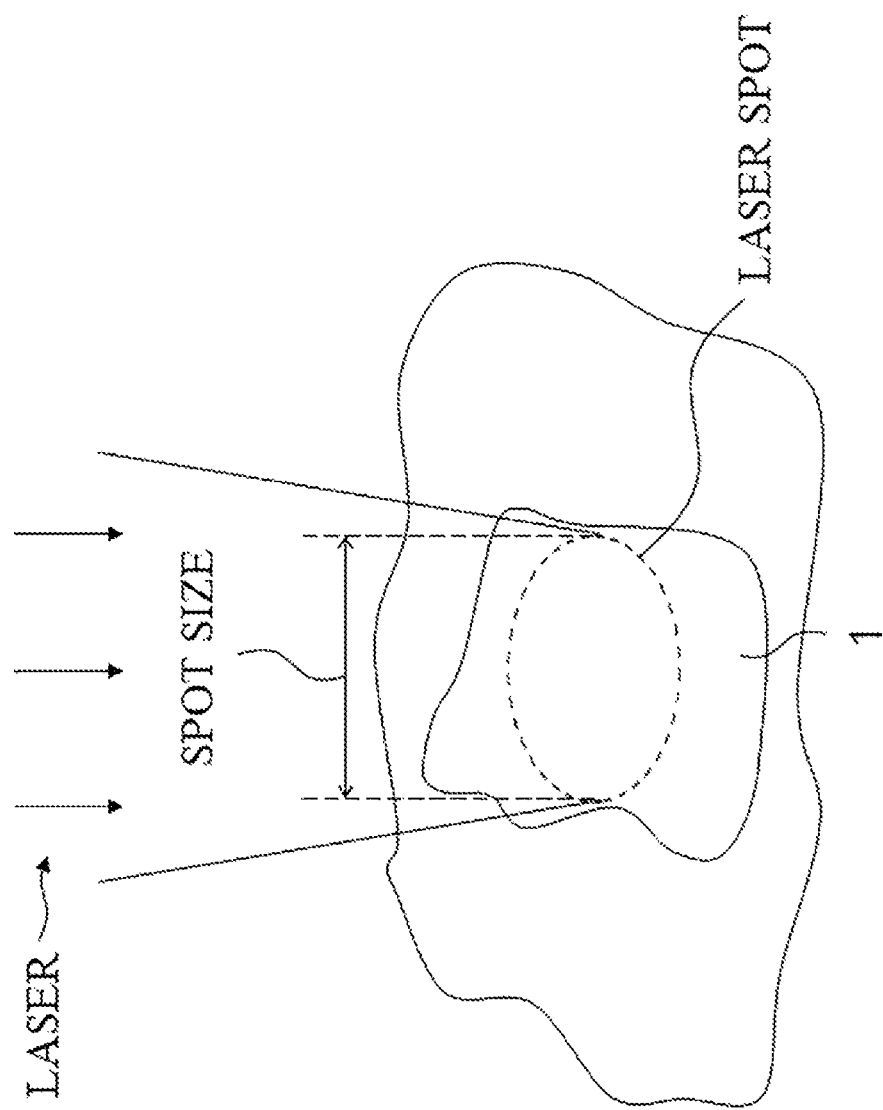

FIGS. 18 and 19 are diagrams illustrating the specimen 1 and a laser spot according to one embodiment of the present disclosure.

Referring to FIGS. 18 and 19, a laser spot may be included or may not be included in the area occupied by the specimen 1 according to a spot size.

A laser spot size may include at least one among a breadth, a width, a diameter, a radius, and an area of a spot according to a shape of the laser spot. Hereinafter, for convenience of description, unless otherwise specified, the spot size may be understood as the diameter of the laser spot, but the present disclosure is not limited thereto.

When the laser spot is larger than the area occupied by the specimen 1, accuracy or reliability of diagnosis on the specimen 1 may be degraded. For example, as shown in FIG.

18, when the laser spot is not included in the area occupied by the specimen 1, the laser is projected such that plasma ablation may be induced in a region of the laser spot which is not occupied by the specimen 1. In this case, the diagnostic system 100 received plasma light generated from the plasma induced from an unnecessary region to perform a diagnostic method such that accuracy or reliability of the diagnosis may be degraded.

Meanwhile, when the specimen 1 is a part of a human or animal body such as lesion tissue including a skin cancer and the like, the specimen 1 is different from a case in which a density or a composition is uniform, such as a metal or an object, in that a shape of the specimen 1 may not be uniform and a component thereof may be different from surrounding materials. Further, in performing therapy, surgery, beauty treatment, or the like by projecting the laser to the specimen 1, the main purpose is to remove a treatment or cosmetic target region, whereas, when diagnosis is performed by projecting the laser to the specimen 1, one of the main purposes is to collect high quality data.

Therefore, as described above, when the specimen 1 is a part of the animal or human body and the diagnosis is performed on the specimen 1, it may be preferable that the laser spot is particularly included in the specimen 1.

Referring to FIG. 19 again, the spot of the laser projected to the specimen 1 may be included in an area occupied by the specimen 1. To this end, the spot size of the laser may be set to be smaller than a size of the specimen 1. Here, the size of the specimen 1 may mean a size of the area occupied by the specimen 1. For example, the size of the specimen 1 may include at least one of a breadth, a width, a diameter, a radius, and an area according to the shape of the specimen 1.

For example, when the spot of the laser has a circular shape, the spot size may be set such that the laser spot is included in the specimen 1. Specifically, when the diagnostic system 100 diagnoses the presence or absence of a skin cancer by setting skin as the specimen 1, since lesion tissue suspected as the skin cancer, i.e., the area occupied by the specimen 1, usually includes a circular region having a diameter of about 6 mm, the spot size of the laser projected to the specimen 1 is preferably 5 mm or less to be included in the area occupied by the specimen 1 in consideration of a unexpected variable such as hand shaking.

Meanwhile, as the spot size becomes smaller, the spot size is easily included in the area occupied by the specimen 1, but, as described below, in order to prevent damage to the specimen 1, it is necessary for the spot size to be set to a predetermined size or more.

In one embodiment of the present disclosure, the laser projected to the specimen 1 should be able to induce the plasma ablation to the specimen 1. Further, in this case, damage to the specimen 1 due to the projected laser should be minimized.

Here, the plasma ablation and/or the damage to the specimen 1 may be in conjunction with power per unit area (hereinafter referred to as a "power density") and/or energy per unit area (hereinafter referred to as "fluence"), which is applied to the specimen 1 due to the projected laser.

For example, when a pulsed laser is used as the projected laser, a power density and fluence may be as follows.

$$\text{power density} = \frac{\text{energy per pulse}}{\text{pulse duration} \times \text{projection area}} \qquad \text{[Equation 1]}$$

The power density may mean energy applied to the specimen 1 per unit area and hour. That is, as shown in Equation 1, the power density of the pulsed laser may be a value obtained by dividing power, which is obtained by dividing power per pulse (laser pulse energy) of the projected laser by a pulse duration, by a projection area.

$$\text{fluence} = \frac{\text{energy per pulse}}{\text{projection area}} \qquad \text{[Equation 2]}$$

The fluence may mean energy applied to specimen 1 per unit area. That is, as shown in Equation 2, the fluence of the pulsed laser may be a value obtained by dividing the energy per pulse of the projected laser by the projection area.

$$\text{fluence} = \text{power density} \times \text{pulse duration} \qquad \text{[Equation 3]}$$

Thus, as shown in Equation 3, the fluence of the pulsed laser may be a value obtained by multiplying the pulse duration by the power density of the pulsed laser, and the power density of the pulsed laser may be a value obtained by dividing the fluence of the pulsed laser by the pulse duration.

In this case, when the laser is projected to the specimen 1 using the pulsed laser, formation of the plasma is in conjunction with the power density of the pulsed laser. Specifically, when a sufficient power density is applied to the specimen 1, the plasma ablation may be generated in the specimen 1.

Further, when the laser is projected to the specimen 1 using the pulsed laser, damage to the specimen 1 may be in conjunction with the fluence of the pulsed laser. Specifically, when the fluence at a predetermined level or more is applied to the specimen 1, damage may be generated in the specimen 1.

Figure 20:
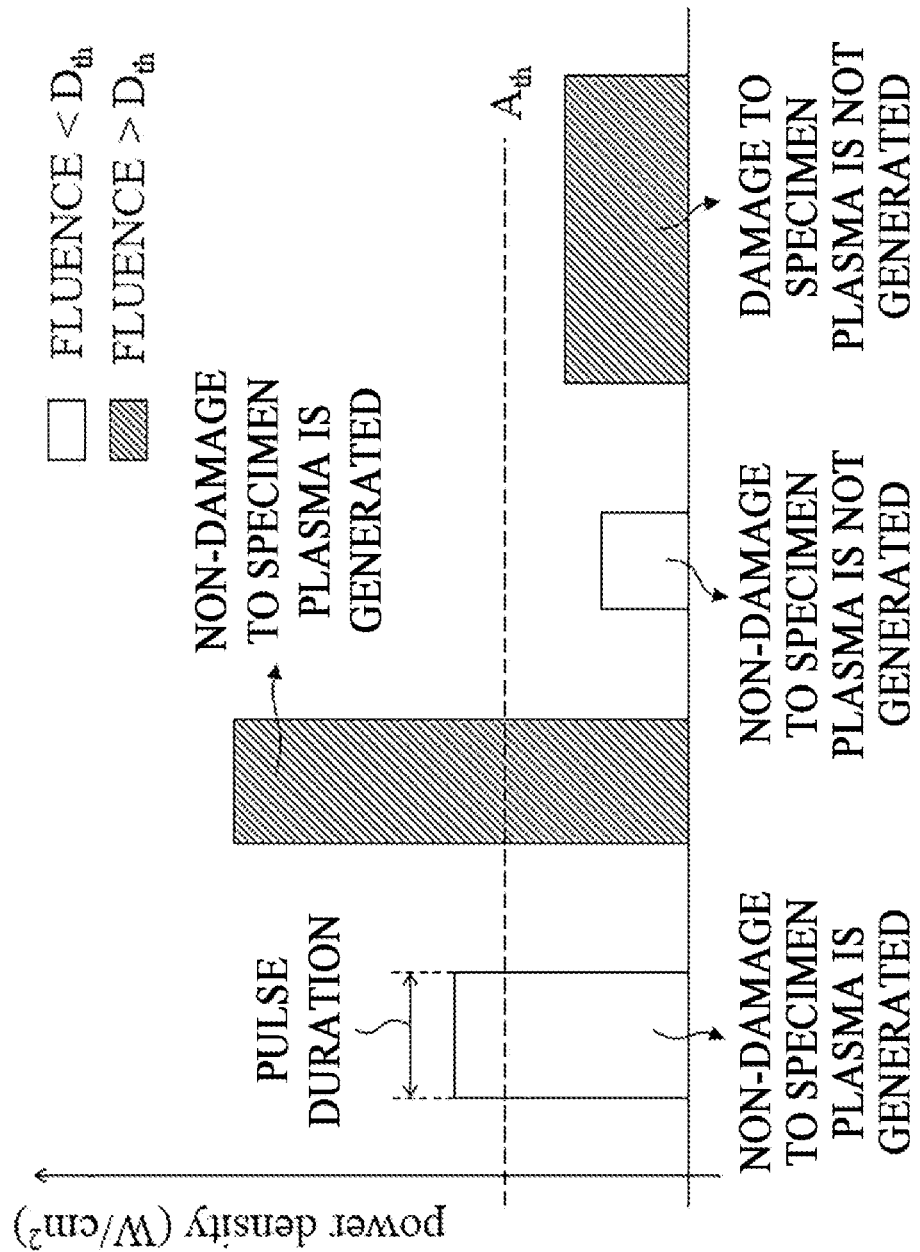
FIG. 20 is a graph showing power density and fluence which are applied to a specimen by several pulsed lasers according to one embodiment of the present disclosure.

FIG. 20 is a graph showing a power density and fluence which are applied to the specimen 1 by several pulsed lasers according to one embodiment of the present disclosure.

Hereinafter, for convenience of explanation, a minimum power density which should be applied to induce the plasma ablation to the specimen 1 refers to an ablation threshold $A_{th}$, and maximum fluence for minimizing damage to the specimen 1 due to the laser projection refers to a damage threshold $D_{th}$.

Referring to FIG. 20, various power densities and fluence may be applied to the specimen 1 according to one embodiment of the present disclosure.

For example, referring to FIG. 20, when a power density of the ablation threshold $A_{th}$ or more and fluence of the damage threshold $D_{th}$ or less are applied to the specimen 1, the plasma may be generated in the specimen 1, but damage due to the laser projection may be minimized.

Alternatively, referring to FIG. 20, when a power density of the ablation threshold $A_{th}$ or more and fluence of the damage threshold $D_{th}$ or more are applied to the specimen 1, the plasma may be generated in the specimen 1, and damage due to the laser projection may be generated to some extent.

Also alternatively, referring to FIG. 20, when fluence of the damage threshold $D_{th}$ or less and a power density of the ablation threshold $A_{th}$ or less are applied to the specimen 1, the specimens 1 may be hardly damaged and the plasma may also not be generated.

Further alternatively, referring to FIG. 20, when fluence of the damage threshold $D_{th}$ or more and a power density of the ablation threshold $A_{th}$ or less are applied to the specimen 1, although damage may be generated in the specimen 1 to some extent, the power density is less than or equal to the ablation threshold $A_{th}$ such that the plasma may not be generated.

That is, although a sufficient power density is applied to the specimen 1, when the fluence is sufficiently low, the plasma ablation may be generated in the specimen 1 without damage to the specimen 1 or with minimum damage thereto. For example, when the diagnostic system 100 diagnoses skin suspected of a skin cancer whether the skin cancer is present and the fluence is sufficiently low even though a sufficient power density is applied to the skin, the plasma ablation is induced only in epidermis of the skin and is not induced in dermis or subcutaneous tissue such that the diagnosis may be performed without damage to blood vessels or peripheries of the blood vessels.

Here, the ablation threshold $A_{th}$ and the damage threshold $D_{th}$ may have different values according to a kind or state of the specimen 1. For example, when the specimen 1 is a part of a human or animal body and a power density applied to the specimen 1 due to the laser projection is 0.1 $GW/cm^2$ or more, the plasma may be formed in the specimen 1. Alternatively, when the specimen 1 is skin and a fluence value of the projected laser is 40 $J/cm^2$ or more, skin tissue may be damaged. Specifically, when the fluence value is 40 $J/cm^2$ or more, a serious situation may occur in which cell damage such as bleeding occurs at a predetermined depth from the surface of the skin and cancer cells or the like metastasize to other parts of the body. That is, the ablation threshold $A_{th}$ may include $GW/cm^2$ and the damage threshold $D_{th}$ may include 40 $J/cm^2$.

Meanwhile, according to one embodiment of the present disclosure, the diagnostic system 100 may adjust the power density and the fluence value so as to prevent damage to the specimen 1 while forming the plasma in the specimen 1 for safe and accurate diagnosis. For example, the LIBS unit 1200 adjusts the energy, pulse duration, and projection area of the laser projected to specimen 1 such that an intensity per unit area of the laser projected to the specimen 1 becomes 0.1 $GW/cm^2$ and energy per unit area applied to the specimen 1 becomes 40 $J/cm^2$ or less. For example, when the above-described fluence and power density are applied to the skin, the plasma ablation is generated in only the epidermis such that non-destructive test may be substantially performed without damage to body tissue such as blood vessels.

Hereinafter, a method of setting the above-described energy, pulse duration, and projection area of the laser and the like according to specifications of a device, a facility, or equipment, and a settable value range according to an embodiment of the present disclosure will be described.

The laser projection module 1210 may set energy and a pulse duration of the laser generated by adjusting a kind of the active laser medium 1212 and energy applied to the active laser medium 1212. For example, the laser projection module 1210 may generate a laser having energy ranging from about 10 mJ to 100 mJ per pulse and a pulse duration ranging from about 1 ps to 1 ms.

The laser adjusting member 1214 may change an intensity or energy of a generated laser using a filter. For example, the laser adjusting member 1214 may allow only a portion of the generated laser to pass through using a translucent or opaque filter to reduce the intensity or energy of the laser.

The laser adjusting member 1214 may include an optical part such as a lens and the like and change a shape or focal length of the laser, thereby adjusting the projection area. For example, when the laser adjusting member 1214 includes a convex lens, the focal length of the laser may become shorter, and, as the specimen 1 becomes away from a focal point of the laser, the projection area may become larger.

The guide member 1216 may change or adjust the projection area of the laser applied to the specimen 1 by setting a projection distance. For example, as the guide member 1216 extends to be long from the laser projection module 1210, the projection distance may become longer, and as the specimen 1 becomes closer to the focal point of the laser, the projection area may become smaller.

As described above, when the spot size is set by the laser adjusting member 1214 and/or the guide member 1216, the power density and the fluence may be considered. Specifically, the laser spot may have a diameter ranging from 1 µm to 10 mm, or the projection area may be set within a range of 0.7 $\mu m^2$ to 70 $mm^2$. For example, preferably, the laser spot has a diameter ranging from 100 µm to 5 mm or an area ranging from 0.01 $mm^2$ to 20 $mm^2$.

Meanwhile, the above-described ranges of the intensity, energy per pulse, pulse duration, and projection area of the laser are merely illustrative, and thus the embodiments of the present disclosure are not limited thereto.

Hereinafter, as the above description according to one embodiment of the present disclosure with reference to FIGS. 21 to 23, a method in which the diagnostic system 100 specifically sets a spot size so as to induce the plasma ablation without causing damage to the specimen 1 will be described.

Figure 21:
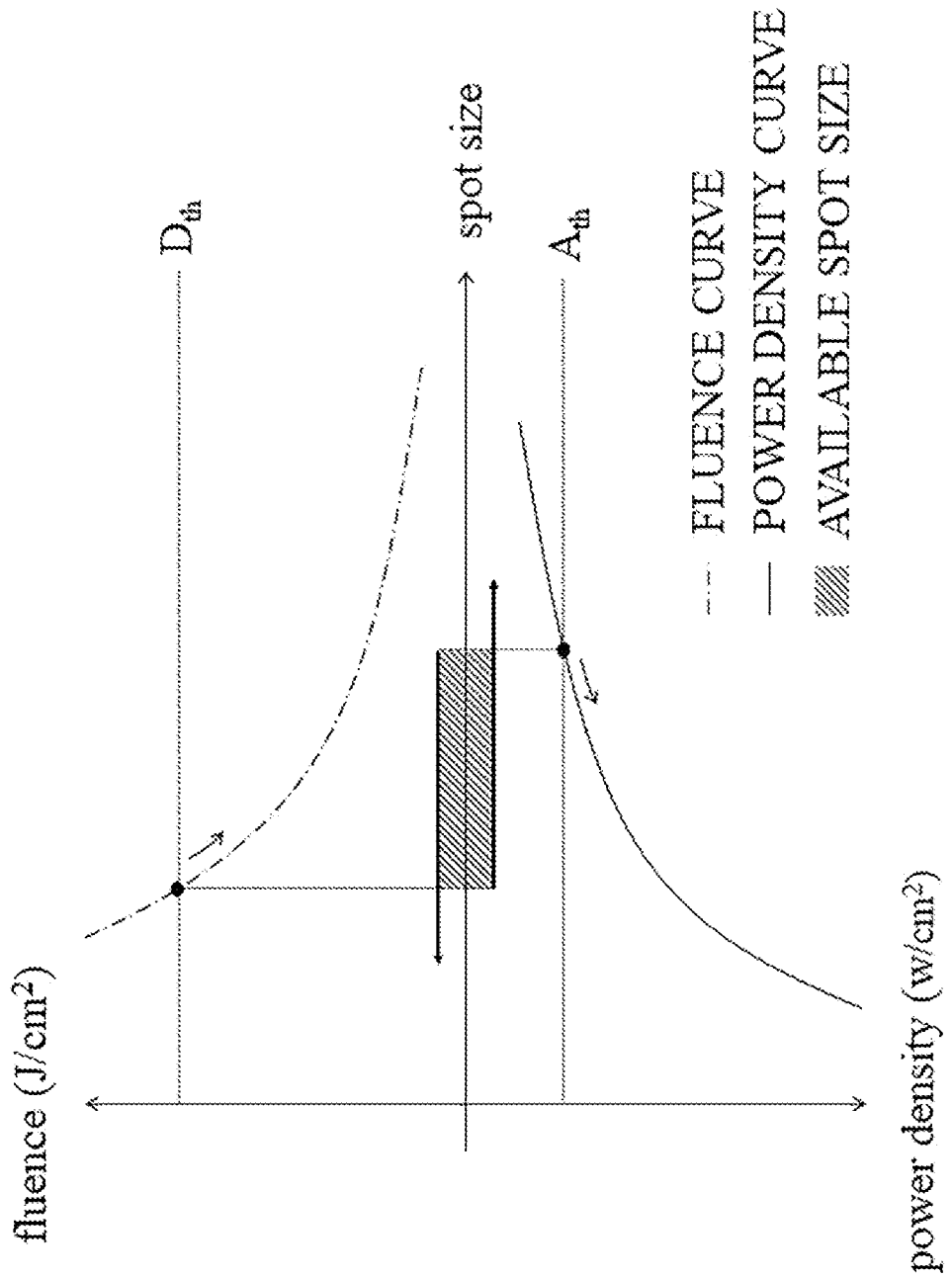
FIGS. 21 to 23 are graphs showing a relationship between a spot size, power density, and fluence according to one embodiment of the present disclosure.
Figure 22:
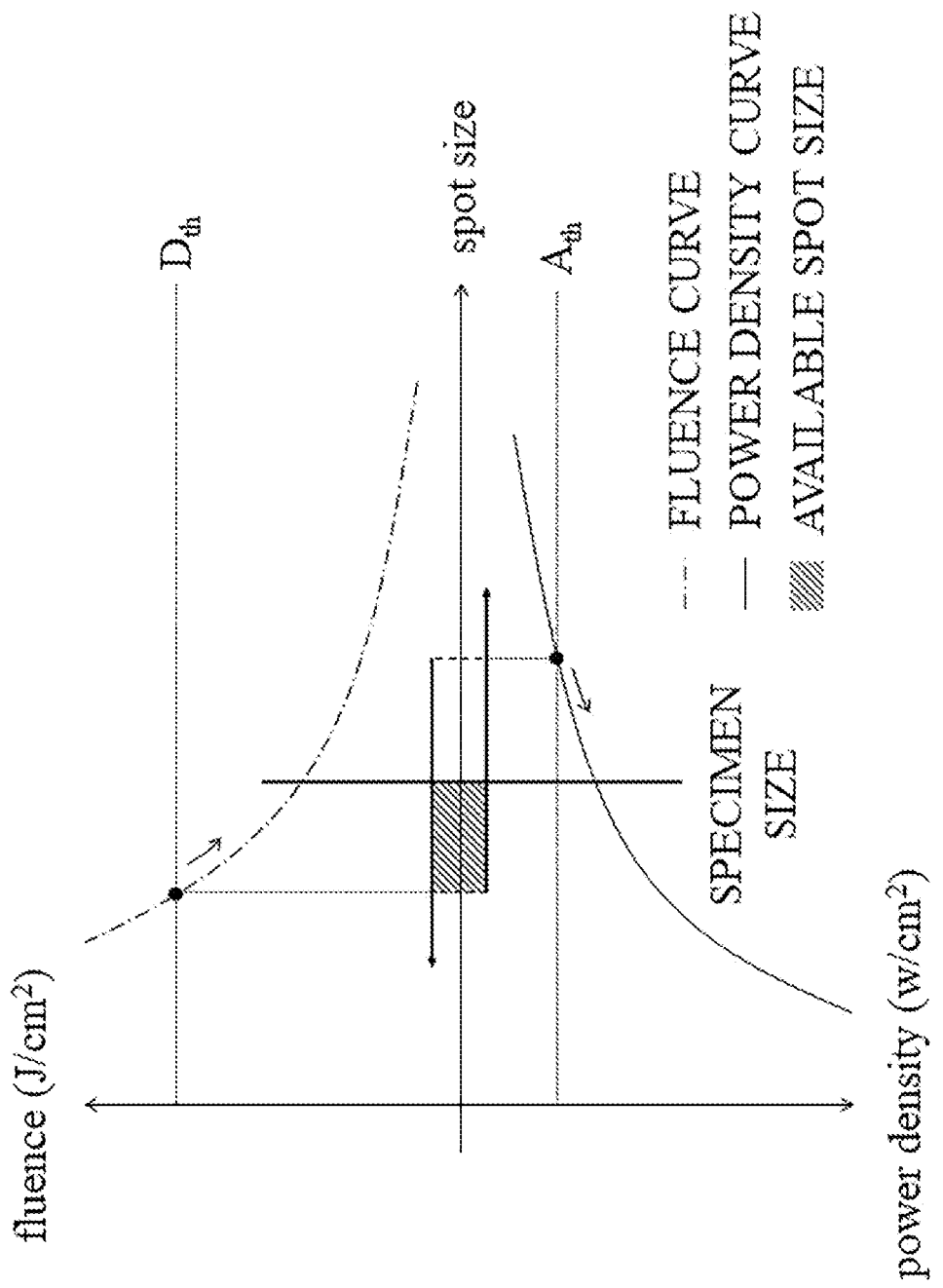
Figure 23:
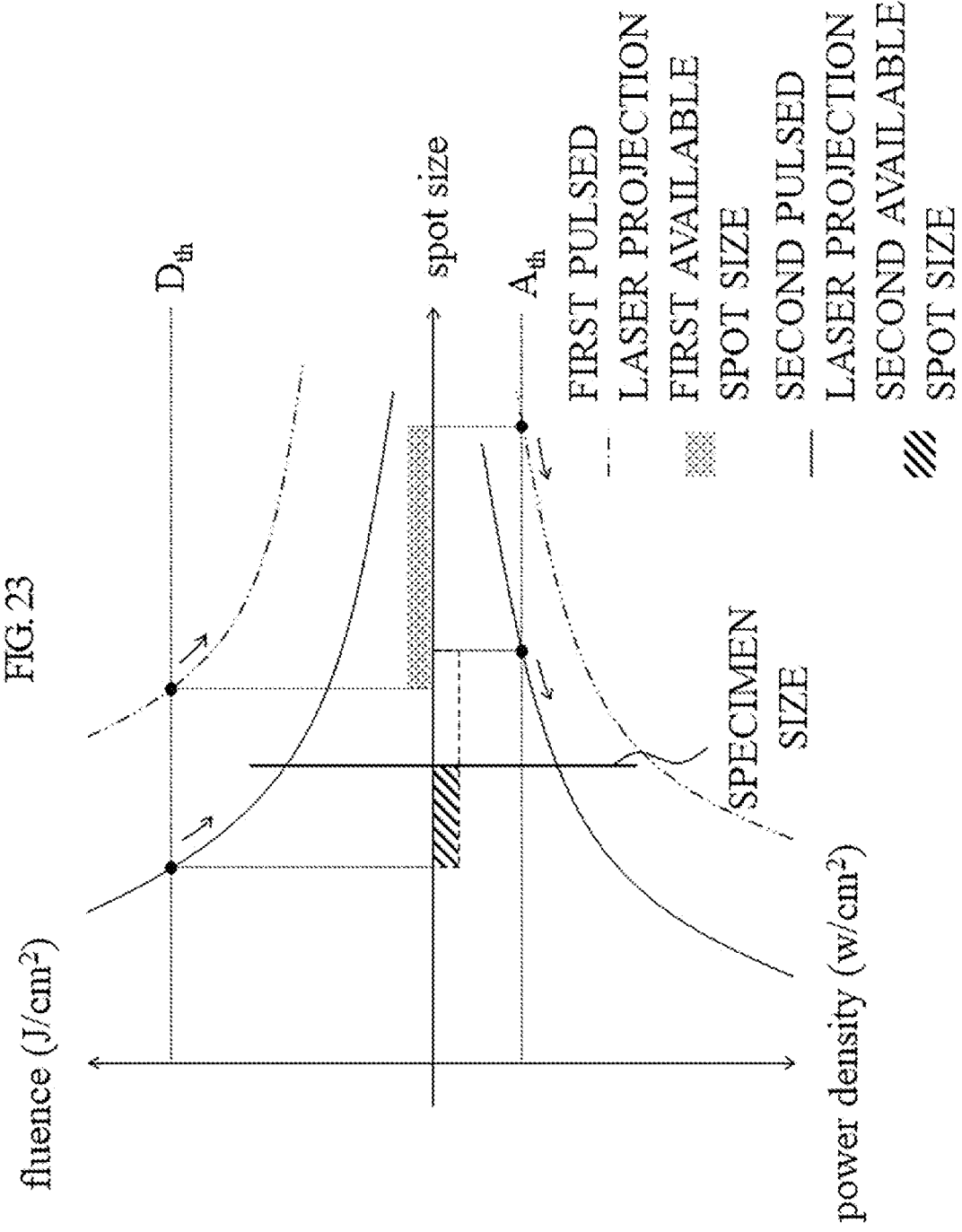

FIGS. 21 to 23 are graphs showing a relationship between a spot size, power density, and fluence according to one embodiment of the present disclosure.

According to one embodiment of the present disclosure, the diagnostic system 100 may select an appropriate spot size on the basis of an effective spot size for inducing the plasma ablation without damage to the specimen 1.

Referring to FIG. 21, as the spot size increases, a power density value may decrease. Further, as the spot size increases, a fluence value may decrease. Here, a positional relationship and curvatures of a power curve and an energy curve may be varied according to energy per pulse of the laser, a pulse duration, and the like.

When an intensity, a pulse duration, or the like of the laser projected to the specimen 1 is set to a predetermined value in the diagnostic system 100, the effective spot size may mean a spot size which is capable of inducing plasma ablation without damage to the specimen 1. Here, the effective spot size may be set by the power curve and the energy curve.

Referring to FIG. 21 again, in order to apply fluence that is less than or equal to the damage threshold $D_{th}$ so as to prevent damage to the specimen 1, the laser projected to the specimen 1 should have a spot size that is greater than or equal to a spot size value corresponding to the damage threshold $D_{th}$ on the energy curve. Further, in order to apply a power density that is greater than or equal to the ablation threshold $A_{th}$ so as to induce the plasma ablation in the specimen 1, the laser projected to the specimen 1 should have a spot size that is less than or equal to a spot size value corresponding to the ablation threshold $A_{th}$ on the power curve. Therefore, a maximum value of the effective spot size may be set to a spot size corresponding to the ablation threshold $A_{th}$ on the power curve, and a minimum value thereof may be set to a spot size corresponding to the damage threshold $D_{th}$ on the energy curve.

Meanwhile, according to one embodiment of the present disclosure, the effective spot size may be set in consideration of the size of the specimen 1. For example, referring to FIG. 22, the minimum value of the effective spot size may be set to a spot size corresponding to the ablation threshold $A_{th}$ on the power curve, and the maximum value thereof may be set to a spot size corresponding to the damage threshold $D_{th}$ on the energy curve. When the size of the specimen 1 is smaller than the spot size corresponding to the damage threshold $D_{th}$, the maximum value of the effective spot size may be set to the size of the specimen 1.

That is, the diagnostic system 100 may select the spot size of the laser projected to the specimen 1 within the effective spot size which is set in consideration of at least one among the spot sizes corresponding to the ablation threshold $A_{th}$, the damage threshold $D_{th}$, and the size of the specimen 1. Consequently, the diagnostic system 100 may perform more safe and more accurate diagnosis on the specimen 1.

Meanwhile, according to a characteristic of the laser projected to the specimen 1, the size of the specimen 1 may be smaller than a minimum value of the effective spot size. Alternatively, at least a portion of the effective spot size may not be included within the size of the specimen 1. Also alternatively, a spot size within the size of the specimen 1 may not be present in the effective spot size. In this case, when the diagnostic system 100 performs diagnosis on the specimen 1, the plasma ablation due to the laser projection is induced in a portion other than the specimen 1 such that accuracy of the diagnosis may be degraded.

Referring to FIG. 23, the effective spot size may be differently set according to the intensity or pulse duration of the pulsed laser used by the diagnostic system 100. For example, when the diagnostic system 100 uses a first pulsed laser for diagnosis and a first effective spot size is set, or when the diagnostic system 100 projects a second pulsed laser having a laser intensity or energy per pulse that are smaller than that of the first pulsed laser for diagnosis, a second effective spot size may be set to a spot size that is smaller than the first effective spot size. Here, a minimum value and a maximum value of the first effective spot size may have values that are greater than those of the second effective spot size.

Referring to FIG. 23 again, the size of the specimen 1 may be smaller than the minimum value of the first effective spot size and greater than the minimum value of the second effective spot size. In this case, the diagnostic system 100 may use the second pulsed laser and set the spot size within the second effective spot size in consideration of the size of the specimen 1, thereby inducing the plasma ablation without damage to the specimen 1. Meanwhile, when the diagnostic system 100 uses the first pulsed laser, even though the minimum value of the first effective spot size is selected as the spot size, the spot size is larger than the size of the specimen 1 such that the laser may be projected to a region other than the specimen 1.

Therefore, the diagnostic system 100 should adjust or set the intensity or the energy per pulse of the laser projected to the specimen 1 such that the minimum value of the effective spot size has a value that is smaller than the size of the specimen 1. For example, as shown in FIG. 23, the intensity or the energy per pulse of the laser may be reduced such that the spot size corresponding to the damage threshold value $D_{th}$ on the energy curve using the first pulsed laser becomes smaller than the size of the specimen 1. More specifically, the diagnostic system 100 may reduce the intensity of the first pulsed laser using the second pulsed laser having an intensity that is smaller than that of the first pulsed laser or using the laser adjusting member 1214.

As described above, when the diagnostic system 100 performs the diagnosis according to one embodiment of the present disclosure, the detailed method in which the effective spot size was set to induce the plasma ablation without causing damage to the specimen 1 has been described. In addition to the above description, a method of setting or adjusting the spot size within the effective spot size will be described in detail below.

Figure 24:
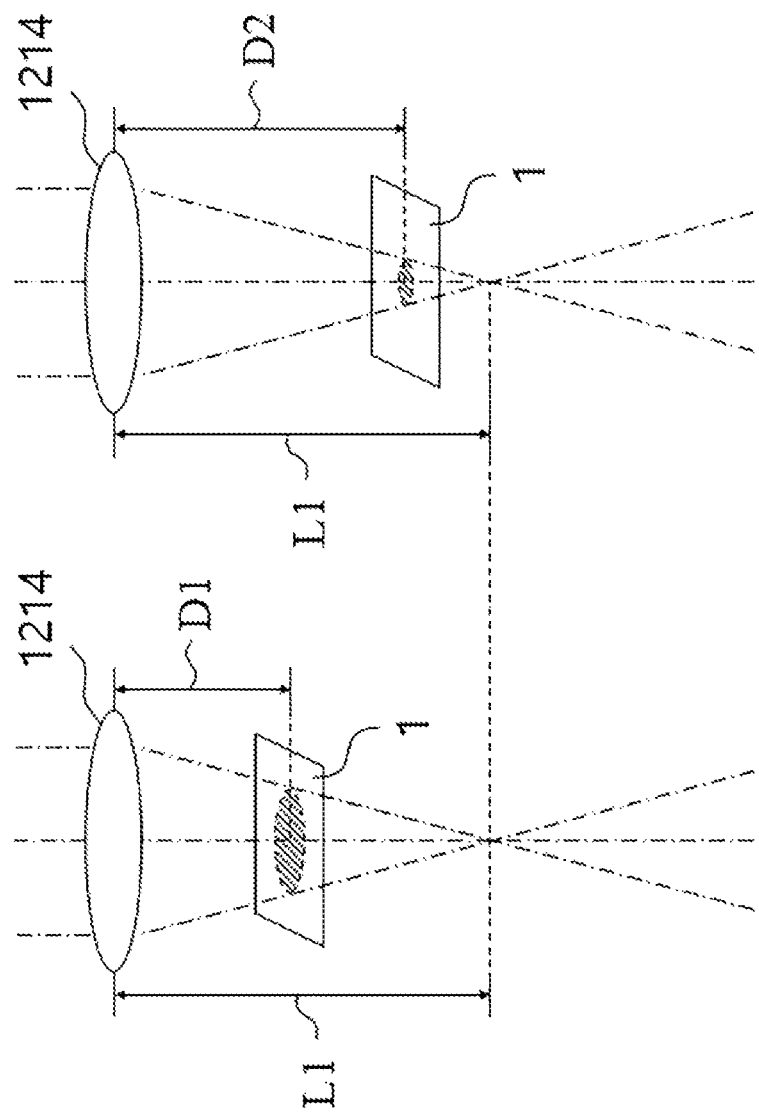
FIGS. 24 and 25 are diagrams illustrating that a spot size of a laser projected onto a specimen is variously set according to one embodiment of the present disclosure.
Figure 25:
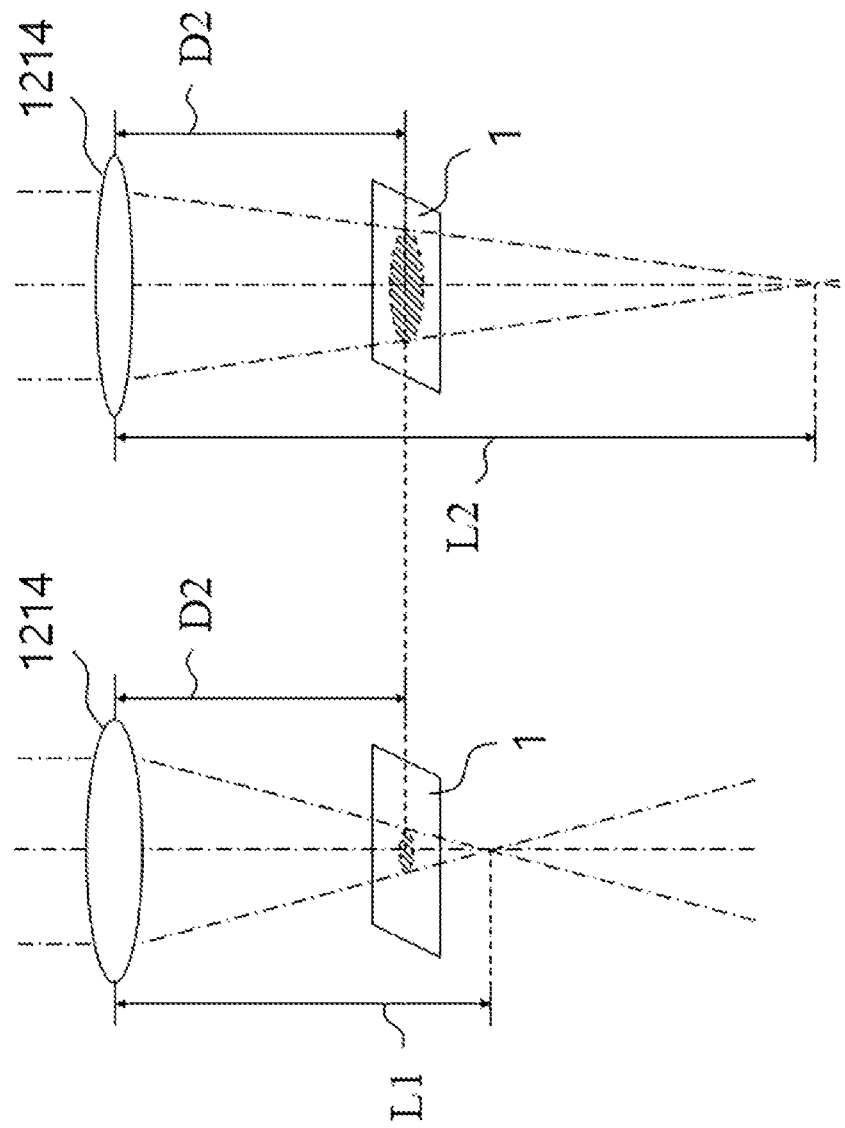

FIGS. 24 and 25 are diagrams illustrating that a spot size of a laser projected to the specimen 1 is variously set according to one embodiment of the present disclosure.

According to one embodiment of the present disclosure, the diagnostic system 100 may set the spot size so as to satisfy a condition for generating the plasma in the above-described specimen 1 or a condition for preventing damage to the specimen 1. Here, unless otherwise specified, the intensity or pulse duration of the projected laser in addition to the spot size is considered to be predetermined by the laser projection module 1210 or the external equipment 10.

Referring to FIGS. 24 and 25, the spot size may be set by the projection distance at which the laser is projected to the specimen 1 and the focal length of the laser.

The projection distance may mean a distance between the laser output from the laser projection module 1210 and the specimen 1. For example, the projection distance may mean a distance between the laser adjusting member 1214 and the specimen 1. Alternatively, the projection distance may mean a distance from the external equipment 10 to the specimen 1.

Meanwhile, the projection distance may be adjusted by the guide member 1216. Specifically, for example, when the guide member 1216 is formed to extend to a predetermined length from one position of the laser projection module 1210 in a projection direction of the laser. The projection distance of the laser may be set on the basis of a predetermined length of the extending portion.

The focal length may mean a distance from the laser projection module 1210 to the focal point of the laser. For example, when the laser is projected to the specimen 1 in the form of a focused beam by the laser adjusting member 1214, the focal length may mean a distance from the laser adjusting member 1214 to the focal point of the laser. Alternatively, when the laser in the form of the focused beam is output from the external equipment 10 to be projected to the specimen 1, the focal length may mean a distance from the external equipment 10 to the focal point of the laser.

Meanwhile, the focal length may be set according to a characteristic of the laser projected to the specimen 1 and an optical characteristic of the laser adjusting member 1214 such as an optical part for changing a shape of the laser. For example, as a wavelength of the laser projected to the specimen 1 becomes larger, the focal length may be increased, and as a refractive index of the lens through which the laser passes becomes larger, the focal length may be decreased.

Referring to FIG. 24 again, when the specimen 1 is located between the laser adjusting member 1214 and the focal point of the laser and the focal length is the same, as the projection distance becomes longer, the spot size may become smaller. For example, a spot size when a laser having a first focal length L1 due to the laser adjusting member 1214 is projected to the specimen 1 located at a first projection distance D1 from the laser adjusting member 1214 may be larger than a spot size when the laser having the first focal length L1 is projected to the specimen 1 located at a second projection distance D2 that is longer than the first projection distance D1. In this case, when the projection distance is the first projection distance D1, the spot size of the laser is included in the effective spot size such that the plasma ablation may be induced without damage to the specimen 1. However, when the projection distance is the second projection distance D2, the spot size of the laser becomes smaller such that the plasma ablation may be induced in the specimen 1 but damage may occur in the specimen 1.

Referring to FIG. 25 again, when the specimen 1 is located between the laser adjusting member 1214 and the focal point of the laser and the projection distance is the same, as the focal distance becomes longer, the spot size may become larger. For example, a spot size when a laser having the first focal length L1 due to the laser adjusting member 1214 is projected to the specimen 1 located at the second projection distance D2 from the laser adjusting member 1214 may be smaller than a spot size when the laser having the second focal length L2 that is longer than the first focal length L1 is projected to the specimen 1 located at the second projection distance D2. In this case, when the focal length is the first focal length L1, the spot size of the laser is not included in the effective spot size such that the plasma ablation may be induced in the specimen 1 but damage may occur in the specimen 1. When the focal length is the second focal length L2, the spot size of the laser is increased and included in the effective spot size such that the plasma ablation may be induced in the specimen 1 without damage to the specimen 1.

Meanwhile, FIGS. 24 and 25 illustrate a case in which the specimen 1 is located between the laser adjusting member 1214 and the focal point of the laser. However, the specimen 1 may be disposed such that the focal point of the laser is located between the specimen 1 and the laser adjusting member 1214. In this case, in contrast to the above description, as the projection distance increases, the spot size may increase, and as the focal length increases, the spot size may decrease.

That is, the spot size is adjusted according to a distance in which the specimen 1 is spaced apart from the focal point of the laser so that the diagnostic system 100 should set the spot size to be included in the effective spot size in consideration of the projection distance, the focal length, and an absolute value of a difference between the projection distance and the focal length.

As described above, the method of adjusting or setting the spot size so as to induce the plasma ablation while preventing damage to the specimen 1 has been described. Meanwhile, even though the spot size of the laser projected to the specimen 1 is set using the above-described laser adjusting member 1214 and the above-described guide member 1216, the laser may be projected to the specimen 1 having a physical defect of a device or a member and having a certain error from a spot size which will be set according to a method of using the device by a user.

Therefore, some embodiments for preventing damage to the specimen 1 due to generation of an error in size of the projection area of the laser projected to the specimen 1 will be described below.

Hereinafter, a method of adjusting the focal length relative to the projection distance so as to perform safe diagnosis on the specimen 1 according to one embodiment of the present disclosure will be described with reference to FIGS. 26 and 27.

Figure 26:
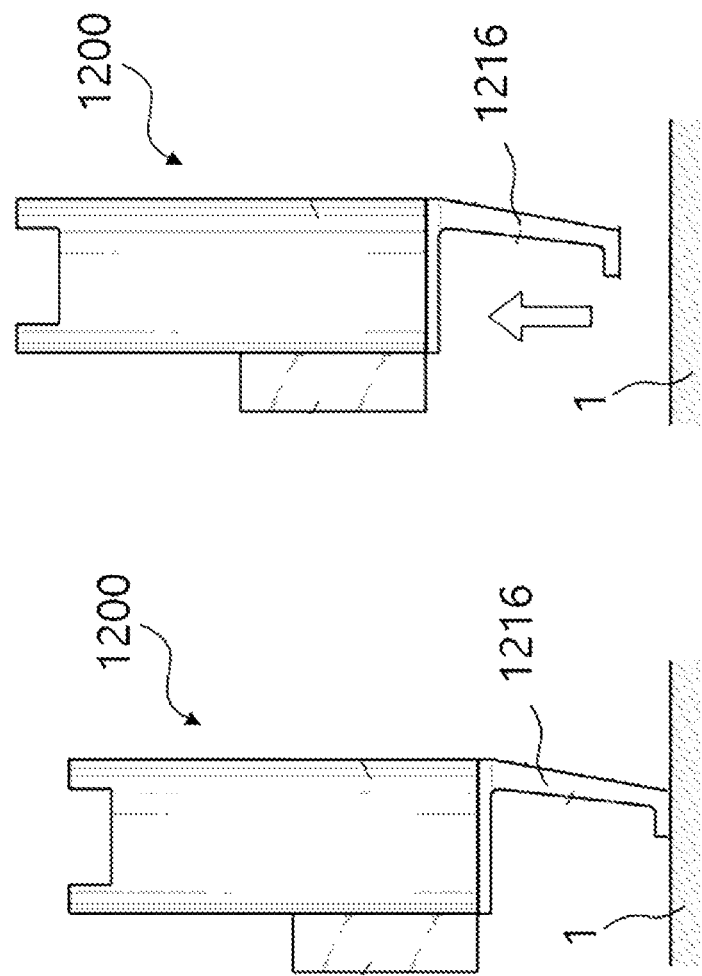
FIG. 26 is an exemplary diagram illustrating that the LIBS unit becomes away from a specimen according to one embodiment of the present disclosure.
Figure 27:
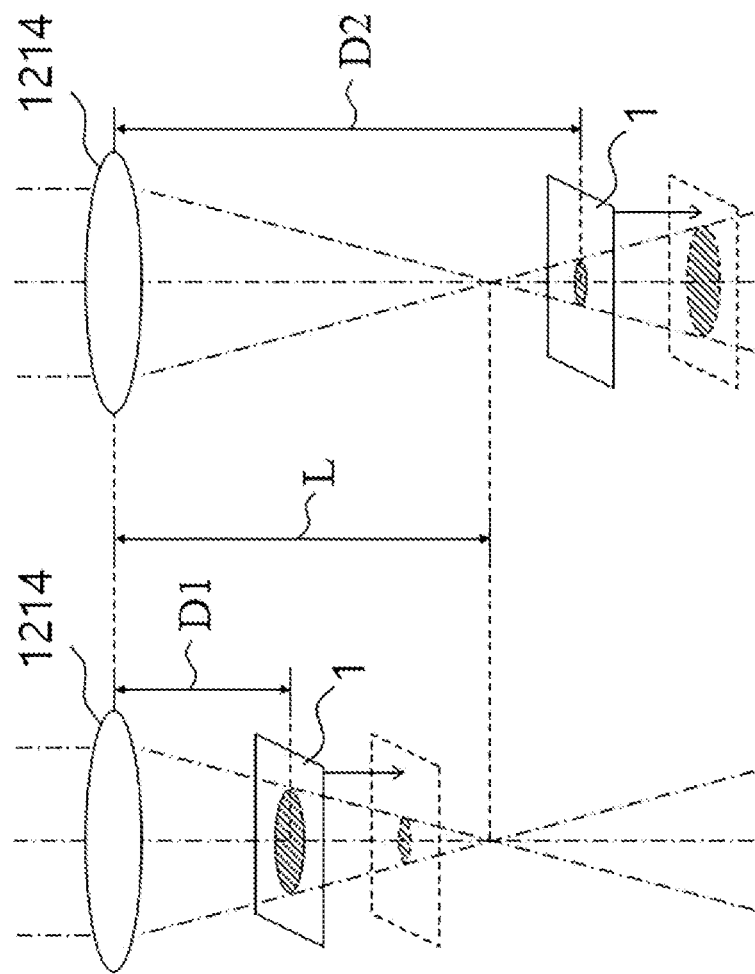
FIG. 27 is an exemplary diagram illustrating a laser spot according to a relationship between a projection length and a focal length of a laser with respect to a specimen according to one embodiment of the present disclosure.

FIG. 26 is an exemplary diagram illustrating that the LIBS unit 1200 becomes away from the specimen 1 according to one embodiment of the present disclosure, and FIG. 27 is an exemplary diagram illustrating a laser spot according to a relationship between a projection length and a focal length of a laser with respect to the specimen 1 according to one embodiment of the present disclosure.

As described above, when the fluence value applied to the specimen 1 due to the laser projection is greater than or equal to a specific value, the specimen 1 may be seriously damaged. However, according to one embodiment of the present disclosure, when the laser projected to the specimen 1 is in the form of a focused beam, the projection distance is adjusted in consideration of the focal length of the laser such that it is possible to prevent the specimen 1 from being damaged due to the laser.

Referring to FIG. 26, according to one embodiment of the present disclosure, the diagnosis by the diagnostic system 100 may be performed in a state in which the guide member 1216 is brought into contact with the specimen 1. In this case, in a state in which the LIBS unit 1200 or the guide member 1216 is moved in a direction opposite a direction of the laser projection due to external factors such as hand shaking or negligence of the user, the diagnostic system 100 may perform the diagnosis. Meanwhile, the guide member 1216 serves to support at least a part of the LIBS unit 1200 with respect to the specimen 1 so as to keep the projection distance constant so that it may be substantially difficult for the guide member 1216 to move in a propagation direction of the laser.

Referring to FIG. 27, the projection distance at which the laser is projected to the specimen 1 may be longer or shorter than the focal length of the laser. Alternatively, the focal point of the laser projected to the specimen 1 may be located to be spaced a predetermined distance from the specimen 1.

According to one embodiment of the present disclosure, the specimens 1 may be disposed to be spaced apart from laser adjusting member 1214 or the external equipment 10 such that energy applied to the specimen 1 due to the laser projection has a specific value or less. For example, the specimen 1 may be disposed to be spaced a specific projection distance from the laser adjusting member 1214 such that fluence applied due to the laser projection has the damage threshold $D_{th}$ or less.

Here, a positional relationship between the specimen 1 and the laser adjusting member 1214 or the external equipment 10 and the specimen 1 may be varied due to some external factors. For example, as shown in FIG. 26, the LIBS unit 1200 is spaced a certain distance from the specimen 1 due to hand shaking or negligence of the user using the diagnostic system 100, and thus the laser projection distance relative to the specimen 1 may be increased.

Here, the spot size of the laser projected to the specimen 1 may be varied according to a variation in projection distance. That is, a fluence value applied to the specimen 1 may be varied. However, as described below, influence of the varied fluence value may become larger or smaller according to an arrangement position of the existing specimen 1.

Referring to FIG. 27 again, the specimen 1 may be disposed between the focal point of the laser and the laser adjusting member 1214 such that the laser has the first projection distance D1 that is shorter than the focal length L. Here, even though the spot size is set within the effective spot size such that the fluence that is less than or equal to the damage threshold $D_{th}$ is applied to the specimen 1 when the laser is projected to the specimen 1, when the projection distance is increased due to external factors, the spot size of the laser may be decreased. Accordingly, the power density and the fluence applied to the specimen 1 may be increased, and, when the increased fluence is greater than or equal to the damage threshold $D_{th}$, damage may occur in the specimen 1.

Meanwhile, referring to FIG. 27 again, the specimen 1 may be disposed to be spaced a predetermined distance from the focal point of the laser such that the laser has the second projection distance D2 that is longer than the focal length L. Here, when the laser is projected to the specimen 1 and the spot size is set within the effective spot size such that the fluence less than or equal to the damage threshold $D_{th}$ is applied to the specimen 1, even when the projection distance is increased due to external factors, the spot size of the laser is increased. Accordingly, the power density and the fluence applied to the specimen 1 may be decreased, and the decreased fluence is less than or equal to the damage threshold $D_{th}$, damage may not occur in the specimen 1.

Therefore, the diagnostic system 100 sets the projection distance of the laser to be longer than the focal length of the laser such that, even when the fluence value applied to the specimen 1 is varied due to the above-described external factors, the damage may not occur in the specimen 1.

Alternatively, the diagnostic system 100 disposes the specimen 1 to be spaced a predetermined distance from the focal point of the laser in the propagation direction of the laser such that, even when the fluence value applied to the specimen 1 is varied due to the above-described external factors, the damage may not occur in the specimen 1.

Hereinafter, when the diagnostic system 100 performs the diagnostic method according to one embodiment of the present disclosure, a method of using a spherical aberration of the laser adjusting member 1214 so as to prevent damage to the specimen 1 will be described with reference to FIG. 28.

According to one embodiment of the present disclosure, the laser adjusting member 1214 may include an optical lens having a spherical aberration. Here, the spherical aberration means a phenomenon in which a position of a formed focal point is varied according to a distance from a center of a lens when parallel light passes through the lens. Specifically, a lens with a spherical aberration may have a different refractive index for each region, and light passing through different regions of the lens may be refracted to pass different focal points. For example, as a region becomes away from a central axis of the lens, a refractive index becomes larger such that a focal point of the light passing through the region may be formed to be closer to the lens. Thus, when the laser passes through the lens with a spherical aberration, the laser may have a focused beam form which is not gathered at any one point.

Figure 28:
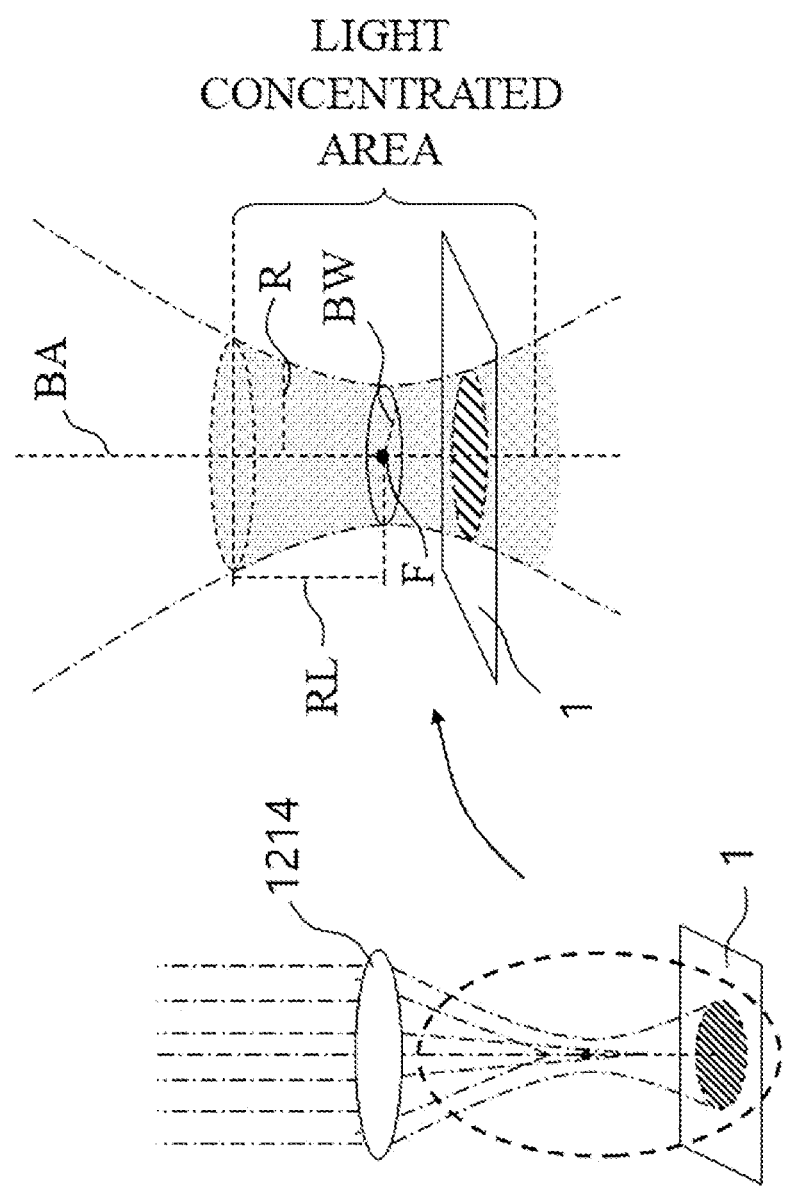
FIG. 28 is an exemplary diagram illustrating a shape of a laser passing through a laser adjusting member having a spherical aberration according to one embodiment of the present disclosure.

FIG. 28 is an exemplary diagram illustrating a shape of a laser passing through laser adjusting member 1214 having a spherical aberration according to one embodiment of the present disclosure.

Referring to FIG. 28, the laser passing through a lens with a spherical aberration may have a light concentrated area in which the laser is concentrated near the focal point of the laser. As light in the form of a focused beam is gathered and scattered based on a focal point of the light, the light concentrated area may be formed in a shape in which the laser gathers and spreads based on the focal point of the laser.

The light concentrated area may be specified by the focal point F of the laser and a Rayleigh length RL. For example, the light concentrated area may include an area within a range of the Rayleigh length RL among areas through which the laser passes in a propagation direction in which the laser passes from the focal point F of the laser and in a direction opposite the propagation direction. Here, the Rayleigh length RL may be calculated on the basis of a refractive index, a numerical aperture NA, or a focal length of the lens and a wavelength of the laser projected to the specimen 1. For example, when the wavelength of the projected laser is 1064 nm, the focal length of the lens is 6 cm, and a diameter of the lens is 3 mm, the Rayleigh length RL may be about 2.17 mm.

In the light concentrated area, the laser may have a light radius R indicating a breadth, a width, or a thickness of the laser based on an optical axis BA.

In the light concentrated area, the laser may have a beam waist BW. The beam waist BW may mean the breadth of the laser or half of the breadth thereof at the focal point F of the laser in the light concentrated area. That is, the beam waist BW may mean a shortest radius of the light radius R of the laser in the light concentrated area.

When the laser is projected to the specimen 1 in the light concentrated area, a spot size may be determined on the basis of the light radius R. Here, a range of spot sizes in which the laser is projectable to the specimen 1 in the light concentrated area may be determined using a maximum value and a minimum value of the light radius R.

According to one embodiment of the present disclosure, the diagnostic unit 100 may perform a diagnostic method in the light concentrated area. Here, the diagnostic system 100 may set a diagnostic condition for preventing damage to the specimen 1 while forming the plasma in the specimen 1. Specifically, when the laser is projected to the specimen 1, the diagnostic system 100 may set the effective spot size in consideration of the intensity or energy per pulse of the laser, the pulse duration, the damage threshold $D_{th}$, and the ablation threshold $A_{th}$, set a light concentrated area having a specific Rayleigh length RL to be included in the set effective spot size, and set a length of the guide member 1216 to locate the specimen 1 within the set light concentrated area.

Meanwhile, the above-described ranges of the light radius R, the Rayleigh length RL, the beam waist BW of the light concentrated area and a size of the projection area are merely illustrative, and thus the embodiments of the present disclosure are not limited thereto.

Hereinafter, a diagnosis operation using spectrum data according to one embodiment of the present disclosure will be described.

In the present disclosure, the diagnostic system 100, specifically, the diagnostic unit 1400, may perform diagnosis on the specimen 1 on the basis of spectrum data. In other words, the diagnostic unit 1400 may determine a state of the specimen 1 on the basis of the spectrum data. Specifically, the state of specimen 1 may be a kind of the specimen 1, a component content of the specimen 1, a health state of the specimen 1, and the like.

Here, for example, when the specimen 1 is a part of the body, the kind of the specimen 1 may include whether the specimen 1 is which body organ such as liver tissue, skin tissue, hair tissue, or the like and whether the specimen 1 is non-diseased tissue or diseased tissue such as a cancer. Further, for example, when the specimen 1 is a part of the body, the component content of the specimen 1 may be a content of harmful substances contained in tissue or cells. Further, when the specimen 1 is a part of the body, the health state of the specimen 1 may mean whether the specimen 1 is in a normal state or an abnormal state (e.g., a disease such as a cancer), a degree of aging, or a nutritional state.

Here, the diagnostic unit 1400 may use various diagnostic algorithms so as to obtain a diagnosis result from the spectrum data. In other words, the diagnostic algorithm may mean an algorithm which receives the spectrum data and outputs a diagnosis result. Such a diagnostic algorithm may be provided physically or logically to the diagnostic unit 1400. For example, the diagnostic algorithm is stored in the second memory 1450 of the diagnostic unit 1400, and the second controller 1410 may obtain a diagnosis result from the spectrum data by processing the diagnostic algorithm in cooperation with the second memory 1450. Alternatively, a physical electrical circuit for implementing the diagnostic algorithm may be implemented in hardware in the second controller 1410 of the diagnostic unit 1400.

In the present disclosure, the diagnosis algorithm may obtain the diagnosis result on the basis of at least one piece of spectrum data. Here, the spectrum data may be obtained from the specimen 1 through an operation of obtaining the above-described spectrum data.

Here, the specimen 1 may include a "target specimen" which is a diagnostic target. For example, when the diagnostic system 100 performs the LIBS on a specific skin tissue to obtain spectrum data on the specific skin tissue and determines whether a skin cancer is present in the specific skin tissue on the basis of the based on the spectrum data, the specific skin tissue on which the presence or absence of the skin cancer is determined may be the target specimen.

Further, the specimen 1 may further include a "reference specimen" for comparison with the "target specimen." For example, in order to determine whether the skin cancer is present in the specific skin tissue, the diagnostic system 100 may determine the presence or absence of the skin cancer of the specific skin tissue on the basis of spectrum data of the specific skin tissue on which the presence or absence of the skin cancer is diagnosed and spectrum data of tissue in which the skin cancer is previously confirmed as not being present. In this case, the specific skin tissue which is a diagnostic target may correspond to the "target specimen" and the tissue in which the skin cancer is previously confirmed as not being present may correspond to the "reference specimen" for comparison with the "target specimen."

Therefore, in the present disclosure, the "specimen" may be interpreted as an object to which the laser is projected and in which a LIBS phenomenon is induced.

Further, the "target specimen" may be interpreted as an object for a target of diagnosis which will be performed by the diagnostic system 100. For example, when the diagnostic system 100 performs disease diagnosis, the target specimen may be an object suspected of having a disease or an object which is a target of disease confirmation.

Further, the "reference specimen" is a specimen other than the object which is a target of diagnosis of the diagnostic system 100. The reference specimen may be interpreted as an object for extracting additional spectrum data which is mainly used to compare or refer to the spectrum data on the target specimen in a process of calculating a diagnosis result by the diagnostic algorithm. In order to refer to the spectrum data of the "reference specimen" or to compare with the spectrum data of the "target specimen," an object of which state is previously confirmed may be used as the "reference specimen." For example, when the diagnostic system 100 performs disease diagnosis, the target specimen may be a suspicious object, and the reference specimen may be an object which is previously confirmed as having a disease or as not having a disease.

As described above, in the present disclosure, the diagnostic system 100 may use various diagnostic algorithms.

For example, the diagnostic algorithm may be provided as a machine learning model. A typical example of the machine learning model may be an artificial neural network. Specifically, a typical example of the artificial neural network is a deep-learning artificial neural network including an input layer for receiving data, an output layer for outputting a result, and a hidden layer for processing data between the input layer and the output layer. Detailed examples of the artificial neural networks include a regression analysis artificial neural network (convolution neural network), a recurrent neural network, a deep neural network, and the like. In this specification, the artificial neural network should be interpreted as a comprehensive sense including the above-described artificial neural networks, various other artificial neural networks, and an artificial neural network in combination thereof and is not necessarily to be a deep learning series.

Further, the machine learning model is not necessarily to be the artificial neural network model. In addition to the description, the machine learning model may include a nearest neighbor algorithm (KNN), a random forest, a support vector machine (SVM), a principal component analysis (PCA), and the like and may include an ensemble form of the above-described techniques or a form in which the above-described techniques are combined in various manners. Meanwhile, in the embodiments described based on the artificial neural network, unless otherwise described, it is noted in advance that the artificial neural network may be replaced with another machine learning model.

Further, the diagnostic algorithm in the present disclosure is not necessarily limited to the machine learning model. That is, the diagnostic algorithm may include various determination/decision algorithms instead of the machine learning model. For example, the diagnostic algorithm may be a non-machine learning algorithm for performing diagnosis by comparing database generated using the obtained spectrum data with the spectrum data obtained from specimen 1.

Therefore, it is noted in advance that the diagnosis algorithm in the present disclosure should be understood as a comprehensive sense including all types of algorithms for performing diagnosis using spectrum data.

Hereinafter, a diagnosis algorithm will be described based on some examples of performing diagnosis from spectrum data using a deep-learning artificial neural network. However, since this is merely for convenience of explanation, it should be noted that the diagnosis algorithm in the present disclosure is not limited to the deep-learning artificial neural network.

In the present disclosure, the deep-learning artificial neural network may be implemented logically or physically. That is, the artificial neural network may be implemented in hardware, software, or a combination thereof.

For example, the artificial neural network may be implemented as a program using an application such as a tensor flow of Google and the like. Here, the artificial neural network in the form of a program is provided with logically implemented layers, nodes, and lines connecting the logically implemented layers to the nodes and may be implemented by processing data through operations of a central processing unit (CPU) or a graphics processing unit (GPU). In the present disclosure, the artificial neural network may be implemented with the second controller 1410 and the second memory 1450 of the diagnostic unit 1400. In this case, the second memory 1450 may store a weight value of each node constituting the artificial neural network, a connection relationship between the nodes, and a configuration of the node, and the like, and the second controller 1410 may input spectrum data to the input layer, calculate a node value at each node, and then calculate a result value at the output layer.

Alternatively, the artificial neural network may be provided as hardware such as a neuromorphic chip implemented with various electrical circuits in addition to an application specific integrated circuit (ASIC) form or a field programmable gate array (FPGA) form for dedicatedly processing the artificial neural network.

In the present disclosure, the artificial neural network may receive spectrum data and output a diagnostic result.

Figure 29:
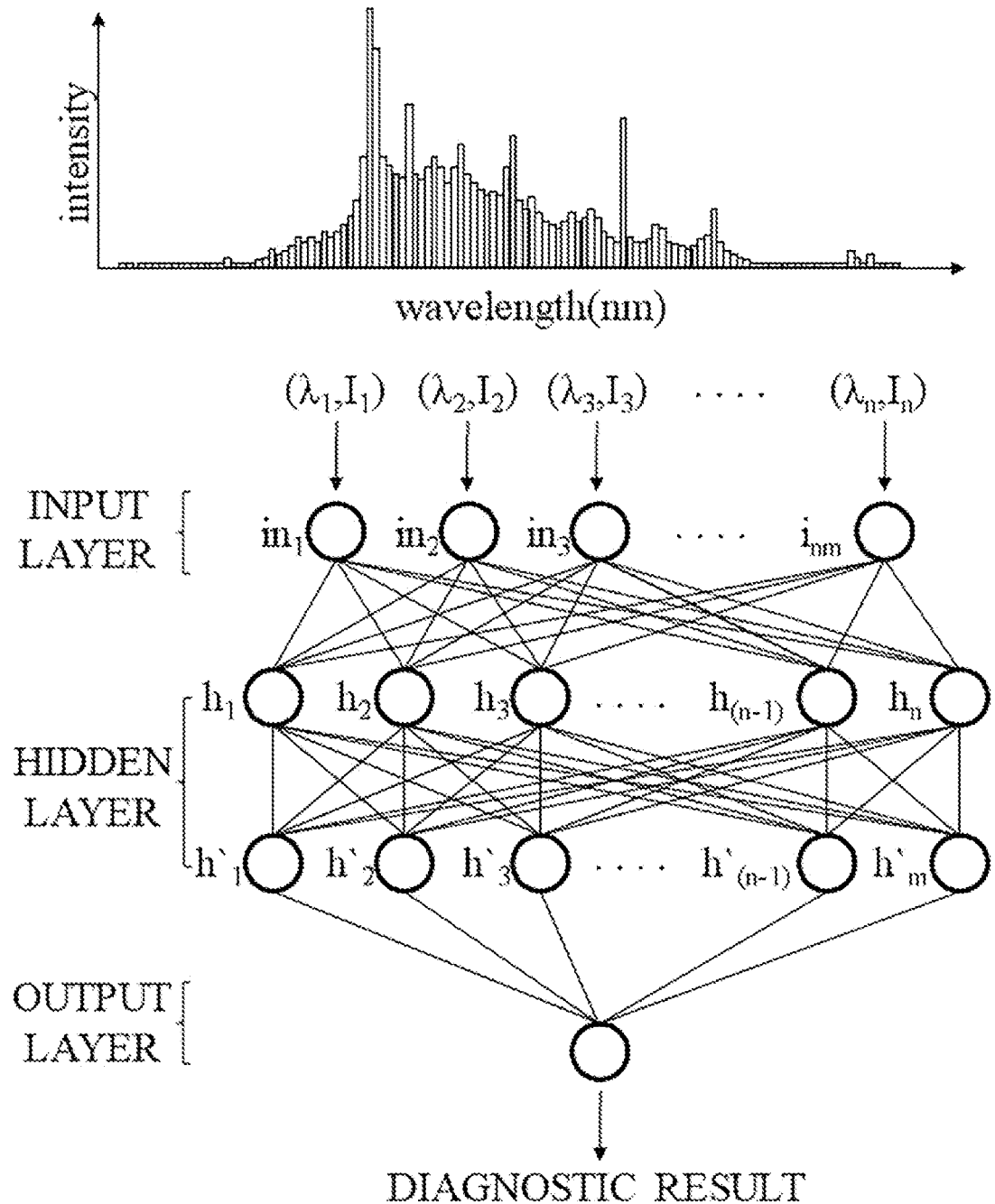
FIG. 29 is an exemplary diagram illustrating an artificial neural network according to one embodiment of the present disclosure.

FIG. 29 is an exemplary diagram illustrating an artificial neural network according to one embodiment of the present disclosure.

Referring to FIG. 29, the artificial neural network may include an input layer for receiving spectrum data, an output layer for outputting a diagnostic result, and at least one hidden layer disposed between the input layer and the output layer.

The spectrum data may be input to the input layer. The input layer may include a plurality of input nodes. An intensity for each wavelength may be input to each input node. In other words, a specific wavelength may be assigned to each input node, and an intensity value with respect to the assigned specific wavelength may be input to each input node as an input value.

In the following description of the present disclosure, the spectrum data input to the input layer refers to input data. Here, the input data may be raw data of spectrum data measured in the LIBS unit 1200 or spectrum data processed from the raw data of the spectrum data measured in the LIBS unit 1200. Further, the input data may be spectrum data on a single specimen, pieces of spectrum data obtained from a plurality of specimens, or a combination of the pieces of spectrum data obtained from the plurality of specimens. A detailed description of the input data will be described below.

The output layer may output a diagnostic result.

For example, when the artificial neural network outputs a diagnostic result in the form of binary classification, one or two output nodes may be included in the output layer. The artificial neural network, which outputs a result value in the form of the binary classification, may mainly perform diagnose on a single disease or a single health state.

Alternatively, when the artificial neural network outputs a diagnosis result in the form of multi-classification, the output layer may include a plurality of output nodes. The artificial neural network, which outputs a result value in the form of the multi-classification, may mainly perform diagnose on a plurality of diseases or a plurality of health states.

Also alternatively, when the artificial neural network outputs a diagnostic result in the form of regression, the output layer may include at least one output node.

The hidden layer may include a plurality of layers, and each of the layers may include at least one hidden layer.

The artificial neural network may be trained using labeling data tagged with previously confirmed diagnostic result and spectrum data as a learning-set. Thus, when the spectrum data obtained from the target specimen is input, the sufficiently-learned artificial neural network may output a diagnostic result.

Specifically, the artificial neural network determining the presence or absence of a disease may be trained using a learning-set in which a value indicating that a disease is present is assigned to spectrum data (hereinafter referred to as a "diseased spectrum data") obtained by projecting a laser to a specimen having a disease (hereinafter referred to as a "diseased specimen") and a value indicating that a disease is not present is assigned to spectrum data (hereinafter referred to as a "non-diseased spectrum data") obtained by projecting the laser to a specimen having no disease (hereinafter referred to as a "non-diseased specimen"). Here, the suffi- ciently-learned artificial neural network may receive spectrum data obtained from the target specimen which will be diagnosed on the presence or absence of a disease and output the presence or absence of a disease as a diagnosis result. In this case, the diagnostic result may be mainly output as a probability value.

Here, some characteristics (attributes) of the spectrum data will be briefly described.

Figure 30:
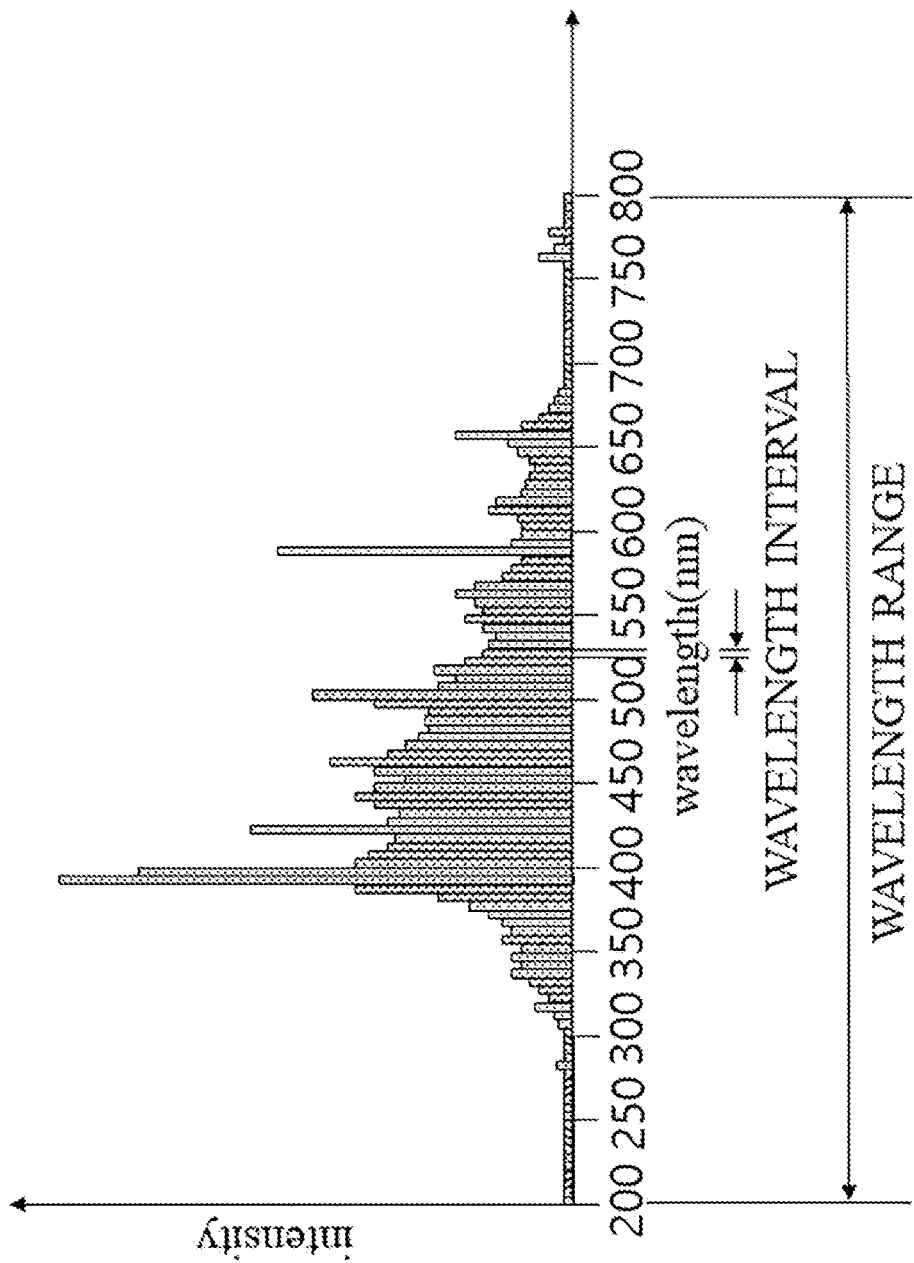
FIG. 30 is a diagram illustrating a structure of spectrum data according to one embodiment of the present disclosure.

FIG. 30 is a diagram illustrating a structure of spectrum data according to one embodiment of the present disclosure.

Referring to FIG. 30, the spectrum data includes a plurality of light intensity values, and each light intensity value may be in conjunction with a specific wavelength or a specific wavelength range. That is, the spectrum data may include an intensity value for each wavelength.

In the spectrum data generated by the above-described spectrum measurement module 1230, the intensity value for each wavelength is determined on the basis of a quantity of light, an intensity of the light, and light energy which are incident on each sensor belonging to each sensor array 1232, and each sensor receives light having a wavelength range corresponding to a position of a sensor disposed on a propagation path of spectroscopically divided light and a light receiving range of the sensor so that the spectrum data is strictly to be expressed as having an intensity value for each wavelength range. However, for convenience of description, in the present disclosure, the spectrum data will be used interchangeably with a term "intensity value for each wavelength."

For example, the spectrum data may be provided in the form of including an light intensity value with respect to a 200 nm wavelength (or a wavelength range of 199.5 nm to 200.5 nm), an light intensity value with respect to a 201 nm wavelength (or a wavelength range of 200.5 nm to 201.5 nm), . . . , an light intensity value with respect to a 799 nm wavelength (or a wavelength range of 798.5 nm to 799.5 nm), and an light intensity value with respect to an 800 nm wavelength (or a wavelength range of 799.5 nm to 800.5 nm).

The characteristic of the spectrum data may include a wavelength range. The wavelength range of the spectrum data may mean a range of a minimum wavelength to a maximum wavelength among wavelengths assigned to intensity values included in the spectrum data. For example, the wavelength range of the spectrum data may be expressed as a range of 200 nm to 1000 nm, a range of 280 to 780 nm, and the like.

Further, the characteristic of the spectrum data may include a wavelength interval. The wavelength interval of the spectrum data may mean an interval between the wavelengths assigned to the intensity values included in the spectrum data. For example, the wavelength interval of the spectrum data may be expressed as 1 nm, 0.7 nm, 2 nm, and the like.

Raw spectrum data is spectrum data obtained from the LIBS unit 1200, and a characteristic of the raw spectrum data may be determined according to specifications of the spectrum measurement module 1230 of the LIBS unit 1200. For example, a wavelength range of the raw spectrum may be determined according to a measurement range of the spectrum measurement module 1230, and a wavelength interval of the raw spectrum may be determined according to resolution or definition of the spectrum measurement module 1230.

According to one embodiment of the present disclosure, it is also possible to directly use the raw spectrum data as input data of the diagnostic algorithm. However, in some embodiments, when the raw spectrum data is directly used as the input data of the diagnostic algorithm, there may be some technical difficulties.

First, when the raw spectrum data is directly used as the input data of the diagnostic algorithm, compatibility between the diagnostic algorithm and the spectrum data may be degraded.

As described above, since the wavelength range or the wavelength interval of the raw spectrum data is determined according to performance or a setting (configuration) of the diagnostic system 100, when a configuration of the LIBS unit 1200 is changed or performance thereof is different, the characteristic of the spectrum data may be varied. For example, even when the spectrum measurement module 1230 is the same product of the same manufacturer, an obtained characteristic of the raw spectrum data may be varied according to a software setting. Alternatively, a characteristic of raw spectrum data obtained using a different-type spectrum measurement module 1230 may be different. Also alternatively, even when spectrum data is obtained using the same-type spectrum measurement module 1230, an offset is generated in a detected wavelength due to a slight difference in performance between the devices such that characteristics of the raw spectrum data obtained from the devices may be different from each other.

As described above, when the characteristic of the spectrum data is varied, a diagnostic algorithm designed to be suitable for the spectrum data having a predetermined characteristic may not perform diagnosis on the spectrum data deviating from the predetermined characteristic or diagnostic accuracy of the diagnostic algorithm may be degraded. Therefore, the diagnostic algorithm directly using the raw spectrum as the input data may be difficult to be widely used because the diagnostic algorithm is sensitive to the specifications of the LIBS unit 1200.

Next, when the raw spectrum data is directly used as the input data in the diagnosis algorithm, external factors act on a diagnostic result such that diagnostic accuracy may be degraded.

Various environmental factors including the intensity of the projected laser, a state of the specimen 1, and sensitivity of the sensor array 1232 due to a temperature and humidity and the like may affect the raw spectrum data obtained by the LIBS unit 1200. For example, when the laser projection module 1210 is a different-type product, the intensity of the laser for inducing the plasma ablation may be different, and thus the light intensity value of the obtained spectrum data may be entirely varied. Here, even when the laser projection module 1210 is the same-type product, the intensity of the laser may be varied due to a temperature or humidity during the laser projection, and, even in an environment in which environmental factors are strictly controlled, the intensity of the projected laser may be minutely varied. Alternatively, even when the laser having the same intensity is projected according to a surface state, hardness, a moisture content, and the like of the specimen 1, a degree of the plasma ablation may be different. Also alternatively, environmental factors such as a temperature and the like affects the sensitivity of the sensor array 1232 such that there is probability in that the light intensity value of the spectrum data is varied. In other words, a difference in light intensity value may occur between pieces of raw spectrum data obtained from the same object 1.

As described above, in the present disclosure, in order to overcome difficulty in performing the diagnosis accurately when the raw spectrum is directly used, as an embodiment, which is not essential, preprocessing may be performed on the raw spectrum data. Hereinafter, some preprocessing according to one embodiment of the present disclosure will be described.

Here, the preprocessing may mean that the diagnostic unit 1400 processes the spectrum data obtained from the LIBS unit 1200. The preprocessing on the spectrum data may be performed to improve the performance of the diagnostic algorithm, such as accuracy, a learning speed, a calculation speed, and the like. The preprocessing may not necessarily be for the above-described purpose and may be performed for various other purposes.

In the following description, opposing that the spectrum data obtained from the LIBS unit 1200 refers to the "raw spectrum data," spectrum data processed from the raw spectrum data through preprocessing refers to "processed spectrum data." The diagnostic algorithm may use the processed spectrum data as input data instead of the raw spectrum data.

The processed spectrum data may be obtained by preprocessing the raw spectrum data. Specifically, the second controller 1410 of the diagnostic unit 1400 may obtain the raw spectrum data from the LIBS unit 1200, perform preprocessing on the raw spectrum data to generate the processed spectrum data, and obtain a diagnostic result from the processed spectrum data using the diagnostic algorithm.

An example of the preprocessing may include standardization.

Here, the standardization means that the raw spectrum data is processed into spectrum data having light intensity values with respect to predetermined wavelengths (hereinafter referred to as "standard wavelengths"). Here, the standard wavelengths may correspond to wavelengths requested by the input data of the diagnostic algorithm. For example, the artificial neural network provided as the diagnostic algorithm may be designed to assign standard wavelengths to the input nodes of the input layer. In other words, standardization may mean the raw spectrum is changed into spectrum data having a standardized specification.

Figure 31:
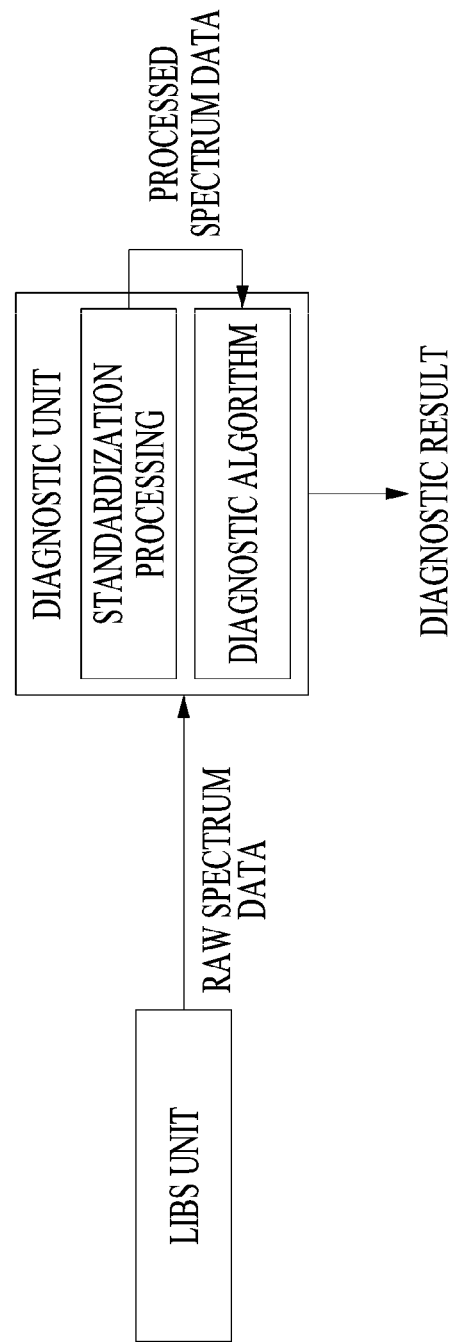
FIG. 31 is a schematic diagram illustrating standardization according to one embodiment of the present disclosure.

FIG. 31 is a schematic diagram illustrating standardization according to one embodiment of the present disclosure.

Referring to FIG. 31, the diagnostic system 100 may perform the standardization to generate processed spectrum data having a standardized specification from the raw spectrum data as the input data of the diagnostic algorithm.

Specifically, the second controller 1410 may obtain the raw spectrum data from the LIB S unit 1200. The second memory 1450 may store standard specification information of the input data. Here, the standard specification information may include a wavelength range, the number of intensity values for each wavelength, a wavelength interval, standard wavelengths, and the like. For example, the standard specification may be a specification requested by the input node of the artificial neural network. The second controller 1410 may process the raw spectrum data with reference to the standard specification information and generate the spectrum data having a specification requested as input data, i.e., in the form of the standard specification, as processed spectrum data.

For example, the second controller 1410 may generate the processed spectrum data having a wavelength interval corresponding to a wavelength interval of the input node of the diagnostic algorithm from the raw spectrum data. Also alternatively, the second controller 1410 may increase the number of intensity values for each wavelength, which are included in the raw spectrum data. Further alternatively, the second controller 1410 may generate processed spectrum data of which wavelength range is adjusted to correspond to a wavelength range requested by the input node of the diagnostic algorithm from the raw spectrum data.

Through the standardization, the raw spectrum data may be processed as the input data of the diagnostic algorithm, and the diagnostic algorithm may use the processed raw spectrum data to calculate a diagnostic result. Hereinafter, specific embodiments of the standardization according to one embodiment of the present disclosure will be described with reference to the drawings.

In accordance with an example of the standardization according to one embodiment of the present disclosure, the diagnostic unit 1400 may generate processed spectrum data having a wavelength range different from that of the raw spectrum data.

Figure 32:
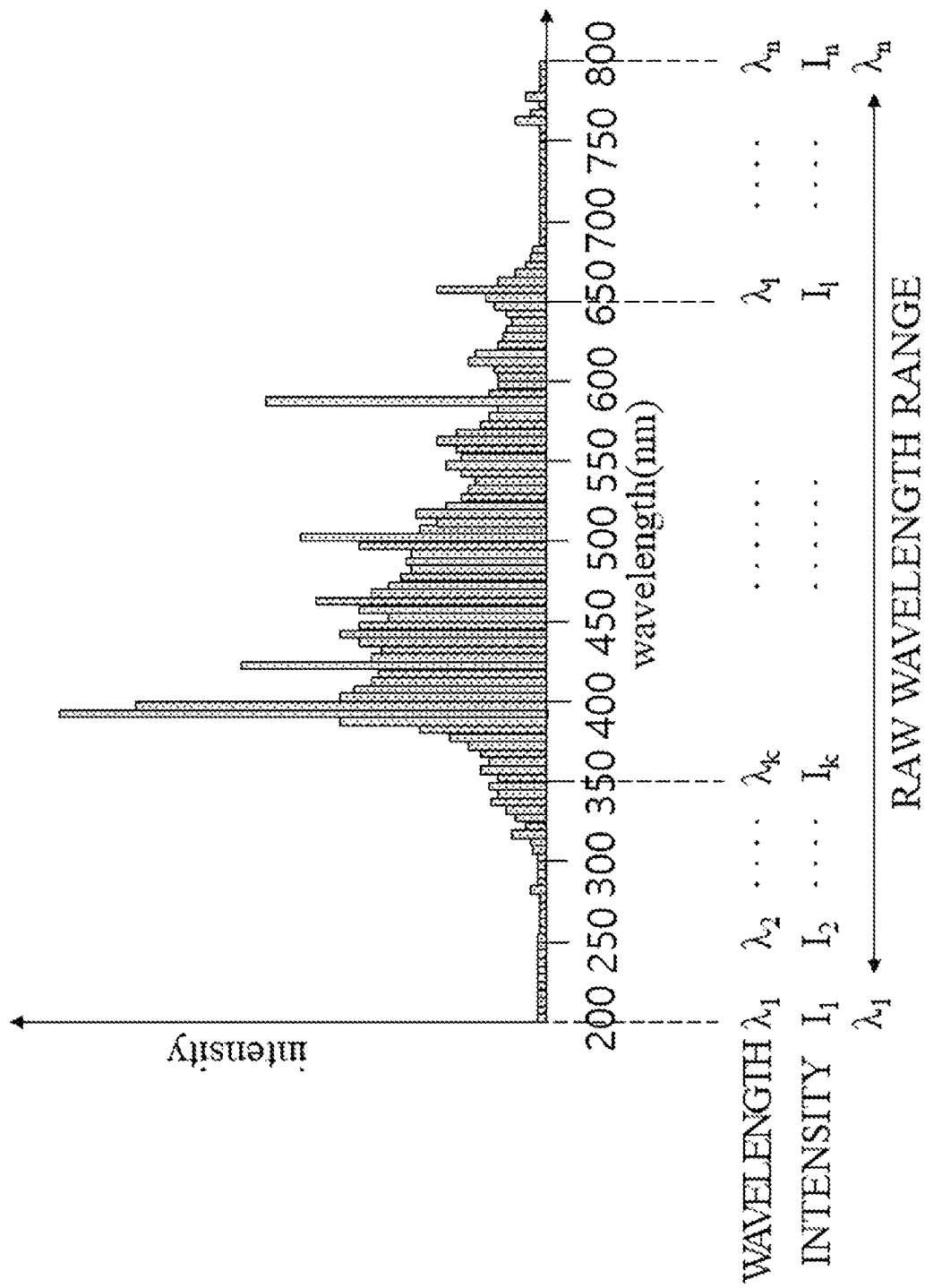
FIG. 32 is a diagram illustrating an example of raw spectrum data having a raw wavelength range according to one embodiment of the present disclosure.
Figure 33:
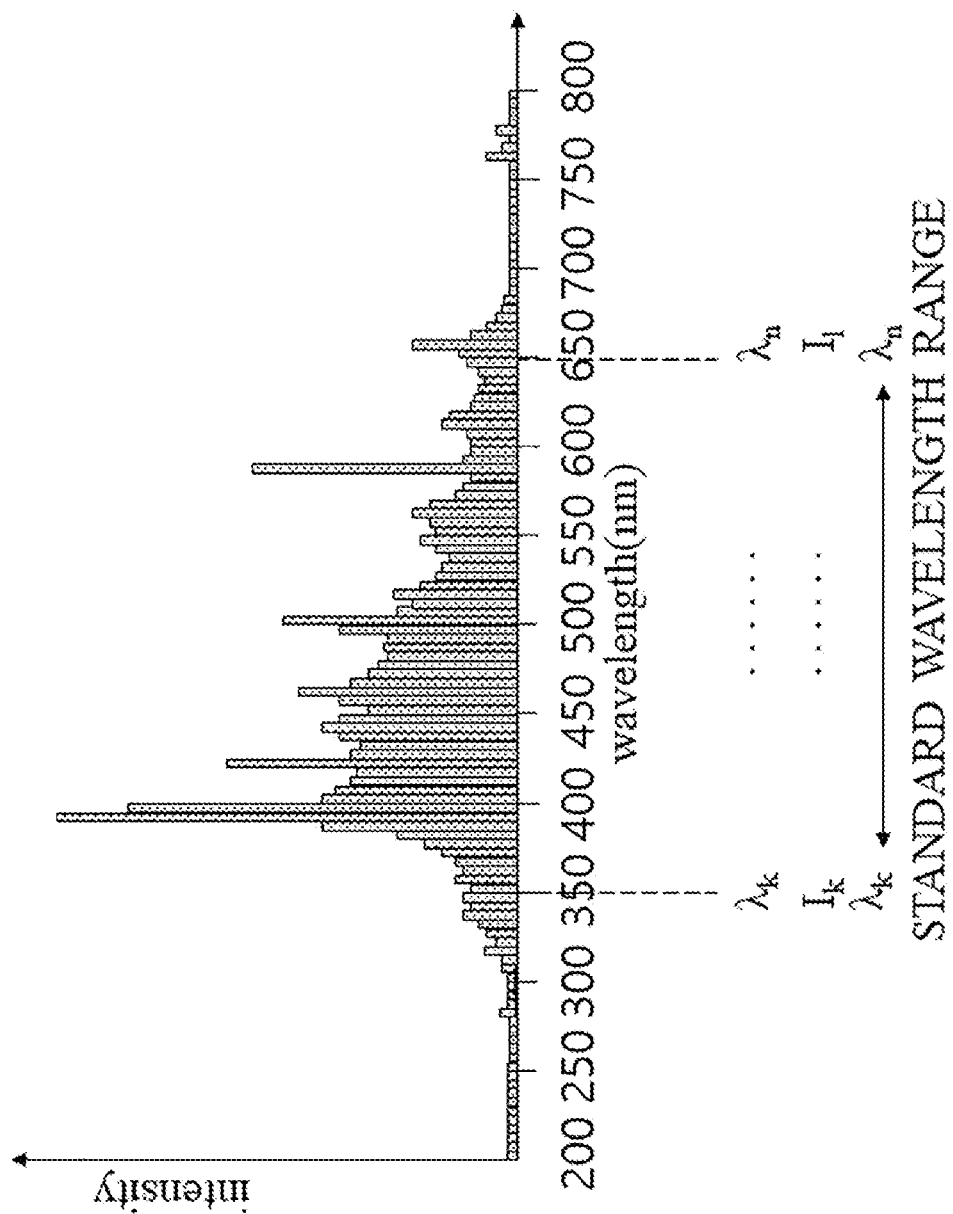
FIG. 33 is a diagram illustrating an example of processed spectrum data having a standard wavelength range according to one embodiment of the present disclosure.

FIG. 32 is a diagram illustrating an example of raw spectrum data having a raw wavelength range according to one embodiment of the present disclosure, and FIG. 33 is a diagram illustrating an example of the processed spectrum data having a standard wavelength range according to one embodiment of the present disclosure.

The raw spectrum data may include an intensity value for each wavelength with respect to a raw wavelength range. The raw wavelength range of the raw spectrum data may be determined according to the specifications of the LIBS unit 1200. For example, when the spectrum measurement module 1230 of the LIBS unit 1200 measures a light intensity value with respect to a wavelength range of 200 nm to 800 nm, as shown in FIG. 32, the LIBS unit 1200 may obtain spectrum data having a raw wavelength range of 200 nm to 800 nm.

The diagnostic unit 1400 may generate processed spectrum data having a standard wavelength range from raw spectrum data having the raw wavelength range. For example, as shown in FIG. 33, when the standard wavelength range is ranging from 350 nm to 660 nm, the diagnostic unit 1400 may generate the processed spectrum data having a wavelength range of 350 nm to 660 nm from the raw spectrum data having a wavelength range of 200 nm to 800 nm.

According to an example, the diagnostic unit 1400 may extract a portion of the raw spectrum data to generate processed spectrum data having the standard wavelength range different from the raw wavelength range.

Figure 34:
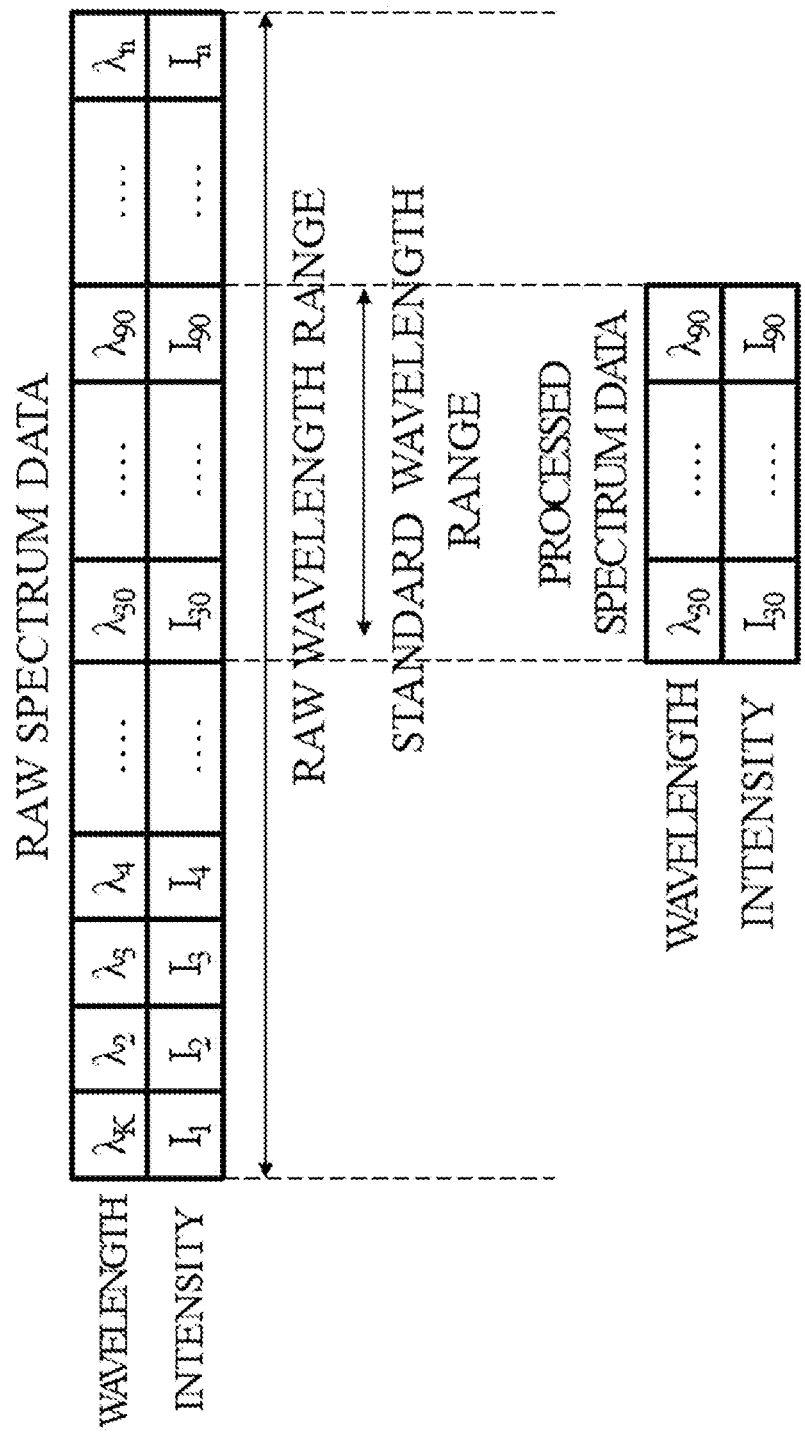
FIG. 34 is a diagram illustrating an example of a process of obtaining processed spectrum data according to one embodiment of the present disclosure.

FIG. 34 is a diagram illustrating an example of a process of obtaining processed spectrum data according to one embodiment of the present disclosure.

Specifically, referring to FIG. 34, the second memory 1450 may store information on the standard wavelength range which is a wavelength range required by the input data. The second controller 1410 may extract the intensity value of each wavelength included in the standard wavelength range among the intensity values of the wavelengths of the raw spectrum data by referring to the information on the standard wavelength range from the second memory 1450 and generate the processed spectrum data having the standard wavelength range using the extracted intensity value for each wavelength.

Alternatively, the diagnostic unit 1400 may generate a spectrum curve from the raw spectrum data and generate processed spectrum data having the standard wavelength range on the basis of the spectrum curve.

FIG. 35 is a diagram illustrating another example of the process of obtaining processed spectrum data according to one embodiment of the present disclosure.

Specifically, referring to FIG. 35, the second controller 1410 may obtain the raw spectrum data and generate the spectrum curve regarding a wavelength-light intensity domain using the intensity values for the wavelengths of the raw spectrum data. Here, the spectrum curve may be generated using various interpolation or extrapolation techniques including nearest interpolation, linear interpolation, polynomial interpolation, spline interpolation, and the like. The second memory 1450 may store information on the standard wavelength range which is a wavelength range required by the input data. The second controller 1410 may extract an intensity value for each standard wavelength from a portion corresponding to the standard wavelength range of the spectrum curve by referring to the information on the standard wavelength range from the second memory 1450 and thus generate the processed spectrum data with respect to the standard wavelength range.

As described above, in one embodiment of the present disclosure, the diagnostic unit 1400 processes the raw spectrum data having the raw wavelength range determined according to the specifications of LIBS unit 1200 into the processed spectrum data having the standard wavelength range required by the diagnostic algorithm.

The standard wavelength range may be differently set according to a target which will be diagnosed and a type of diagnosis. For example, in order to determine a composition of a specific medicine, spectrum data on a wavelength range of 320 nm to 550 nm may be used, and in order to determine a composition of another medicine, spectrum data on a wavelength range of 200 nm to 250 nm may be used. Alternatively, when skin cancer diagnosis is performed by performing LIBS on skin tissue, the diagnosis may be performed using spectrum data on a wavelength range of 270 nm to 800 nm.

As described above, the standard wavelength range may be set according to various criteria.

For example, when a diagnostic result is obtained using the intensity value for each wavelength of the spectrum data as the input data, the standard wavelength range may be determined on the basis of feature importance for each wavelength of the spectrum data.

Here, the feature importance for each wavelength may mean a degree of influence of a specific wavelength on the diagnostic result of the diagnostic algorithm. An intensity value of the wavelength having high feature importance may be interpreted as having high necessity as the input data of the diagnostic algorithm. On the contrary, an intensity value of the wavelength having low feature importance may be interpreted as having low necessity as the input data of the diagnostic algorithm.

FIG. 36 is a diagram illustrating feature importance for each wavelength included in spectrum data according to one embodiment of the present disclosure.

Referring to FIG. 36, a plurality of wavelengths included in the spectrum data may each have feature importance with respect to a diagnostic result. Here, the feature importance may be calculated as a correlation factor between the diagnostic result of the diagnostic algorithm and the intensity value for each corresponding wavelength. For example, a correlation factor between a specific wavelength and a diagnosis result may be obtained from a difference between diagnostic accuracy obtained by inputting the spectrum data excluding the specific wavelength into the artificial neural network learned through a learning-set in which the spectrum data and the diagnostic result are tagged with each other and diagnostic accuracy obtained by inputting the spectrum data including the specific wavelength into the artificial neural network. Alternatively, in addition to the above description, the feature importance may be obtained by using various feature selection techniques or various feature extraction techniques, which are used in the field of machine learning.

The standard wavelength range may be set to include wavelengths having high feature importance. For example, the standard wavelength range may be set to include wavelengths having feature importance that is larger than a threshold and to exclude wavelength ranges having feature importance that is smaller than the threshold. Alternatively, the standard wavelength range may be set to a range between a minimum wavelength and a maximum wavelength among the wavelengths having feature importance that is larger than the threshold FIG. 37 is a diagram illustrating an example of setting a standard wavelength range on the basis of feature importance according to one embodiment of the present disclosure.

Figure 37:
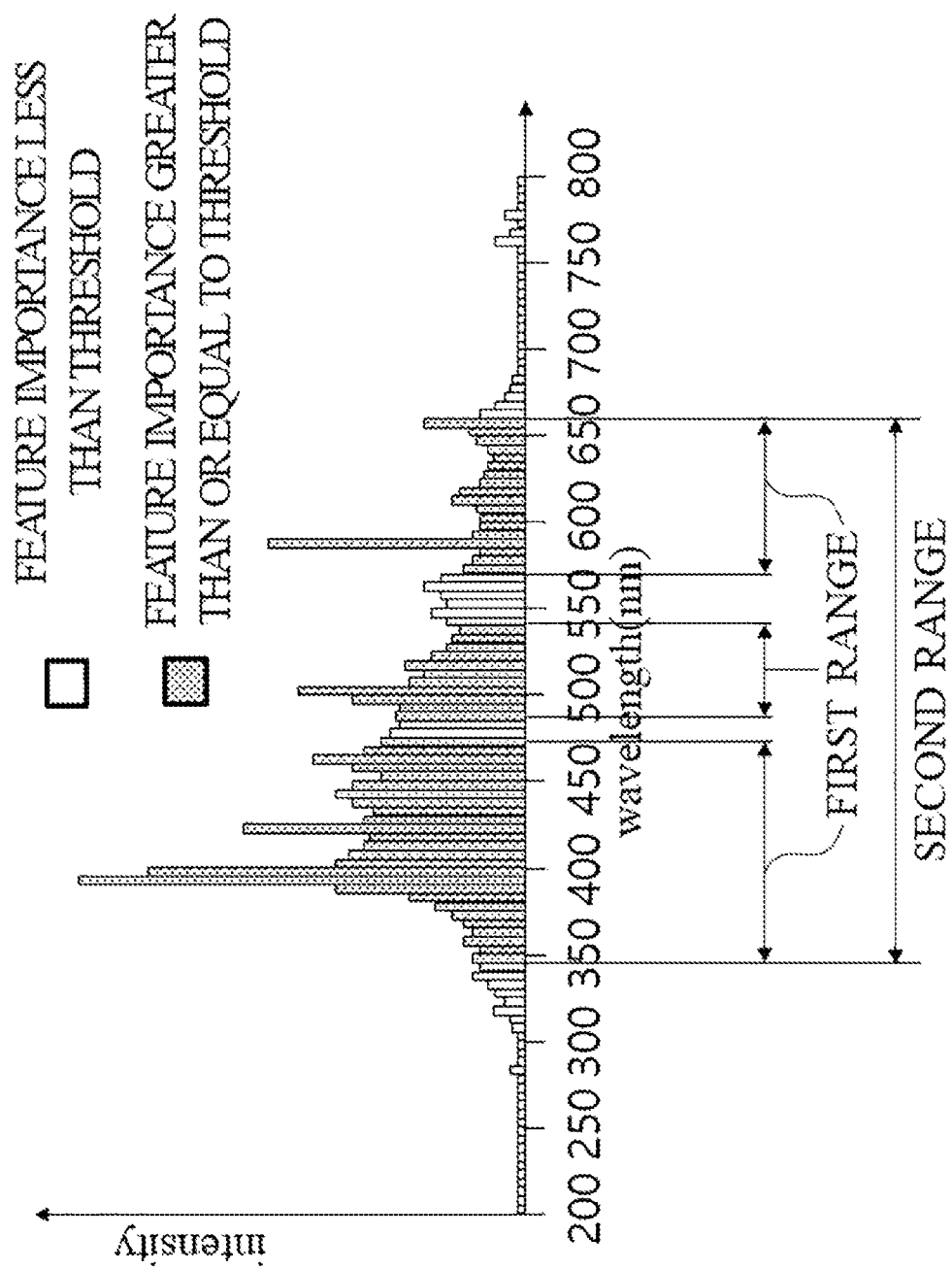
FIG. 37 is a diagram illustrating an example of setting a standard wavelength range on the basis of feature importance according to one embodiment of the present disclosure.

FIG. 37 shows the spectrum data on a wavelength-light intensity axis and illustrates whether feature importance for each wavelength included in the spectrum data is larger or smaller than the threshold. In this case, the standard wavelength range may set to a first range including wavelengths having feature importance that is larger than the threshold and excluding wavelengths having feature importance that is smaller than the threshold or set to a second range including wavelengths between the minimum wavelength and the maximum wavelength among the wavelengths having the feature importance that is larger than the threshold.

Meanwhile, in the above description, the standard wavelength range has been described as being set on the basis of the feature importance with respect to all the wavelengths of the spectrum data. Alternatively, the standard wavelength range may be set on the basis of the feature importance with respect to some of the wavelengths included in the spectrum data. Here, for example, some of the wavelengths included in the spectrum data may be wavelengths corresponding to element peaks and, alternatively, may be wavelengths, each having an intensity value of a predetermined magnitude or more.

Figure 38:
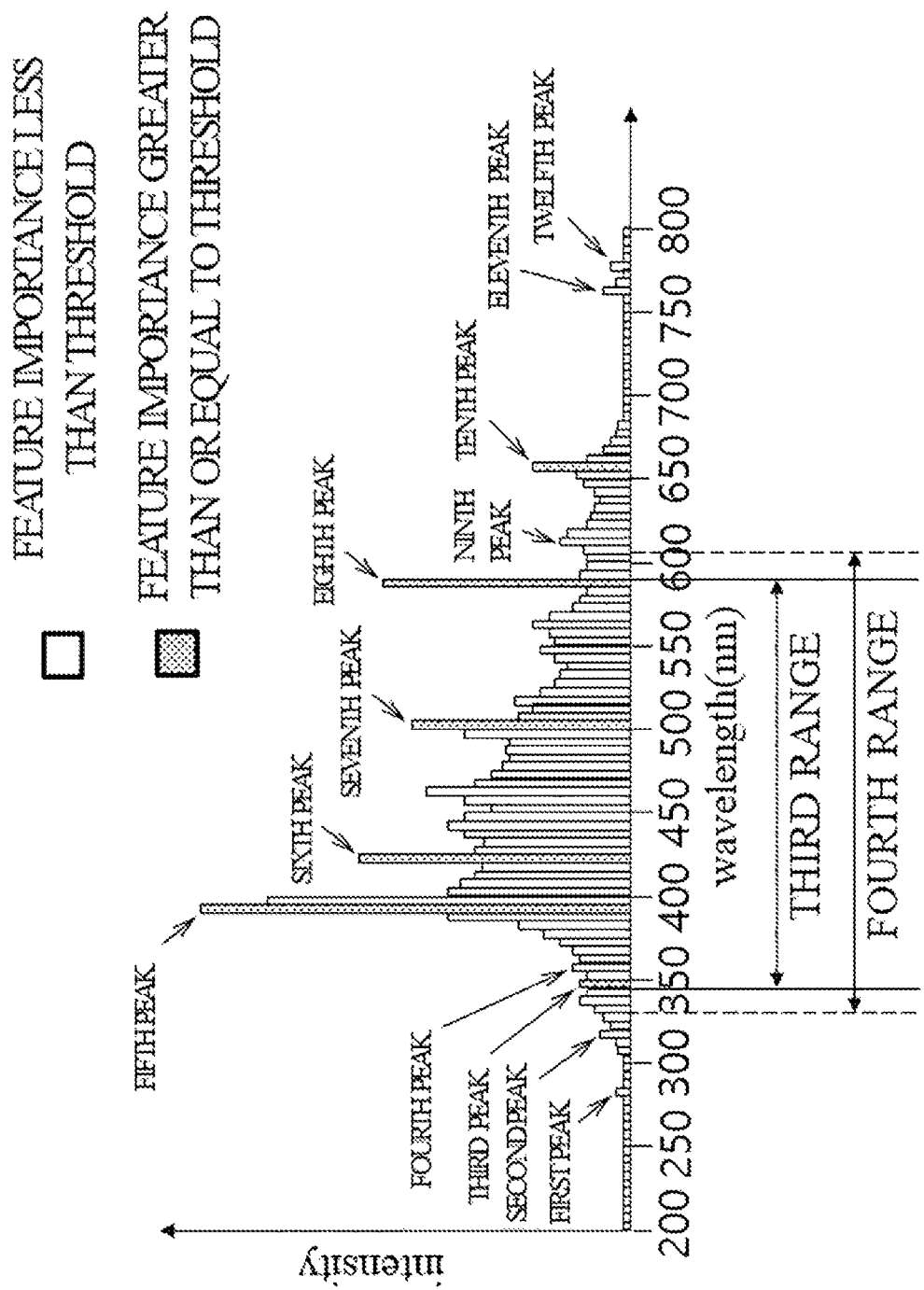
FIG. 38 is a diagram illustrating an example of setting a standard wavelength range to some wavelengths on the basis of feature importance according to one embodiment of the present disclosure.

FIG. 38 is a diagram illustrating an example of setting a standard wavelength range to some wavelengths on the basis of feature importance according to one embodiment of the present disclosure.

FIG. 38 illustrates setting of the standard wavelength range on the basis of wavelengths having feature importance that is larger than the threshold among the wavelengths corresponding to the element peaks. Specifically, FIG. 38 shows that the spectrum has a plurality of element peaks and whether the feature importance for wavelengths corresponding to the plurality of element peaks is greater than or equal to, or less than or equal to the threshold. In this case, the standard wavelength range may be set to a third range between a minimum wavelength and a maximum wavelength among wavelengths of the element peaks having feature importance that is greater than or equal to the threshold or set to a fourth range in which a buffer region is added to a lower limit and an upper limit of the third range.

In case of using as small as hundreds of intensity values for wavelengths or as many as thousands of intensity values for wavelengths as the input data, since calculating the feature importance for all the input data requires much effort and time, it may be advantageous in many ways to calculate the feature importance for only some wavelengths instead of all the wavelengths and to obtain the standard wavelength range on the basis of the calculated feature importance.

As another example of criteria for setting the standard wavelength range, the standard wavelength range may be determined on the basis of the intensity value for each wavelength of the spectrum data.

For example, the intensity value for each wavelength used to set the standard wavelength range may mean an average intensity value for each wavelength of the spectrum data used as the learning-set. Here, preferably, the spectrum data used as the learning-set may be spectrum data undergoing normalization, which will be described below. Therefore, the intensity value for each wavelength may also be an intensity value for each wavelength after the normalization.

Figure 39:
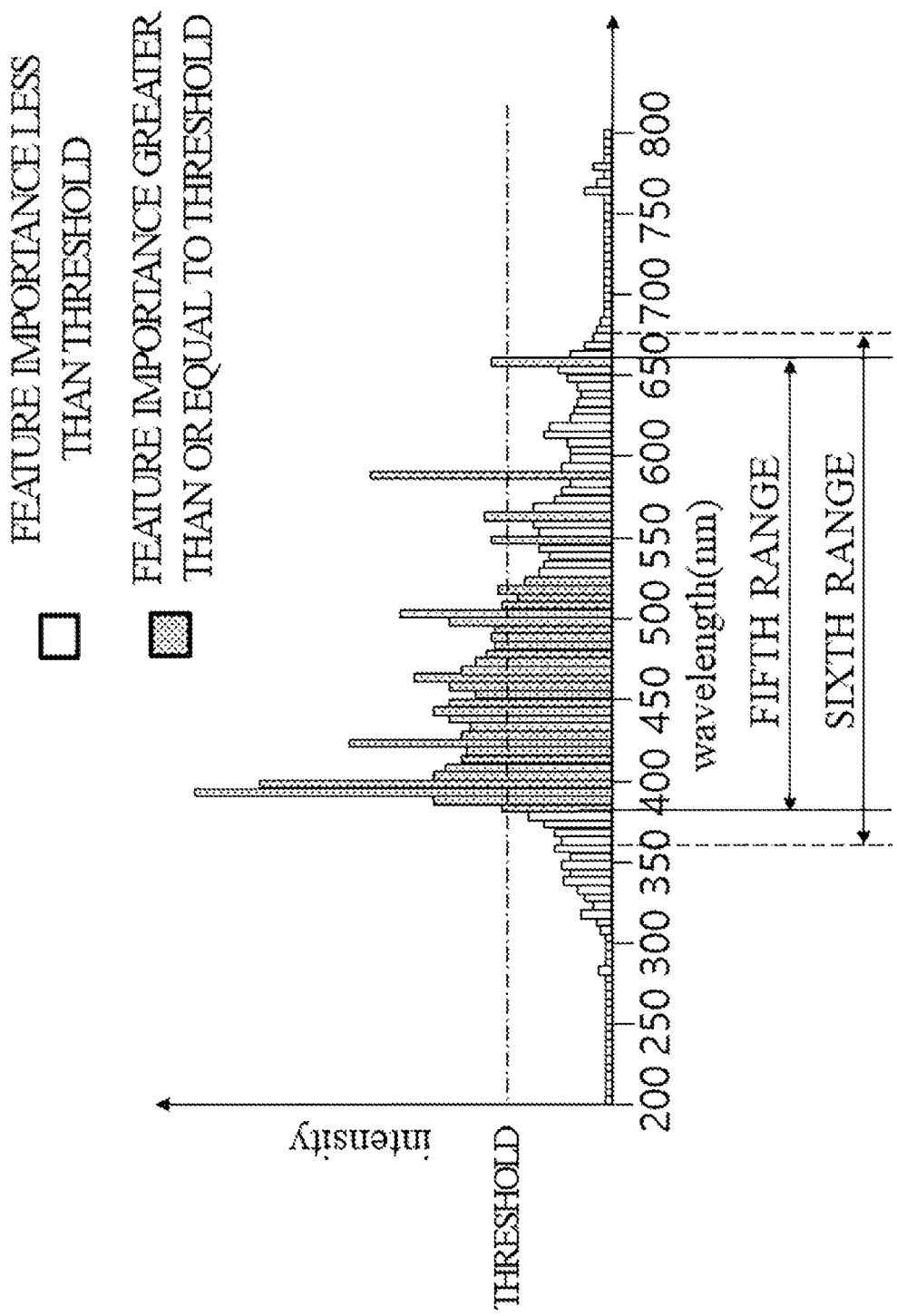
FIG. 39 is a diagram illustrating an example of setting a standard wavelength range on the basis of an intensity value for each wavelength according to one embodiment of the present disclosure.

FIG. 39 is a diagram illustrating an example of setting a standard wavelength range on the basis of an intensity value for each wavelength according to one embodiment of the present disclosure.

FIG. 39 shows an average of the spectrum data used as the learning-set represented on the wavelength-intensity axis. The standard wavelength range may be set to a fifth range between the minimum wavelength and the maximum wavelength among the wavelengths having feature importance that is greater than or equal to the threshold or set to a sixth range in which a buffer region is added to a lower limit and an upper limit of the fifth range. Here, the threshold may be determined as a value obtained by multiplying the sum of the intensity values of overall pieces of spectrum data or some pieces thereof by a predetermined ratio or determined as an arbitrary value.

As still another example of the criteria for setting the standard wavelength range, the standard wavelength range may be determined in consideration of the element peaks of the spectrum data.

For example, the standard wavelength range may be set to include element peaks having high relevancy with the diagnosis result and to exclude element peaks having low relevancy therewith or may be set to a region between a minimum wavelength and a maximum wavelength among element peaks having high relevancy with the diagnosis result or to a range to which a buffer region is added.

Figure 40:
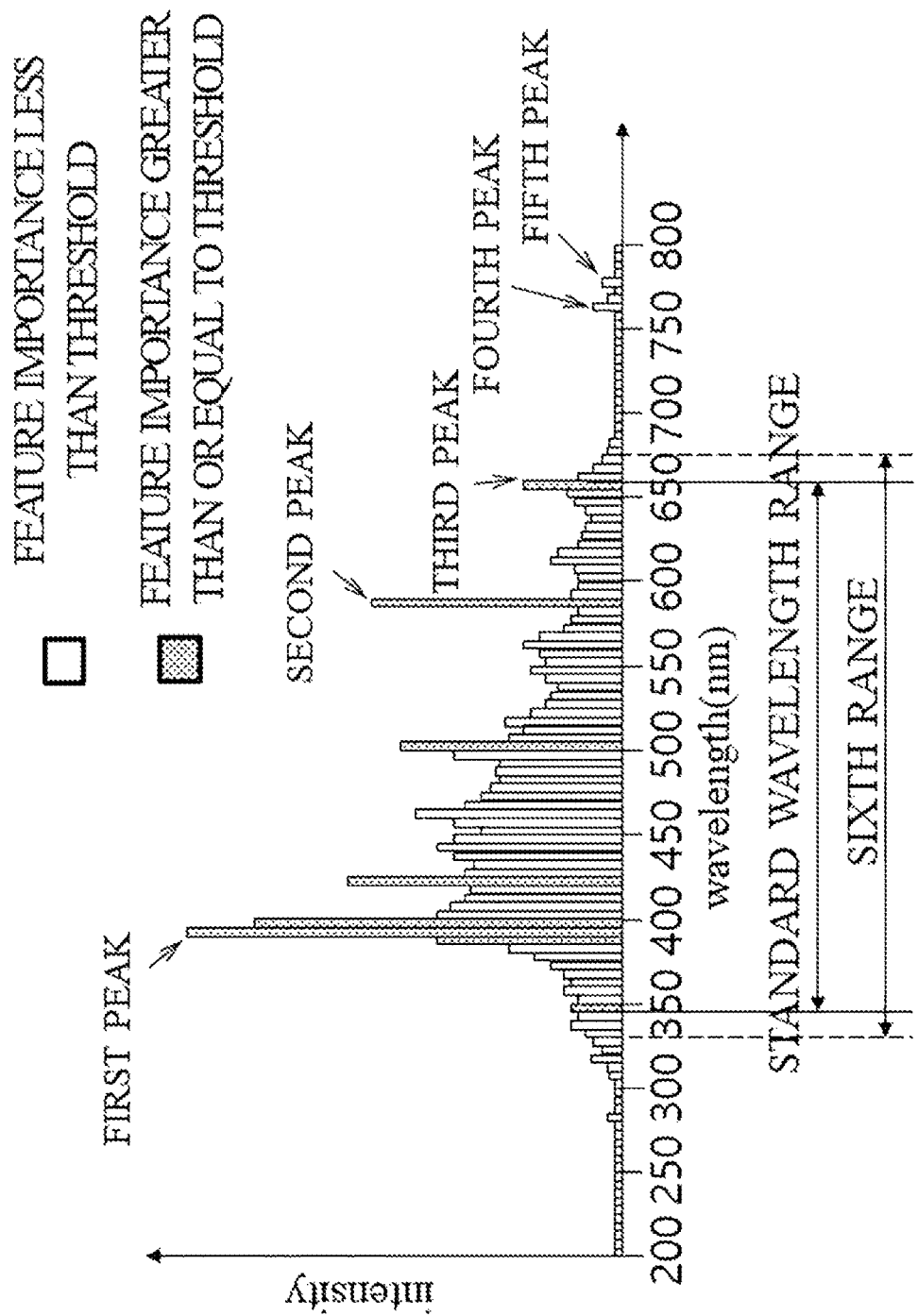
FIG. 40 is a diagram illustrating an example of setting a standard wavelength range on the basis of diagnostic relevance of an element peak according to one embodiment of the present disclosure.

FIG. 40 is a diagram illustrating an example of setting a standard wavelength range on the basis of diagnostic relevance of an element peak according to one embodiment of the present disclosure.

FIG. 40 illustrates spectra obtained for performing a cancer test on skin tissue. In this case, since contents of a first peak related to calcium, a second peak related to sodium, and a third peak related to hydrogen are significantly different between a cancer cell and a non-diseased cell, it may be determined that skin tissue, which is a target of diagnosis, is high relevant with whether the skin tissue is a cancer cell or a non-diseased cell. On the contrary, since a fourth peak related to oxygen or a fifth peak related to potassium do not have large differences in content between the cancer cell and the non-diseased cell, the fourth peak and the fifth peak have low relevancy with whether the skin tissue, which is a target of diagnosis is the cancer cell or the non-diseased cell. Thus, the standard wavelength range may be set to essentially include the first, second and third peaks having high relevancy.

Meanwhile, some of the element peaks in the spectrum data may be element peaks for the same element. For example, when a part of an object which is a target of the LIBS is ablated and transitioned into a plasma state, elements included in the ablated object may be excited to have different energy levels. Thus, even in the case of the same element, a wavelength of an emitted spectrum may vary according to the excited energy level.

Therefore, when the standard wavelength range is set on the basis of the relevancy of the element peaks, it may be further considered whether the element peaks overlap.

Figure 41:
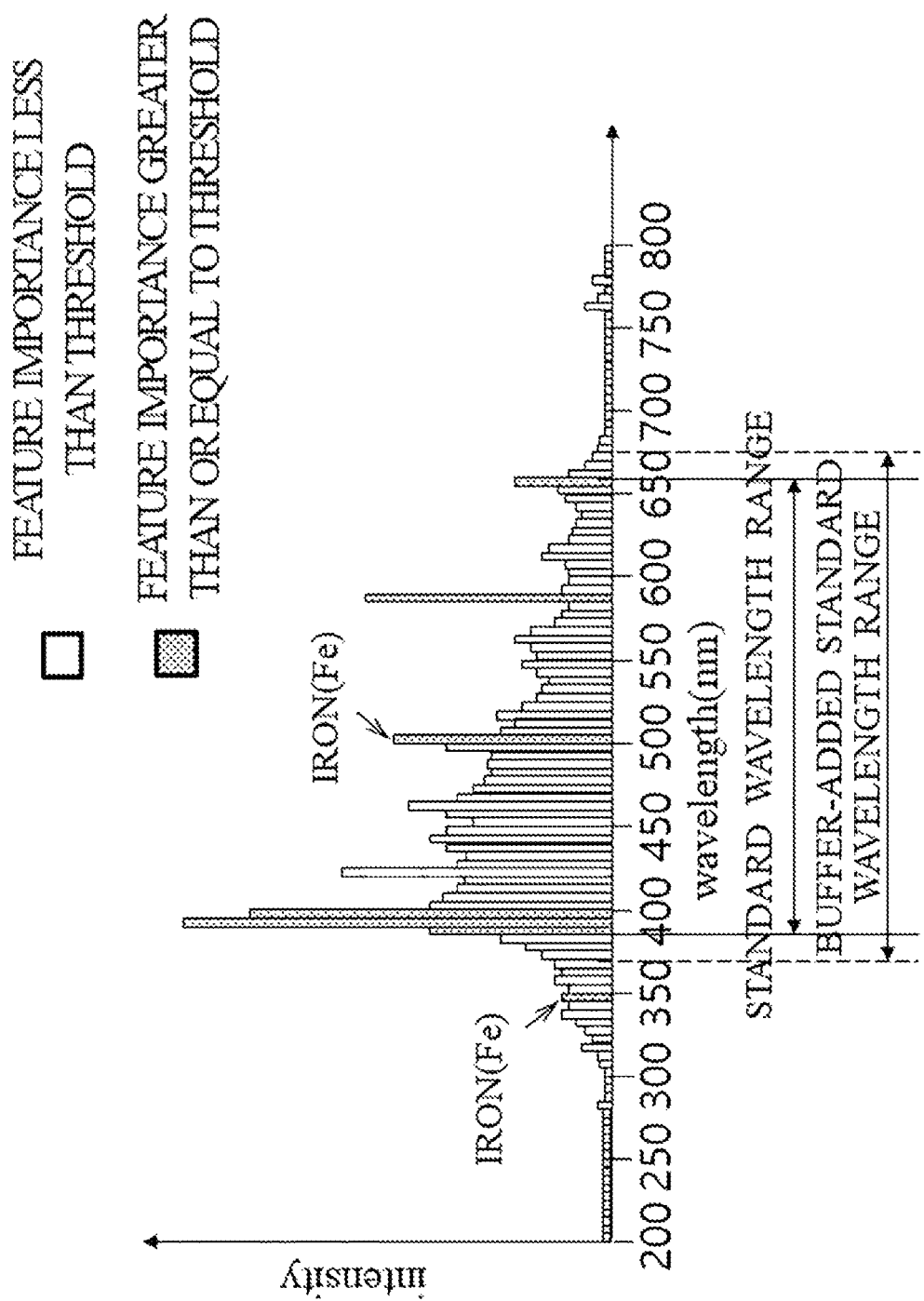
FIG. 41 is a diagram illustrating an example of setting a standard wavelength range by further considering a duplicated element peak according to one embodiment of the present disclosure.

FIG. 41 is a diagram illustrating an example of setting a standard wavelength range by further considering an duplicated element peak according to one embodiment of the present disclosure.

FIG. 41 illustrates spectra obtained for performing a cancer test on skin tissue. In this case, iron (Fe) is an element peak having high diagnostic relevancy with respect to the cancer cell or cancer tissue but may be overlappingly generated at wavelengths of 340 nm and 660 nm. In this case, when the standard wavelength range is set, only one of the wavelengths may be included. For example, as shown in FIG. 41, when elements related to element peaks having 380 nm or less except for iron have low diagnostic relevancy, an iron-related element peak of 340 nm may be excluded from the standard wavelength range.

In summary, the standard wavelength range may be set such that the remaining element peak except for one of the duplicated element peaks among the elements having high diagnosis relevancy is not included in the standard wavelength range. When diagnosis is performed through the LIBS, since resolution of the input data may be improved as the wavelength range become smaller, an element peak which will be excluded from the standard wavelength range among the duplicated element peaks may be mainly selected as the duplicated element peak out of the wavelength range which is set as a single element peak except for the duplicated element peaks among the element peaks related to the diagnosis-related elements.

As described above, some criteria for setting the wavelength range have been proposed, but the criteria for setting the wavelength range are not limited to the above-described examples. Further, the above-described examples may be used alone for the wavelength range setting and used by being appropriately combined.

Meanwhile, the above-described standard wavelength range setting may be performed by the diagnostic system 100 or the diagnostic unit 1400 or by a computer device which develops a diagnostic algorithm applied to the diagnostic unit 1400 or a server periodically updating the diagnostic algorithm of the diagnostic unit 1400. Further, the set standard wavelength range may be stored in the second memory 1450 of the diagnostic unit 1400, and the second controller 1410 may refer to the set standard wavelength range when generating the processed spectrum data from the raw spectrum data.

Meanwhile, the standard wavelength range may be different according to a kind of desired diagnosis. Specifically, a standard wavelength range for diagnosing a skin cancer may be differently set from a standard wavelength range for diagnosing skin age. Therefore, in the diagnostic system 100 which performs a plurality of diagnosis, a standard wavelength range for each diagnosis is stored in the second memory 1450, and, when the second controller 1410 obtains a user input for a kind of diagnosis, the second controller 1410 may change/set the standard wavelength range for each diagnosis, which will be performed, with reference to the second memory 1450 on the basis of the user input.

According to another example of the standardization according to one embodiment of the present disclosure, the diagnostic unit 1400 may generate processed spectrum data having the number of intensity values for each wavelength different from that of the raw spectrum data.

In the case of a nonlinear machine learning algorithm such as the artificial neural network, as an amount of information included in the reference data used for learning of the artificial neural network is increased, model performance may be improved. Thus, even in the present disclosure, diagnostic accuracy may be improved by increasing the number of input nodes of the artificial neural network.

In this case, the raw spectrum data according to one embodiment of the present disclosure may have the number of intensity values for each wavelength limited within the wavelength range determined according to the specifications of the LIBS unit 1200. In this case, the artificial neural network may be trained with the reference data having pieces of information that is larger than a limited number within the wavelength range set to be suitable for learning of the artificial neural network. In this case, the diagnostic unit 1400 increases the number of intensity values for each wavelength in the wavelength range required as the input data of the artificial neural network included in the raw spectrum data, thereby generating the processed spectrum data having the number of intensity values for each wavelength in the wavelength range, which corresponds to the wavelength range and/or the number of the input nodes of the artificial neural network.

Hereinafter, for convenience of description, the number of intensity values for each wavelength of the spectrum data will be referred to as the number of pieces of data.

For example, guessing data may be generated through the standardization of the raw spectrum data. In this case, the guessing data may mean a new derived variable generated by processing the raw spectrum data. For example, the guessing data may be an intensity value at a specific wavelength extracted from the above-described spectrum curve.

The generated guessing data may be used for learning of the artificial neural network or input to the input node of the artificial neural network. Thus, the intensity value for a wavelength other than the wavelengths included in the raw spectrum data may be generated as the guessing data and used in the artificial neural network. Consequently, accuracy of the diagnostic result of the artificial neural network may be improved, and the number of intensity values for each wavelength of the raw spectrum data may be varied to correspond to the number of pieces of the input data within the wavelength range required by the input node of the artificial neural network.

Hereinafter, generating the processed spectrum data having the number of intensity values for each wavelength different from that of the raw spectrum data according to one embodiment of the present disclosure will be described with reference to the accompanying drawings.

Figure 42:
FIG. 42 is a diagram illustrating a table that relates to changing of the number of intensity values for each wavelength of raw spectrum data through standardization according to one embodiment of the present disclosure.
Figure 43:
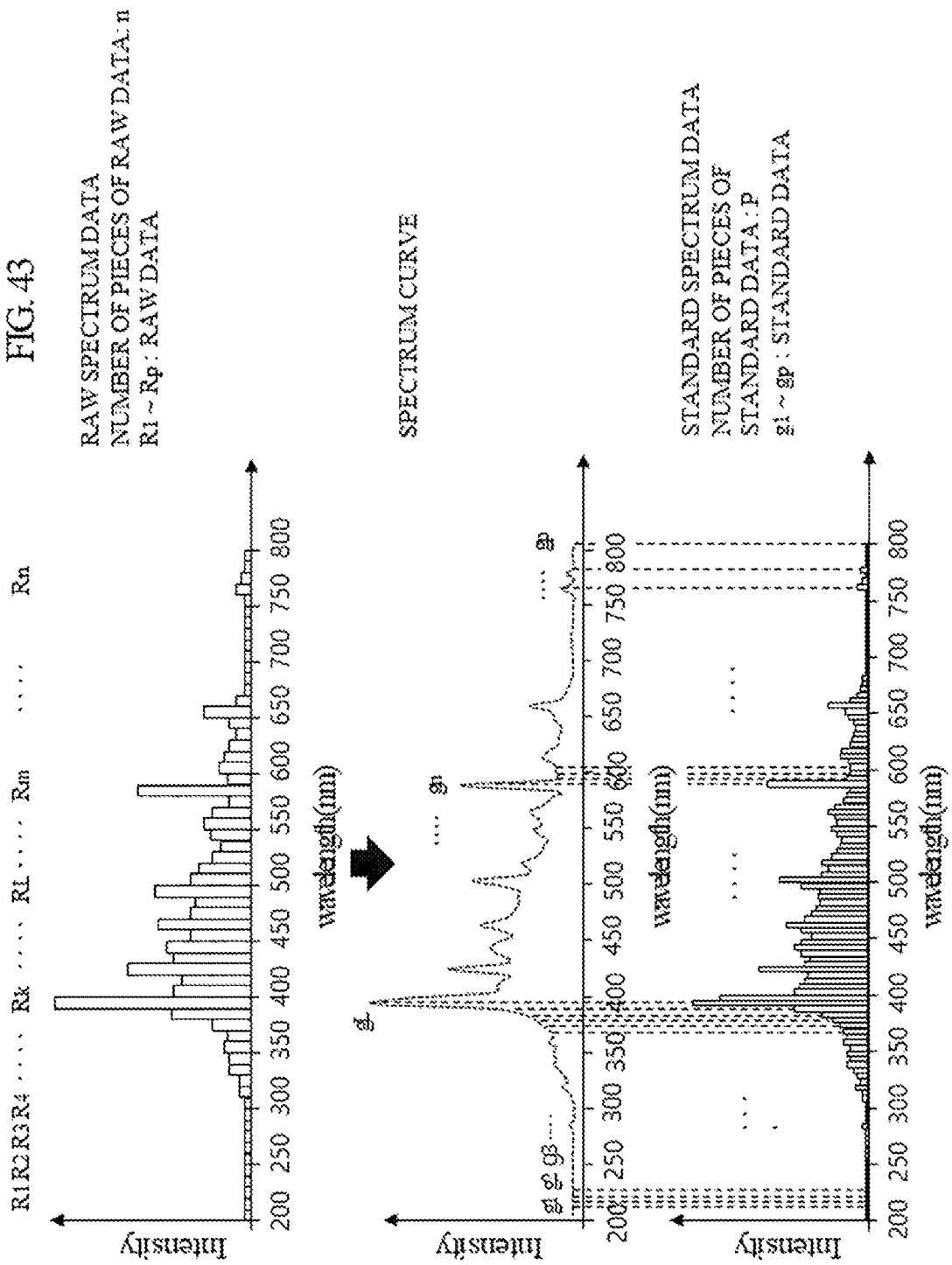
FIG. 43 is a graph showing the changing of the number of intensity values for each wavelength of the raw spectrum data through the standardization according to one embodiment of the present disclosure.

FIGS. 42 and 43 are diagrams showing changing of the number of intensity values for each wavelength of the raw spectrum data according to one embodiment of the present disclosure.

FIG. 42 is a diagram illustrating a table that relates to changing of the number of intensity values for each wavelength of raw spectrum data through standardization according to one embodiment of the present disclosure, and FIG. 43 is a graph showing the changing of the number of intensity values for each wavelength of the raw spectrum data through the standardization according to one embodiment of the present disclosure.

According to one embodiment of the present disclosure, the diagnostic unit 1400 may generate processed spectrum data having the number of pieces of data different from that of the raw spectrum data on the basis of the raw spectrum data. Hereinafter, for the convenience of description, the number of pieces of data included in the raw data refers to "the number of pieces of raw data," and the number of pieces of data included in the processed spectrum data refers to "the number of pieces of standard data." The number of pieces of processed data may coincide with the number of input nodes of the artificial neural network.

Specifically, referring to FIGS. 42 and 43, the second memory 1450 may store information on the number of pieces of standard data which is the number of intensity values for each wavelength required by the input data. The second controller 1410 may generate the guessing data by processing the raw spectrum data with reference to the information on the number of pieces of standard data from the second memory 1450 and generate the processed spectrum data having the number of pieces of standard data including the guessing data.

Further, the second memory 1450 may store standard wavelength information on wavelengths corresponding to the intensity values for each wavelength required by the input data. Here, the number of pieces of standard wavelengths may be greater than the number of pieces of raw data. The second controller 1410 may process the raw spectrum data by referring to the standard wavelength information from the second memory 1450 to generate the guessing data having an intensity value corresponding to the standard wavelength and generate the processed spectrum data having the number of pieces of standard data including the guessing data.

Here, the number of pieces of standard data may be variously set. For example, a predetermined number may correspond to the number of input nodes of the artificial neural network.

As a detailed example, referring to FIG. 42, the second controller 1410 may generate the processed spectrum data having the number of intensity values for each wavelength about 2 times while having the same wavelength range as the raw spectrum data. Here, the processed spectrum data may include the guessing data.

Here, when the raw spectrum data includes the intensity values for each wavelength corresponding to some of the standard wavelengths, the processed spectrum data may include the guessing data having intensity values corresponding to the remaining standard wavelengths in addition to intensity values corresponding to some of the standard wavelengths included in the raw spectrum data.

Further, when the raw spectrum data does not include the intensity values for each wavelength corresponding to the standard wavelengths, the processed spectrum data may include only the guessing data having an intensity value corresponding to the standard wavelength.

The guessing data may not be included in the raw spectrum data but may be a value derived on the basis of the intensity values for each wavelength included in the raw spectrum data. More specifically, the second controller 1410 may process raw spectrum data having 60 wavelengths in a wavelength range of 200 nm to 700 nm to generate processed spectrum data having 120 wavelengths in the wavelength range of 200 nm to 700 nm.

Further, the guessing data may be a value generated by interpolating the intensity values for each wavelength included in the raw spectrum data. For example, the guessing data may be a median value between intensity values of adjacent wavelengths or a value generated by interpolating the intensity values of the adjacent wavelengths. For example, the guessing data may be extracted from the wavelength-light intensity spectrum curve of the intensity values for each wavelength included in the raw spectrum data.

Referring to FIG. 43, the diagnostic system 100 may generate processed spectrum data having the number of intensity values for each wavelength different from that of the raw spectrum data using the spectrum curve. Specifically, the second controller 1410 may extract the guessing data from the spectrum curve on the basis of the intensity values for each wavelength included in the raw spectrum data and generate the processed spectrum data having the number of pieces of standard data including the guessing data.

Further, according to another example of the standardization according to one embodiment of the present disclosure, the diagnostic unit 1400 may generate processed spectrum data having wavelength intervals different from those of the raw spectrum data.

As described above, owing to the change of the setting of the diagnostic system 100, when the wavelength intervals of the spectrum data are varied or an offset is generated in a detected wavelength due to a minute difference in performance between the devices obtaining the spectrum data such that the wavelength intervals of the obtained spectrum data are varied, diagnostic accuracy of the diagnostic algorithm may be degraded. In this case, in order to improve the accuracy of the diagnostic algorithm, it is necessary to process the spectrum data such that the wavelength intervals of the spectrum data are compatible with the diagnostic algorithm. Further, as the wavelength intervals are varied within a specific wavelength range of the spectrum data, the number of pieces of data in the spectrum data may be varied.

Hereinafter, generating the processed spectrum data having wavelength intervals different from those of the raw spectrum data according to one embodiment of the present disclosure will be described with reference to the accompanying drawings.

Figure 44:
FIG. 44 is a diagram illustrating a table that relates to changing of a wavelength interval of spectrum data through standardization according to one embodiment of the present disclosure.
Figure 45:
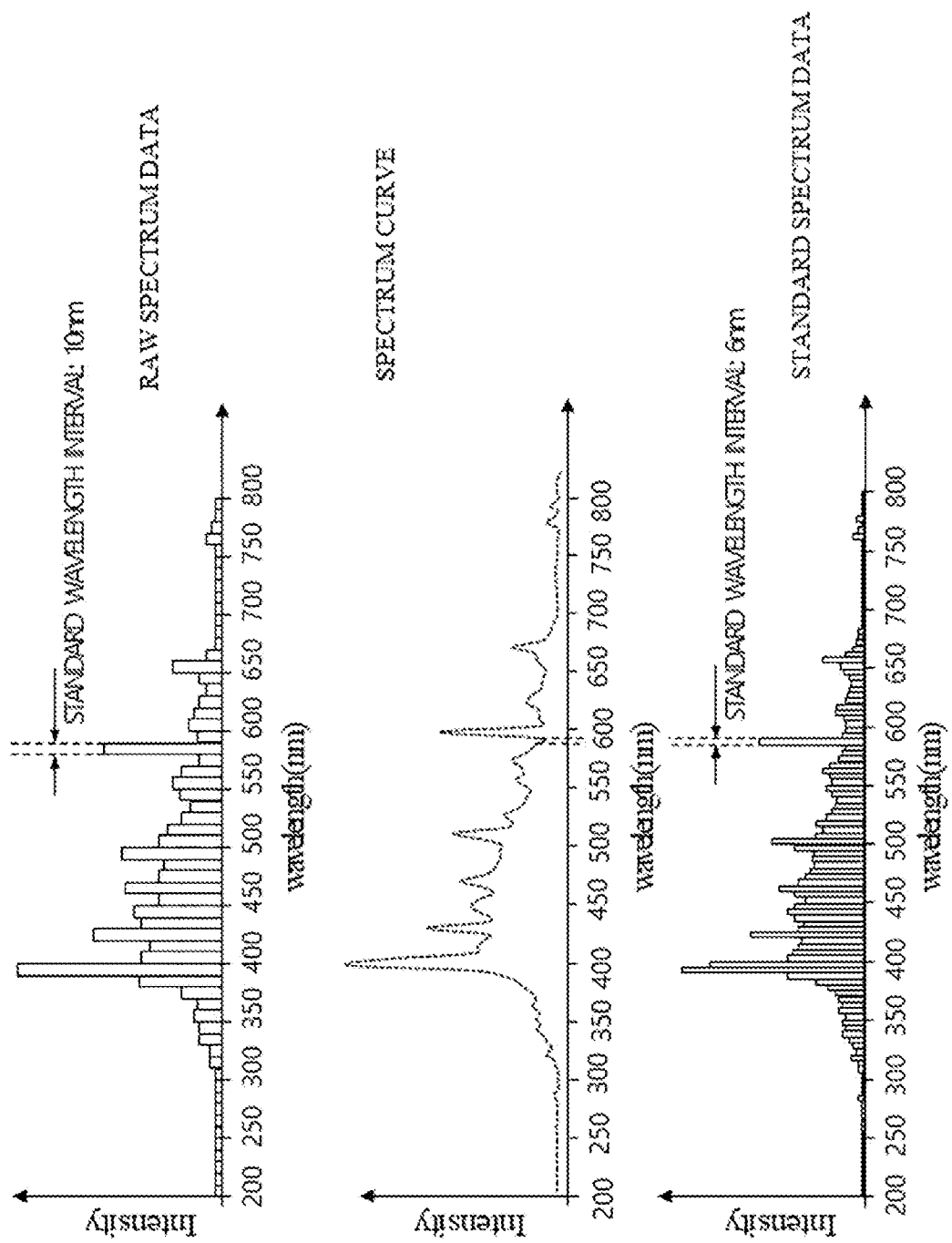
FIG. 45 is a graph showing the changing of the wavelength interval of the spectrum data through the standardization according to one embodiment of the present disclosure.

FIGS. 44 and 45 are diagrams for changing wavelength intervals of the spectrum data according to one embodiment of the present disclosure.

Specifically, FIG. 44 is a diagram illustrating a table that relates to changing of a wavelength interval of spectrum data through standardization according to one embodiment of the present disclosure, and FIG. 45 is a graph showing the changing of the wavelength interval of the raw spectrum data through the standardization according to one embodiment of the present disclosure.

According to one embodiment of the present disclosure, the diagnostic unit 1400 may generate processed spectrum data having wavelength intervals different from those of the raw spectrum data on the basis of the raw spectrum data. Hereinafter, for the convenience of description, the wavelength interval included in the raw spectrum data will be referred to as a "raw wavelength interval," and the wavelength interval included in the processed spectrum data will be referred to as a "standard wavelength interval." A processed wavelength interval may coincide with a wavelength interval of the input data of the artificial neural network.

Specifically, referring to FIGS. 44 and 45, the second memory 1450 may store information on the standard wavelength interval which is a wavelength interval required by the input data. The second controller 1410 may generate processed spectrum data having the standard wavelength interval by processing the raw spectrum data with reference to the information on the standard wavelength interval from the second memory 1450.

Here, the standard wavelength interval may be variously set. For example, the standard wavelength interval may correspond to a wavelength interval of the input node of the artificial neural network.

As a detailed example, referring to FIG. 44, the second controller 1410 may generate processed spectrum data having a wavelength interval of B nm different from A nm which is a wavelength interval of the raw spectrum data. Specifically, the second controller 1410 may process raw spectrum data having a wavelength interval of A nm to generate processed spectrum data having a wavelength interval of B nm. Thus, the processed spectrum data may include a larger number of pieces of data than that of the raw spectrum data.

Referring to FIG. 45, the diagnostic system 100 may generate processed spectrum data having a wavelength interval different from that of the raw spectrum data using the spectrum curve. Specifically, the second controller 1410 may extract the guessing data from the spectrum curve from a wavelength on the basis of the intensity values for each wavelength included in the raw spectrum data, which corresponds to the standard wavelength interval on the spectrum curve between the intensity values for each wavelength and generate the processed spectrum data including the guessing data.

Hereinafter, offset correction between spectrum data through the above-described wavelength interval adjustment will be described with reference to the drawings.

Figure 46:
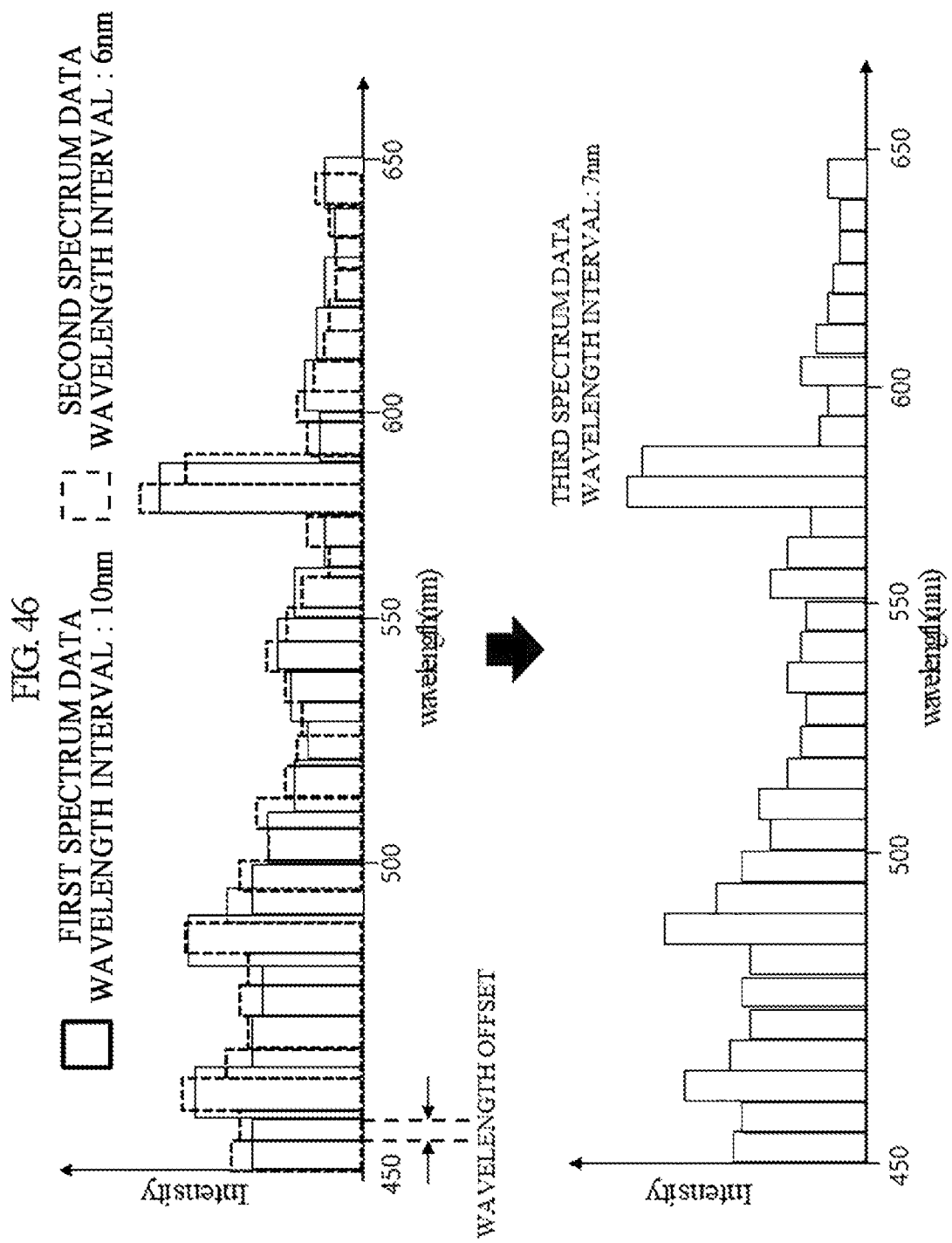
FIG. 46 is a diagram illustrating wavelength off-set correction according to one embodiment of the present disclosure.

FIG. 46 is a diagram illustrating wavelength off-set correction according to one embodiment of the present disclosure.

FIG. 46 illustrates first and second spectrum data which is measured for the same object in a plurality of LIBS units 1200 having the same specifications and/or settings and in which an offset is generated.

For example, even when diagnosis is performed from the spectrum data using diagnostic units 1400 which store the artificial neural networks equally learned and programmed, owing to mechanical causes of the plurality of LIBS units 1200 measuring the spectrum data, an offset is generated in the spectrum data measured in the same object such that obtained diagnostic results may be affected.

Alternatively, when the LIBS unit 1200 measuring reference spectrum data included in the learning-set of the artificial neural network and the LIBS unit 1200 measuring the raw spectrum data so as to perform the diagnostic algorithm have the same specifications and/or settings, owing to mechanical causes between the LIBS units 1200, a wavelength offset may be generated.

In this case, the wavelength interval of the spectrum data is adjusted such that pieces of spectrum data having different wavelength intervals may be set to have the same wavelength interval. That is, the second controller 1410 may generate processed spectrum data having the standard wavelength interval by adjusting the wavelength interval of the obtained spectrum data.

Referring to FIG. 46 again, owing to a wavelength interval difference of 4 nm between a first spectrum data having a wavelength interval of 10 nm and a second spectrum data having a wavelength interval of 6 nm, which are measured in the same object, a wavelength offset may be generated. In this case, as exemplarily shown, the second controller 1410 may generate third spectrum data which is set to have the same wavelength interval of 7 nm by adjusting the wavelength intervals of the first spectrum data and the second spectrum data. The above-described wavelength interval is an exemplary value. It is obvious that the measured wavelength interval of the first spectrum data is 1 nm, the measured wavelength interval of the second spectrum data is 0.6 nm, and the second controller 1410 may adjust the measured wavelength intervals to an interval of 0.7 nm.

The above-described standardization according to one embodiment of the present disclosure may be performed such that one element included in the spectrum data corresponds to a standard or a plurality of elements correspond to a standard specification and may be sequentially performed such that the plurality of elements correspond to the standard specification For example, the second controller 1410 may obtain the raw spectrum data and generate the spectrum curve on the wavelength-light intensity domain in conjunction with the raw spectrum data. When the spectrum curve is generated, the second controller 1410 may generate processed spectrum data by processing the raw spectrum data to have the standard wavelength range using the generated spectrum curve. When the processed spectrum data having the standard wavelength range is generated, the second controller 1410 may generate the processed spectrum data having the standard wavelength interval by adjusting the wavelength interval of the processed spectrum data having the standard wavelength range. Thereafter, the second controller 1410 may generate input data by extracting the number of pieces of standard data corresponding to the standard wavelength interval from the spectrum curve using the processed spectrum data having the standard wavelength range and the standard wavelength interval.

As described above, the standardization is performed such that the wavelength interval of the raw spectrum data may be processed to correspond to the input node of the artificial neural network, and thus diagnostic accuracy of the diagnostic algorithm may be improved.

An example of the preprocessing may include normalization.

Here, the normalization means processing of the sum of all or some of the intensity values for each wavelength included in the raw spectrum data into spectrum data having a predetermined intensity value (hereinafter referred to as a "reference value"). Here, the reference value may be a value corresponding to the intensity value for each wavelength included in the reference spectrum data of the learning-set which will be used for learning of the artificial neural network.

According to one embodiment of the present disclosure, it may be desirable for the artificial neural network to be learned using a learning-set constituted of reference spectrum data include less influence of the above-described environment variables. For example, spectra observed from plasma ablation generated from the same object by a laser having large energy and a laser having small energy may have a similar pattern but may be different in intensity values for each wavelength. Alternatively, spectra observed from objects plasma ablation generated form objects having the same material and different surface states (e.g., surface moisture and the like by lasers having the same energy may also have a similar pattern but may be different in overall intensity values for each wavelength. Therefore, it is necessary to equalize magnitudes of the overall spectra while maintaining the patterns of the spectra.

The artificial neural network is trained using the reference spectrum data of which intensity values are corrected to correspond to specific reference values and in which influence of the environmental variables is reduced, and the input data also corresponds to a specific reference value using the spectrum data of which the intensity value for each wavelength is adjusted is used such that sensitivity and/or specificity of calculation for diagnosis may be improved.

In this case, in order to reduce the influence of the environmental variables as well as match a scale with the reference spectrum data constituting the learning-set used for learning of the artificial neural network, it may be preferable to correct of the intensity value for each wavelength of the spectrum data used as the input data of the artificial neural network using a reference value corresponding to a specific reference value which is a correction reference of the intensity value for each wavelength of the reference spectrum data.

In summary, in order to remove the influence of the environmental variables on the spectrum data used in the artificial neural network according to one embodiment of the present disclosure and match the scales between the spectrum data used as the input data of the artificial neural network and the reference spectrum data used for learning of the artificial neural network, it may be necessary to normalize the intensity value for each wavelength included in the spectrum data.

Figure 47:
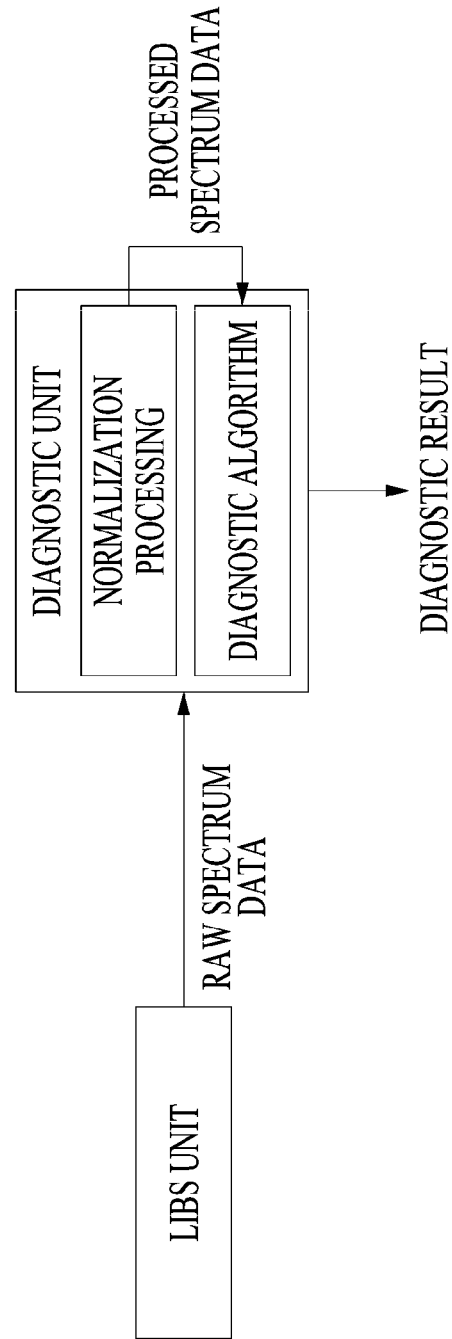
FIG. 47 is a schematic diagram illustrating normalization according to one embodiment of the present disclosure.

FIG. 47 is a schematic diagram illustrating normalization according to one embodiment of the present disclosure.

Referring to FIG. 47, the diagnostic system 100 may perform the normalization to generate processed spectrum data having a normalized reference value from the raw spectrum data as the input data of the diagnostic algorithm.

Specifically, the second controller 1410 may obtain the raw spectrum data from the LIB S unit 1200. The second memory 1450 may store reference value information of the input data. The second controller 1410 may process the raw spectrum data on the basis of the reference value information stored in the second memory 1450 to generate processed spectrum data having the spectrum data containing an intensity value corresponding to the reference value.

Here, it may be preferable to normalize a ratio between light intensity values for each wavelength included in the processed spectrum data and a ratio between light intensity values for each wavelength included in the raw spectrum data to be substantially the same as or similar to each other. That is, when the second controller 1410 processes the raw spectrum data to generate normalized processed spectrum data, the second controller 1410 may generate the processed spectrum data to have a waveform substantially the same as or similar to that of the raw spectrum data.

Here, the reference value may be variously set. For example, the reference value may be a value in conjunction with an intensity value for each wavelength at a specific wavelength. As a detailed example, the reference value may be a value in conjunction with a specific intensity value of at least one specific element peak included in the spectrum data. Alternatively, the reference value may be a value in conjunction with the sum of intensity values for each wavelength in a specific wavelength range. Also alternatively, the reference value may be a value in conjunction with a partial area extracted from the spectrum curve. Further alternatively, as described above, the reference value may be a specific reference value which is a reference for correction of the intensity value of the reference spectrum data which is used for learning of the artificial neural network.

That is, the second controller 1410 may generate processed spectrum data in which intensity values for each wavelength within a wavelength range of a normalization target are varied based on the intensity values at the specific wavelength from the raw spectrum data.

Further, the second controller 1410 may generate processed spectrum data in which the intensity values for each wavelength within a wavelength range of a normalization target are varied based on the sum of the intensity values for each wavelength within the specific wavelength range from the raw spectrum data.

Further, the second controller 1410 may generate processed spectrum data in which the intensity values for each wavelength within a wavelength range of a normalization target are varied based on area values of some regions in the spectrum curve with respect to a wavelength-light intensity generated using the intensity values for each wavelength of the raw spectrum data.

In the present disclosure, through the normalization, the raw spectrum data may be processed as the input data of the diagnostic algorithm, and the diagnostic algorithm may use the processed raw spectrum data to calculate a diagnostic result.

Hereinafter, detailed examples of the normalization according to one embodiment of the present disclosure will be described with reference to the drawings.

According to an example of the normalization according to one embodiment of the present disclosure, the diagnostic unit 1400 may generate processed spectrum data by adjusting magnitudes of the intensity values for each wavelength on the basis of the intensity value of the specific wavelength included in the raw spectrum data.

Figure 48:
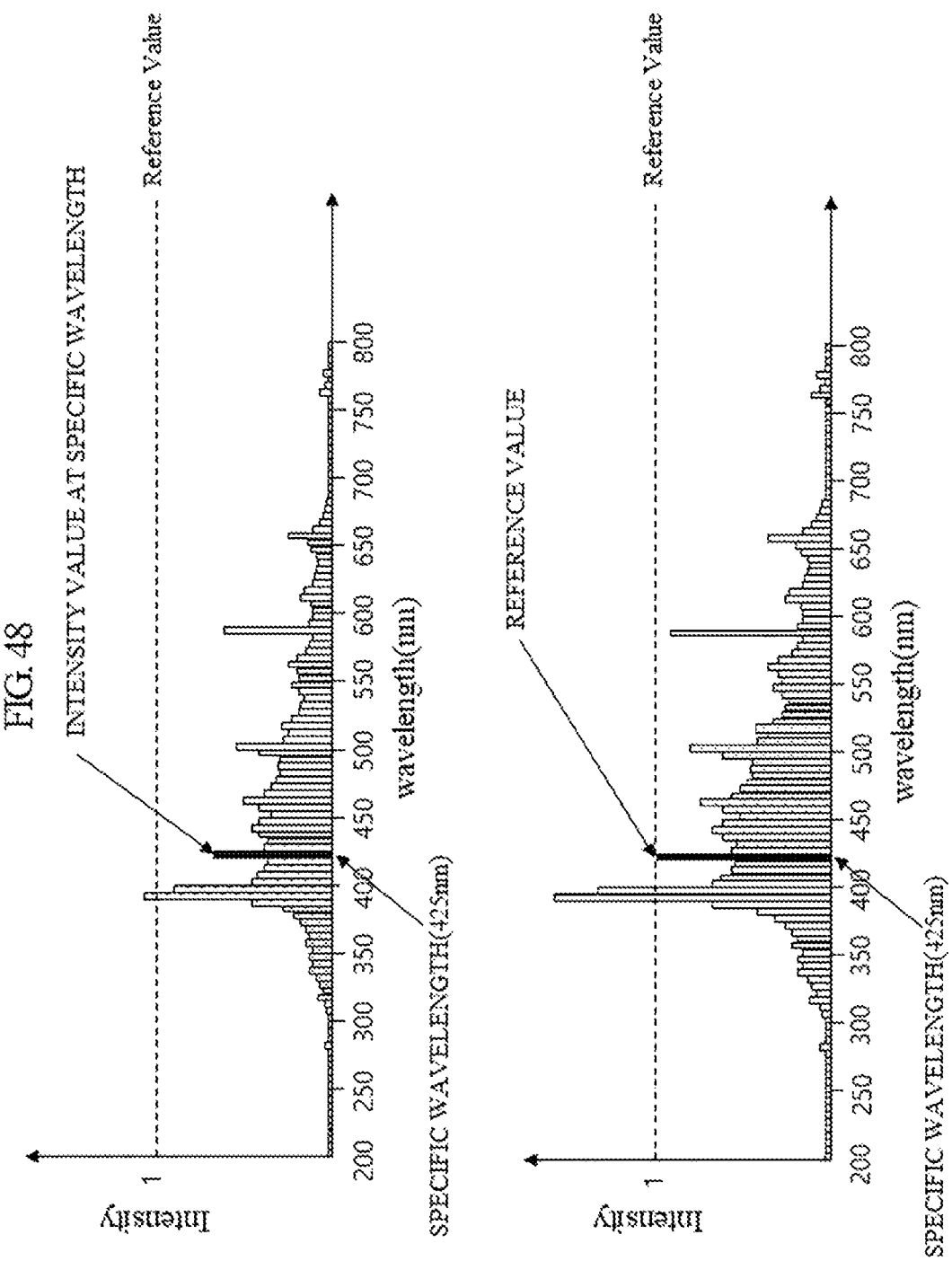
FIG. 48 is a diagram illustrating an example of normalization on the basis of an intensity value of a specific wavelength according to one embodiment of the present disclosure.

FIG. 48 is a diagram illustrating an example of normalization on the basis of an intensity value of a specific wavelength according to one embodiment of the present disclosure.

Referring to FIG. 48, at least one specific wavelength and a reference value for the specific wavelength may be set in the second memory 1450. The second controller 1410 may obtain the raw spectrum data and adjust the intensity values for each wavelength of the raw spectrum data such that the intensity value at the specific wavelength among the intensity values for each wavelength included in the raw spectrum data coincides with the reference value. Specifically, the second controller 1410 may calculate a ratio between reference values for intensity values corresponding to the specific wavelength among the intensity values for each wavelength of the raw spectrum data and multiply the intensity values for each wavelength of the raw spectrum data by the ratio between the reference values for the intensity values corresponding to the specific wavelength, thereby adjusting magnitudes of the intensity values for each wavelength.

In this case, the specific wavelength may be a wavelength corresponding to the element peak. Further, the specific wavelength may be generally selected as the wavelength of the element peak having a largest intensity of the standard wavelength range used for diagnosis.

The specific wavelength may be provided as a plurality of specific wavelengths. In this case, the magnitudes of the intensity values for each wavelength may be adjusted using an average value of ratios between reference values for intensity values corresponding to the specific wavelengths among the intensity values for each wavelength of the raw spectrum data.

According to another example of the normalization according to one embodiment of the present disclosure, the diagnostic unit 1400 may generate processed spectrum data by adjusting magnitudes of the intensity values for each wavelength on the basis of the intensity value of a specific wavelength range included in the raw spectrum data. When the normalization is performed using the wavelength range, it is more robust to external variables or errors than when the normalization is performed on the basis of the intensity values at a single wavelength or several wavelengths.

According to an example, the normalization may be performed using the sum or an average of the intensity values for each wavelength included in the specific wavelength range.

Figure 49:
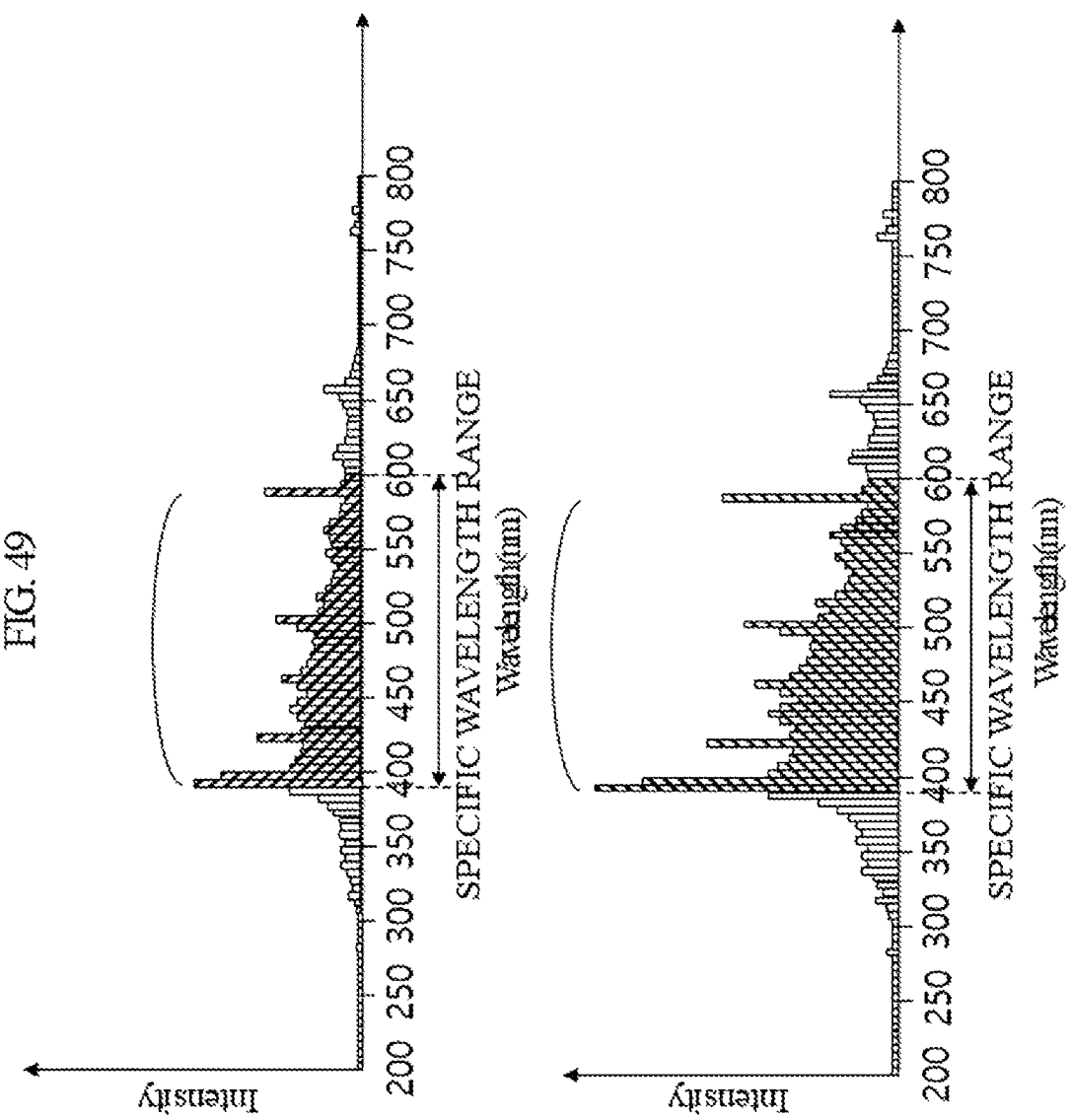
FIG. 49 is a diagram illustrating an example of normalization on the basis of an intensity value of a wavelength range according to one embodiment of the present disclosure.

FIG. 49 is a diagram illustrating an example of normalization on the basis of an intensity value of a wavelength range according to one embodiment of the present disclosure.

Referring to FIG. 49, a specific wavelength range and a reference value for the specific wavelength range may be set in the second memory 1450. The second controller 1410 may obtain the raw spectrum data and adjust the intensity values for each wavelength of the raw spectrum data such that the sum of intensity values in the specific wavelength range among the intensity values for each wavelength included in the raw spectrum data coincides with the reference value. Specifically, the second controller 1410 may calculate a ratio between reference values for the sum of intensity values included in the specific wavelength range among the intensity values for each wavelength of the raw spectrum data and multiply the intensity values for each wavelength of the raw spectrum data by the ratio between the reference values for the sum of the intensity values included in the specific wavelength range, thereby adjusting magnitudes of the intensity values for each wavelength.

Here, the specific wavelength range may be selected as an arbitrary range. For example, the specific wavelength range may coincide with the standard wavelength range used as the input data. Alternatively, the specific wavelength range may be an entire wavelength range observed in the LIBS unit 1200. Also alternatively, the specific wavelength range may include the standard wavelength range used as the input data and may be a range included in the wavelength range observed in the LIBS unit 1200.

In the above description, the sum of the intensity values for each wavelength included in the specific wavelength range is used, but an average of the intensity values may be used instead of the sum thereof.

According to another example of the normalization according to one embodiment of the present disclosure, the diagnostic unit 1400 may perform the normalization on the basis of energy (or a power density) of the observed spectrum.

Figure 50:
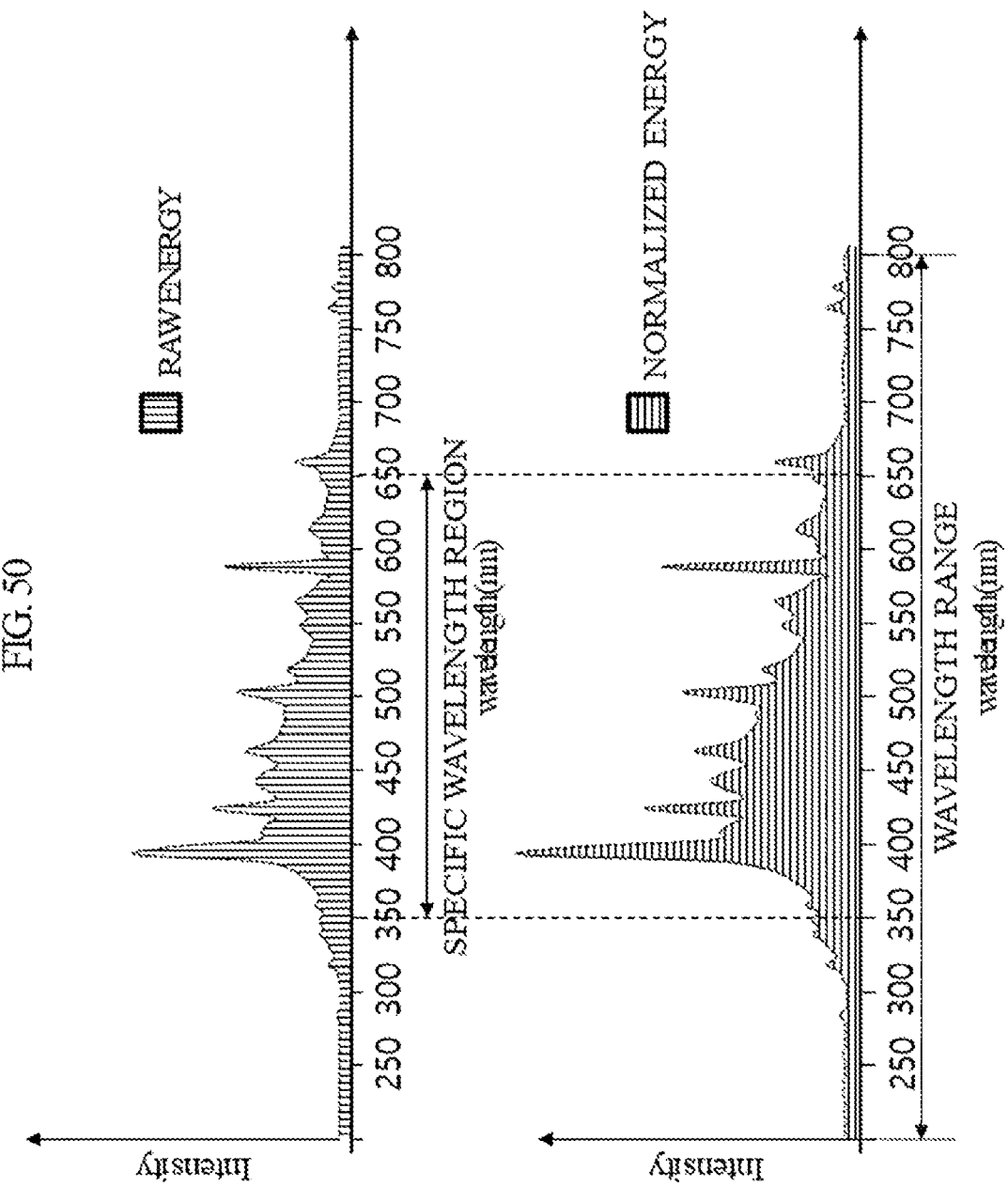
FIG. 50 is a diagram illustrating an example of normalization using a spectrum curve according to one embodiment of the present disclosure.

FIG. 50 is a diagram illustrating an example of normalization using a spectrum curve according to one embodiment of the present disclosure.

The diagnostic unit 1400 may generate a spectrum curve on the wavelength-light intensity axis from the raw spectrum data, calculate energy (or power density) by integrating the spectrum curve, and perform the normalization using the calculated energy.

For example, the second controller 1410 may generate a raw spectrum curve from the raw spectrum data on the basis of the wavelength-light intensity with respect to the raw spectrum. The second memory 1450 may store a specific wavelength range and/or a reference value. For example, the second controller 1410 may calculate the energy (or power density) of the raw spectrum by integrating the raw spectrum curve with respect to the specific wavelength range stored in the memory 1450. The second controller 1410 may calculate a ratio of the reference value to the calculated energy (or power density), multiply a magnitude of the raw spectrum curve by the ratio of the reference value to the energy (or power density) to generate a processed spectrum curve, and obtain light intensity values for standard wavelengths from the processed spectrum curve, thereby generating processed spectrum data.

Alternatively, the second controller 1410 may calculate the energy (or power density) of the raw spectrum. The second controller 1410 may adjust the magnitudes of the intensity values for each wavelength by multiplying the intensity values for each wavelength of the raw spectrum data by the calculated ratio of the reference value to the energy (or power density) of the raw spectrum.

Here, the specific wavelength range may be selected as an arbitrary range. For example, the specific wavelength range may coincide with the standard wavelength range used as the input data. Alternatively, the specific wavelength range may be an entire wavelength range observed in the LIBS unit 1200. Also alternatively, the specific wavelength range may include the standard wavelength range used as the input data and may be a range included in the wavelength range observed in the LIBS unit 1200.

The above-described standardization and normalization, which are examples of the preprocessing, may be performed separately or by being combined with each other. Hereinafter, an embodiment of generating the processed spectrum data used as the input data of the machine learning model from the raw spectrum data using the above-described examples of preprocessing will be described.

Figure 51:
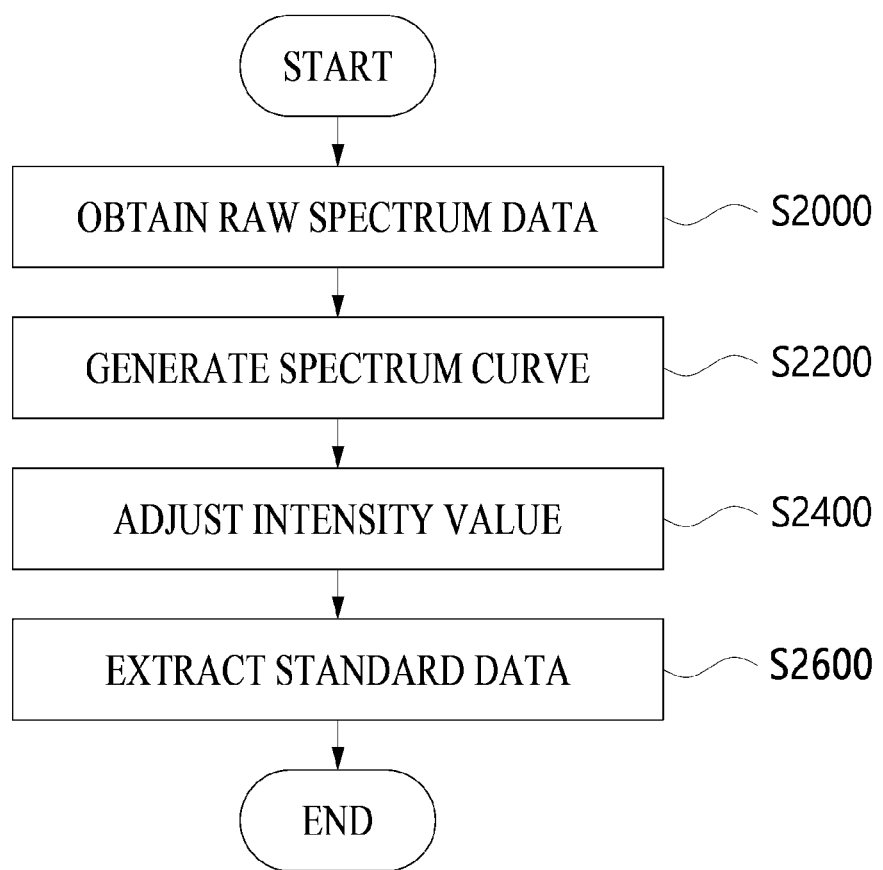
FIG. 51 is a flowchart illustrating an example of a method of generating processed spectrum data used as input data of a machine learning model according to one embodiment of the present disclosure.

FIG. 51 is a flowchart illustrating an example of a method of generating processed spectrum data used as input data of a machine learning model according to one embodiment of the present disclosure.

A method of generating processed spectrum data according to one embodiment of the present disclosure may include obtaining raw spectrum data (S2000), generating a spectrum curve (S2200), and adjusting intensity values with respect to the generated spectrum curve (S2400), and extracting standard data from the spectrum curve of which intensity values are adjusted (S2600).

The diagnostic unit 1400 may perform the method of generating processed spectrum data.

First, the diagnostic unit 1400 may obtain the raw spectrum data (S2000). Specifically, the second controller 1410 may obtain the raw spectrum data from the LIBS unit 1200.

Next, the diagnostic unit 1400 may generate the spectrum curve (S2200). Specifically, the second controller 1410 may generate the spectrum curve on the wavelength-light intensity domain on the basis of the intensity value for each wavelength of the raw spectrum data.

Then, the diagnostic unit 1400 may adjust the intensity value of the spectrum curve (S2400). Specifically, the second controller 1410 may generate the spectrum curve of which intensity is adjusted by adjusting the intensity value of the spectrum curve in conjunction with the raw spectrum data to correspond to a reference value with reference to reference value information stored in the second memory 1450.

Next, the diagnostic unit 1400 may extract standard data corresponding to a specification of the input data of the artificial neural network. Specifically, the second controller 1410 may generate processed spectrum data by extract standard spectrum data corresponding to a standard specification of the input node of the artificial neural network from the spectrum curve of which intensity value is adjusted with reference to standard specification information stored in the second memory 1450.

When the processed spectrum data is generated, the diagnostic unit 1400 may obtain a diagnostic result from the processed spectrum data. Specifically, the second controller

1410 may input the processed spectrum data to an input layer of the artificial neural network with reference to the artificial neural network stored in the second memory 1450, thereby obtaining a result of whether a disease is present from the processed spectrum data.

In addition to the above examples, it is also possible for the diagnostic system 100 according to one embodiment of the present disclosure to perform a preprocessing process by combining standardization with normalization. Here, one preprocessing process may be performed and then another preprocessing process may be performed. In this case, a subsequent preprocessing process may be performed on the processed spectrum data generated in the previous preprocessing process instead of the raw spectrum data.

Hereinafter, some examples of determining the diagnostic result from the spectrum data using the artificial neural network according to one embodiment of the present disclosure will be described.

Figure 52:
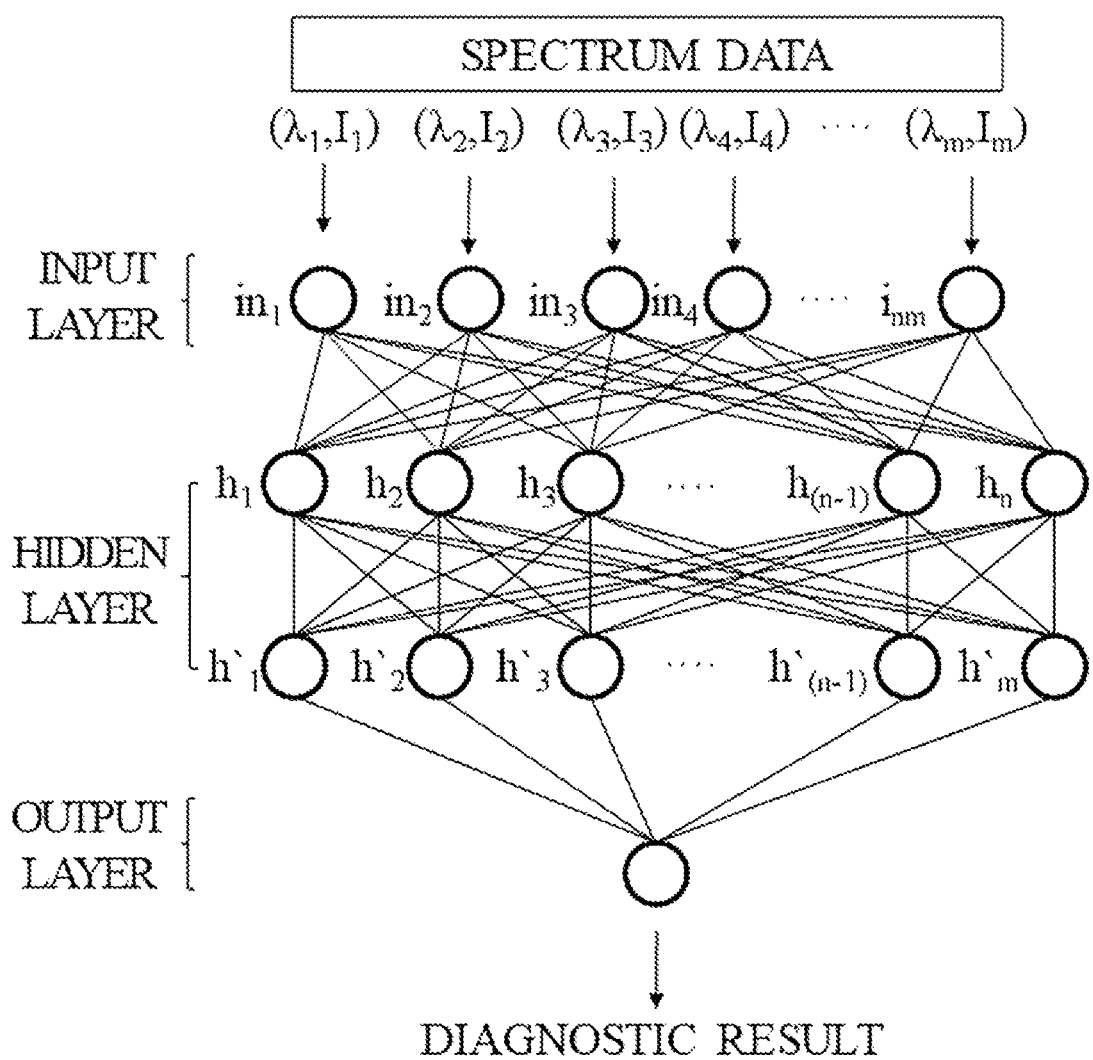
FIG. 52 is a diagram illustrating an example of determining a diagnosis result from a single piece of spectrum data using an artificial neural network according to one embodiment of the present disclosure.

FIG. 52 is a diagram illustrating an example of determining a diagnosis result from a single piece of spectrum data using an artificial neural network according to one embodiment of the present disclosure.

Referring to FIG. 52, the diagnostic unit 1400 may perform diagnosis on a target specimen from a single piece of spectrum data obtained from the target specimen using the artificial neural network.

Specifically, the second controller 1410 may input raw spectrum data obtained from the target specimen to the input layer of the artificial neural network as input data using the artificial neural network stored in the second memory 1450 and obtain a diagnostic result for the target specimen according to a computational result which is performed by the artificial neural network on the basis of the raw spectrum data obtained from the target specimen.

Here, the artificial neural network may be trained using a learning-set constituted of reference spectrum data tagged with the diagnostic result for each single piece of spectrum data. For example, the artificial neural network may be trained using a learning-set including large amount pieces of data (about 4000 or more) containing a single piece of spectrum data tagged as having a disease at an intensity value for each wavelength with respect to a diseased specimen and/or a single piece of spectrum tagged as having no disease at an intensity value for each wavelength with respect to a non-diseased specimen.

Further, the spectrum data input to the artificial neural network may not only be directly input as the raw spectrum data, but may also be processed spectrum data on which the preprocessing is performed. That is, when the diagnostic unit 1400 obtains the single piece of raw spectrum data from the LIBS unit 1200, the diagnostic unit 1400 may not only obtain a diagnostic result for the target specimen from the single piece of raw spectrum data by inputting the obtained single piece of raw spectrum data to the artificial neural network, but may also obtain a diagnostic result for the target specimen from a single piece of processed spectrum data by inputting the single piece of processed spectrum data, which is obtained by processing the single piece of raw spectrum data obtained from the LIBS unit 1200, to the artificial neural network.

Here, the single piece of spectrum data does not mean the spectrum data measured only once with respect to the target specimen in the LIBS unit 1200, but is a single piece of spectrum data generated using pieces of spectrum data measured with respect to the same target specimen. For example, the single piece of spectrum data may be an average value or the sum of the pieces of spectrum data measured with respect to the same target specimen. That is, the diagnostic unit 1400 may obtain the spectrum data measured multiple times with respect to the same target specimen from the LIBS unit 1200 and use the average value between the obtained spectrum data or the sum value of the obtained spectrum data as the input data of the artificial neural network. As described above, the pieces of spectrum data measured multiple times with respect to the same target specimen are processed into a single piece of spectrum data and then the single piece of spectrum data is used such that influence of error factors which may be included in the spectrum data may be effectively reduced rather than using the spectrum data measured only once with respect to the target specimen. However, when the pieces of spectrum data measured with respect to the target specimen are used, it may be preferable to adjust intensity values of the pieces of spectrum data, that is, to preferentially perform the above-described normalization.

In the following description of the present disclosure, for convenience of description, exemplary embodiments of diagnosing a skin cancer using the artificial neural network will be described. For example, when skin cancer diagnosis is performed from the single piece of spectrum data using the artificial neural network according to one embodiment of the present disclosure, the target specimen may be tissue suspected of a skin cancer, and the diagnosis result may be a result of whether the skin cancer is present in the target specimen. However, owing to the above description, it should be understood that the diagnosis according to the present disclosure is not limited to the skin cancer.

As described above, the obtaining of the diagnostic result from the single piece of spectrum data in conjunction with the target specimen using the artificial neural network has been described. However, when only the single piece of spectrum data with respect to the target specimen is used and the artificial neural network performs calculation, the artificial neural network may have low ability to cope with various situational factors which may be included in spectrum data. For example, even between spectrum data obtained from the same skin tissue of various patients, the spectrum data having different characteristics may be measured according to specificity such as age, gender, race, and an environment of each patient having the tissue. As a detailed example, according to the race of the patient, an intensity value of an element peak, which indicates a specific element included in the skin tissue, included in the spectrum data may be differently measured. In this case, when specificity of a patient between a patient population which is a reference for measuring reference spectrum data used for learning of the artificial neural network and a patient which will be a target of actual diagnosis is varied, accuracy of the diagnostic result may be degraded. In this case, when a diagnosis result is obtained from combined spectrum data in which the pieces of spectrum data obtained from a plurality of objects are combined, influence due to specificity of a patient is reduced such that the accuracy of the diagnostic result may be improved. For example, a difference value between spectrum data measured from tissue in which a skin cancer is present and spectrum data measured from non-diseased tissue may include only a significant difference between the non-diseased tissue and tissue of the skin cancer without being affected by specificity of a patient such that the accuracy of the diagnostic result may be improved using the difference value.

Alternatively, diagnosis may be performed on an object, which is a target of the diagnosis, from pieces of spectrum data using the artificial neural network.

Figure 53:
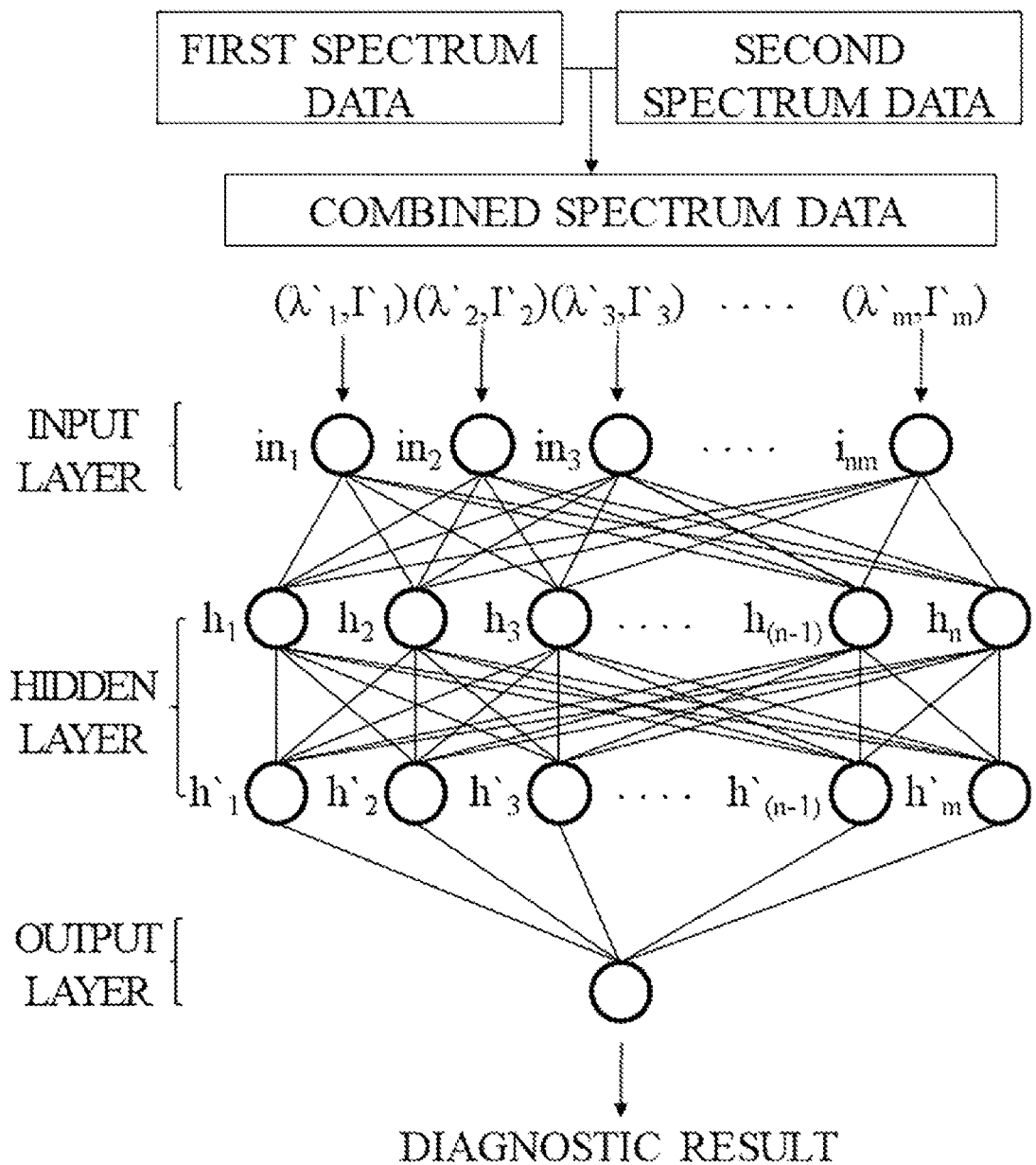
FIG. 53 is a diagram illustrating determination of a diagnosis result from spectrum data combining pieces of spectrum data using the artificial neural network according to one embodiment of the present disclosure.

FIG. 53 is a diagram illustrating determination of a diagnosis result from spectrum data combining pieces of spectrum data using the artificial neural network according to one embodiment of the present disclosure.

Referring to FIG. 53, the diagnostic unit 1400 may perform diagnosis on a target specimen from spectrum data in which the pieces of spectrum data are combined using the artificial neural network.

Specifically, the second controller 1410 may obtains pieces of raw spectrum data from the LIBS unit 1200, generate combined spectrum data in which the pieces of raw spectrum data are combined from the obtained pieces of raw spectrum data, and input the generated combined spectrum data to the input layer of the artificial neural network as input data of the artificial neural network, thereby obtaining a diagnostic result for the target specimen according to a computational result which is performed by the artificial neural network on the basis of the combined spectrum data.

Here, the artificial neural network may be trained using a learning-set constituted of the reference spectrum data tagged with the diagnosis result with respect to the combined spectrum data in which the spectrum data obtained from the target specimen and the reference specimen are combined. For example, the artificial neural network may be trained using a learning-set which includes the spectrum data tagged as the presence of a disease with a difference value between the measured spectrum data measured from the diseased specimen and the non-diseased specimen and/or the spectrum data tagged as the absence of a disease with a difference value between the measured spectrum data measured from the non-diseased specimen and another non-diseased specimen.

Further, the combined spectrum data may be generated in various manners. For example, the combined spectrum data may be a difference value of intensity values for each wavelength at wavelengths corresponding to each other of two or more pieces of spectrum data. Alternatively, the combined spectrum data may be a ratio value between intensity values for each wavelength at wavelengths corresponding to each other of two or more pieces of spectrum data. Also alternatively, the combined spectrum data may be a sum value of intensity values for each wavelength at wavelengths corresponding to each other of two or more pieces of spectrum data. Further alternatively, the combined spectrum data may be a multiplication value of intensity values for each wavelength at wavelengths corresponding to each other of two or more pieces of spectrum data.

Further, the spectrum data used to generate the combined spectrum data may be the above-described processed spectrum data as well as the above-described raw spectrum data. That is, the raw spectrum data may be preprocessed before being processed into the combined spectrum data, and the processed spectrum data may be processed into the combined spectrum data. Alternatively, the raw spectrum data may be first processed into the combined spectrum data, and the combined spectrum data may be preprocessed and processed into the processed spectrum data. That is, the input data of the artificial neural network may be the processed spectrum data obtained by preprocessing the combined spectrum data or may be the combined spectrum data obtained by combining the processed spectrum data. As described above, the present disclosure is not limited to the exemplary embodiments described herein, and the raw spectrum data may be preprocessed and/or combined in various orders or manners. A detailed content related to the processing of the pieces of raw spectrum data will be described below.

Further, the pieces of spectrum data may be spectrum data obtained from various objects. For example, when the pieces of spectrum data includes spectrum data obtained from the target specimen and spectrum data obtained from the reference specimen, the target specimen and the reference specimen may be distinguished according to a position at which each object is located or a disease state of each object.

Figure 54:
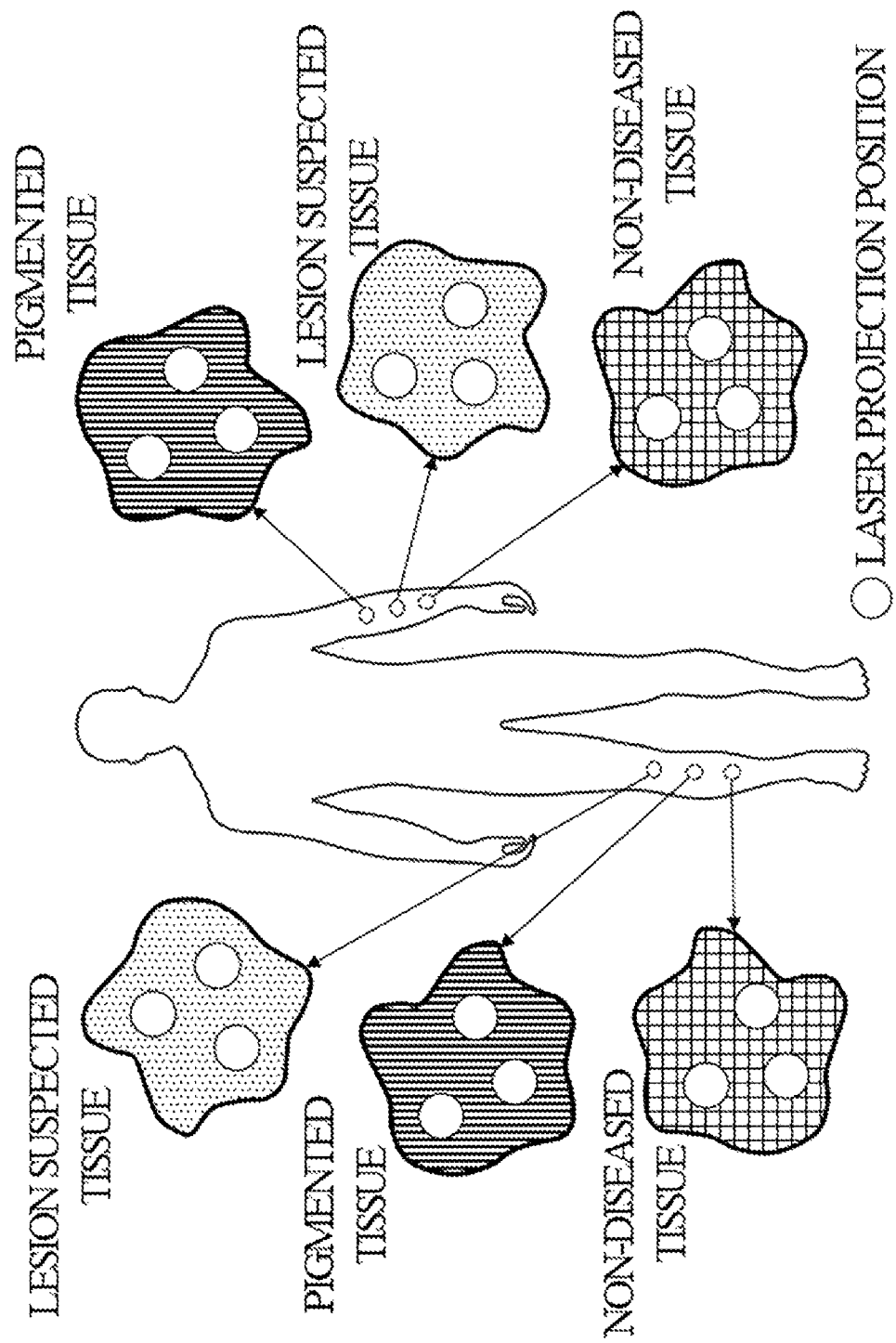
FIG. 54 is a diagram illustrating points at which pieces of spectrum data are obtained according to one embodiment of the present disclosure.

FIG. 54 is a diagram illustrating points at which pieces of spectrum data are obtained according to one embodiment of the present disclosure.

According to one embodiment of the present disclosure, the target specimen is an object which is a target of diagnosis and may be tissue suspected of having a disease. Further, the reference specimen may be a specimen for comparison or reference with the target specimen and may be tissue in which the presence or absence of a disease has been confirmed. For example, the reference specimen may be pigmented tissue such as a spot confirmed as non-diseased tissue. Alternatively, the reference specimen may be non-diseased tissue. That is, when the target specimen is determined, the reference specimen may be selected as tissue which may be easily compared with the target specimen among pieces of tissue in which the presence or absence of a disease has been confirmed.

For example, when skin cancer diagnosis is performed using a difference value between spectrum data of the target specimen and the reference specimen, as the artificial neural network is trained with reference spectrum data including a consistent difference value between the target specimen and the reference specimen, predictive performance of the artificial neural network may be improved so that it may be preferable to select a non-diseased specimen (or pigmented tissue), which has a consistent difference in spectral characteristic with a skin cancer tissue, as the reference specimen.

Specifically, as the normal tissue (or the pigmented tissue) is located to be closer to the skin cancer tissue, probability in that properties (e.g., a moisture content, hardness, ultraviolet rays exposure, a skin color, and the like) of the skin cancer tissue and the non-diseased tissue (or the pigmented tissue) are commonly included in the spectrum data may be increased. Therefore, when a spectral difference between the skin cancer tissue and the non-diseased tissue (or the pigmented tissue) located close to the skin cancer tissue, only a significant spectral difference in conjunction with a disease from which the nature of skin tissue is excluded, which is affected by the general environment between the skin cancer tissue and the non-diseased tissue, may be derived. That is, the reference specimen may be located within a predetermined distance from the target specimen such that the artificial neural network should be learned with the reference spectrum data dominantly including the significant difference related to a disease between the non-diseased tissue and the skin cancer tissue.

Further, according to one embodiment of the present disclosure, pieces of spectrum data obtained from the same target specimen or the reference specimen may be used for diagnosis. The pieces of spectrum data obtained from the same target specimen or the reference specimen are used such that it is possible to reduce a cause of an error included in the spectrum data.

As described above, it has been described that the diagnosis result for the skin cancer may be obtained from the combined spectrum data using the artificial neural network. In addition to the above examples, it is also possible for the diagnostic system 100 according to one embodiment of the present disclosure to obtain the input data by combining the preprocessing, such as the standardization and the normalization, with a process of combining the spectrum data, thereby obtaining the diagnostic result. Here, after one preprocessing process is performed, the spectrum data may be combined before another preprocessing process is performed, or after all preprocessing processes are performed, the spectrum data may be combined. In this case, instead of the raw spectrum data, a subsequent preprocessing process or the process of combining the spectrum data may be performed on the processed spectrum data generated in a previous preprocessing process, or the preprocessing process may be performed on the combined spectrum data.

Hereinafter, in a method of determining a diagnosis result from pieces of spectrum data using the artificial neural network according to one embodiment of the present disclosure, some detailed examples in which a process of preprocessing the pieces of spectrum data and a processing process of generating the combined spectrum data are performed in combination will be described with reference to the drawings.

Figure 55:
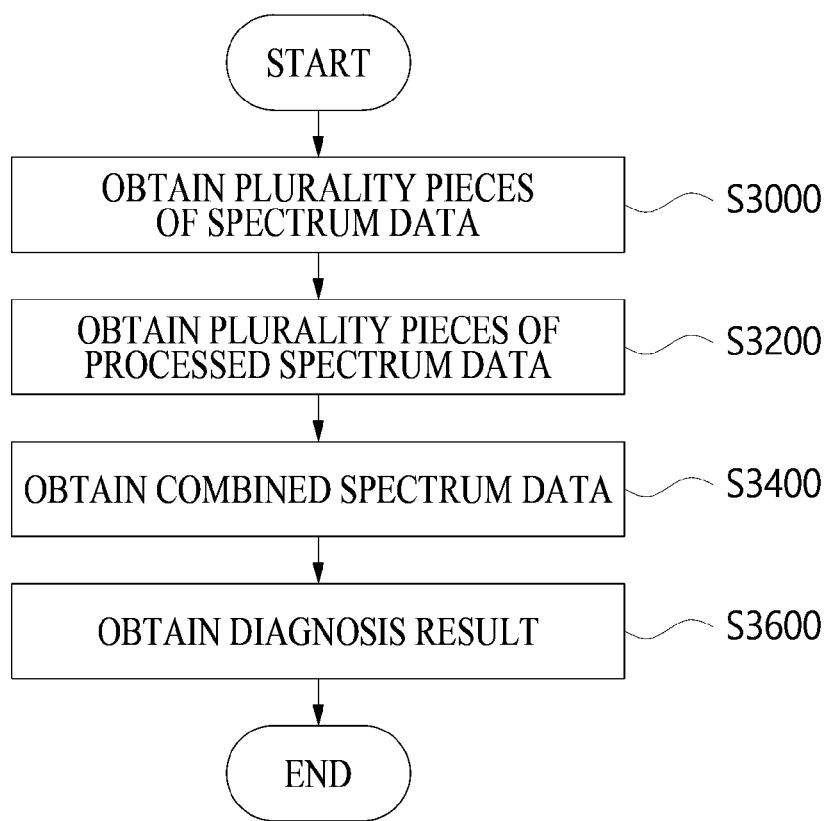
FIG. 55 is a flowchart illustrating a first detailed example of a method of determining a diagnosis result from pieces of spectrum data using the artificial neural network according to one embodiment of the present disclosure.

FIG. 55 is a flowchart illustrating a first detailed example of a method of determining a diagnosis result from pieces of spectrum data using the artificial neural network according to one embodiment of the present disclosure.

According to one embodiment of the present disclosure, the method of determining a diagnosis result from pieces of spectrum data using the artificial neural network may include obtaining pieces of raw spectrum data (S3000), obtaining pieces of processed spectrum data (S3200), obtaining combined spectrum data (S3400), and obtaining a diagnosis result (S3600).

According to one embodiment of the present disclosure, the diagnostic unit 1400 may perform the method of determining a diagnosis result.

First, in the obtaining of the pieces of raw spectrum data (S3000), the diagnostic unit 1400 may obtain the pieces of raw spectrum data from the LIBS unit 1200. Specifically, the second controller 1410 may obtain raw spectrum data in conjunction with the target specimen and raw spectrum data in conjunction with the reference specimen, which are obtained in the LIBS unit 1200.

Thereafter, in the obtaining of the pieces of processed spectrum data (S3200), the diagnostic unit 1400 may obtain the pieces of processed spectrum data by preprocessing the plurality of raw spectrum data. Specifically, the second controller 1410 may obtain the pieces of processed spectrum data by normalizing and standardizing the raw spectrum data in conjunction with the target specimen and the raw spectrum data in conjunction with the reference specimen. Here, the normalization and the standardization may be performed in a manner the same as or similar to that described above.

Then, in the obtaining of the combined spectrum data (S3400), the diagnostic unit 1400 may obtain the combined spectrum data by combining the pieces of processed spectrum data. Specifically, the second controller 1410 may obtain the combined spectrum data by combining processed spectrum data in conjunction with the target specimen and processed spectrum data in conjunction with the reference specimen. Here, the process of combining the pieces of processed spectrum data may be performed in a manner the same as or similar to that described above.

Thereafter, in the obtaining of the diagnosis result (S3600), the diagnostic unit 1400 may obtain the diagnosis result from the combined spectrum data using the artificial neural network. Specifically, with reference to the artificial neural network stored in the second memory 1450, the second controller 1410 may input the combined spectrum data to the input layer of the artificial neural network and obtain a diagnostic result value derived according to calculation of the artificial neural network.

Figure 56:
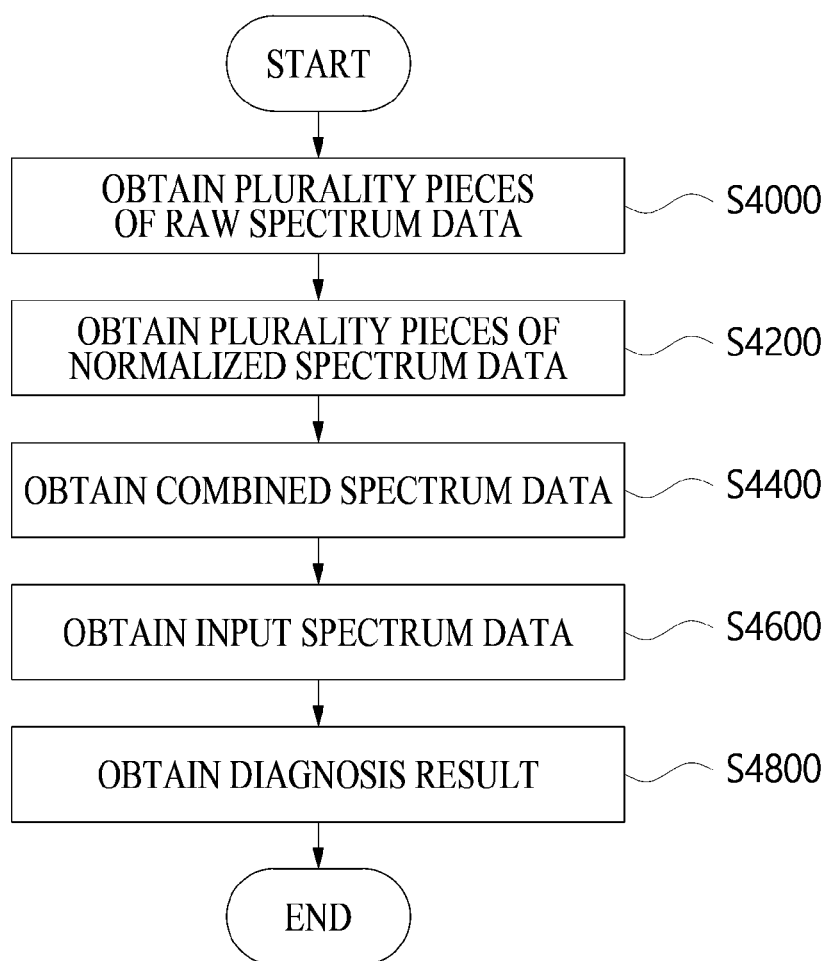
FIG. 56 is a flowchart illustrating a second detailed example of a method of determining a diagnosis result from pieces of spectrum data using the artificial neural network according to one embodiment of the present disclosure.

FIG. 56 is a flowchart illustrating a second detailed example of a method of determining a diagnosis result from pieces of spectrum data using the artificial neural network according to one embodiment of the present disclosure.

According to one embodiment of the present disclosure, the method of determining a diagnosis result from pieces of spectrum data using the artificial neural network may include obtaining pieces of raw spectrum data (S4000), obtaining pieces of normalized spectrum data (S4200), obtaining a combined spectrum data (S4400), obtaining an input spectrum data (S4600), and obtaining a diagnosis result (S4800).

According to one embodiment of the present disclosure, the diagnostic unit 1400 may perform the method of determining a diagnosis result.

First, in the obtaining of the pieces of raw spectrum data (S4000), the diagnostic unit 1400 may obtain the pieces of raw spectrum data from the LIBS unit 1200. Specifically, the second controller 1410 may obtain raw spectrum data in conjunction with the target specimen and raw spectrum data in conjunction with the reference specimen, which are obtained in the LIBS unit 1200.

Thereafter, in the obtaining of the pieces of normalized spectrum data (S4200), the diagnostic unit 1400 may obtain the pieces of normalized spectrum data by normalizing the pieces of raw spectrum data. Specifically, the second controller 1410 may normalize raw spectrum data in conjunction with the target specimen and raw spectrum data in conjunction with the reference specimen to obtain first processed spectrum data in which the raw spectrum data in conjunction with the target specimen is normalized and second processed spectrum data in which the raw spectrum data in conjunction with the reference specimen is normalized.

Then, in the obtaining of the combined spectrum data (S4400), the diagnostic unit 1400 may obtain the combined spectrum data by combining the pieces of normalized spectrum data. Specifically, the second controller 1410 may obtain the combined spectrum data by combining the first processed spectrum data with the second processed spectrum data.

Then, in the obtaining of the input spectrum data (S4600), the diagnostic unit 1400 may obtain the input spectrum data by standardizing the combined spectrum data. Specifically, the second controller 1410 may standardize the combined spectrum data to obtain input data corresponding to a input standard of the artificial neural network.

Thereafter, in the obtaining of the diagnosis result (S4800), the diagnostic unit 1400 may obtain the diagnosis result from the input data using the artificial neural network. Specifically, with reference to the artificial neural network stored in the second memory 1450, the second controller 1410 may input the input data to the input layer of the artificial neural network and obtain a diagnostic result value derived according to calculation of the artificial neural network.

As described above, the examples of obtaining the diagnosis result from the combined spectrum data by combining the pieces of spectrum data using the artificial neural network have been described. However, in addition to the above description, according to one embodiment of the present disclosure, a diagnostic result may be obtained by inputting the pieces of spectrum data to the artificial neural network without combining the pieces of spectrum data.

Figure 57:
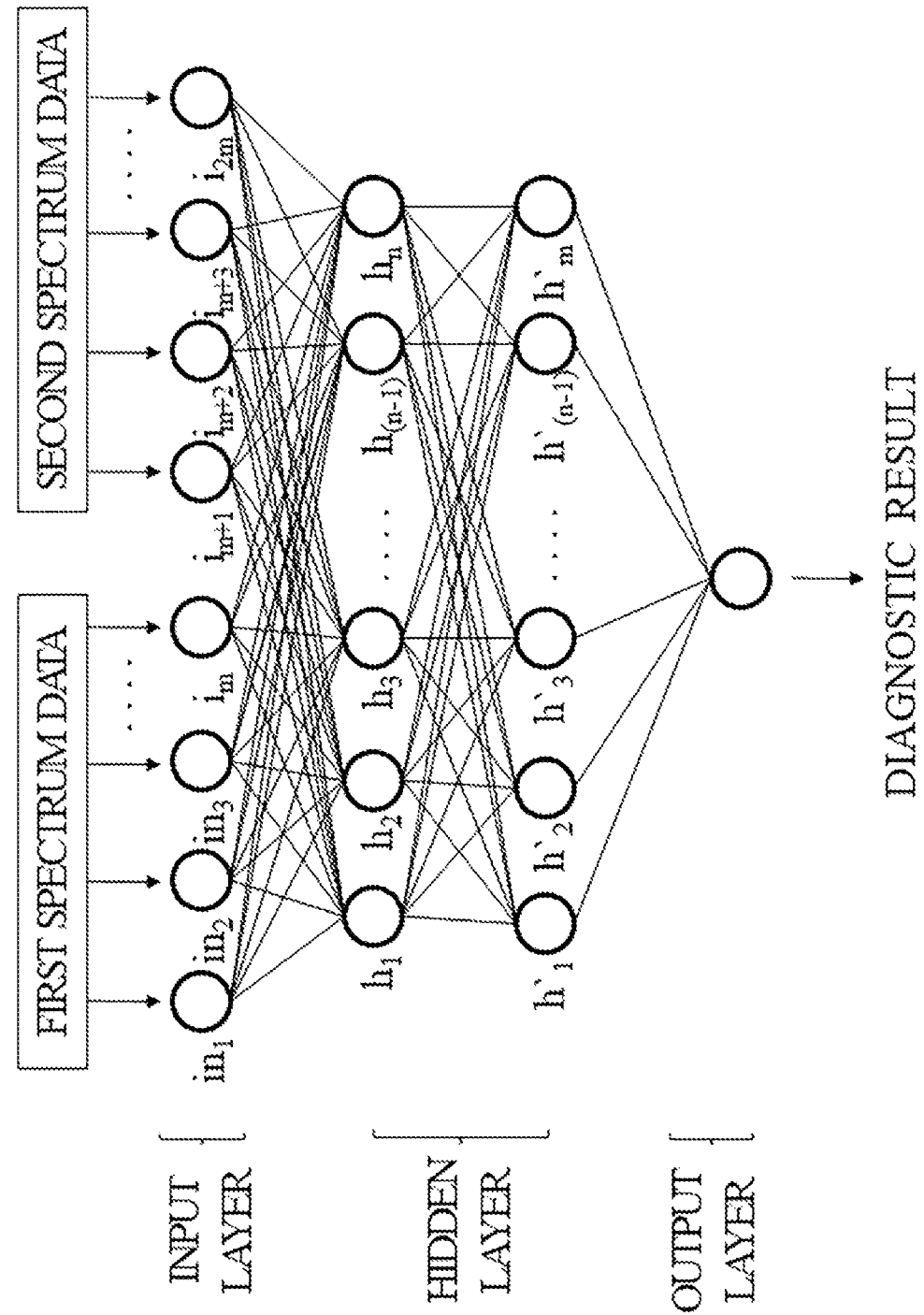
FIG. 57 is a diagram illustrating another example of determining a diagnosis result from pieces of spectrum data using the artificial neural network according to one embodiment of the present disclosure.

FIG. 57 is a diagram illustrating determination of a diagnosis result from pieces of spectrum data using the artificial neural network according to another embodiment of the present disclosure.

Referring to FIG. 57, the diagnostic unit 1400 may perform diagnosis on a target specimen from the pieces of spectrum data using the artificial neural network.

Specifically, the second controller 1410 may obtain raw spectrum data in conjunction with the target specimen and raw spectrum data in conjunction with the reference specimen from the LIBS unit 1200 and input the obtained raw spectrum data in conjunction with the target specimen and the obtained raw spectrum data in conjunction with the reference specimen to the input layer of the artificial neural network as input data of the artificial neural network, thereby obtaining a diagnostic result for the target specimen according to a computational result which is performed by the artificial neural network on the basis of the pieces of raw spectrum data.

Here, the artificial neural network may be trained using a learning-set constituted of reference spectrum data tagged with the diagnosis result with respect to all the pieces of spectrum data obtained from the target specimen and the reference specimen.

Here, the raw spectrum data may include processed spectrum data. That is, the second controller 1410 may directly use the raw spectrum data in conjunction with the target specimen and the raw spectrum data in conjunction with the reference specimen or may perform a preprocessing process on each of the pieces of raw spectrum data to generate pieces of processed spectrum data with respect to the pieces of raw spectrum data and use all the pieces of processed spectrum data.

As described above, the obtaining of the diagnosis result from the combined spectrum data obtained by combining the pieces of spectrum data using the artificial neural network or from the pieces of spectrum data has been described. Here, the raw spectrum data in conjunction with the target specimen or the raw spectrum data in conjunction with the reference specimen may be spectrum data generated using the spectrum data measured multiple times with respect to the same target specimen and/or reference specimen in the same or similar manner as described above. For example, the raw spectrum data in conjunction with the target specimen and/or the reference specimen may be an average value or a sum value of the pieces of spectrum data measured multiple times with respect to the target specimen or the reference specimen.

In addition, each of the pieces of spectrum data does not need to be obtained in the same manner and may be obtained in various manners. That is, the spectrum data obtained from the target specimen and the spectrum data obtained from the reference specimen may be obtained in various manners. For example, the spectrum data obtained from the target specimen may be spectrum data generated using values measured multiple times, and the spectrum data obtained from the reference specimen may be spectrum data measured only once. Alternatively, the raw spectrum data obtained from the target specimen may be generated using spectrum data measured multiple times with respect to the same point in the target specimen, and the raw spectrum data obtained from the reference specimen may be an average value of pieces of spectrum data measured with respect to various laser projection points in the reference specimen. Also alternatively, the combined spectrum data may be generated by combining the raw spectrum data in conjunction with the target specimen measured with respect to various laser projection points in the target specimen and the raw spectrum data obtained measured only once with respect to the reference specimen.

Hereinafter, various examples of obtaining the diagnosis result from the spectrum data using the artificial neural network according to one embodiment of the present disclosure have been described. However, owing to various causes (e.g., a flash), an effect of an error which cannot be corrected even when a preprocessing process such as normalization is performed may be included in the intensity value for each wavelength of the spectrum data. When an error occurs in the intensity value for each wavelength having high feature importance, accuracy of result prediction of the artificial neural network may be degraded. Therefore, when an error which cannot be corrected is present in the spectrum data, it may be inevitable to obtain the spectrum data again.

Figure 58:
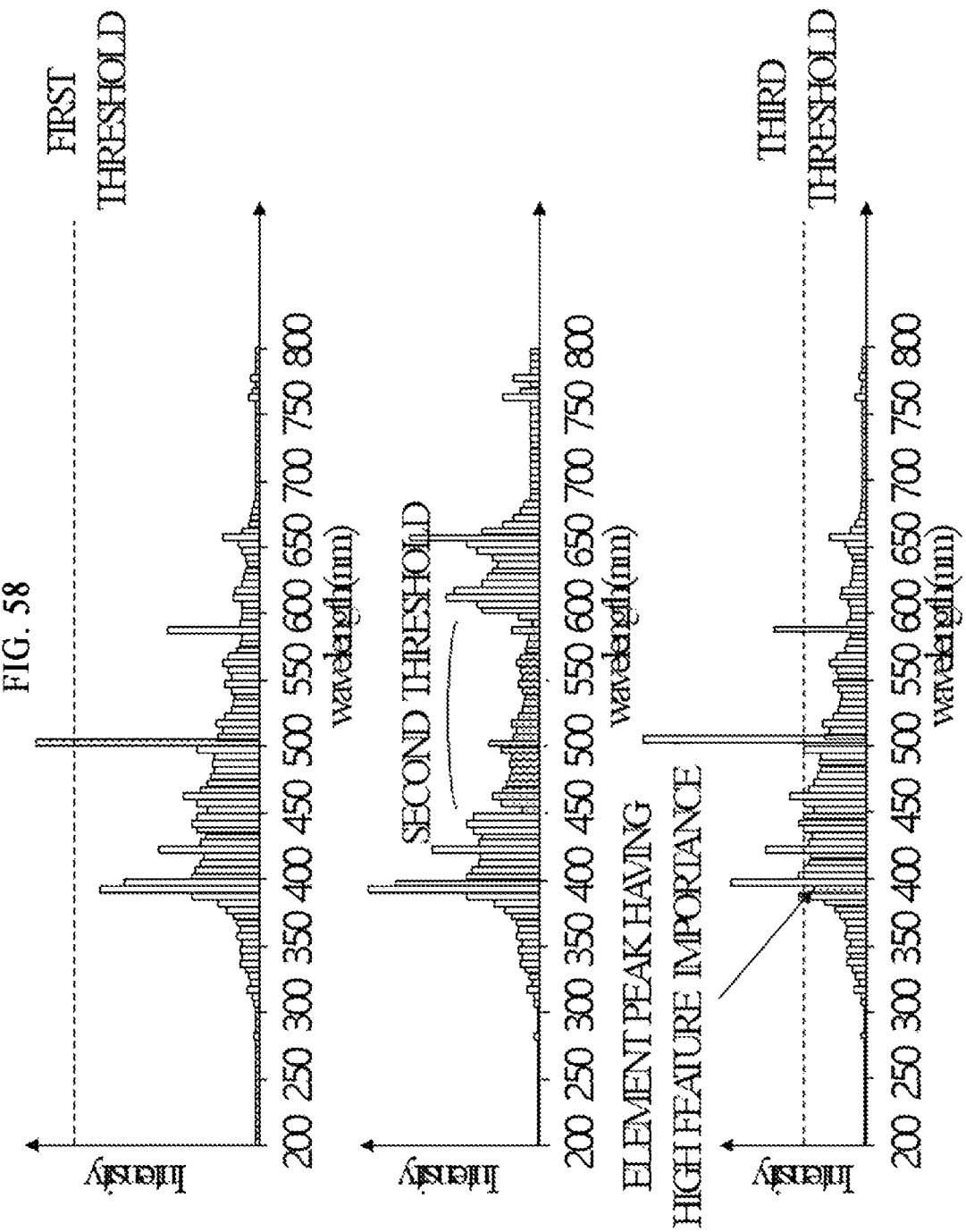
FIG. 58 is a diagram illustrating an error of spectrum data according to one embodiment of the present disclosure.

FIG. 58 is a diagram illustrating an error of spectrum data according to one embodiment of the present disclosure.

According to one embodiment of the present disclosure, the diagnostic unit 1400 may determine whether an error is present in the spectrum data and transmit a signal according to the determination result to the LIBS unit 1200.

Specifically, the second memory 1450 may include threshold information in conjunction with the error of the spectrum data. The second controller 1410 may obtain the raw spectrum data from the LIBS unit 1200, determine whether the obtained raw spectrum data includes an intensity value error for each wavelength above or below a threshold with reference to the threshold information in conjunction with the error of the spectrum data stored in the second memory 1450, and transmit a signal according to the determination result to the LIBS unit 1200.

Here, the signal according to the determination result may be transmitted to an output part. The output part obtaining the signal according to the determination result may provide information on the presence of the error in the spectrum data or provide a notification regarding laser re-projection.

Referring to FIG. 58, the threshold which is a determination reference for determining whether the error is present in the spectrum data may be variously set.

For example, the threshold may be a first threshold which is set on the basis of the intensity value for each wavelength. The first threshold may be a reference on a strong measurement result of any intensity value for each wavelength included in the spectrum data such that correction by the preprocessing is impossible.

Alternatively, the threshold may be a second threshold which is set on the basis of a sum value of intensity values for each wavelength in a specific wavelength range. The second threshold may be a reference on a weak measurement of any intensity value for each wavelength included in the spectrum data such that correction by the preprocessing is impossible.

Also alternatively, the threshold may be a third threshold which is set on the basis of an intensity value at a wavelength having high feature importance. The third threshold may be a reference on a weak measurement of any intensity value for each wavelength having high feature importance such that correction by the preprocessing is impossible.

Hereinafter, a mechanical structure of the LIBS unit 1200 according to one embodiment of the present disclosure will be described.

Figure 59:
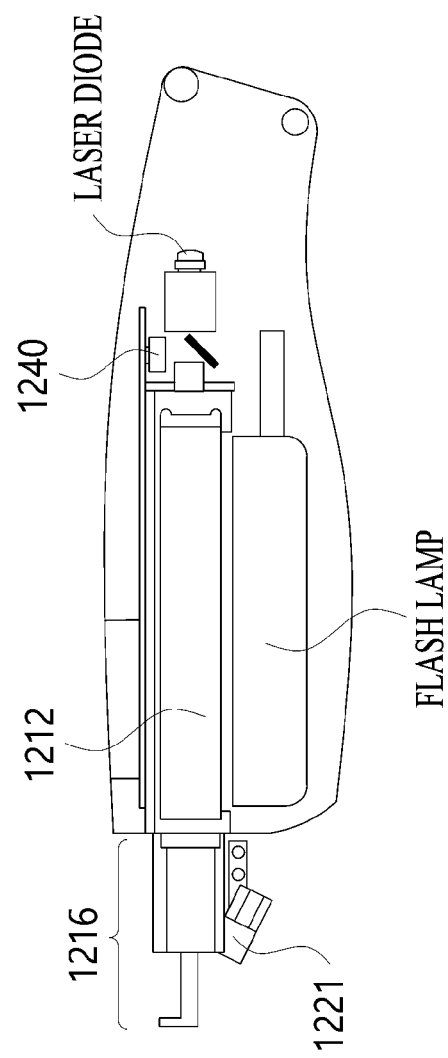
FIG. 59 is a diagram illustrating an exterior and an interior of the LIBS unit according to one embodiment of the present disclosure.

FIG. 59 is a diagram illustrating an exterior and an interior of the LIBS unit 1200 according to one embodiment of the present disclosure.

According to one embodiment of the present disclosure, the LIBS unit 1200 may include a housing, the active laser medium 1212, a flash lamp, the triggering module 1240, and a laser diode.

The housing may include an interior space for accommodating the active laser medium 1212, the flash lamp, the triggering module 1240, and the laser diode and include an opening facing the specimen 1. Further, the guide member 1216, which extends from one end of the housing toward the specimen 1 and an end portion of the guide member 1216 is in contact with a periphery of the specimen 1, may be formed outside the housing. Further, the light receiving member 1221 for receiving light due to plasma ablation induced in the specimen 1 may be disposed outside the housing.

The flash lamp may supply energy to the active laser medium 1212 to oscillate a laser. The flash lamp may be disposed adjacent to the active laser medium 1212 in the housing so as to supply the energy to the active laser medium 1212.

When the LIBS unit 1200 projects the laser to the specimen 1, the laser diode may emit an indication beam indicating a location at which the laser is projected. The laser diode may be disposed inside or outside the housing such that the laser emitted by the active laser medium 1212 and the indication beam emitted from the laser diode meet at the specimen 1. Alternatively, the laser diode may be disposed inside or outside the housing such that the indication beam emitted from the laser diode is located within a predetermined range from a point at which the laser by the active laser medium 1212 is projected to the specimen 1.

Here, when the active laser medium 1212 is located between the laser diode and the specimen 1, the indication beam emitted from the laser diode may be projected to the specimen 1 by passing through the active laser medium 1212.

The triggering module 1240 may be disposed inside or outside the housing to perform a triggering operation.

Here, the triggering module 1240 may be disposed inside or outside the housing.

According to one embodiment of the present disclosure, the triggering module 1240 may be disposed inside the housing and receive light reflected from the specimen 1 to perform a triggering operation. For example, the triggering module 1240 may receive the light reflected due to the indication beam emitted from the laser diode and projected to the specimen 1 to perform the triggering operation. Also alternatively, the triggering module 1240 may receive the light reflected due to the laser emitted by the active laser medium 1212 and projected to the specimen 1 to perform the triggering operation.

Here, the triggering module 1240 may indirectly receive the light reflected from the specimen 1 through a mirror without directly receiving the light. For example, a reflective member may be disposed between the laser diode and the active laser medium 1212 and the triggering module 1240 may receive the light reflected from specimen 1 through the mirror. In this case, the reflective member disposed between the laser diode and the active laser medium 1212 may allow at least a portion of the indication beam emitted from the laser diode to pass therethrough and reflect the remaining thereof. Thus, the triggering module 1240 may receive the light reflected from the specimen 1 without being disposed on a path of the indication beam emitted from the laser diode.

Meanwhile, the triggering module 1240 may be disposed inside the housing, located between the active laser medium 1212 and specimen 1, or disposed outside the housing.

As described above, although it has been described that the LIBS unit 1200 includes the housing, a module for projecting a laser to the specimen 1 was included in the housing, the guide member 1216 for guiding the laser to the specimen 1, and the light receiving member 1221 for receiving the light due to induced plasma are disposed outside the housing, the structure of the LIBS unit 1200 is not limited thereto, and the components located inside and outside the housing may be disposed differently from the above description as necessary.

The method according to the embodiment may be implemented in the form of program commands executable through various computer means and be recorded in a computer-readable medium. The computer-readable medium may include program instructions, data files, data structures, and the like in alone or a combination thereof. The program instructions recorded in the computer-readable medium may be specially designed and configured for the embodiment or may be effective to those skilled in the computer software. Examples of the computer-readable recording media include magnetic media such as a hard disk, a floppy disk, and a magnetic tape, optical recording media such as a compact disc read only memory (CD-ROM) and a digital versatile disc (DVD), a magneto-optical medium such as a floptical disk, and hardware devices specifically configured to store and execute program commands, such as a read only memory (ROM), a random access memory (RAM), a flash memory, and the like. Examples of the program instructions include machine language codes generated by a compiler, as well as high-level language codes which are executable by a computer using an interpreter or the like. The above-described hardware devices may be configured to operate as one or more software modules so as to perform an operation of the embodiment, and vice versa.

In accordance with the present disclosure, a continuous spectrum of light generated from plasma, which is generated by projecting a pulsed laser to living tissue, is obtained and analyzed using an artificial neural network such that it is possible to accurately diagnose the presence or absence of a disease in the living tissue.

In accordance with the present disclosure, plasma emission and element specific emission exhibiting when a laser is projected to a specimen are collected and analyzed such that accurate or reliable disease diagnosis can be performed on a patient.

In accordance with the present disclosure, light having a continuous spectrum and a line spectrum exhibiting due to laser projection to the specimen is received and analyzed using an optical sensor operating before generating plasma to the specimen such that disease diagnosis can be performed on the patient.

In accordance with the present disclosure, a pulse duration, an intensity, energy per pulse, and a projection area of a high power pulsed laser are appropriately adjusted so as to apply only a level of energy which prevents damage to the specimen while the high power pulsed laser has a power density sufficient to induce local plasma generation such that the disease diagnose can be performed on the patient through LIBS analysis without damage to the body.

In accordance with the present disclosure, when the laser inducing plasma in the specimen is projected, a projection distance is made to be longer than a focal length and, when the projection distance is increased due to external factors, a spot size of the laser with respect to the specimen is increased such that the disease diagnosis can be safely performed to avoid damage to the specimen.

Further, in accordance with the present disclosure, when the laser inducing the plasma in the specimen is projected, energy applied to the specimen is controlled to minimize damage to the specimen through a lens having a predetermined spherical aberration such that the disease diagnosis can be safely performed.

In accordance with the present disclosure, an artificial neural network determines the presence or absence of a disease from a comparison value of spectrum data obtained from a suspicious specimen and a non-diseased specimen using LIBS such that a specificity factor of the patient can be reduced and thus the disease diagnosis can be universally performed on patients with different conditions such as race and gender.

In accordance with the present disclosure, a trigger signal is provided by projecting the laser to the specimen and detecting the projected laser or laser-derived light generated from the projected laser such that light detection for LIBS analysis can be started at an appropriate time.

In accordance with the present disclosure, a diagnostic result is obtained from the spectrum data using the artificial neural network and a variable due to influence of the surrounding environment is removed by adjusting a light intensity value included in the spectrum data such that the disease diagnosis can be universally performed even when the disease diagnosis is performed in various environment.

In accordance with the present disclosure, the diagnose disease is performed using the artificial neural network on the basis of the spectrum data and influence of a mechanical offset generated in a spectrum acquisition device is minimized by adjusting a data specification included in the spectrum data such that an accurate diagnostic result can be obtained.

The effects of the present disclosure are not limited to the above-described effects and other effects which are not described can be clearly understood by those skilled in the art to which the present disclosure pertains from the following description and the accompanying drawings.

As is described above, while the present disclosure has been shown and described with reference to the specific embodiments thereof, various changes and modification may be derived by those skilled in the art from the above description. For example, even when the described techniques may be performed in a different order than the described method, and/or elements of the described systems, structures, devices, circuits, and the like may be coupled to combined in other forms, or replaced or substituted by other components or equivalents, appropriate results can be achieved.

Therefore, other implementations, other embodiments, and equivalents to the appended claims fall within the scope of the following claims.

What is claimed is:

1. A laser-induced breakdown spectroscopy (LIBS) device, the device comprising:
   a laser projector configured to project a pulsed beam to a target;
   a light receiving module configured to receive a target light, wherein the target light includes a light in connection with plasma ablation induced at the target by the pulsed beam;
   a spectrometer optically connected to the light receiving module and configured to obtain a spectrum data related to the target light received from the light receiving module, the spectrometer comprising:
   a spectral member for separating light received from the light receiving module; and
   sensor arrays configured to detect the separated light from the spectral member in a predetermined wavelength band, wherein the sensor arrays include a plurality of image sensors arranged to measure a plurality of intensities of the separated light corresponding to a plurality of specific wavelength bands included in the predetermined wavelength band,
   wherein the sensor arrays are configured to alternately and repeatably operate 1) a plurality of exposure periods for accumulating electrical energy according to the detected light and 2) a plurality of reset periods for initializing the electrical energy accumulated during the exposure period and the sensor arrays configured to generate the spectrum data related to the detected light in the exposure period,
   wherein the sensor arrays are configured to be set for the exposure period to have a predetermined duration such that the spectrum data related to the target light includes 1) first spectrum information related to the continuum emission having overall intensity values for the predetermined wavelength band and 2) second spectrum information related to the element specific emission having intensity values of one or more spectral peaks within the predetermined wavelength band; and
   a controller configured to:
   obtain a plurality of spectrum data corresponding to the plurality of exposure periods of the spectrometer,
   select a specific exposure period based on an occurrence of the projection of the pulsed beam,
   obtain the target spectrum data of the target light generated in connection with the plasma ablation from the selected specific exposure period, and
   provide, by using an artificial neural network, diagnostic information on whether the target is related to a disease based on the spectrum data.

2. The device according to claim 1, further comprising:
   a triggering module configured to transmit a triggering signal to the spectrometer in response to the occurrence of the projection of the pulsed beam, and
   wherein the controller configured to select the specific exposure period based on the triggering signal.

3. The device according to claim 2, wherein the triggering module includes a photo diode which outputs the triggering signal when light above a preset intensity is received.

4. The device according to claim 2, wherein the controller is further configured to:
   receive the trigger signal from the triggering module; and
   select the specific exposure period among the plurality of exposure periods based on the reception time of the triggering signal.

5. The device according to claim 2, wherein the triggering module is disposed adjacent to the laser projector for detecting the occurrence of the projection of the pulsed beam.

6. The device according to claim 1, wherein the artificial neural network has been trained based on a spectrum data for training which reflects 1) first spectrum information related to the continuum emission having overall intensity values for the predetermined wavelength band and 2) second spectrum information related to the element specific emission having intensity values of one or more spectral peaks within the predetermined wavelength band.

7. The device according to claim 1, wherein the predetermined duration of the exposure period is set to be longer than 1 ms.

8. A method for providing a medical information using a laser-induced breakdown spectroscopy (LIBS) device, the method comprising:

projecting, by a laser projector, a pulsed beam to a target;

separating, by a spectral member, light generated in connection with a plasma ablation induced at the target by the pulsed beam;

alternately and continuously repeating, by a sensor array, 1) a plurality of exposure periods for accumulating electrical energy according to received light and 2) a plurality of reset periods for initializing the electrical energy accumulated during the exposure period;

generating, by the sensor array, a plurality of a spectrum data, which is related to the plurality of exposure periods, including a plurality of intensity values of the separated light received from the spectral member in predetermined wavelength band;

selecting, by a controller, the target specific exposure period among the plurality of the exposure periods; and obtaining, by the controller, the spectrum data related to the specific exposure period from the sensor array, providing, by the controller, diagnostic information on whether the target is related to a disease based on the spectrum data by using an artificial neural network, and wherein the sensor arrays configured to be set for the exposure period to have a predetermined duration such that the spectrum data includes 1) first spectrum information related to the continuum emission having overall intensity values for the predetermined wavelength band and 2) second spectrum information related to the element specific emission having intensity values of one or more spectral peaks within the predetermined wavelength band.

9. The method of claim 8, further comprising:

generating, by a triggering module, a triggering signal in response to an occurrence of the projection of the pulsed beam; and wherein the selecting the specific exposure period is further based on the triggering signal.

10. The method of claim 9, wherein the triggering module is disposed adjacent to the laser projector for detecting the occurrence of the projection of the pulsed beam.

11. The method of claim 9, wherein the triggering module includes a photo diode which outputs the triggering signal when light above a preset intensity is received.

12. The method of claim 8, wherein the artificial neural network has been trained based on a spectrum data for training which reflects 1) first spectrum information related to the continuum emission having overall intensity values for the predetermined wavelength band and 2) second spectrum information related to the element specific emission having intensity values of one or more spectral peaks within the predetermined wavelength band.

13. The method of claim 8, wherein the predetermined duration of the exposure period is set to be longer than 1 ms.

14. The method of claim 8, wherein the disease comprises a skin cancer.

* * * * *